(12) United States Patent
Merkulov et al.

(10) Patent No.: US 6,562,593 B2
(45) Date of Patent: May 13, 2003

(54) ISOLATED HUMAN TRANSPORTER PROTEINS, NUCLEIC ACID MOLECULES ENCODING HUMAN TRANSPORTER PROTEINS, AND USES THEREOF

(75) Inventors: Gennady Merkulov, Baltimore, MD (US); Karl Guegler, Menlo Park, CA (US); Marion Webster, San Francisco, CA (US); Karen A. Ketchum, Germantown, MD (US); Valentina Di Francesco, Rockville, MD (US); Ellen M. Beasley, Darnestown, MD (US)

(73) Assignee: Applera Corporation, Norwalk, CT (US)

( * ) Notice: Subject to any disclaimer, the term of this patent is extended or adjusted under 35 U.S.C. 154(b) by 0 days.

(21) Appl. No.: 09/740,041

(22) Filed: Dec. 20, 2000

(65) Prior Publication Data

US 2002/0082190 A1 Jun. 27, 2002

Related U.S. Application Data

(60) Provisional application No. 60/251,035, filed on Dec. 5, 2000.

(51) Int. Cl.$^7$ .......................... C12N 5/10; C12N 15/63; C12N 15/12; C12P 21/02; C07H 21/04

(52) U.S. Cl. ................... 435/69.1; 435/320.1; 435/325; 536/23.5

(58) Field of Search ............................ 435/69.1, 320.1, 435/325; 536/23.5

(56) References Cited

U.S. PATENT DOCUMENTS

2002/0098473 A1 * 7/2002 Edwards et al.

* cited by examiner

*Primary Examiner*—Gary Kunz
*Assistant Examiner*—Stephen Gucker
(74) *Attorney, Agent, or Firm*—Applera Corporation; Lin Sun-Hoffman

(57) ABSTRACT

The present invention provides amino acid sequences of peptides that are encoded by genes within the human genome, the transporter peptides of the present invention. The present invention specifically provides isolated peptide and nucleic acid molecules, methods of identifying orthologs and paralogs of the transporter peptides, and methods of identifying modulators of the transporter peptides.

23 Claims, 38 Drawing Sheets

```
   1 TCAGAGGTGC CCCTCATTCA AAATGCCTTT TAAAGCATTT GATACCTTCA
  51 AAGAAAAAAT TCTGAAACCT GGGAAGGAAG GAGTGAAGAA CGCCGTGGGA
 101 GATTCTTTGG GAATTTTACA AAGAAAAATC GATGGGACAA CTGAGGAAGA
 151 AGATAACATT GAGCTGAATG AAGAAGGAAG GCCGGTGCAG ACGTCCAGGC
 201 CAAGCCCCCC ACTCTGCGAC TGCCACTGCT GCGGCCTCCC CAAGCGTTAC
 251 ATCATTGCTA TCATGAGTGG GCTGGGATTC TGCATTTCCT TTGGGATCCG
 301 GTGCAATCTT GGAGTTGCCA TTGTGGAAAT GGTCAACAAT AGCACCGTAT
 351 ATGTTGATGG AAAACCGGAA ATTCAGACAG CACAGTTTAA CTGGGATCCA
 401 GAAACAGTGG GCCTTATCCA TGGATCTTTT TTCTGGGGCT ATATTATGAC
 451 ACAAATTCCA GGTGGTTTCA TTTCAAACAA GTTTGCTGCT AACAGGGTCT
 501 TTGGAGCTGC CATCTTCTTA ACATCGACTC TGAACATGTT TATTCCCTCT
 551 GCAGCCAGAG TGCATTAAGG ATGCGTCATG TGTGTCAGAA TTCTGCAAGG
 601 TTTAGTGGAG GGTGTGACCT ACCCAGCCTG CCATGGGATG TGGAGTAAGT
 651 GGGCACCACC TTTGGAGAGA AGCCGACTGG CCACAACCTC TTTTTGTGGT
 701 TCCTATGCAG GGGCAGTGGT TGCCATGCCC CTGGCTGGGG TGTTGGTGCA
 751 GTACATTGGA TGGTCCTCTG TCTTTTATAT TTATGGCATG TTTGGGATTA
 801 TTTGGTACAT GTTTTGGCTG TTGCAGGCCT ATGAGTGCCC AGCAGCTCAT
 851 CCAACAATAT CCAATGAGGA GAAGACCTAT ATAGAGACAA GCATAGGAGA
 901 GGGGGCCAAC GTGGTTAGTC TAAGTAAATT TAGTACCCCA TGGAAAAGAT
 951 TTTTCACATC TTTGCCGGTT TATGCAATCA TTGTGGCAAA TTTTTGCAGA
1001 AGCTGGACCT TTTATTTGCT CCTCATAAGT CAGCCTGCTT ATTTTGAAGA
1051 GGTCTTTGGA TTTGCAATAA GTAAGGTGGG TCTCTTGTCA GCAGTCCCAC
1101 ACATGGTTAT GACAATCGTT GTACCTATTG AGGACAATT GGCTGATTAT
1151 TTAAGAAGCA GACAAATTTT AACCACAACT GCTGTCAGAA AAATCATGAA
1201 CTGTGGAGGT TTTGGCATGG AGGCAACCTT ACTCCTGGTG GTTGGCTTTT
1251 CGCATACCAA AGGGGTGGCT ATCTCCTTTC TGGTACTTGC TGTAGGATTT
1301 AGTGGCTTCG CTATTTCAGG TTTTAATGTC AACCACCTGG ACATTGCCCC
1351 ACGCTATGCC AGCATTCTCA TGGGGATCTC AAACGGAGTG GGAACCCTCT
1401 CTGGAATGGT CTGTCCCCTC ATTGTCGGTG CAATGACCAG GCACAAGACC
1451 CGTGAAGAAT GGCAGAATGT GTTCCTCATA GCTGCCCTGG TGCATTACAG
1501 TGGTGTGATC TTCTATGGGA TCTTTGCTTC TGGGGAGAAA CAGGAGTGGG
1551 CTGACCCAGA GAATCTCTCT GAGGAGAAAT GTGGAATCAT TGACCAGGAC
1601 GAATTAGCTG AGGAGATAGA ACTCAACCAT GAGAGTTTTG CGAGTCCCAA
1651 AAAGAAGATG TCTTATGGAG CCACCTCCCA GAATTGTGAA GTCCAGAAGA
1701 AGGAATGGAA AGGACAGAGA GGAGCGACCC TTGATGAGGA AGAGCTGACA
1751 TCCTACCAGA ATGAAGAGAG AAACTTCTCA ACTATATCCT AATGTCTGAG
1801 AGGCACTTCT G (SEQ ID NO:1)
```

FEATURES:
5'UTR: 1-22
Start Codon: 23
Stop Codon: 1790
3'UTR: 1793-1811

HOMOLOGOUS PROTEINS:
```
gb|AAF76223.1|AF271235_1  (AF271235) differentiation-associat...   866   0.0
ref|NP_065079.1|   differentiation-associated Na-dependent in...   864   0.0
ref|NP_064705.1|   brain-specific Na-dependent inorganic phos...   836   0.0
pir||I59302   brain specific Na+-dependent inorganic phosphat...   835   0.0
ref|XP_008922.1|   brain-specific Na-dependent inorganic phos...   830   0.0
ref|XP_006115.1|   differentiation-associated Na-dependent in...   543   e-153
pir||T43650   probable sodium-dependent inorganic phosphate c...   491   e-137
sp|P34644|YOQ6_CAEEL HYPOTHETICAL 52.2 KD PROTEIN ZK512.6 I...     491   e-137
gb|AAF51256.1|   (AE003583) CG9887 gene product [Drosophila m...   456   e-127
gb|AAF55770.1|   (AE003730) CG4288 gene product [alt 1] [Dros...   377   e-103
```

EST:
```
gi|2064553 /dataset=dbest /taxon=9606 ...                          505   e-140
```

EXPRESSION INFORMATION FOR MODULATORY USE:
gi|2064553  Pooled human melanocyte, fetal heart, and pregnant uterus Tissue expression:
Human leukocytes

FIGURE 1

```
  1 MPFKAFDTFK EKILKPGKEG VKNAVGDSLG ILQRKIDGTT EEEDNIELNE
 51 EGRPVQTSRP SPPLCDCHCC GLPKRYIIAI MSGLGFCISF GIRCNLGVAI
101 VEMVNNSTVY VDGKPEIQTA QFNWDPETVG LIHGSFFWGY IMTQIPGGFI
151 SNKFAANRVF GAAIFLTSTL NMFIPSAARV HYGCVMCVRI LQGLVEGVTY
201 PACHGMWSKW APPLERSRLA TTSFCGSYAG AVVAMPLAGV LVQYIGWSSV
251 FYIYGMFGII WYMFWLLQAY ECPAAHPTIS NEEKTYIETS IGEGANVVSL
301 SKFSTPWKRF FTSLPVYAII VANFCRSWTF YLLLISQPAY FEEVFGFAIS
351 KVGLLSAVPH MVMTIVVPIG GQLADYLRSR QILTTTAVRK IMNCGGFGME
401 ATLLLVVGFS HTKGVAISFL VLAVGFSGPA ISGFNVNHLD IAPRYASILM
451 GISNGVGTLS GMVCPLIVGA MTRHKTREEW QNVFLIAALV HYSGVIFYGV
501 FASGEKQEWA DPENLSEEKC GIIDQDELAE EIELNHESFA SPKKKMSYGA
551 TSQNCEVQKK EWKGQRGATL DEEELTSYQN EERNFSTIS (SEQ ID NO:2)
```

FEATURES:
Functional domains and key regions:
Prosite results:
--------------------------------------------------------------------
[1] PDOC00001 PS00001 ASN_GLYCOSYLATION
N-glycosylation site Number of matches: 4
    1    105-108  NNST
    2    106-109  NSTV
    3    514-517  NLSE
    4    584-587  NFST
--------------------------------------------------------------------
[2] PDOC00004 PS00004 CAMP_PHOSPHO_SITE
cAMP- and cGMP-dependent protein kinase phosphorylation site 544-547  KKMS
--------------------------------------------------------------------
[3] PDOC00005 PS00005 PKC_PHOSPHO_SITE
Protein kinase C phosphorylation site Number of matches: 4
    1      8-10   TFK
    2     57-59   TSR
    3    151-153  SNK
    4    541-543  SPK
--------------------------------------------------------------------
[4] PDOC00006 PS00006 CK2_PHOSPHO_SITE
Casein kinase II phosphorylation site Number of matches: 8
    1      8-11   TFKE
    2     39-42   TTEE
    3     40-43   TEEE
    4    280-283  SNEE
    5    285-288  TYIE
    6    290-293  SIGE
    7    476-479  TREE
    8    569-572  TLDE
--------------------------------------------------------------------
[5] PDOC00008 PS00008 MYRISTYL
N-myristoylation site Number of matches: 17
    1     20-25   GVKNAV
    2     83-88   GLGFCI
    3     91-96   GIRCNL
    4    130-135  GLIHGS
    5    147-152  GGFISN
    6    183-188  GCVMCV
    7    193-198  GLVEGV
    8    226-231  GSYAGA
    9    230-235  GAVVAM
   10    353-358  GLLSAV
   11    370-375  GGQLAD
   12    398-403  GMEATL

FIGURE 2A

```
13   414-419  GVAISF
14   451-456  GISNGV
15   457-462  GTLSGM
16   499-504  GVFASG
17   564-569  GQRGAT
```
---
[6] PDOC00262 PS00290 IG_MHC
Immunoglobulins and major histocompatibility complex proteins signature

```
     270-276  YECPAAH
```

Membrane spanning structure and domains:

| Helix | Begin | End | Score | Certainity |
|---|---|---|---|---|
| 1 | 81 | 101 | 1.532 | Certain |
| 2 | 137 | 157 | 1.403 | Certain |
| 3 | 164 | 184 | 1.595 | Certain |
| 4 | 228 | 248 | 1.668 | Certain |
| 5 | 254 | 274 | 2.110 | Certain |
| 6 | 315 | 335 | 0.815 | Putative |
| 7 | 358 | 378 | 1.655 | Certain |
| 8 | 397 | 417 | 1.281 | Certain |
| 9 | 420 | 440 | 2.197 | Certain |
| 10 | 458 | 478 | 1.651 | Certain |
| 11 | 489 | 509 | 1.657 | Certain |

FIGURE 2B

BLAST Alignment to Top Hit:

```
>CRA|155000001887002 /dataset=nraa /length=582 /altid=gi|8515881
        /def=gb|AAF76223.1|AF271235_1 (AF271235)
        differentation-associated Na-dependent inorganic
        phosphate cotransporter [Rattus norvegicus] /org=Rattus
        norvegicus /taxon=10116
        Length = 582

Score =  889 bits (2271), Expect = 0.0
 Identities = 426/582 (73%), Positives = 497/582 (85%), Gaps = 4/582 (0%)
 Frame = +3

Query: 42    DTFKEKILKPGKEGVKNAVGDSLGILQRKIDGTTEEEDNIELNEEGRPVQTSRPSPPLCD 221
             ++ K++IL PGKEG+KN  G SLG + R ++    +  IEL E+G+P++         PLCD
Sbjct: 2     ESVKQRILAPGKEGIKNFAGKSLGQIYRVLEKKQDNRETIELTEDGKPLEVPEKKAPLCD 61

Query: 222   CHCCGLPKRYIIAIMSGLGFCISFGIRCNLGVAIVEMVNNSTVYVDGKPEIQTAQFNWDP 401
             C C GLP+RYIIAIMSGLGFCISFGIRCNLGVAIV+MVNNST++  GK  +  A+FNWDP
Sbjct: 62    CTCFGLPRRYIIAIMSGLGFCISFGIRCNLGVAIVDMVNNSTIHRGGKVIKEKAKFNWDP 121

Query: 402   ETVGLIHGSFFWGYIMTQIPGGFISNKFAANRVFGAAIFLTSTLNMFIPSAARVHYGCVM 581
             ETVG+IHGSFFWGYI+TQIPGG+I+++ AANRVFGAAI LTSTLNM IPSAARVHYGCV+
Sbjct: 122   ETVGMIHGSFFWGYIITQIPGGYIASRLAANRVFGAAILLTSTLNMLIPSAARVHYGCVI 181

Query: 582   CVRILQGLVEGVTYPACHGMWSKWAPPLERSRLATTSFCGSYAGAVVAMPLAGVLVQYIG 761
              VRILQGLVEGVTYPACHG+WSKWAPPLERSRLATTSFCGSYAGAV+AMPLAG+LVQY G
Sbjct: 182   FVRILQGLVEGVTYPACHGIWSKWAPPLERSRLATTSFCGSYAGAVIAMPLAGILVQYTG 241

Query: 762   WSSVFYIYGMFGIIWYMFWLLQAYECPAAHPTISNEEKTYIETSIGEGANVV-SLSKFST 938
             WSSVFY+YG FG++WYMFWLL +YE PA HPTI++EE+ YIE SIGE AN++  + KF T
Sbjct: 242   WSSVFYVYGSFGMVWYMFWLLVSYESPAKHPTITDEERRYIEESIGESANLLGAMEKFKT 301

Query: 939   PWKRFFTSLPVYAIIVANFCRSWTFYLLLISQPAYFEEVFGFAISKVGLLSAVPHMVMTI 1118
             PW++FFTS+PVYAIIVANFCRSWTFYLLLISQPAYFEEVFGF ISKVG+LSAVPH+VMTI
Sbjct: 302   PWRKFFTSMPVYAIIVANFCRSWTFYLLLISQPAYFEEVFGFEISKVGMLSAVPHLVMTI 361

Query: 1119  VVPIGGQLADYLRSRQILTTTAVRKIMNCGGFGMEATLLLVVGFSHTKGVAISFLVLAVG 1298
             +VPIGGQ+AD+LRS+QIL+TT VRKIMNCGGFGMEATLLLVVG+SHT+GVAISFLVLAVG
Sbjct: 362   IVPIGGQIADFLRSKQILSTTTVRKIMNCGGFGMEATLLLVVGYSHTRGVAISFLVLAVG 421

Query: 1299  FSGFAISGFNVNHLDIAPRYASILMGISNGVGTLSGMVCPLIVGAMTRHKTREEWQNVFL 1478
             FSGFAISGFNVNHLDIAPRYASILMGISNGVGTLSGMVCP+IVGAMT++K+REEWQ VFL
Sbjct: 422   FSGFAISGFNVNHLDIAPRYASILMGISNGVGTLSGMVCPIIVGAMTKNKSREEWQYVFL 481

Query: 1479  IAALVHYSGVIFYGIFASGEKQEWADPENLSEEKCGIIDQDELAEE---IELNHESFASP 1649
             IAALVHY GVIFY +FASGEKQ WADPE  SEEKCG I +DEL EE    I N+ ++ +
Sbjct: 482   IAALVHYGGVIFYALFASGEKQPWADPEETSEEKCGFIHEDELDEETGDITQNYINYGTT 541

Query: 1650  KKKMSYGATSQNCEVQKKEWKGQRGATLDEEELTSYQNEERN 1775
             K   SYGATSQ      W+ ++    +  E  +Y ++R+
Sbjct: 542   K---SYGATSQENGGWPNGWE-KKEEFVQESAQDAYSYKDRD 579 (SEQ ID NO:4)

Hmmer search results (Pfam):
Scores for sequence family classification (score includes all domains):
Model      Description                                        Score    E-value  N
--------   -----------                                        -----    -------  ---
PF01777    Ribosomal L27e protein family                        1.4          9  1

Parsed for domains:
Model      Domain  seq-f  seq-t    hmm-f  hmm-t     score   E-value
--------   ------  -----  -----    -----  -----     -----   -------
PF01777    1/1        11     18 ..      1      9 [.    1.4         9
```

FIGURE 2C

```
   1 AACCTCTTTT TGTCTGAGTT TCCTGCCAGT AAAATTGGGG AAAATAAGAA
  51 GTTATTTACC ACAGAGTCTT GCTGGGAAGA TTGTGGTGAT ACTTAAAGAG
 101 TGCTTAACAC AGAGCCAGGA CCCTAGAAAG AACTCAAAAG ATATTAGCAA
 151 TATTTAGCCT ACCAAGGATT CAGCACGGAC TTAGTTGAAC TTAATTCAAA
 201 TTTTGGATAA TTTGGACAGT GGCTTGCAGA GGATATTGAC TGGTCTTGTG
 251 GAAATGACTC CTGGGGAGCC TGAGAGCCTA TAGCCTATGA TTTGTCAGTC
 301 GCATGCAGAC TGGAGGATTG AACACAGGA GCCTCAAAGA TGAAGAGTTT
 351 TTTTTCCACC GCAGCAGCAT TTACAGAGGC GTCATCCTGC TGCCCATAAA
 401 TGTGGCCACA ACTTGCAGCG TTTCAGCCCC AGTTCAACAA GTATTTAGGT
 451 AACGCCCACT CCCTGCCAGG CTCTGCTAGG GCAGAGGACA GGTGATTTGG
 501 AGGCACAGAG GAGGGACATC TCACCTTGCC CATGCAGTTT TCTAGAGGAT
 551 TGATATCTTA GCATGACCTT AGAACCCCTA GAAGTTACCC AGTTGAAGGG
 601 GTGCAGAGAG TTACCCAGGC AGAGGGCATA GCTTGAGTAA AGCCCAGAGG
 651 CAATAGGGAG CTTGCTGAGT TCAGTGAAAT GAGGATGTGG AAAGCAGAGT
 701 GACAAGAAGA AAGACTTAGG GTCCCAGGGA AAGGCCTTGT GTGCCATGAT
 751 AAAGAATTGT ATTGTAAATA GTGCTGCAAT AAACATACGT GTGGATGTGT
 801 CTTTGTAGTA GAATGATTAG AATACATGGA TACAGAGGG GGAACATCAC
 851 ACACCGGAGC TGGTCAGGGG TTGGGGGGCA AGGAGAGGGA GAGCATTAGG
 901 ACAAATACCT AATGCATGTG GGGCTTAAAA CCTAGATGAT GGGTTGATAG
 951 GTGCAGCAAA CCACCATGGC ACATGTATAC CTATGTAACA AACCTGCATG
1001 TTCTGCACAT GTATCCTGGA ACTTAAAGTA AAAAAAAAAA AGTCCATCTA
1051 GAGGGAGAAA AGGGGAAAAA ACAAAAATAA TTTTATTTAT CCTGAGGACA
1101 ATGAGGAGTC AGTGGAGAGT TCTAAGCAGG TTCTAGATAT CTTCCGGCTC
1151 AGAAATCTTC AATTAGATGG TCCCAAATGG CATCTACGTA TCATACTTTG
1201 AGAGAGCCTG CTCTGTTGAT TAGGAGCAAA TAAATGTCCT CCTGGATGTA
1251 TGTGGCCTGG GTTTTGCATT TGGGCTACTC AAATGCAAGT TCCTCGTGGG
1301 ACCACATCCA TGCTAGTGGC TGGCTGAAAA ACGGCTTCAT GACTCTCATG
1351 AGGGGAATAA AAGGCATGGA GTGGTGGCTG TGAGCCTGTC TGCAGGGCCA
1401 GACCTCAGAA AAGCAAAGGG CTGTAAATGT TTCATAAATT TCTCTCTGGG
1451 TGCCTGCTCT GGCTGAGAGC CCATTCATAA GCCCAGGCGG CTGAGGGGCA
1501 GGTATTGTGC CGGTTACTAT AGCATCACCT TGGAAAGTCT CACTTGGTGA
1551 GAGCGGCAGG CGAGCTGGGG TGGGGCAGGA GGGGGACGCG GCTGGCTGGA
1601 GGGGCTGGAG CTAGGCCACG GATACTGCTG CTGGTCTCAG GACTCCTGGT
1651 GGTCCGGAGC TCATGTTAGC GTCCCCAGCT GCAGCCCAGG GAGGGAGAGA
1701 GGCTGCGCTC AGTCTGAGAG TGGCTGCCTG AGACAGCTGC CACAGGCTGC
1751 TGCAGAGCGT GCAGCTTTTG CAAGGGACTG AATTCCCAGC CAGACACCCC
1801 TTGGACTCTT TTTTGGAGGG GTGGGGAGCA GAGAGAGGAG GGAGTTGTCT
1851 TATCTTGGAA GATCCGAGCT GGGTTCATC TCCTTTTTGA TTTTGAGTAG
1901 TTCCCTCCAC GAGAACTGAC TTCCAGGTGT TCACCAAGGG AAACAAGGTG
1951 GTTCTCACAC TGGAAATGAG GAAGGATGAC AGTTTTTGAG ACTGACTGTT
2001 AACGGCTCAG AGGTGCCCCT CATTCAAAAT GCCTTTTAAA GCATTTGATA
2051 CCTTCAAAGA AAAATTCTG AAACCTGGGA AGGAAGGAGT GAAGAACGCC
2101 GTGGGAGATT CTTTGGGAAT TTTACAAAGG TAAAGTTTGA ATGCGAACTT
2151 TAGTTCCTTT CTGAGTAGCT TCGTATTGCC AATGTGTGAG AGACTTGGTA
2201 TCACGTTTTT AAAACCACAC TTTAATGAGG AGAGGATGGG TCAGATTAGA
2251 TCCTTCTGGA GCCCCTTCTA GCTCCAGTAG TCTATGCCTG GAGGAAAAAC
2301 AGATGCATGA ATAGTATTGG GTTGTATTAG GAAAAGATCA AGACAAATAT
2351 GCTGTTTATA TAGCTGGATT AGCACTTTCT GGAGATGATG ATATTGCATA
2401 TGGTATGTTT GCATTGAATT TAGAAAATAT TTAGGGAGAT AATATTTTAT
2451 GTTAACTCAT TAGTAATGAC AAATATGCCT TGAACTGAAA TAATTTTTAT
2501 GTTTTTCACT GAATCCACTA TAAATGAAAA TTAAATATTT GCAATTTTTA
2551 GCTTATTTAA TAAAATACAT AAAGTGGTTC CTGATTGTAT AGTTTGCAAA
2601 GAGAAGGATA GTTACACATT AATTTGAAGG AAGTAACTTA AAAAATGTCT
2651 TTGAAGCAGA AAATCTCACA TAATTGCAGT GGGAAAATGT TAAGTACTAT
2701 CACTGAATTG AATGAGATTT TAGTCCAAAC CAAAAAGTAA ATATTTTTTA
2751 AAGTAAAATA TATTAATGGA AGGAGAGTTT GCTATAAATG ATTGAATTAA
2801 TGTGACAGTT TAATTTATGA ATTTTTATAG ACATAGTAAA TGCCTTCTCA
2851 AATTATATAA ATGATTTCAT AAGTGGTCCT TATGTGCAAG GTAAAATGAC
2901 TGCTTTATCT CTCTGATATA AATAAATGTG AAAATAACT TTGATACACT
2951 TTTTATTTGT TTGGATGATT ATTTCTAATC CTGGTGAGTG AAAATGCCAT
3001 CTGGTGTGTC CTTTTAACTT TTCTATTATC TCTTAAATTT AAAACTTTT
3051 TCATTTAAAT GACTATTTCC AGGCAATCTG AGATTCATCC CATTTCTTGT
3101 GTTTTAAAAC ACATATGCTC CTGTCAGTGT TAAATTTTCC CATGGTATCA
3151 CTGTTAATAT TAACTTTCCT AATAAGAAAA AAGAGTTGGA CACCTTATTA
3201 TTTTAGTAAT TAGAAACAAA AAGCTTCAA TCAGACCTAC ACTGAATTAG
3251 CATGTCTAGA TGAAAACCTA GCTCAGTGAC AGCAGCATAA ACCAGCCAAA
3301 TATAGAAAAA ATTACAATAA CATTTTTTTC AGAGTGTTTT ATCCTTCCGT
3351 TGAGCACTCC CCAGGTAACG TCTTATTGTG TTGGCGTTCA TTTGATTAGA
3401 AACGCAAAAA TAATTTTTGC ATAATAAGCA CGATAGCTTA ATTGGCTTAT
```

FIGURE 3A

```
3451 TCAAGTAATG ACAAAGGAAT CTGGCAAAGT CAAGAATAAA AACCATAGGC
3501 CGGGCGCAGT GGCTCACGCC TGTAATCCCA GCACTTTGGG AGGCGGAAGT
3551 GGGAGGATCG CTTGAGGCCA GAAGTTCGAG ACTAGCCTGG GGAACATAGA
3601 GAGACCATGT CTCTACAGAA ATACAAAAAA TTAGCCAGCA TGATGGTGCA
3651 TGCCTGTCAT CTCAGCTTCC CAAGAAGTGG GAGTATTGCT TGAGCCCAGA
3701 CATTCAAGGT TGCAGCGAGC CAAGATTGCG TCTCTGCACT CCAGCTAGGG
3751 TGACAGAGTC AGACTCTGTC TCAAAAAATA AAAAAATAAA ATAAATTTAA
3801 AAACCTATGA CGTTGGGCCA TAGTCACCAT TATAAACAGC AAACTCTGCC
3851 TTCATTTATA AAATATTTGA TATAAAAATA CTTAGGAATT TTCTTTTCAA
3901 CCTTAAGTTT AATTGCTTTT TGTGAAATTT GATTGCTTTT TTCAATAGGA
3951 ATTATTGATC GAAGAGCCGG TTTTGCTATG TTTGATTGGA GGAGCTACAT
4001 GGAGATCTTT TTGTTTACAA AATTGATTTG CTTAGGGATA TAACAAAATT
4051 GGCGATTTTC CAAATTGTGT GACCTCAACC AGAAATTGGG CTATGTGTCT
4101 AGGACTGTTT GAATAGTTTC CTCAGAACAA TAGAAAAACA GCTAGCACAG
4151 TACTAGGGAC AGAGAATGCA CTAAACAAAT GCTAGATATT GTCATGGTTG
4201 TCCTAATTGT AGAATGGCTT TAGAAAAAAT AAAGCCAAGG TCAAATCCCT
4251 TTTTTCAGTG ATCTATAGAG AGAAATTATT GGCAGAAGAA ACGAAAACAG
4301 ACATTGCTTG AGCGGTGATC CAAGTTGATC CTCAGTTCTA GTGAGGAATT
4351 ATCAAGACCA GCTCTGCCAC GTGTTTGGCA TTAATCACAG GTGTATAAGG
4401 TAATTGTATG TAAATGACCC TGCCCAGAGC CTGGCACATA CTGGGCATTT
4451 CCCTCTCATT TCACTGCTTT TCACGTAAAA CCAGTTGACA GAATCCCATG
4501 TAAAAAAATC ACAAAGAACT GTTTTCTGTT TTGTAGGAGC TTTTGGAAGC
4551 TAGAAGCCCC TACATTGTAA CTTAGAAGGC AATGTAAATC ACAGCTGTCT
4601 AATAATGTTT GAGGCTGAGG TCATCATCTA AATGGAATTC TTGAGATGCT
4651 TTTTAATCAC AGTGTTCCTC ACAGTCAGGG GAGTGGCAAT TGCACAGGGA
4701 AGCATTTGAG AGTTCGCACA CAGGCTTGAT TACAGTCAGG CATGATTAGC
4751 TTTCCTGGAA AACAGTCATT GATAAGAAGC AGCTGAGCAA TTAATCAGCT
4801 AAAGGTAAAA TAATATTTTA GAAGTGCAGG AAGAAAGAAG ATGCACTCAT
4851 TTATAGTTTA GTATTGAATT ATATAGATGA CATAGAAAGC ATTAAACTTG
4901 GAAACTAATG TCCAGAAAGT GACATGCAGA TTTGTTCAAT TTAAATTACA
4951 ATTTATGTGT CCTTTAATTG TTCATGTCTA AAAAACATAA CAGTGACAAA
5001 ACAGTATCTT TCAGACACTG TAAACTCATT TAATTCTATT AAAATCCCCA
5051 TGAAGAGGGG ATTACTATAA TTACAACTTT TCTTTTTTTT GGGATAGGGT
5101 CTCACTCTGT TGCCTAGGCT GGAGTGCAGT GATGTGATCA TAGCTCACTG
5151 CAGCCTCAAA CTCCTGGCCT CAAGCCATAC TGCCTCCTTG GCCTCCCAAA
5201 GTGCTAGGAT TACAGGCATG AGCCACAGCA TCTAGCAATA ATTTTACAGA
5251 TGAGAAAACT GAGGCACAGA GAGGTTAAGT AGCTTGCCCA AGGTCACACA
5301 GCTATAAATG GAAGAGCTAG GTTTCAAACC AGATGTTCTA TGCCCATCAT
5351 TCTTAATCAC TACATTATGT TACCCCTGTA ATCAAGTGTC TTTCCTCTTC
5401 CCACTCACTG TCTTGATATT GGGCCACTTA TTTAGGTTTA GGGAGGTCTA
5451 CTTGGACTGC AATGTAGCCA GCAACTTCTG GATCTGCTGT CAAGTGTGGG
5501 CTATTCTCCT AATCAGTTGC ATCTTTATTG AAGGCTTTCT CCAAGGGAGG
5551 CTTAAGGGGA GTCTGGTCTC CTTACAAGTA TGTCTATCTT CCCTTTAAAT
5601 GAAACTAGTC CCTGCATCGT GTCTGTCTTC AGCATTCAGG AGTGTGCCAG
5651 ATATGCACTT CCTGCTCCAT CAACAAAGGT GAGTGTGTTA AAGCTTGCTC
5701 TGAGATCAGG TGATCCTGGG TTCCAACTGC TGCAACATCC TTTACTTCCC
5751 TGCCTGCATG ACCTCAGGCA ACTTGGCTGC AATGGGGTGA CTCTAGGAAA
5801 CCAAGTCAGA TCACATCTCA CCCCTGCTCA AAACTACCTC ACTCAGAGTT
5851 AAAGCCAGTG CCCTTTCAAT GGCCTTCAAG GACCTCTGTG ATCTAGGACT
5901 TTTGGAAGGC TCTCTGAGTT CATCTGTGAC ATTTTCCTGC CTCACTCTAC
5951 TCTGGATTCA CGGGCCTCCT GGCTCTTATT AGAACTCCCC CAGATTCACT
6001 CCTGTCCCGG CTTTCGCCCT GTTTCTTTTG CTTAAATGCT TTCCTCCCAG
6051 ATAGCCTGAT GGCTCATTCC CTCGCTTTCT TCAAGTATGT GCTCAAAGAT
6101 CCCCACTTTC CTGGCCATTC TATTTAAACA TGAAGCTCAC CTGCCCTCCT
6151 CCTCCTGCCC TCTTCTCTGT CCCTCTTTCC TGCTTTACTT CACCTCTGTC
6201 TTAGGTAGGT TCCCTAAAAA GCACAGCCTG AGACAGGGAT TTGGGTGAGC
6251 CTAGAATGTG ATTTAATGAG CTCTTCCTGA AAAAACTGGG AGGGAGTAAA
6301 ACAAGAAGGG AAAGGAGAGG CTGGGTGTGG TGGCTCACGC CTATAATCCT
6351 AGCATTTTGG GAGTCCGAGG CAGGCAGATT GCCTGAGCTC AGGAGTTTGA
6401 GACCAGCCTG GGCAACATGG TGAAACCTGT CTCTACTAAA AGACAAAAAA
6451 TGAGCCAGGC ATAGAGGCAT GTGCCTATAG TCGTAGCTAC TCAGGAGGCT
6501 GAGGCAGGAG AATTGCTTGA ATCCGGGAGG CAGAGGTTGC AGTGAGCCGA
6551 GATCACACCA CTGCACTCCA GCCTGGACGA CAGAGGGAGA CTCCATCTCC
6601 AAAAAAAACA AACAAAAAA AAACAGAAAG GAGAAAGAGC CAAGCAAGGA
6651 TGCATGCTCA CAATGCCCAG TGGCCAGATC CAAAGGGGAA GGCTCTGGAG
6701 CACAAGCGAT GTGCTGAGTC CTTCCTTTGG GGCAAGTGGG GCAGCCTTTT
6751 ATATCTCTGC CTCAGTCAGT CATCAGCTCT GGGCTGATGG GGGTGGGTGA
6801 GGGGTTTATT TGGAGGCCAC TGAGCAGTGG GAAGTTCTCC AGGGTTCCTC
6851 ATGCCAGGAC TAGAAGCCCA GGCAAGGAGT CACCATGGTG GCAAGGGTCA
```

FIGURE 3B

```
 6901 TGGGTCCTGA TCCTCAGGAG GAACCAGAAC TGTCACCTCA TCACGGGAGC
 6951 AGGAAGAGAT GTGTTTGGCA CTGAGGTGGT CCACTCGGAC ATCTCCTGAT
 7001 ACTGCCTGGG CTAGTTTTAT TTATTTTTTT ATTTTAATTT TTAAAATAAT
 7051 AGAGATGGGG GTCTCACCAT GTTGATTAGG CTGGTCTTAA ACTCCTGGGC
 7101 TCAGGAGATC TTCCTGCCTT GGCCTCCCAA GTGCTAGAAT TACAGGCATG
 7151 AGCCACCGCA CCCTGCCTAG TTTTAACTGC AAATGGGAAA ATACAGCAAC
 7201 CGTGACCTGC TAGCAGCTCT GGAAGTAGAA GTGTGCTTGC CCATCAAGGG
 7251 GAACTGGGGA GTGTGCTATG GTGTCTATGA CAGCCCACCC ACTGCACCGC
 7301 TCAGATCAAC TTGCTTCTCA CATGAAGTTC ACTCCATCCA GGTACAGCTT
 7351 CTCCAAGACT CTATGGTTGT AATTCCTGAG GAGCCTTCCA AGAAGAGTT
 7401 ATTAAGACAG ACTCCAGGCC CCACTGTGAT GACTGGTCCC TCCTCTCCAC
 7451 CCCTTTTTGA TTTCCCTCAC TTCTGTTTGC TTGTCTGATG GGTTGCCCCA
 7501 GATCTTCATC CCTGAGAGGT CTAAATCCCT GGTTAACATA ACCTCACCAG
 7551 GTCATGGTTG CTGTATTTGC CCACTGACAG TTAAAAACTA GCCAAGGCAG
 7601 TATCAGGAGA GTGTCCCAGCA GATCATCTGG GTGCCAAACA TATTTCTTCC
 7651 TGCTCCCATG ATGAAGCGAC AGTTCTGATT CCTCCTGAAG ATTAGGATCC
 7701 ATGACCCTTA TCACTGTAGT GACTTCTTAC CATGTCTTCT GGTCTTGGCA
 7751 CGAGGACCCC AAAGTGACTG AGCAGCAGTC GTAACCATAT GTTGACTAGG
 7801 ATTTCCATTG TGTTCCTAAA TGGAAGAATT CTTCCTTGTG AATCGGGATT
 7851 TCTAGCTCCT CAGAGCCTAA GCTGAAGAGA TGAGATATTC CTCAGGTGGG
 7901 TTACTGGGAA TGATGGCGAG TGGGCCACT CCTTCTCTCA TGCCTTGTTT
 7951 CTTTGACCTG TGTGTTCTGC CCACTGGGCA CACAGCACCA TATCATAACT
 8001 GTTGGGTTTT TTGTTTGTTT GTTTGGGATG GAGTCCCACT CTGTCGCCCA
 8051 GGCTGGATGC AGCGGCTTGA TCTCAGCTCA CTGCAACCTC TGCCTCCTGG
 8101 GTTCAAGCAA TTCTCCTGCC TCAGCCTCCT GAATAGTGGG ATTACGGGCA
 8151 CCCACCACCA TGCCCGGCTA ATTTTGTATT TTTAGTAGAG ATGGGGTTTC
 8201 GGTATGTTGG TCAGGCTGGT TTCAAACACC TGACTTCAAA TGATCCACCC
 8251 GCCTTGGCCT CCCAAAATGC TGGCGTTACA GGTGCATAAC TGTTGATTTA
 8301 TGGAATATAC TGCATCCTGG AAGATAGCAC CTTACCCTCC CAGGGTTTCA
 8351 TCTCCAAGCT GATGTCGCAG CTGCATCTTT AAGAAGCTTC TTCAGAGGCC
 8401 AGGTGCCATG GCTCACACCT GTAATCCCAG CACTTTGGGA GGCCAACGCA
 8451 GATGGATCAT TTGAGGTCAG GAGTTGGAGA CCAGCCTGGT CAACATGGTG
 8501 AAACATATAT TTTCTACTAA AAATACAAAA AATTGCCAGG CGTGGTGGTG
 8551 GGCACCTGTA ATCCCAACTA CTCAGGAGGC TGAGGCAGGA GAATTGCTTG
 8601 ATTAAACCCA AGGGGGAAGA GGTTGCAGTG AGCTGAGATA GAGCCACTGC
 8651 ACTCCAGCCT GGGTGATAGA ACAAGATTCC ATCTCAAAAA AAAAAAAAA
 8701 AAAAAAAGCT TCTTTAGCTC TGGCAGGCTG TCAGCTTCTG GATGGTGTGG
 8751 TATATGGTGG GGCTTGTGCA TCCCATTGTC ATGTGCCCAC TGCTATGCCA
 8801 TCTTCACCAT AAATTGGGTG TTTTGGTCTG AAAAAATGTG ATGTGAGATC
 8851 CCATGTTGAG AAATGACAGA CTGAATCCTC AGATAGTGAT GTTGGCTGAG
 8901 ACTTGTAGTC TGAATAGGCA AACTCATACA TGGAATATTT CAACCCCAGT
 8951 CAGGATGAAT TGCTACCCTT TCCAGGATGG AAGGGGTCTG TTACAAACAA
 9001 CTTCTGACCA AGAGACTGGT TTGTCCCCTC AGGAATTGTG CCATCTCAGG
 9051 GGCTCAGCAT TAGTCTTGTT GCTGACCGCA GCAGGAGCTA GCTCAGTCCT
 9101 GGTGAGTGGG AGCTCCGACA TAGCCTCCAT CCCTGCTGCC ATGGTTACTC
 9151 TGTTCATAAG TGCACTGCTC TAGCACTGGG TGGCTGAGGA CGGAAGCTAG
 9201 CTGACATCAA CTGGCCAAGT CAGCCTGCCT ATCGTCTGTT TTGTGCCTCT
 9251 TCCAAGTGGC ATGTGATAAT GTGCAATCAG GAGAGCTCAT ACTAGGCATC
 9301 CACTCATAGA TTGATCCACA TCTCTTCCCC AGATCTTTTT CCCAGTCCTC
 9351 CAATATTGCT TTAAATGTCC CCTGACCTCC AGTGAGGTCA TTCACCACTG
 9401 CCTATGAGTC CATGTATATC CTTACCTTTG AATGTTCTC TTTTCATACA
 9451 AAATGTGTGG CCAGGAGACT GCTCAAAACT CTGCCTATTG GGAGGCTTTC
 9501 CCCCTCACTG TCCTTCAGGG CCATCCCTGG GTGGGCTGAA GTATAGCAGC
 9551 AGTCCATTTG CAACATGCTC TAACATGACA AATTGACCAG CTCTGGACCA
 9601 AACTAAGTTT TTTTTCCTCC TGTAATTTGT TCACAGGTGT GAGCTCATGG
 9651 AGAGGCATTG GTATAGTAGA TATAGGTCAG GTGGAAAACT GGCCCCTCTG
 9701 ACATGGGATT ACTTGTGTCC TGTGGCCCTG CTGGTGTTAG ATTCCAGATG
 9751 GACCACTTCC GTCTTATGAT GGACAGTTGG ACTTCTCAGG TCTGATAGAA
 9801 CCTAGCTCCT GATGGGTCGT TTTGGCTGCA TGGTCTCTTG ATATTCCATG
 9851 GTCAGATGCT GTGTCTCCAC CAGGACTCAG TAACATGCCA TGAGATGTTT
 9901 TTTGTCTGTT GTATATTTCT CTACTATAGA TGACAAGGCC TTGTCCCAGA
 9951 ATCCTAAGGC TCTATGCTAT ATTTCTCCTA TTGAGTTTTG CCAGAAACCT
10001 CATATAGTGT CTTTTCCTAT TCAGATGACT TTAGTACCAA GGGTATGCTG
10051 GAGAATACAG CCCTAGTGGC AAGATCACCC TTATTGCAGC CTAGACTTGC
10101 TACAGAACAT TTTCTTGTTT TTGGATTTCA TTAAAAACCA GCAGCCTTTT
10151 ATGTCATGGA ATAAGTGGGT TAGAACAATA TTCCCAAGTG TTGAATACAC
10201 TGCCTCAAAA ACCCAAAGAG GTCTGCCAAC CATTGTGCTT CTTCCTTAGT
10251 GGCAGGAAGT TCAAAGCACA ATAACTTTTC CTTCACTTTG AAGGGAATGT
10301 TCTGGAATGT CTCAAACACT AGACTCCTGT GAACTTCGCC CACGTGATGG
```

FIGURE 3C

```
10351 ACCTGTGATC TTTGTAGCAA TTATTTCTGG AGCACACATG TCTTACTGAG
10401 GCATCCAGAG TACTTGTCAA TTCTTGCTCC TGAGGTCTAA ATAACATAAT
10451 GTCATCTATT GGTCATAATA GATCAATGTG ATGTTCTGCA GCAGGTCCAG
10501 AAGGTCTCTC TGACTATATT ATGAGAGAGA ACAATCCACG GATATATACT
10551 GTCATTCATC TCATGTCATT GTGAATTTCT TAGCCTCCTT TCTAATGGAT
10601 ATGGAAGAA TGCACCAGAT CAAGACAGGC AAGCTATGTA CATGAGTTAA
10651 GAGTGTGGTA GTTCCCTGTC ATCCACCGTG ATCCCTTCTT TTTTTTTTTT
10701 TTTTTTTTTT CAGGGGTAG GCTGGTGAAT TACCTTGGGA TCCAATGGGG
10751 GCTACCACCC CTGCATCCTT TAAATCTCTG AAGGTGCAAT AATCTCTGTC
10801 ATTCTGCATA ATATAATACT GTTTTTGATT TATCTTCTTA CACAGGGATG
10851 ACAGTTTTAA GGACTTCCAT TTGACTTTTT TCTATTACAA TAGCTTTTAT
10901 TCTACAAGTC AAGGAACCAC GGAAAGCGTT TTCCAAATGC TAGGTGTCTC
10951 TCTTCCAATT ATACATGTGG GAATTATACA TGGGGAATG ACCACTGGAT
11001 GGGTCCATGG ACATGAACTC ACTATGAGAC GATCCTGTGC CAGGACTCCA
11051 CTTATTACCT GACCCTTATA AGCCCCACTC TAATGGAGGA AGAATAGTGC
11101 TATAAATCTC TGAGTATCAA CATCAATTTG CCCCTTTATC AAAAGTCTG
11151 CAAAAGATAG AGGTATTTCT CTTTCTTCAG TGTATGTTTA CCCAAATTAA
11201 TGGTGGTAGA GTCCTTTGGG AAGGACTGT GGGCATCATG ACTGCATTTC
11251 CTTCTGTGGT GTTGCAGGTT CCTTAGTCAC GGAACCTTCG GTCTTCTCCT
11301 TCAGTCTTTG GATTCTGGCC TAGAAACTGG GCAAGAGAGT GTGACTTTCC
11351 ACTGGGGTGG CCAGCCTCAG CCTACTGCCC ATTCATCAGC TCTTTATCTT
11401 TTCTGGTTTT ATGTATATGA AGCAATACCC TTATTGGCTG CCCATTTTAT
11451 TTTTGTTCCT TGGAGCACCA TGTTCTGTGA GTCATCTCTG AGATTCCTAT
11501 GGGCTGATTC CCTAACTGTA GTTCTGAATT TTCTGCCCTT ACCTATGATG
11551 GTTAAGTGCT CCCAATCATC CCAATTGCCA CTGGTTCTGG AGCAGCACCT
11601 TCTACTGTGA GCCTCAGCCA GAAGAGGACA GCAGCTTCTG AGCATCAGTG
11651 GTGCCTGTGG CCCCATCACC ACTGCATTCC TTATTATCTT AAGAGCAGGA
11701 GTATTCCTCA GGCCTCCTGA GAAATATAGT TCGTTTGTGG GTTTTCTGGT
11751 CTTATATAGA AAATCCATTC CTGCATAGTC ATTTATTTGA GGCTTTTGAT
11801 CTTTCTTTAT AATCTGCTGT AACAGTTCCC AACATTTCTC ATTTTTAAAG
11851 AAAATAAGTT AAAGAGAGAC CTTTTAATTG ATCAAGAGTG TGATCAACAT
11901 TAAAGATATA ACAATTATGG AATTCTTATA TTCCAAATAA TAGAGATCAA
11951 AACTTTACTT AAAGGAATAG AAGATAGCCA ATTTAATTAT CAGTAATTCA
12001 TCGCTATGAC TGGTTCAAAT TCAGCAATTT TTATACCAGG CATTAAAAAA
12051 TGAAATAGGC TTGTAAATTA GGTTTATATA ACAATGAAGG AAAAGAGAGG
12101 ATGTAGACCT GGACCAACCA AAATAAGGAC ACTCTTGTGG CCTTAGGCAT
12151 TCTCTCCTGG AATGGATAAT TTTTTATTCT TTTATTTATT TATTTATTTA
12201 TTTGAGACAG GGTCTCACTC TGTCACCTAG GCTGGAGTGC AGTGGCACAA
12251 TCATACCTCA CGGCAGCCTC AACCTCCCAG GCTCAAGTGA TCCTCCCACC
12301 TCAGCCTCCT GAGTAGCTGA GACTACAGTT GCGAGCCACC ATGCTTGGCT
12351 AATTTTTAAA ATATTCTGTA GAGACGAAGG TCTCGCTATG TTGCCTAGAA
12401 TGGTCTCGAA CTCCTGGGCT CAAGCCATCC TCCCACCTCA GCCTGCCAAA
12451 TTGCTGGGAT TACAGGCGTG AACCCCTGTG CCCAGCTTTC AAGTTATTTT
12501 TTTTAAAAGT CATGGTGGCC ATATCCTGTA TCTCTGTGTA TAATGTAATA
12551 ATGACTAGAA ATTAGTACAG AATTATATTT TAAAAGTCAC CAGGCTACTC
12601 TGGACATATC TATTTTGTTT AAGTTTCCAA GAACCGTATT AGCAGTTTAT
12651 CAGGATCATT TCTCTTAAGG CCTTTGCCGG GATGTTGAC CCTGTGTCAT
12701 GGGACCATGC CCCCTTTATT AGTTTCCTAG GGCTGCTGTA ACAAAGTACC
12751 ACAAACTAGG TAGCTTAAAA CAACAGAAAC TTATTCTCTC ACAATTCTGG
12801 AGACCAGAAG TCCAAACCCA AGGTGTTGGC AGGGCCAAGC TCCTCCTGAA
12851 GGCTCTTAAG GAGGCCTCAT GCTTGCCTCT TGCTGGCTGC TGGTAGCTGC
12901 TGGGAATCCC AGGCGTGCCT TGGCTTGTGG ATGCATTGCT CCAATTGCTG
12951 CATTTGTTGT CACATGGTCT TCTCCCCTGG TGTCTGTGTC TATGATTTCA
13001 AATTCCCCTC TTCTTATAAG GACACCAGTC ATGAAATCAA TCTATTATGA
13051 CCTCATGTTA ACTTGATTAC ATCTGTGAAG ACTCCATTTC CAAATAAGGC
13101 TACATTCACA GGTATCGGGG GTTAGAACAT CAACATATCT ATTTTGGAGG
13151 ACAGAATTCA ATCTACCTCC CATATTGATG AACTCTCCCT TATCCAACTT
13201 TATTACCCTA CTCCCTCCAA ATCTAGTACA TTCAGGATCC ATTCCCGGGC
13251 ATACTTTCCT GCTTCTTGAT GTAAATGTTC ATCAGATTCT ACGACTCCTG
13301 CTCCCAGTAT CTTTTCTTAG CTCAAAAGTG TATTTTCTCA TCTAAAGTTT
13351 ATATTCTCTC CTTTTACAAC TTCTCCCAAG TACTTTTACA ACAATCAAAT
13401 TTTCTAAGTG CTTCTTAAAG GTTAGTAAGG CCTATAGATT CAATACCTAC
13451 AGAGTAAAGC AACCATATTA TATATTTTGA CATAGACACA CTACATATTA
13501 ACACATAGAA ATAGGCTCCA CTTCTGCAAG GAAATATGTT GTATCATTCA
13551 AAGTTCTTAG TTGCAATCAA CAGAATACAC TCTAGCTAAA GTGGAATGAA
13601 ATTTCGTAAA GAATGTTAAG AATTGGGCTG GGGCAATGG CTCATCCCTG
13651 TAATCCCAGC ACTTTGGGAG GCCAAGGCAG GGAGAGGATC ACCTGAGGTC
13701 TGGAGTTTGA GACCAGCCTG GCCAACATGG TGAAATCCCA TCTCTACTAA
13751 AACTACAAAA ATTAGCCAGG CATGGTGGTA CGTGCCTGTA ATCCCAGCTA
```

FIGURE 3D

```
13801 CTCAGGAGGC TGAGGCAGGA GAACTGCTTG AACCCAGGAG GCAGACGTTG
13851 CAGTGAGCCG AAATCCCACC ACTGCACTCC AGCCTGGGCA ACAGAGCAAG
13901 ACTCCATCTC AAAACCATAA ATTAATAAAA AATAAAAGAA TGTTAGGAAT
13951 TGTTCAGACT TCCTGGAAGG ATCAGGTCTG GATGCTGTAT TCTCCAGGAA
14001 AAAGCAGCAG AGAACATATA CTGCTAGACT GTTCTGGATA AAACACAGCT
14051 GCCACCACTG CCTGCTTCTA AGTGTTGATT ATATTGATGA CTTGTTCCAG
14101 AAATTCTGCC ACAGCAGTCA CAGAGGAGCC AGTTGCCTCT GTTGCATTTG
14151 AAACCATCTG CACTGCCATT CCCCTGCATG CTGTATCCTC TTCTTGTTCT
14201 GTCCCGTATC TAAATCTCAT TCAAGTGCTT TGGATTTAGC AGAGTCCACC
14251 TCTCATGCCT GCATTGTAGC TGCAAGAGAG CCTAGGAAAA GTAGGTGTTT
14301 TTTTTGTTTT TGTTTTGTT GTTTTTATT TTGTTTGTT TTTGCTGCTC
14351 CAGCAAGATT CAAAATATCA AGAATTCATT AAGATATTGG ACAGCTATAA
14401 ATGATGGTTG TCTGCTACAT ATGTGTGCTA CTAGTCTAAT TTTTATTTTT
14451 CAACTTTTGA TACAGACATG GGTACAAAAC ATATTTTTCT AATGTCTTGA
14501 TTTTAACTAC TAGAAAAGTA ACAGTGCAAG TATAACGTTA AATGGCAACT
14551 GAGCTCACTA TGGAAGTGAC AATAGGGAGT GGTGGGGACT GTGGTAAATT
14601 GAGAGCCAAT TGTAGCCATG ACAGAGTGAG AGCTTGATTA TTTCAGGTCT
14651 TCAGATTTTT CAAAATGAAC AAGAAATCCA AAGTTTTATA TGTTTGCTTG
14701 TTTCTGCTTT TTTGAGCTAT CTCCTGATAT TTATTTATTT TTTTATTTAT
14751 TTAATACAAT TTTTAAAAGT AGAGATGGGG GTCTTACTAT GTTGCCCAGG
14801 CTGGTCTCAA ACTCCTGGCC TCAAGCAATC CTCTCACCTT GGCCTCCCAA
14851 AGTTCCAGGA TTACAGGTGT GAGCCACTGT GCTGGGCCTT GGTTTTTAAA
14901 CTCTGTCAAT TAATCTAAAT TTATTTTTA TTTTTTATTT TTTATTTTTG
14951 AGATGGAGTT TTGCTCTTGT CACCCAGGCT GGAGTGCAAA GGCACAATCT
15001 CAGCTCACTA CAACCTCTGC CTCCTGGGTT CAGGCGATTC TCCTGCCTCA
15051 GCCTTCTGGG TAGCTGGGAT TACAGGCATG CACCACCATG TCCAGCTAAT
15101 TTTGTATTTA TAATAGAGAT GGAGTTTTGC CATGTTGGCC AGGCTGGTCT
15151 TGAACTCCTG ACCTCAAGTG ATCTGCATGC CTTGGCCTAC CAAAGTGCTG
15201 GGGTTACAGG CATGAGCCAC CGTGCCCAGC CAATTAATCT AAATTCTAAA
15251 AAAAAAAAAA AAAAAAAAAG CAAAGACCCA TACACACATT ATACCAGATA
15301 AACAAAACAT GGCTATGGGC CACATATGGC CATTGGGCTT TCAGCTTGTC
15351 ATCTGTGACT TAGGCTTTTA AAGCCATAGA GACTATCTTT TTTTCCTCTT
15401 GTTCATCTAA TGATCCCTGC TGAGGTAAGA AGCAGTGAGT CTCTGCTTAA
15451 ATGGGGGGAT AGGAAAGGGT CAAATTACCA GGAGGAAACA AAAACAGCAT
15501 AGGTTAATAC CTCAAAATCT ATGAAGCTGG GCTGAGTGCT AGGGATTTTT
15551 GGTTCCTGAC TTTCTGAAAT TATAATCTAC TGGAAGAGGC AAATATTAAT
15601 TTAAAAATGA GAGACATAGA TACTGGGGGA GCATTGACTG GGCTGGCGTT
15651 GGCCAGGTGC ACTTTATTGA GCTCCTTTTG AATGTGGTGT GCTGAAATCC
15701 ATGCTGATAA GATCCTATTT CAAATCTCAA ACTAGCTCTG GGGATCGTAT
15751 TTTAAATTCT CCTTCCTTTC TTTAAAATTT ACCATTTATT GATTATTTAT
15801 CAAGTGCCAG GAATTATGCT AAGCATTTTG TAACTCGGTC TCATTTAACG
15851 TTCACAGTAG TCCCATCTTC CTTTCATAAA TGAGGGAACT CAGGTTGAGG
15901 GAAGTTAGGT AATTTGCTCA AGGCCACATA CCTAATAAAT ACCACAGTCA
15951 GCATTGAACC CAGTACTGTC TGTCTCCAGG GCATGTTCTC TGAATCCCAC
16001 TGCAATACTC CTCCAGAACC TTTAAAAAAA AGTCTCTGTA GGTAAAGCAC
16051 TCGCCATTCG TCAGGCGCTT TCTGATTAGT TCGTGTGGCA CACTGGTAGC
16101 AATAGGCTGG ATAGCAAATC TCAGTTGTGT TCTCCCTTCA CCAGCTGCAG
16151 CTGGATGATC CTTGGGCAAG TTTTTTTTGT TTGTTTGTTT TCTTTTCTTT
16201 TGTTTTGTTT TTAAGTCAG AGTTCTCACT CTGTCACCCA GGCTGGAGTG
16251 CAGTTCACTG CAACCGCCAC CTCCCAGGTT CAAGTGATTC TCCTGCTTCA
16301 GCCTCCTGAG TAGCTGGGAT TACAGGTGCT TGCCAGCACA CCCGGCTAAC
16351 TTTTTTGTAT TTTTAGTAGA GATGGGTTTT CACCATGTTG GCCAGGCTGG
16401 TCTTGAACTC CTGACCTCAGG TGATCCAGTT CCTTGAACCT TCCAAATTGT
16451 TGGGATTACA GCCGTGAGCC ACCGTGCCCA GCTGGGCAAG GTTTTAAATA
16501 TTCTGAGTGT CTCAGTCTTC TGAGCGTCTC AGTCTTCTGA GCAGTAAGAT
16551 GGGGATATCT CCTATTTGTC AAGACTATTT TGAGAATTAA GGGAGATAAT
16601 ATATATTTTA TAGAAACCTC GTGGAGTCCC TAGAGTGTAG CAAGTAGTCA
16651 ACGTCCTTCA GTTAATTTTC TTCTTCCAGT AGAATAGCAA CTCAAGGATC
16701 GTGTAAAAGA CAACATGAGC TAAATGGGAC CTTTTCAGAG GGCAAATTTG
16751 AATGCTGTAT TTGTTTGCTA GGGCTGCCAC AACAAAATAC TACAGAATGG
16801 GTGGCTTAAC AAACAGAAAT TTATTTTCTC ACAGTTCTGG AAGCTAGAAG
16851 TCCAAGATCA AGGTTTGATT TCTCCTGAGG CCTTTGTCCT TGGCTTGCAG
16901 ATATTGCCTT CTTGCTATGT CCTCAGATGG CTTTCCTCTA TGCATATGCA
16951 TCCCTGGTGT CTCTGTGTGT CCAAGTCTCT TTTTATTTAT GTATTTTTTT
17001 GAAACAGGGT CTCACTCTGT CACCCAGCCT GGAGTGCAGT GGCGAGATCA
17051 TAGTTCACTG CAGTGTCCAA CTCCTGGGCT TAAGTGATCC TCTCCCCTCA
17101 GCCTCCCAAG TAGCTGGGAC CACAGGCATC CATGCCACCA CACCTGGCTC
17151 AAATGTCCTC TTCTTATAAG GACATTATTC ATATTAGATG AGGGCCCACC
17201 CTAAGGGCCT CATTTAACCA TAATTACGTC CTTAAGCACC TCATCCTAAA
```

FIGURE 3E

```
17251 TATAGCCACA TTTGGTGGTA CTGGGGGTTA AGACTTCAAC ACATGAATTT
17301 TGGGTCACAC ATTTCAGTTC ATACCAAATA CAGTGAGCAA GTAAATTGAT
17351 TTAAAAATAC TGTTTTATAT ATATATTTAA CTTTAGATAG GCTCTCTCTA
17401 TATTGCCCAT GCTGGTCTCG AACTCCTGGG CTCAAGGGAT CCTCCTGCCT
17451 CAGCGTCCCA AACTGCTAGG ATTGCAGGCG TGAGCCACCA CGCCCAGCCA
17501 GTAAATGGAT TTTTAAAATA CGTAAAATTA TCTGCAAGTT CTCTCACTTT
17551 GTGCTCCAAA TGTTGATCTT ATTACCTATG AAACAAAACA AAACAAAACC
17601 TTTTCCGCAA TTAGTGGGAA CATTTGAATT GCAAAGAAAT AGTTCTTTAA
17651 GTGCCTAAGG ACTAGTTAGC ATATCTTAGG CAATTAGACC CCTGGGGCTT
17701 GGATGTTTGC TGGACAACTG TGCCTGAGAA CAGAGAGCAG GCACCTCCCT
17751 AGTGTGCAGA GGGCCAGCAG TCTGCAGACC GCGGCTGTCT ATATTTGGAG
17801 AAACAACAAT GAGAATGTCA CTCTAGAAAG AATGAAGATT CTCTGATCTA
17851 AAAGACCAAC TGCAGTCAAG CAGGGAAGGA AAACGAAATG GGATAAATAG
17901 CTATTATGGA TAATTAAAGT CCTCCAACTC CTAAGAAATG AGTTCGTTTT
17951 TCTTCTCTTA TTCTTAAATA ACTTTCTGTT CTCCTCCCCT TTTTATAAAG
18001 CCTTTTTTCT GGGCAGGATG AATAGATCCT TAACCCTGTC TGTAAGTGCT
18051 TCAAGCCAGG AGTGATGTCT GGAATTGATC CACCAATTCC ATTCAGTTGG
18101 ACAAGGATTC ATTGCTTCCA GGCACGATGC TGAACATGGA GAATAAAGAT
18151 GAGTTGGAAA TGGTCCTGGG ATCAGGGAGA CCTTCATTCA TATATGGACA
18201 CAAATCAGTG ACTTTTTTTT TTTTTTTTT TTTTTCCGAG ACAGAGTCTC
18251 GCTCTGTCAC CCAGGCTGGA GTGCAATGGC ACCATCTCGG CTCACTGCAA
18301 CCTCCGCCTC CTAGGTTCAA GAGATTCTCC TGCCTCAGCC TCCCGAGTAG
18351 CTGGGATTAC AGGTGCCAGC CACTATGCCC AGCTGATTTT TGTATTTTTA
18401 GTAGAGACGG GGTTTCATTC ACCATGTTGG TTAGGCTGGT CTCGAACCCC
18451 TAATTTCAGG TGATCCTCTC GCCTCAGCCT TCCAAAGTGC TCAGATTACA
18501 GGCATGAGCC ACTGTGCCTG GCCCAAATCA GTGGCTATTT ACTTAGCACC
18551 TATGCTGCTG AATGAAAATG ACTCTAACTC CATGTGAGAA GTGTTCTAAC
18601 AGAGGAATGT ATAAAATGCC AAGGAAACAC CAGGGATGGC AGAGACCCTA
18651 ACGTTCAGGC AATGTCTATT CATTTATTGG TGATAATGTG TTAGTCTTTG
18701 TAGGGTCGGC TCATGTATCT CTGTGAGATA AATATTTATT GTACAGAAGA
18751 GGATATGTGA GATTCAGAGA GGCCAGGTTA TTTGCCCCCA AGTCACACAG
18801 CTCGCGTATC AGTGGCAGAG CTGGAAATCA AATCCAGGTT ATCTGACTGC
18851 CCAGAAGCCT GGTGTGTTCC ATGATACAGG GTGAGGGGT TCTGTCTTCC
18901 TCTGTGAGCT AGGCTATACA AGAAATGGCC TGCTATTTGA ATGCTTTTAA
18951 AACAAATCAA ATCTGGTCAG GCATAGTGGT TCACACCTAT AATCCCAACA
19001 CTCTGGGAGA CTGAGATGGG TGGATTGCTT GAGGCCAGAA GTTCCACACC
19051 AGCCTGGCCA ACACGCTGAA ACCCTGTCTC TACTAAAAAT ACAAAAATTA
19101 GCCGGGCGTG GTGGCCTACG CCTGTAATCC CAGCTACTCG GGAGGCTGAG
19151 GCACAAGAAT TGCTTGAACC TGGGAGGCGG AAGTTGCAGT GAGCCAAGAT
19201 TGCGCCACTG CACTCCAACC TGGGTGACAG TGCAAGACTC CGTCTCAAAA
19251 AAATAAATAA AACAAAACAA ATCAAATCTG ACTCTGAGCC CCCTGCCTGG
19301 GGGAAGTTAG ATTTCTGTTC ATTTTGATGC TCCCCTTTTG CCACAGCAAT
19351 ATTATGCAAA GGACTCACAA ACAACTCAGG AGGTCCTGCT AATTATTGAT
19401 CCTCATTTGC TCCTGAGCCC ATGATCCCTT GAAGTGGTGG CTCAGCTGCC
19451 ACTTTGGGCA AAGAAAAGTG AGATCCTGTG CTCAGACCCC TCCCCACAGC
19501 TCCTGATATC CCATCTCCAA CTGGAGAGCT GCTGTGAGGG CTGGCTTCA
19551 GGTCAGCCAG CTGTAGGTCC TGCTTCTTGT GGAGCCCACA GCTCCTTCTT
19601 TCAGGGCTTT CCCTTTGATC GTTACTTTCC CCTTCTTTCT CCCCATCTCC
19651 CATACTGTAT GTCTTCCCTC TGGAAAGTCT CGGGATGTCT AAGATGACAC
19701 TGTGCACACA GAGGGTGCTT GTGTTGGTTC AGGTCTTCCA AGAAAGCAGA
19751 TACCAAGACA GGACTCGGCA CATACGAGAT ATGGTCTCGC TCTGTTTTCC
19801 AGGCTGGAGT GCAGTGGCAC AATCACAGCT CACTGCAGCC TCAAACTCTT
19851 GAGCTCAAGT GATCTTCCTG CCTCCGCCTC CCAAAGTACT TGGATTACAG
19901 GCATGAGTTA CTACACCTGG CCAAGAGATT TATTGAGGGA AAATGGGGAA
19951 GGAGCTGGAG GAGGCTGGGG GAGCATTCAA ACTGCTACCT GTGTAGGAGA
20001 GAGGGAAGGA AGAAAAGCTA GGTGGGAAGA CTTTCAGACT ATATTACAAT
20051 ACTGGGACAT TTTGGCATGG CCAGTGCAGA GTCCTAGAGC CAGTCGCTGT
20101 CAGAGGAGTC CTGCCTCTGG CAGGAAAGAA CGGCCTCACA TCCCTGCGGT
20151 GCTCAGTTCT TGGCAGAATA ACAGCCTGTG AGAAAGAGGC GCTGTCCCCA
20201 CGCCAAATGG GTGGTTGATT CAGAGCACAG CAGCTGGGGC TGTCTGCAAT
20251 TAAGCAGTGC AAAGCTCCAC AGCGCTTTCA GTTTTCATTA GCCTTCATCT
20301 AAAGCATCTG CATGTATATA GAGAGCGCTA AGCTTATGAC TGGTGACACT
20351 TTATTAATAG CAATAGTGAT AGTACTTACC ACTTATTAAT ATAAAGCACT
20401 TTTTACGTAC CAGGCACTGC CGTGAATCAT TTACATGCAT CAATCATTGA
20451 ACAACCCTAT GAGATACCCA TTACGATTAG CCCAGTTTAG AGATAGGGAT
20501 TCTTATGGGC TGAATTGTGT CTTCATATGG ATCTGCCCAA ATTCATTATG
20551 GTGAAATTCT AACCCTCAGT ACCTCAGAAT ATGAGTATAT TTGGAGATAG
20601 GGTCTTTAAA AAGGTAATTA AGGTTAAATG AGGTCCTTAC GGTAGGCCCT
20651 AATCGAATAT GACTGATGTC CTTATATGAA GAAAAAATTG GGACACACGG
```

FIGURE 3F

```
20701 ATACATAGAA GGAAGACTAT GTGAAGGCAC AGGGAGAAGA GAGCCATCTG
20751 CAAGCCAAAA AGAAAGGCCT CAGAAGAAAC CAAGGCCTGC TGAAACCTGG
20801 ATCTCAGATT TCTGGCTCTA GAATTGTAGG AAAATACATT TCTGTTGTTT
20851 AGGCCACCTA GTTTGTGGTG CTTTGTTACA GCATCCCTGG AAGACTAGTA
20901 GAAGGTCAAG TAACTTAGCC AAAGTCACAG AGCTAGCACA AGGGAGAGAT
20951 AGCACTGGGC ATCTCTCAGT CCAGAGTCCA TTCTCTTCCC CTGCTCTTCT
21001 GAGTCATGAT GGCTGCGCAA GGACTACAAA GTAACAGGTA CAGATGACAA
21051 AGTGACTCAG GAAGATCATT GAGAAGGAGC ATGGCCTGGT GTGCTGGGAA
21101 CACACAGGAA AGTGGTCCAA GGAACCTAGA CAGCAAAGGA GAAGGGTTTC
21151 ATATCTTGCC TCTACCCACT AAGGGCTGTG TGACCTTGGC CAATTTGTTC
21201 TTGCTTTCTG AACTACAGTT GTATTTTGTG TCAAATGGGA GTATTAGATT
21251 TCCCATGTCT CACTGAGCTG TATTAATGAT CAAATAAGAG AATTACATGA
21301 AAGTATCTGT AGAGGAGGGC AGAGGGAGAG AACTGAATTT GCCTCATACA
21351 ATATTACTGT GGTTGTTACA TATTATCCTT GTTTTAGCTG CTAGGAATAT
21401 ACTATTATAG TAATGTGTCA ATATTAGAGC TCAGTTTTC TTTCTTTTCT
21451 TTTCTTTTTT TTGAGATGGA GTCTCACTCT GTTACCCAGG CTGGAGTGCA
21501 GCAGTGCAAT CTCAGCTCAC TGTAACCTCT GCCTCCAAGG TTCAAGTGAT
21551 TCTCATGCCT CAGCCTCCGG AGTAGCTGGG ACTACAGGTG CTCGCCACCA
21601 TGCCTGGCTA ATTTTTGCAT TTTTAGTAGA GACGGGGTTT TGCCGTGTTG
21651 GTCAGTCTGG TCTCGAACTC CTGACCTCAG GTGATCTGCC CACCTCAGCT
21701 TCTCAAAGTG CTGGGATTAC AGGCGTGAGC TACCACGCCA GGCCTAGAGC
21751 ATCAGTTTTC CATCCTACTT AAGTTACACG TATTTGGTTG CCAGAAATTC
21801 ATGGAGACTA CTAGGGCAGC CCATTATAAA GTCCTATCAT CCAACTGCCT
21851 CTCAGAGCTA ATGGCATCAA TGCTAAGTCT AGCATCATAG ACTCATTAAG
21901 TGACGGTGAG GATTAACGTA ATAAAAATAG CTGGTATATG TTGCTTTTTA
21951 TTATGTGGCA AGTTCTGTTC TAAATTACCT AAGTTTGATA ACTCATTTAT
22001 GACAATCCTA AGAACAACCC TATGAAGAAG AAACTATTAT AATTCCTAGC
22051 TTACAGATGA AGAAACTGAA GTCCAGGGAG TTTAAGTAAT TAGGCTAAAG
22101 TCACACAGCT GAGTAAGTGG GCGACTCAAC ATTCAAAGTA AGGTACATGA
22151 GCTCCTCAGT TGGACATAGA TTGGAGAAGT GAGGCATCCA AGATGGCTTC
22201 AAGATATATA TATATATATA TTTTTTTTTT TTTTTTTTTT TTGAGACGGA
22251 GTCTCACTGT CATGAAGACT GGAATGCAAT GCCGCTATAT CAGCTCACTG
22301 CAGCCTCCGC CTCCCAGATT CAAGTGATTC TCCTGCCTCA GTCTCCCGAG
22351 TAGCTGGGAC TACAGGCGCA TGCCACCACG GCCAGCTAAT TTTTGTATTT
22401 TTAGTAGAGA CGGAGTTTGC CATGTTGGCC AGGCTGGTCT CGAACTCCTG
22451 ACCTCAGGTG ATCTACCTGC CTTGGCCTCC CAAAGTGCTG GGATTACAGG
22501 CGTGAGCCAC CGCGCCCAGC CTGATGGCTT CAAGATTTTT GCTGGAGCAA
22551 CCAAAGTAGC AAAATTGTCA TTACTTATGA TGAGAATAAC TTCAGGAATT
22601 AATTTTTTTT TAGGGGAAGT CAGTTTGGAC ATGTTAAGTT TAAGCTGCCT
22651 TTTAGGTGTC CAAGGAGATG TCAGATAAGT CTAGTTATAA AGATTGGGAG
22701 CTGTTAGCAT ATACATGGTA TCTAAAGCCC AGAGCCTGCT TAGATGTCCA
22751 GAGGGCATAG ACAGAAAGCA AGAGACCCGA GAATGGAGTC CTAGGCATTC
22801 TAGTGTATAT AGGTTGAGGT AAGAAGGAAT CAGCTATAAG AGATAAAACA
22851 GAAGAATTAG GAGGATGACC AAGTGTTTTC CTGGAAAAAC ATAAAATGGC
22901 CAAGAAAGAG AAAGTGGTCA ATTGTATCAA ATGCTGCTGC TAGGTTGATT
22951 AAATCAGATG AGGACTGAAA ATGACCTTTG GACTGAGCCA TGAGGAGGGC
23001 ATTGATAACC TTAAGTAGGG CAGTTTTGGG GGCTCAGGTT GGGAATACCT
23051 GGCTGGAGTG GGTCCAGGAG AGAACAGGAG GAGAGGAATT GAAGACAGTC
23101 ATTTCTTTCT TAAAAAAAGG AAAATGAGAA ATAGGAGGAT AACTGAAAGA
23151 GAAAATGTCT TTTATTTTAG ATTCTAATAT GGGAGGAATA AAAGCTTATT
23201 TATAGGCAAC AGGAATGATC TATTATACTA GGGAGGAGAA CATAATGAAT
23251 GAAGCGTGGG GGTGGGGATT TCTGGAGCAA TATTCGTGAG GGGATAAAAG
23301 GGGACAAGAT CTAGTGTCCA GGGAAAGGGG CTGGACTTAG CTAGAAGCAT
23351 GGACAACTGC ATAGACCCCA TCAGTATAAA TGCAGGCCGG CAGGTAGGTA
23401 GGTACATTGG TAGGGAAATG GTTAGGTTCT TTTCCAATTG CTTTAATGTT
23451 CTGGCACATT TACTAAGCTT CTACTCTGGG CTCACCGGTT GAAATTCAAA
23501 GCTCCTTCCC TTGTTCTACC ATTGCTTTTC ACTTTGATTT CAATAAAACC
23551 CACATCATCC AGTAATTATA GCTGCTTGTA TATGTGTCTT TCTTCCCCAT
23601 CAGCCTAAGA GCTGGAAGAA GGCAGATAAT ATGTCACGTT GTCTATTGCT
23651 CCCCAATACT TAGCCCAGTA CCTGAGACAC AGTAGGCGCT CAATATATAT
23701 CTGATGAACT GAATTGAATC CAGTGTATTT GTTTCTCTAT ACTTGTGCCG
23751 GAAATTTGAT TTCCTTGAGT CATAAGAACC TGCCAAGGTG CCGGGGCGG
23801 TGGCTCACGC CTGTAATCCC AGCACTTTGG GAGGCCAAGG TGGGCGGATC
23851 ACGAGGTCAG GAGATCGAAA CCATCCTGGC CAACATGTTG AAACCCCGTC
23901 TCTACTAAAA ATACAAAAAT TATCTGGGTG TGGTGGCGCA TGGCTGTAAT
23951 CCCAGCTACT CAGGAAGTTG AGGCAGGAGA ATTGCTTGAG CTAGGGAGTC
24001 AGAGATTGCA GTGAGCCGAG AATCGTGCCA CTGCACTCCA GCCTGGCAAC
24051 AGACCGAGAT TCCGTCCCCA AAAAAAAAAA AAAAAGAACC TGCCAAGGTT
24101 ATCTTTCATA TGAACTTGTG GGCAAATGAC TTGTGTTTTA TCCAAACTAT
```

FIGURE 3G

```
24151 TGGGTTAACC ATTATATTAG CTATTTATCA CTGCATTTAA TATTTATGAA
24201 AACTTGCAAG CTTTAATTAT TTTTAAAAAG ACTTGGACCT TAAGTGGGCC
24251 ATGACAGTAT CCTCAGAAAG ATGACAATAA GTAAGAGGAT ACAACTTCCT
24301 TTATAATTGA CAGATAGGGT TCCGTTTGTC CAATTACTTT TTTTTTAAAA
24351 GAAGAGATAA ATTCACTGTA ATGAATGTGC CATAATTGGA ATCTATAGAG
24401 GTCTACCATT TGAATAAAAG GTGCTGGATG ATCACCTCCT TAGAGGAACC
24451 ATCTAAGGAG AAAAGGATAT ACAACCAAAT GGGTGTGCAT TGTGATAGAA
24501 AATGTCCCTC TCCACCTCCA CTTAGTATTT TATTAAGACT TAGAAAAATT
24551 AGGCCGGGCA CAGTGCCTCA CACCTATAAT CCCAGCACTT TGGGAGGCTG
24601 AGGCGGGCGG ATCATCTGAG TCGGGAGTTT GAGACCAGCC TGACCAACAT
24651 GGAGAAACCC CGTCTCTACT GAAAATACAA AAATTAGCCT GGCATGGTGG
24701 TGCAGACCTG TAATCCCAGC TACTCAGGAG GCTGATGTGA GAGAATCGCT
24751 TGAACCTGGG AAGCAGAGGT TGCGGGGAGC CGAGATCGTG CCATTGCATT
24801 CCAGCCTGGG CAACGGGCAA CAAAAGCAAA ACTCCGTCTC AAAAAAAAAA
24851 AAAAAAAAAG ACTTAGAAAG GTTAAGGTCA ACTGTATCAG CTGGGTCGAG
24901 CAATGTGAAC AAAGTCTGTC AATGCTCTTT CAGCAGGAAA TGCAGTATAG
24951 CATATTGTTT TAGACATAGA CTCTGGACTT GGGCCTCTAT CCTACCTCAA
25001 ATGACTTAGT TTCCTCATCT ATAAAATGAC ATGATGACAC TGTCTACCTC
25051 ATGGGGTTGT TATAAAATTT AAATGATTGA TTGAATGTTT ATAAAAGTCC
25101 CACACAATAC CCAGAACATC AGTAGTTTTA GCCACTATAA CTTACTTTAA
25151 TAATAATAAT AATATTTAAT AATAATAATA ACTTACTTTA ATAATAATAG
25201 TAATACCTCC ATAGTATTCT ACTATGGGTC TTCCTTTTTG TTTTTCATCT
25251 GCTGGTACCT TTTTTCTTTT TGCTTAGTAT ACTTTCTTTT TCCTTTAATC
25301 CTGGCTTTTA TTTTCTGCCT ATCCTTTTTC CCATGTAGAA AAATCGATGG
25351 GACAACTGAG GAAGAAGATA ACATTGAGCT GAATGAAGAA GGAAGGCCGG
25401 TGCAGACGTC CAGGCCAAGC CCCCCACTCT GCGACTGCCA CTGCTGCGGC
25451 CTCCCCAAGC GTTACATCAT TGCTATCATG AGTGGGCTGG GATTCTGCAT
25501 TTCCTTTGGG ATCCGGTGCA ATCTTGGAGT TGCCATTGTG GAAATGGTCA
25551 ACAATAGCAC CGTATATGTT GATGGAAAAC CGGAAATTCA GGTTGGTATC
25601 AGTCCATGGT GGAAGACTTT TCTTTTTGAG ACAGGGTCTC GCTCGGTCTC
25651 CCAGGCTAGA GTACAGTGGC ACGATCTTGG CTTACTGCAG CCCCAACCTG
25701 CCAGGTTGAA ATTAACCTCC CATCTCAGCA TCCTCCCATT TCAGCATCTC
25751 AGATAAGTAG CTCCTCCCAT CTCAGCATCT CAGCATCTCA GCATCTCAGC
25801 ATCTCAGATC AGTAGCTGAG ACTACAATCC TGAGGAAACT GTTGACTGCA
25851 GCTGTGTCAA TACTTTGCTC CTTGAGAGAA AGCCCTGCAA TTCCTTCAGT
25901 GATATGACAA AAATGGAGAG TGGCTACTTG TGCTGGGCAT TGTGCAGAAT
25951 GATGGGGATA GAAAGGTGAA TGACCTAGAC TGAGCCCTGT CCTCATGGAG
26001 ACAAGTAAGT GATGACAGTT TGAGGGGGTA GGTGCCACGT TGGAGGTACA
26051 CAGGATTCTT GGGCTCATAG GAGAGGGCAC AGCCCAGACT TCCCTATTGT
26101 GAACAAATTC CCAAAGTGAT GGCTGGACCA GGCAAAGAGG GTGTGGTGTG
26151 GTGGGAAGAA GAATGTTTGA AGAAAAAGGT ACTGTGAAGG ACTGTAAGAA
26201 AGAGACAGAG AGAGAGAGAG AGAGAGAGAA CGTACACATG CTATGTAGGT
26251 ATATTTTAGG AACTGAAACA GGAGCTCATC ATCTTTTCTG TGTCATGGAC
26301 TCCTGGAGAT GACTAATGAA CCTTTGCCAA AGTAATGTTT TAAGTTCTTA
26351 AAATAAAACA CAAAGGATGA CAAAAGAAGC CAATTATATT AAAATATAAA
26401 TACCAAAACA TTTAAAAATC ACATTTGTGA CATAGAAACA TATGGGCTTC
26451 TTTAGTAGTA CATCAGTGAC AAAATCTAGT ATTGGGTCTA ACATTTACTC
26501 TGATTTTAAG TTGGAATGTA TGCCATTGTT GGAAATAGTG GCCATGACTG
26551 TAATACGATT TGAACATATT TGCTATTTCC ACGTGGGACA CAGTCATAGG
26601 TACTAGTCAT ATGACGGTGG CTTGTTGCCT ACATTCATAA TGGCAGAAAA
26651 TGCTAAATTT TGGTTAAGAG TGAAAATAAA GATGCATGTT TTCTTCCCAT
26701 CCAAGTTCTC AGATGCACAG GATTCCATCC ACAGACTCCA GGTTGAGAAC
26751 TCCCAGTGAT TGGGTAGAGC ACGTTGAGGT GGAGGCAGCG AAGTAAATAG
26801 GGGGCTGATC ATCCATAGCC TGGTAGGCAT GTAGCAAGGG CTGCAAGCA
26851 TGGAATGATC ACATCTGTGC TCCAGATTGT TCACTGCCCC ATTGCAGGGG
26901 GCCAGATTGA GGTAAGATAG GAATGGAGGC CACAGGGCCA GTTCAGAGGC
26951 CATCATAGTT ATAAGCAAGG ATACTTCGAA GTGACTTAAA TAGTATTGTT
27001 TTAGGAATCA CTGGAAACAT AAAATCTGGT TTGCTGCTTA AACGATAGAC
27051 CTAGAGAAGT ACTGAGGTTA TGGGTAAAA GAAACAAACA AAAATGTCTG
27101 CCCAGTGGAC ACCCCATAAA TGCATGTTTC ATCGTACTAA ACTCACACAC
27151 TGCAATGACT CATGCAGAAA TCCGTTCATC TGCAGAGAGA CATTTAATAG
27201 TTCTCTGGTC CCTCCCTCTA TTTGAAGAAA CATTTAGATC ACAGTTTTTT
27251 GAACTAGTGT CTGGGAAATC ACTGCACTGC AGGCTGTGCC ATGAAGAAGG
27301 CAGTGCGAGA CCTGGAGCCC ATACTGTGCT GTGTCTTATG AGACTTTCCA
27351 AGAGGGAGAC GTGGTAGGCA ATATTTTCTG GACTGACTTG ATCATAGAAT
27401 GCTCTCTTTC ATGCCATATC TATTAGCATC ATCTGGCACA GTCTCCTGCC
27451 AGGCACTGGT TTGAGAAAAT TTGATTTCAA TCTGTCAAAA GAAGTCTTTA
27501 GTTGGTCTGC AAGCTATTTG TTTTTGCTTT TTTCAAACCA AGAGATTATT
27551 CTGCCAGAGG AAAACAGCAC CATGGAGATC CTCCTAACTA GTCTCTATTT
```

FIGURE 3H

```
27601 GATGCCACAG CCAAATCTGT CCTAAAAGGA TATCCTGTCT TTTGTGGGGT
27651 GTGGGGGATA GAGGTAGAAG GGCATATCAT GCGTTTTTAA AATAAAGAAT
27701 GATGTATATT AGCAAGGTTT CAGATGTGTA TCACATGCAT TCTTTCAGCC
27751 TTTTGTGAGC AAGACCAGCT AATTAAAACT TGTCTGCTGA GGCCCAGATC
27801 AAAATGAGAT GCTGTTTTGC ATTTGTTTGT TGCCTGAAAA GATAGACCTT
27851 GGTCAATAGA GTCTGCTCTG AGGCATATGG AAAAGACATT TTGATTAACC
27901 CGAGGAACAA TGCTAGTGTG CGCTCTCTAG TTTCTACGGC TGTGCCCTCT
27951 GGAGTCTTAG AGAAACTGAT TAAAATCTGA AATATGGTTT AAATTTTTTT
28001 CCTCTGGACT CAGGAGTAGG AATTTAGTAT CAGTAACTCT AGTACAGCTC
28051 TAATTTATAG CAGATTATTT CTCTTGTCCG CCTAGAACAA AGCTTAGATA
28101 TCAAGTGAGC ATGTTCAACC AAATGACAAA TACTTTGCTA ATTGTATTAA
28151 GAAAGGCTCT GAATGGCTGG TATGTTTGTT TGGTTTTTCT GTTTTAAGGG
28201 AAAAACTAGA TATTTGGCAC TGAGATATCT TTAAATCTTT ATTTCAAAAG
28251 AAGGAGAGAA ATAAGCAGTA TGAATAGGTA GATCTTTCAA ATATGTGGCA
28301 TATGTTCTAC AAGGGGTATG AAGAGTGATT TTAACTAAAG CGTGAACACT
28351 TTTTTTTTTT TTTGAAACGG GATCTCTGTT GCCCAGGCTT TAGTGAAGTG
28401 GTGTGATCAT AGTTCACCGC AGCCTTGACC TCCTGGGCTT AAGTGATCCT
28451 CCCACTTCAG TTTCCAAGTA GCTGGGTCCA CAGGCTCATG CCACCATTCT
28501 TAGCTAATTA AAAAAAATTT TTTTAGAGA TGGGATCATG CCATGTTGCC
28551 CAGGCTGATC TCAAACCCCT GGCCTCAAGG GATCCTCCTG CCTTGGTCTC
28601 CCAAAGTGCT GGGACAAGCA TGCACCACTG TGCCTGGCCC ATATTTTAAA
28651 TTTAATAGTT ATGAGTTAAA ACATGTGAAC TCTTAGAAAA GTGTTTGGCA
28701 TATAGTAAGA AAATAAAATG ACCGAAGTTT GAGAAACTTG TGATTTTGTT
28751 TTCTCATTAC TCTCAGGAAA AGTCCAAAGT TCTTCCCATG GATTGTGGGC
28801 CCTGTAGGAT TCAGAGCATG GGCTTTGGAA CTGGCCAGAC CTGGTTTTAA
28851 TGAGCTCTGG GACCTTGAAT AAGTTGCCCT TGTGTCCTGG TCAGAGATTG
28901 CTGGTTGCGA AGAAATGGC AGTGAACTG GCTCGAGTTA AAAGGGGATT
28951 ATTGGGGCCC GGCATGGTGG CTCATGCCTG TAATCCCAGC AATTTGGGAG
29001 GCCAAGGTGG GTGGATCACC TGAGGTCAGG AGTTCTAGAC TAGCCTGGCC
29051 AACATGGTGA AACCCCATCT CTACTAAAAA ATACAAAAAA TTTGGCCAGA
29101 CATGGTGGCG CACACCTGTA GTACCAGCTA CTTGGGAAGC TGAGGCAAGA
29151 GAATCCTGGC AGTTGGAGGT TGTAGTGAGT CGAGATGTGT GAGACTCCAT
29201 CTAAACAAAC AAACAAACAA ACAAAAAATG GTAGTGGGGA TTATTGTAGG
29251 GCTGTAAGAG GATCTCGTGA AAGCCAAGGG CAGAAAGCAG GTCTGTGGTG
29301 TATGTGTGCA GTCTGCACCC AGGACGCAGA AGCCAGCCTG AGGTGGGGCT
29351 GAAACCCAGG CTGTCCTCCA CCCTGAGGAG GGAAGGGAGT CTTTATGTAA
29401 TTCTTTCTGA GGCCGCAGGA CAGGCCCTGC CAGAAGTGCT GAATGGAGCT
29451 TTCCCTCGTG GGAACTAGAG AAGCCTTTGC TAAGGTCTCC AGCTTGCTTG
29501 CCCCACAGAG TCTTTCATTG GCTTTTCTTG GAGTCAGCTC CGTTTTCCCT
29551 GGTCCTTCAT GGACTGCTTT CTTTCCTCTT CCCTGGCTTC TCACTGCCCT
29601 CCACAGTGGA AGTGCCTTGA GCCTTTGTCT TGCTAGGAAG CTGATTTACT
29651 TGGCCCTGAC TCTGTGACTC CGTGGGACTT ATTTGGGTTC AAGAGTGCAC
29701 TATTGTCTAA CTAGAATCTC TGTGGGTTTG GGTTGCTGTC TCTCTCTCTC
29751 TCTCTGTGTG TGTGTGTGTG TGAGAGAGAG AGAGAGAGAG AGAAAGAGAA
29801 AGAGACAGAG ACACAGAGAG AGGGAGAGGC TGACTGGCTG AGCCTAGCCT
29851 ATGGCTTTGC TGTCTTAAAC ATTTTTTTTT TTTTTTTTTT TTGAGACAGA
29901 ATCTTCCTCT GTTGCCCAGG CTGGAGTGCG GTGACATGAT CTCAGCTCAC
29951 TGCGACCTCC ACCTCCCCGG TTCAAGCGAT TCTACTCCTT AGGCTATCAA
30001 GTAGCTGGGA TTACAGGTGC ATGCCACAAC GCCCAGCTAA TTTTCGTATT
30051 TTAAAAATAG AGACGAGGTT TCACCATGTT GGCCAGGCTG GTCTTGAACT
30101 CCTGACTTCA GGTGATCTGT CCACCCCGGC CTCCCAAAGT GCTGGGATTA
30151 CAGGCGTGAG CCACCACACC TGACTGGCTT GGCTGTCTCT ACTCAGGTGT
30201 CCAGTCAGCT GTGGTAGTCA GTCGGGGAGA ATCCCATGTT GCGGGGGAAG
30251 GTGCAATCCT CTCAGAAGTG TGAGCAGACA GGAACTGACA TTTCTAGAAG
30301 TTCCTTGCTA ACCCTCATTG CCCTTATTGT GAAATGGGAA TAAAAGGACT
30351 GCTTTGAAGA TCAAATAAGC TAACCTATAT TAAATACCTA TATTAGTTCC
30401 CTAAGGCTGC CGTAACATAT TACCACAAAC TTGATGGCTT AAAACAATAG
30451 AAATTTATTC TCTCAGAGCT GTGGAGACCG GAAGTCTAAA TCAAGGTGTT
30501 GGCAGCACCT CATGCCCTCT GAAGACTCTA GCAGAGAATC TTTCCTTGAC
30551 TCTTCTAGCT TCTAGTGGCT GCAGCAGATC CTCGGTGTGC GACAATGTCA
30601 CTCTCATGTC TGCCTCCATC TTCACGTGGA CATCTTTCTG CGTGTCTCCT
30651 CTTTTGTCTC AAATCTCCAT CTGTCTTTCT CCTATAAGGA CACTTGTCAT
30701 TGGGTTTAGG GCCCAGCTGG ATAGTCCAGA TATCTCATTT TAAGATTCTT
30751 GACATTTTCA CATCAGCAAA GACTTGTTTT CCAGATAAGG TAGCATTTAT
30801 AGGTCCTGGG GATTTGATGT GGATATCTTT TGGGGCCAT TTTTTGGCCT
30851 TTCACAATAT CTGACACAGT GTTTGGTTTA TTATAGTGAT GGTCCATATA
30901 CAGGGCCATT TTTTTAAAAA TTTATAATTT TAAAAAATTT TATTGTGATA
30951 AGAATGCTTA ACATGAGAGC TACTGTTTTA ATAAAGTTTT TAGTGTACAA
31001 TACATTATGG TTGACTCTAA GTACAATGTT GAATAGCAGA TCTCTAGAGC
```

FIGURE 3I

```
31051 GTGTTCATTT TGCTTGACTG AAACTTTTTC CCATTAATTA GTAACTCCTC
31101 ATTTCCCCCT CCCCCAGCAC CTGACAACCA TCATTCTACT CTTCAAGTCT
31151 ATGAATTTGA CTATTTTAGG TATGTCATGT AGGTGGAATC ATGCAGTATT
31201 TGTCTTTCTG TGACTGGCTC ATTTCACTGA GTGTAATGTC CTCCAGGTTC
31251 ATGCCAGTTG TTACATCTTG CAGAATTTTC TTCTTTATAA AAGATGAATA
31301 GTATTCCATT GGTGTGTATA CCACATTTCC TTTTTTTTTT TTTTGAGATG
31351 GGGTCTTACT CTGTCACCCA GGCTGGAGTG CAGTGGCACA ATCTTGGCTC
31401 ACTGCAACTT CCGCCTCCCA GGTTCAAGCG ATTCTCCTGC CCCAGCCTCC
31451 TGAGTAGTTG GGATTACAGG CATGTGCCAC CATGCCAGGC TAATTTTTAT
31501 ATTTTTAGTA GAGACGGGGT TTCACCACAT TGGCCAGGCT GGTCTGAAC
31551 TCCTGACCTC AAGTGATCTA CCCGCCTTGG GCTCCCAAAG TGCTGGGATT
31601 ACAGGCATGA GCCACTGCGC CCAGCCACAT TTTCTTTATT CATCTGTCAA
31651 CGGGCATTCA GGTTTTTTCC ACGTCTTGGC TATTGTGAAT AATGCTTCAG
31701 TGAACATGGG GGTACTAATA TCTTTTTGGA TCATGATTTC AACTCTTTTG
31751 GATAAATACC CAGAAGTGGG ATTGCTAAGT CATACATTCG TTCTGTTTTT
31801 AAGTTTTGGA GGAACCTCTG TACTGTTTCC ATGGTGGCTG CACCCATTCC
31851 CACCAACAGT ATATAAGGGC TTTATTTTCT CTTCATCCGC ACCAACACTT
31901 CTTGTCTTTT GTTTTTGATA ATGGTCATCC TAACAGGTAT AAAGTGACGT
31951 CTTATGGTGG TTTTGATTTG CATTTCCCTG ATGGTTAGTG ACATTGACCG
32001 CCTCTTCATG TAGATATTGG CCATTTATTG GTCTTCTTTG GAGAAATGTC
32051 TATTCAAGTC TTTAGTCCAC TATTATGGTT TTAATGGGTC TCAAATGACA
32101 ATGAAAGTCA GTTCTCAGCA GCCTAGGGGC TCTTCTTCAT GTATTATTTC
32151 TTTCAGAGAT TGACAGAAGC ACTATTTCCC CAGAGAGAAA GGCATGAGAA
32201 AGGGATGTTG TGATTGACAA TTAGCAGCTG GTTGAAGTGG GAGTTAGAGA
32251 AAGGGTCTAG TTCTCCCTCT GTCTTGGATC CTCAGGTAAT TCTGTGGATC
32301 TGGGCAAAGA AGTCTTGTCT CTCCTTAGTG AGAAAATTAA GTCTCTCCAA
32351 GCAATAGAAA GAATATCGTG TTTTGGGGTT AGGCAGATGA GAGGTTTTGT
32401 GTCCCCTTTT CCTTGCAAAT AGTTGTATGA CCTTGGACAA GTAAACTAAT
32451 CTCTCTAAGC CTTAGTTTCC TCATTTGCAA TTACCTCTAG GTGTTTTAAA
32501 GATTAAAGGA GGAAATCTGT AGAAAGCACC TTAGTGAAAT CATATTCCAC
32551 CTCTGCTCAA ATTTTCCAAT GGTTTTCATT TCTCTTTGTT TAAAAGCCAG
32601 AGTTCCGGTG ATGTCTTAAA GAACCCTTCA TCATTGTAAC CTCTCTTGCA
32651 TTAACACCTA TTCTCTTCCT CCTCATTCAT TACCCTCCAG CTGTACTGAC
32701 ATACTGCTTT TCCTCTAACA CGCAAGACAC AACCCTACCT TGGGTCCTTT
32751 GTACTTGCTG TTTCTCTGCC TGGAAAGCTC ACATCTCAAA TGACCATATG
32801 ACTTGCTCCC TTCCTTTCTT TAGGTCTTTA CTTAAAACTC ATCTTCTCAG
32851 TGAAGACTTC CCTGGCCGTT CTATCTAAAA TTTACCCCAC CACACTGCCA
32901 TCCAACACTT CATATTCCCT TCCCTTCTTT ATTTTTTCAT CTTATTGCTG
32951 GTTACCATCT AACTCTGCCT GTAATTGTTT ATCACCTGCT ATCTCCACTG
33001 GCATCTTCAA AATGGCAGGA GTCACTACAG CTGTTCACTG CTGTACCCCA
33051 GTGCATAGAA CTATGCGTGT TACACAATAA ACACAAAATA CAGATTTGGT
33101 GAGCTGATTT GAATTAATGA TAGCTAGCTA GTTCCTTTTT ACCATTGAGC
33151 TTCAACTTTC TAATCCGTAA ATGAGAAAT AGAGAGTATA GGCCAAAGTG
33201 GCTTGGACTG TGAGCTCCTA GAAGGCAAAG ACAATGCTTG TTTGAGTCTG
33251 TATTTACACT GTCCAGCACC TAACATTGCA TTCAGAAGC ACAGGACGAA
33301 CGTTGAACAG ATGGGCGGAT AAATATGTAA TAACTTGTGA CAGGAAAATA
33351 AGATAAGCAG TGATGAAAAT TTATAAAACA TAGTATGTTA ATAATTAGGA
33401 ACCCTCTTAC TCCATATTTG CATTTTGATA TCAAAAAGCT TTACAAAGCC
33451 ATTCATTTAT TCATTCATTT GGCGAATACA CACTTGTACC TTCTATGTTC
33501 CCAGGCGTTT GATTTAGGTA CTAAGACTAT AAGTCAAACA GGACATGGCT
33551 GCTATCTTAG AGTTTCTTGG TGCCCTGTGT GGGAAATTGA CATGTGGATG
33601 TCCATTCACT GAAGACAGCA CTGTGTTGGT GCCATGGCTG TGGGACCAAA
33651 GGTCTGTAAG ACAAGCCCAA GAAAAAGGGA CCAGTTCAAT TTTCGGGATT
33701 CAGGAAGTTT CCTCTGAGGA AGGACCATTT ACAATGAGTC TAAAAAGAAT
33751 GAGTTACTTT ACCTGGGAAA GAATATGAGG AAAGGGATTC CAGCCCTAGA
33801 GAATCACATT TTCAATGGCC TAAGGGTTGT GGAAGGTTGT GTTGTTGCTA
33851 TTGCCATCAG CATAGTATCA GTAATGGCTG CTAACATTTA TTGAGTCTAC
33901 ACTGTGTGCC AGTCACTATC CTAATCTGTT ACATGCAAAA TCTCTAAGCA
33951 GAGAGATAAC CTACTAGAAA TATTCATGCC ATTTATCCCC ACACATCCTA
34001 TGGATAGGTA GAATGGGCTT TATTGTCCTC ATTAAGAAAT GAGAGACTTA
34051 AGACTCTAAT TCTCTTTGTG CTATCACAAA ACTGGCATCT GAATAATGTA
34101 GTAAATAACT TAGTAGCCCC CCAAAACCCC ATTTTTTGTT TTATTCACAA
34151 GCTATTTTAT TTTCTCCTTA GCATTCATTG CTATTTTGTG TTTTTTCTCT
34201 CTGTGTATAT ACATATATAC ACACACATTA TATATATTAT ATATATATAG
34251 AGAGAGACAC ACACACATTA GATATATGTA TTTTTAGAGA CAGGAGCTTG
34301 CTCTGTCACT CCCCACTGGG TGCAGTGTGT GTTTGTAGCT TACCTTAACC
34351 TTGACCAACT CCTGGGTTCC AGGGATCCTC CCATCTCAAC CTCCTGAGTA
34401 GCTAGGACTA CAGGCACACA CCACCACACC TGGCTAGATT TGTATTATTA
34451 TTATTATTAT TATTATTATT ACTATTGAGA TGGAGTCTCT CTCAGTCACC
```

FIGURE 3J

```
34501 CAGGCTGGAG TGTAGTGGTG TGATCTTGGC TCACTACAAC CTCTGCCTCT
34551 TGGGTTCAAG TGATTCTCCT GCCTCAGCCT CCCAAGTAGC TGGGATTACA
34601 GGCGTCTGCC ACCACACCCA GCTGATTTTT ATATTTTTAG TAGAGATGGG
34651 ATTTCACCAT GTTGGCTAGG CTGGTCTCAA ACTCCTGACC TCAAATGATC
34701 CACCCACCTC TATCTCCCAA AGTGCTGGGA TTACAGGCGT GAGCCATTGC
34751 ACCTGGCCTA GCTGGCTAGA TTTTTGATTT TTTGTAGAGA TGGGGTCTCG
34801 CCACGTTGCC CAGGCTGGTC TTGAGCTCCT GGCCTCAAGT AATCCTCTTG
34851 CCTAGGCCTT CCAAAGCATT GGGATTACAG GTGTGAGTCA CCATGACCAT
34901 TAATATAAAT ACATATATAT TTAAATTTGT ACATAATCTC TTATTACAAG
34951 GTGAAATCTA TGAGAGCAGG GACTTTTGTT TGTTTGTTTC ATTTTTTTTT
35001 TTTGAGATGG AGTCTCACTC TGTTGCCCAA GCTGGAATGC AGTGGTGCAA
35051 TCTCAGCTCA CTGCAAATTC CATCTCCCAG GTTCATGCCA TTCTCCTGCC
35101 TCAGCTTCCT GAGTAGCTGG GAGTACAGGT GCCCGCCACC ACGCCCGGCT
35151 AATTTTTTTT GTATTTTTAG TAGAGATGGG GTTTCACCGT GTTAGCCAGG
35201 ATGGTCTGGA TCTCCTGACC TCGTGATCCA CCCGCCTCAG CCTCCCAAAG
35251 TGCTGGGATT ACAGGTGTGA GCCACCGCAC CCGGCCGGTT TTGTTTTTTA
35301 AGATGGGGTT TCACTCTGTT GCCCAGGCTG GAGTGCATTG GCACTATCTT
35351 GGCTCACTGC AGCCTTGACC TCCTGGGCTC AAGCCAGGAG GCTCAAGCCA
35401 GGCTGAGGTC CCACCTCAGC CTCCTAAATA ACTGGGACTA CAGGCACACA
35451 CCACTACGCC TGGCCCAGGA CTTTTGCTTG CTGCTATCCC CAAGTATGTA
35501 AGATGCCCTC CATAAGTATG TGTTAAATAA ATGAAAAAAG AAAGACCTCA
35551 TGAGGTAATT ATTGTGTAGG CTCATTGGTA AAAAATGGTT GTCAGCCTTT
35601 TTCTAACAAA CACAACTATA TCTGATTTCT CATTTCCAGA CAGCACAGTT
35651 TAACTGGGAT CCAGAAACAG TGGGCCTTAT CCATGGATCT TTTTTCTGGG
35701 GCTATATTAT GACACAAATT CCAGGTGGTT TCATTTCAAA CAAGTTTGCT
35751 GCTAACAGGT AAGATAAATT GATATAACAT GATACAAACC AATGAAATGT
35801 GGCTTTGTAC CTATAAATTC TGCATAGCTG GCTCTCAATT TGGGGGTGCA
35851 GAATGAAAAA CAGGAGCCAT CTGGATAGAT GCAATTCACA GATACTGATC
35901 CCAAATGACC CTGATCTTAA TTTATTTTTA TTTTTATTTT TGAGACGGTG
35951 TCTCACTCTG TCACCCAGGC TGGAGTGCAG TGGTGTGATC TTGGCTCACT
36001 GCAACCTCTG CCCCACCCCC TCCCCACCCC CACTCGGCAT TCAAGCAACT
36051 CTGGTTCCTC AGCCTCCTGA ACAGTGGGA TTAAAAGTGT GCACCACTAC
36101 ACCCAGCTAA CTTTTGTATT TTTGGTAGAG ACGAGGTTTC ACCATGTTGG
36151 CCAGGCTGAT CTCAAACTCT TGACCTCAAG TGATCCACCC GCCTTAGCCT
36201 CCCAAAGTAC TGGGATTGCA GGCGTGTGAG ACACCAGCGC CCAGTCAAGA
36251 GTTTCTTTTT ATTTCGTTTT TCATCCAATT AAATTTACCT TGCAACTCTT
36301 CAAGTGATTA TGTGGTAAAA AGACCAATCA ACTCTGAGTC AGGAGAAATG
36351 GTTCCTGCCC CCTAACTGGA TCACTGGGTG ACCTCTATTG AGTCACTTTC
36401 CTTCCCTCCC TGGGCCTCAG TTTCTTCATC TGTGAAATGA AACATTGGAC
36451 TAGATTGTAT TTCAGTTCCC CTTGACCAGT GACATTCTGT AATCTTAGGT
36501 TAATATCACC CAGTACCATA AAGGTTTTCT CAGATGAGTG GTGGGGGCTT
36551 GCCTCTAGAC TGCAAGATGT GTCTCTAATG TCCTTGAGAC TCTGTAGTGG
36601 GTGTTTGAGC AATTAAAAGT ACCCAAGAAC AGAGTGAGCT GTCTCAAGAA
36651 GCAGTGAGTT CTCTGTCACC GGAGGTATTC AAGCAGAGGA GGATGGCCAC
36701 TTGGGGGAGA TGTTGTAGAA TGTATCATGT ATTAGAAAAG GAGTGAACTA
36751 AATCTCTCCA GGTCGCTTCC AATTGTATTT CCCATATGAC TTTCCATAAA
36801 TGGATTTCAT GAAGTGCATT CCATTTTTAA AAAGTGGTTT TTTTTTTCAA
36851 ATTCTAAAGC ACAACTCATT AGATAGTTGT GAAAACAATA TAATGATTTA
36901 CCAATGAGCA TTTTTAAAAA AGAGAAGAAA AGAAGAAAAG ATAATCAAAT
36951 AGAATAAAAT AGAAAATATC TGAATGCATT GCACATAAGG GTAAATATTG
37001 GTTTTTGAGA CTTGTTTCAG TTACATTTGT ATGTATGAGT ATGGACTGGG
37051 TTGCAATATA AAATATATTT TGTTTATGGG TTAAGGTAAA AAAATTGGAA
37101 GCCACTACCA TAAGATCTAA ATAGGAATAA GCATATATTT ATTTAGGTTC
37151 TTGTCTAATT TATGTCTTTT ATTTATTGTT AGTTATCTAT TGTATTCTTT
37201 TTAAAAAGTG ATAAAATATT GGTTGCTATG GTTTCCTGGG TTACCGCTTA
37251 CACCTCAGCC TTGAAAAAAA ATCAGCACATA ATCTAATTTC CCAGCACATA
37301 AAAAGAGTGG AAACATCATC AACATAAGTG AGAGGGGAAG AAAATGCTGC
37351 TTGCTCTCTT TTCCCAGGGC ACCCTGAGCT GGCCAGGAAA TGGGAGCTAA
37401 GACAGGTACA CAACCTGTCT TGTGCTTGGC TGGTCCCAGG ACATACAATG
37451 CTTCTTGGAT AGTCAGTGTT TCTGACTCTG GAAGCAGGA AACAACCTCA
37501 AACATACAGT AACAGTCAGA AAAGATCAGT CGGTGGGAA CCAGGCAGGA
37551 TGGTAGGTCT CTAGCAAGCT TACCTGAACC TGGCCAATCT CCAACTTTTC
37601 AGGACATCAT CCAGGCAGGA CATCCCTGTG CCACCAAAAA TTTGTTCATA
37651 GTTGGTCCAG GGGCCAGAGC TTGGGAATCA AAGAAGCCCA AGAGTCTAGC
37701 TTGGGGTGCA CTAGACCCTA ACACATCTAT TTCTCCAAAT TACAGGTGCC
37751 AGCCGCCATG CCTGGCTAAT TTTTTGTATT TTTAGTAGAG ATGGGGTTCA
37801 CCATGTTGGC CAGGCTGGTC TCAAACTCCT GACCTCAGGT GATCCACCCA
37851 CCTCAGCCTC CCAAAGTGCT GGGATTACAG GTACGATCTT TCCACAGGGA
37901 TTTCCACAGG GATCTTTCAT GAACTGTTAG GTTTGTTTCT GGTGCTTAGC
```

FIGURE 3K

```
37951 TGAAGTAGCA CATCCATCAG CAGACCTGCC GAATAACACA ATGCTTTGGT
38001 CCCCCAGGGT CTTTGGAGCT GCCATCTTCT TAACATCGAC TCTGAACATG
38051 TTTATTCCCT CTGCAGCCAG AGTGCATTAC GGATGCGTCA TGTGTGTCAG
38101 AATTCTGCAA GGTTTAGTGG AGGTAGGAGA TACTTTCCTT ACAGTTTTTG
38151 ATATTGCTAG AGACAGCGCA GTCCTTTAGA AAATTCACCT TCTGAAGAAA
38201 ATCCCCTTTA CTCAGTTTTT TTCTATATTT TCTTCCTTTT CCTGCTGTTT
38251 CCATTCTCTG GTAATGGCTA AAATTGCAAG AATTTTAATT AAAATGCCTT
38301 GTGTGATTTT ACATTTATGA ACAATAAAGT ACCCTTGCAT AATGATCTTA
38351 GAGATAATCT AACCTGACCC TCTTCATTTT AATAGATAGT GTAACTGAAG
38401 CCCAAATCTA CAGTTCACAT AGCAGAGGCT CATTCCACTA AAACAATTTA
38451 AGTGGATTCA TTAATAAATC TGTACATTTT CAAGGGTGTA GTCTGATGCA
38501 GAGATTTAAT TCAATGAAGG AGGCAGCATG ATATGGAGCC AGAAGGTAAA
38551 TATTTGGAC TTTACAGGCC TTACAGTGTC TGTTGCATCT ACTCAACCCT
38601 GCTGTTATAG TGCAAAAGCA GCCAGAGACA ATATGGAAAC AAATGGGCAT
38651 GGCTACGTTC CAATTAAACA TTTTACAAAC TGAAATTTGA ACTTCATATG
38701 ATTGTTGTGT GCCATTAAAT ATTACTCTTC TTTTGATTTT TTTTCTCACC
38751 ATTTTAAAAT GTAAAAAAGA TTCTTAGCTT GTGGGCTATA CAAAAACAGA
38801 TGGTGAACCA ATTGGCCCAT AGTTTGCCAA CCCTCGATAT ACAGCAATGT
38851 TTCCCAAACA CAGTCATTCA CCTCTGACCT TCGCCAGTTT GTTATGCCCA
38901 TGTACAACTT GTACTATTAT TTGCCTATTG TTTTCCCCTA GATCGACTCA
38951 TTTAAAACAA AAAACAAAAG ATACCTATTA CTCTAAGCAA TACCATCTTT
39001 GAAATCATGG GTTTGATGTG TTAGTTACAT CTTTTCCTTT TTTTTTTTTT
39051 TTTTTTTGAG ATAGAGTCTC GCTCTGTAGC CCAGGCTGAA GTGCGGTGGC
39101 ATGATCTCGG CCCGTTGCAA CATCTGCCTC CCAGGTTCAA GCGATTCTCC
39151 TGCCTCAGCC TCCTGAGTAG CTGGGACTAC AGGTGCCAGT TACCACACCC
39201 GGCTAATTTT TTGTATTTTT AGTAGAGATG GGGTTTTACC ATGTTGGCCA
39251 GGCTGGTCTT GAACTCCTGA CCTCAGGTGA TCCGCCCACC TCAGCCTCCC
39301 AAAATGCTGG GATTACAGGT GTTAGCCACC ACACCCAGCC ACTAGTTACA
39351 TCTTTTTCAA AGCATACATA TATATAGTAG AATTATATAT AAATTTAATT
39401 ATATATAGAT TAATTATAAC ATATATACTA GTGTATATAT GTATATATAA
39451 TATATACATA TATAGTATAT ATATAATATA TATAGTGTAT ATATATACTG
39501 TATCATATAT AGTGTATGTA TATAATATAC ATACACTAGT ATATATATTA
39551 TAATTAAAAA TGTAAGTTGT TATATCATTT CAAATCCAAC TCTAGTCCCA
39601 CTAGAGGGAC ATATATGACA CTTTGGGATG TACCCGTGTA GTGGAAAGAA
39651 CACGATATTA GCATCCATGA AGACTAAATT TTAGTCACTT AACAGCCCTG
39701 AGTCTCAGGT TCTGTATCTT GAAATGAGTG GATGGACCAA CTGATTGTGG
39751 AAGGCTCTTC CTACACTGAT AGTCTATGAT AATATGAAAT ATAAATATAA
39801 AGACCTTTTC CCCCATCTCC TACCATGCTT ACATGTGAAG TGTATTTGAA
39851 TTTCAGCATC TGTACTGTGA GTCAAAATAG CTCAATCATG CTGTTTAGTG
39901 TCTGTTTTAG TCCATTTGGG CTTCTACAGA ATACCATAAA CTAGGTAGGT
39951 TATAAACAAA AGAATTTTTT TTTTTTTTT TGAGACAGAG TCTCACTGTG
40001 TCACCGAGGC TGGAGGCAGT GGTGTGATCT CAGCTCACTG CAACCTCTGC
40051 CTCCCAGGTT CAAGCGATTC TTCTGCTTCA GCCTCCTGCA TAGCTGGGAT
40101 AACAGGCACA TGCCACTGCA CCCGGCTAAT TTTTGTATTT TTGGTAGAGA
40151 TAGGATTTTG CCATGTTGGC CAGGCTGGTC TCGAACTCCT GACTTAGGTG
40201 ATCCGCCCAC CTCGGCCTCC CAAACTGTTG GGATTACAAG CATAAGCCAC
40251 TGTGCCTGGC CTTTTTTTTT TTTCAGTCTC GCTCTGTTGC CCAGGCTGAA
40301 GTGCAGTGGT GCAATCTCAG CTCACTGCAA TCTCTGCCTC CTGGGTTCAG
40351 GCGATTCTTG TGCCTCAGCC TCCCAAGTAG TTGGGATTAC AGGCATGCAC
40401 CACCATGCCC AACTAGTTTT TGTATTTTTA GTAGAGATGG GGTTTCATCA
40451 CGTTGGCTAG GCTGGTCTTG AACTCCTGGC TTCAAGTGAT CCACCCACCT
40501 CGGCCTCTCA AAGTGCTGGG ACTACAGGCG TGAGCCACCG CTCCTGGCCT
40551 AGAAATGTAT TTCTTACAGT TCTGGAGGCT GAGGAGTCAA AGATCAAGGT
40601 GCTGGCAGAT CGGTGACTTG GGAGAGCTAG CTTCCTGGTT CATAAACAAC
40651 TACCTTCTCT TTGTCTGCCC ATGGCAGAAC GGATGAGGGA GCTCTCTGGA
40701 GTTTCTTTTA CAAGGCACTA ATCTCATTCA TGAGGGCTAC ACCCTTATTA
40751 CTTAGTCACT TCCCAAAGGT CCATCTCCAA ATACCATCAC ATTGGGAATT
40801 AGGTTTTAAC ATAGGAATTT GGTGGGGACA CAAACATTCA ACCTACAACA
40851 GTGTCTGTAA ATTGGGCTTT TATATTGTAG CCTGTGTGAA GAAGCAGCAT
40901 CCATATTTTA AACACAAGCA GAAACTACAG TCAAATCAAC TAATCTATTT
40951 TCAACTCTTC TGCCAGGGTG TGACCTACCC AGCCTGCCAT GGGATGTGGA
41001 GTAAGTGGGC CCCACCTTTG GAGAGAAGCC GACTGGCCAC AACCTCTTTT
41051 TGTGGTGGGT ATATTAGAAT CGTAACAAAT TTTATTTATG AATGCTTTTT
41101 TTGGGTTCAT GCAGTGGCTC ACGCCTGTAA TCTCAGCACT TTAGGGAGGC
41151 CGAGGCAGGA GGATCCCTGG AGCCCAGGAG TTCGAGATCA GCCTGGACAA
41201 TATAGTGACA CTTCGTCTTT AAAAAAAAAA AAAAAATTA GCCGAGCATG
41251 GAGGTGTGTG CCTGGGATCC TAGCTACTAG GGAGGCTGAG GCAGGAGGAC
41301 TGCTTGAGCC TGGGAGGTTG AGGCTGCATT AAGCTATGAT GGCCACAGCA
41351 CTCCAGCCTG AGTGACAGAG TGAGACCTTG TATCTAAAAA GAAAAAGAA
```

FIGURE 3L

```
41401 AAAAGAAATG GAATGCTTTT TTGGCTTCAA GCAACTGAAA ACCCTACTAA
41451 GGGCCTTAAA ATGAGTCTAT TTATTTTATA TAACAGAATT CTAAAGGTGA
41501 GTGGTGGCTA GTGTTGGTTC TGCTGCTCAA AAATCCATCC AGGGCCTAGG
41551 CATGTTCTGA CTTTCTACTC TGCTATCCTC AGACATAGCT TTTTATTTAC
41601 TTCTGTGCTT ATTCCATCTG TCCCTTTCAT CAGGAAAACA AAAGCTTTCC
41651 CAAAGCCCCC TACCAACCTT CCACTTTAAT TTCTTTGGCC CTAACTGTAT
41701 CATATGCTTT ACTAAATGCA GAGGAGGCTA GGCAAGCAGA TGCCTAGCTT
41751 CACCAGCCTC TTCAGGAGTG AAGGGGAAGG GAGAAAGGGT TGGAAGTGGT
41801 TGTTGGATTA GCCAACAAAT GACATTTGCT AAGGACAAAA GTGGAAAGAT
41851 GGGATCATCA AGCATCCCAC GCCTCTTCTT TTTATATGAA ACTAAAGTTC
41901 AGTGACTTGC CCAAGATCAT GGAGCTAGAA CAAGACCTGA ACTGTTGATC
41951 TGGAACTTTC CTTACTTCAC GCTCCTACCA TGTACACATT GTCATATAGA
42001 AATGTAAATT AATTTTTGTC ATTATATCCC AGATAATAAG AAGTAGAGAC
42051 CATCCATCTT ATCTGAAAGT AAATGAGTAG CCCCCAAGTA GTATGTGACT
42101 TTAATTCCTG CATCTCCAAA CTTCACCTTG CTGAGGTTGC CATCTCCAAG
42151 CTACCCCTGT GGGACAGGCC TCTCTAGGTG TGGCTGGGTC CCTAGGAATC
42201 AATCAACAAC AGAACAACAA CAGCACATGC CGCTGCCATC AACACAGTGG
42251 TAAATGTGTC GGGGGAAGGG GCCCATGAAG GTAAAAGTAC CTTAGACCAG
42301 CCAGGCATGG TGGCTCACAC CTGTAATCCC AGCACTTTGG GAGGCTGAGG
42351 TGGAGGATTG CTTGAGCCTA GGAGTTTGAG ACCAACCTGG GCAACATGGT
42401 GAAACCCCAT CTCTACCAAA AATACAAAAA ATTAGCTGGG TGCGGTGGCT
42451 CATGTCTGTG GTCCAGCTA CTCAGGAGGC CAAGGTGGGA GGATCGCTTG
42501 AGCCCGGAGG TGGAGGTTGC AGTGAGCCGA GATCACACCA TTGTACTCCA
42551 GCCTGGGTGA CAGAGGAAGA CCCCGTCTCA AAAAAAAAAA AAAGTACCTT
42601 AGACCACAAA AGTCACAGTG TGGCCTAGGC AGTGTGAATT ACAGCTTAGG
42651 TCTGTCTGAT TTTCAAACTA GCACACTTTT CCTAAGATAT TCTTCTTTGC
42701 TAAAGGGAGA AAGATAGCTT TCTATTTATT TCTGCATATG TTTTAATTTT
42751 CCTCTTCCTG CTGGCCTTTT ACCTCCTTGA AATAATAATA AAGTAATCCT
42801 GAGAATGTGG TGTGAGGTAT TCACCGCTAT GCCTACTTTG TGCCTCGTTG
42851 GGAATTGCAT GCTCAGCTGA GATGTCTTTA CATATTCAGT GTCTCTTGTC
42901 CTTAGAAACC ATCTCCATCC GCTCATTTGC AGTTTAAGCA TCTCCATCCC
42951 TACTACTGTG CTTATACCAA CTCTAGAAGA GGATAAGACT CACCCCAGCT
43001 GGCCTTGTGG CTTGTTAGAT CCTTGACCTT ACTTTCTTTG GATGGTTTAT
43051 TTGTAAGACC TTTCATTTTG ATTTGCCAGC AAAATGAGCA TGACTAGCAG
43101 CCACTCCCCA TTCTTAGTGT GTTTTTATAG CCCTAAAAGG GCTGATTTAA
43151 GAAATGGTTT GACTCTCAAG GAAAGTTACC TGATCAAGGA CACAGGCCTC
43201 ATTACATGTC CCAGCTAAGG TGTGGCCTTG GTTTCAAAGA ACAGCCAAAG
43251 GAAAATGTGG AAGAAGGAAA CCCAGGCTTG GAGTGTATAA ATTCTTAATC
43301 TCAAAAGATA TTGGAGTTAG AAGGGATTCT AGAAAACATC CAGTGATATG
43351 GTTTGGCTCT GTCGCCACCC AAATCTCATC TTGTAGCTCC CATAATTCCC
43401 ATGTGTTATG GGAGGGACCT GGTGGGAATT GATTGAATCA TGGGGGTGGG
43451 TCTTTCCCAT GCTTTTCTCG TGGTAGTGAA TGGGTCTCAT GAGATCTGAT
43501 GGTTTTAAAA ACGGGAGTTT CTCTGCACAA GCTCTCTCTT TGCTTGCCGC
43551 CATCCACGTA AGATGTGACT TGCTCTTCTA TGCCTTCCGC CATGATTGTG
43601 AGGCCTCCCC CGCCACGTGG AACTGTGAGT CCAATTAAAC CTCTTTCTTT
43651 TGTAAATTGC TCACACTTGG GTTTGTCTTT ATCAGCAGCA TGAAATCAGA
43701 CTAATACATC CAGTTACAAC CCATTGTTTT ATAGTTGAGG AAACTGAGGC
43751 TGAGGGAGGA AAAAAGATTT AAATTCTTAC AGCTAGTGAG GGCCGAACCG
43801 GGGGCTCTTT CTCACCCCCA GTTCTGTTCT TCCTTCTTTG CATACCATTC
43851 AACAATCATC TGAGGCCCAG GGGACTGAGC TGCAGTCTGC TCCCCAGGGC
43901 AGTCTGGGAG CAGCTGGGGG CAGCTGCAGT AAGGGCTGAG TGCCCTGTTG
43951 TTTGCTCAAG GGGCTGTGTC TAATAGGAAC TGACATTGGA GAATGTCTAA
44001 AAGGATGAGG AAGATTTTTT CTGATAGAAA AGAAGGGTAG TTTAGGTCAC
44051 ATTGTGTATT AGTCTGTTTT CACATAACTA TAAAGAACCA CCTGAGACTG
44101 GGTAATTTAT AAAAGAAAGA GGTTTAATCA ACTCACAGTT CTGCATGGCT
44151 GGGGAGGCCT CAAGGAACTT ACAATCACGG CAGGAGGCAA AAGGGGAGGC
44201 AAGGCACATC TTACATGGTG GCAGGAGAGA GAGAGAGAGA GTGAAGGGGA
44251 AGGTGCCACA CTTTTAAACC ATCAGATCTC ATGAGATCTC ACTCACTATC
44301 GTAAGAACAG CACGGGGGAA ATCCGCCCCC ATGACCCAGT CACCTCCCAC
44351 CAGGTTCTTC CCTCAACACA TGGGGATTAC AATTTGAGAT GCAATTTGGG
44401 TAGGGACACA GAGCCAAGCC ATATCACATT GTAAAGTTTC CCCAATGATA
44451 GAATGCTTTT TACTATGTAA GGGGAATTAT TAGGTGCTTT TGAGTGAAGG
44501 AGGCATGACT GAATGATTAA ATAAGAGTAA GGGCTTTGGG GTTCCACAGA
44551 CCTGGGCTCC TGTCCTGTGA CTTGTCACTT CTACCTGTGT GACCTCAGGC
44601 AATCTGCCTC CCCTCCTCCA GCCTGGCTTT CTCCTTATAA AATGGGGGTC
44651 ATATTGGTAC TTACCTTGTC AGGTTGAAGG AGAGTTAAAC AAAGTCATAG
44701 GTACAGTATA CTTAGCATGG TACTAGGCAC CCAGAAAGCA CTCAGTGCAT
44751 CTTAGTTGGT GGGGTTATTC TCTACCTGCC CCTGTCCCAG GCATTCTTTT
44801 GCATTACCTA AACCAGACTC ACCCACCCCA CCTCCCAGGG TATTTGGCCT
```

FIGURE 3M

```
44851 GGGGACAAAG GCCACCCTAT CTCCACGCAC AGCAGAATGA GACCTGCAGC
44901 CCATTTTCAA CACATGCCTG GAGTGCTCAC CTTATTGGTT TGAGGAGCCC
44951 TGAGATTGTT TTTTGAGTGT GTTGTCATTC TGTACATGAT AATAGCGGTA
45001 ATAGCTGGCA TTTGTGTAAC CCATTATAGC TTACAAAGCA TCTTCACATA
45051 CATAGTTTAT TTGAATCTCA AAACAACCCC TTGAGATGGA TATTTCATTC
45101 CCATCTTATC TCTGAGGAAA ATGAGTCTCT TGACTTCCTC GGGTGTCATG
45151 ATGTTCAGAT TCCAGATCTC AGGCTGGGCC TTTCACCGAG GGTCAGGCTC
45201 ACCTTGGAAA GATGTGATTT AATCTATTTC TCTGGAAGAT CCCCAACCTC
45251 CCATTTCCTA AAGATCTTCC TTAGCATCAA ATTCTGGGAT ATAGAATTTC
45301 CTTTCACCAC TCACTTTTTC TGAAGCAAGA GTTTTTTCAT TCACAGCCCA
45351 GGGGGAGTTT CAGAGAGTAA CTTCTCCTTT CAGCTAATAA CTCCCAATAA
45401 TGGGAGGTCA CAGGGCTCAT CTTTCCCTAC CAGACGTCCA GAGGATAGCA
45451 GAGGTCAGCT CACTGCCTCT AGTCACAATT ATCTTGTCTA GACAAGATAA
45501 ACATTCACAC ACAGGTAAGC ATTTGCAAGG TTAAGTTTTA CAAAGTAAGA
45551 AATACATGTA AAAATGTACC CATTCAGGAG CTGAATGGAG ACAGCAGCCC
45601 TCTTGCCATC TGGAATTTAA TTGTTCACCC CTCACCTTTT TTTTTTTTTT
45651 TTTTTTTGAT ACAGTCACTC TGTCACCCAG GCTGGAGTGC AGTGGTGAGA
45701 TCTTGGCTCA CTGCAACCTC CGCCTCACGG GTTCAAGCAA TTCCCGTGCC
45751 TCAGCCGCCC AAGTAGCTGG GATTACAGGC ACGCGCCACC ATGCCAGGCT
45801 AATTTTTTGT ATTTTTAGTA GAGATGGGGT TTTGCTATGT TGACCAGGCT
45851 GGTCTTGAAC TCCTGGCCTC AAGTGATCTG TCCACCTCAG CCTCCCAAAG
45901 TGTTAGGATT ACAGGTGTGA GCCACCGTGC CTGGCAACCC TCTCCTTTTT
45951 TTTTTAATC AAGACTTTAA AAATCATGAT CTTTTAAATA ATTCAATGTC
46001 CCTCATTTAA AGATCTGGAT GAGAATCCTC CCAGTCCTCC TAAGCAAATT
46051 TTGTATGTTC CTTTGCTTGC TCTTTTTAGC TTCCAATATT GCGCCTGGTT
46101 GAATTTTCAA AATTTCTCTT AGATTTTTT CATCTTCTGA TTCCATTCTC
46151 TCATGTAATT CCAAACTGTG ATGCTGGAGC AATCTTTGTC TAAATCCTGT
46201 GTGGTCTCTG GATGAAGTTA AAGGGCATCT TGGTGACCTT CCTCTCCTGG
46251 AAGCCCTGTT CTGTGGCACA CTGGGAGTTT GCCTGTCTCT GCACGGAGGC
46301 AGTCTGATTC CTGCTCAGTT TGATTAATTC CTGACTTTAC CATATGAATT
46351 CTAAATGAGC TGAAAAGGCT TGCATGATGA TTGGTCAGAT TCCCTCAATC
46401 TTTTCTTGTT CCAGGTTCCT ATGCAGGGGC AGTGGTTGCC ATGCCCCTGG
46451 CTGGGGTGTT GGTGCAGTAC ATTGGATGGT CCTCTGTCTT TTATATTTAT
46501 GGTGAGTGAT TTGACTTCAC AAGTTCACAT GTGACTCATA GAGATGGTAT
46551 TTTACTGCAT ATGGGTTTGG CTCAGAGTTC ATTACATCAA AATAGAGATT
46601 ACTAAAACAA GTTTATTGTA TAAATGGAAT ACTTTATCTA TGATTTGATT
46651 AATATTTATA TTAAAGTTGA CCTAAAAAAA TAAGTAGAAC ATTGTCTTTC
46701 TTTAAATACC AGTTAACAAG AGGAACGTCA ACAAAATACT TACCCCTAGC
46751 TGAACATACT GCCATTTGGA AATATTGTAA AGATCCTTTT GTAGTTCATA
46801 AATGTGATAA TTGGGTGTTC ACGTGCATGT ATGAGATGTC TGAGTCCCTC
46851 AAACCTTGTT ACAACATTGG TACATTACCC ATTTTACCTG AAAAAAATAT
46901 ATATGGTAAA AATTGAAAAA TTTAGAAACG GAAGAAAATG AGACCATATA
46951 ACCCAGCCTT TTCTTTTTTA ACTGCAGGCA TGTTTGGGAT TATTTGGTAC
47001 ATGTTTTGGC TGTTGCAGGC CTATGAGTGC CCAGCAGCTC ATCCAACAAT
47051 ATCCAATGAG GAGAAGACCT ATATAGAGAC AAGCATAGGA GAGGGGGCCA
47101 ACGTGGTTAG TCTAAGTGTA AGTATAAAAA GTCAGATGAA GACTTACCTT
47151 TTTTCATAAG TGATTGTGTT GCCTTCTTAC AGAAAAAATG TCAATATCTT
47201 TACTAAAAAT ATCATGGTAT TTTTACTCCC TAGAAATTTA GTACCCCATG
47251 GAAAAGATTT TTCACATCTT TGCCGGTTTA TGCAATCATT GTGGCAAATT
47301 TTTGCAGAAG CTGGACCTTT TATTTGCTCC TCATAAGTCA GCCTGCTTAT
47351 TTTGAAGAGG TCTTTGGATT TGCAATAAGT AAGGTAAACA CACAGATGCT
47401 CCAAATATTT TTGAACTTTA AATCTCTTGA TTCTACAGAG AATAACTTTG
47451 TATGATAAAA TAATTAAATT GCTGATCATA ATTCATAACA GTTCTGTGAC
47501 ACCTAATAGC CTGGCTGTCA GACAAGTTAT ACATTCTATG CATAGTATGC
47551 ATAGCTGTTT AATTTCTTCT TAGCAAGGAT CAGAGCCGTA TTAAGCTGCT
47601 TTAAAGATTT ATGTTGTACC CAATCTTAGA GTGTTTTTGA AGCTAGCTCA
47651 AGGACGGCAT ATTAGGCAAG GATAAAAAGA TTTGAGGGTG TGGGTTTTCT
47701 TTTTTTCCTG TAAGCTACTC AGTGAGTAGC AGTAAGAACC TTACCATTCA
47751 TTTTGCAGAA CACCCCTTCT CCATAATGGT GGCTATAGCA GTAACAATCA
47801 TTGCTTGCAA TGGGTTAGAA AGAACCTCTT TCTGCCAGGC GTGGTGGCTC
47851 ACGCCTATAA TCCCAGCATT TTGGGAAGCC AAGGCTGGCG GATCACCTGA
47901 GGTTAGGACC AGCCTGACCA ACATGGCAAA ACCCTGCCTC TACTAAAAAT
47951 ACAAAATTA GCTGGGCGTA GTGATGCACA CCTGTGATCC TAGTTACTCA
48001 GGAGGCTGAG ACAGGAGAAT CACTTGAACC CAGGAGGCAG AGGTTGCAGT
48051 GAGGCGAGAT TGCACCACTG CACTCCAGCC TGGGCAACAG AGCAAGACTC
48101 TGTCTAAAAA AAAAAAGAA GAAGAAAAA TAAACAGAAA AAAAAGAAAG
48151 AACCTCTTTC AATGCTCCCA GACATTATCA TCAAGCCAAT TGTGTTTTAG
48201 GGAGGAAGGG TGTGGATAGT GAATCATCAA CCATCATCAT AAGATAAACC
48251 TCTTTCCTAC AAGGGAAAGA ACAGCAGCCG AGCAAACACA AATGTCTGCC
```

FIGURE 3N

```
48301 TAGCTACAGA TACTGTCAGA AGTGACCATG GAAGAGCTGG CATAATCATG
48351 AAATGGTGGC TGTCATCAGT CATCAGTGCT CACTGGGTGC CAAGTGCTTT
48401 ATCTCCCATG TGCCATGCCC TCTGTGATGA ATAAAAGTCA TCGCTGCCCT
48451 CAAGGAGCTT CCAATCTGGT AGAGGACACA GATAGGTCTA AAATCATTCG
48501 CTCATTCATC ATTTATTTAT TATGAAATTC AGGCCTACCC AGCTCCCACA
48551 TAATTAGATG CTTAAATTTG GTGGTGGTAG GTAGGGGGC TGTGGAGTGG
48601 AGGTGGGCAA GGGAATTAGG GAGGCCCCTC TCTCAGAAAT AATGACAAAC
48651 TGCTTACTGT TTCTTTCCCT TCCAGGTGTG TCTCTTGTCA GCAGTCCCAC
48701 ACATGGTTAT GACAATCGTT GTACCTATTG GAGGACAATT GGCTGATTAT
48751 TTAAGAAGCA GACAAATTTT AACCACAACT GCTGTCAGAA AAATCATGAA
48801 CTGTGGAGGT ACTGTGGATT TCATAGATGG CTTAGGCAGC TTTTGTAGAA
48851 TTAGGGTAAA CTGAACTGCA GAGCATATAT TAAGAAGTGA CATTTAGTCA
48901 TTGGAGTGGA TCTTAAAGAC CTCTAAGTCT GTCCCTCAGC AGACACTTGA
48951 GTGTTGTCCA TCACAGTGCT GCCAAGAGGT CATCCAGCTG GGACCTTTCC
49001 ATACATCCTT CCACATTTAT TGTTTGCTTA TGTAGTTTAT TCCCTTCTCT
49051 GCTTACCTTT CTACCTATCC ATATGTTTTG GTAAGAAACA GAAGAAAAGT
49101 AGTCTTTCCT CCTAGCCTAT GCTTGTGCAT GGGACACACA CACACACACA
49151 CACACACACA CACACACACA CCATTTTCTT TCTTGATTTT ATTTAGCTCC
49201 TGCTTTATGT TTTAATTTTG TAAAGACAAA GTGAATGTTA GGTGATTTCC
49251 CAAAAGAGGT AGGCGAAAGT AATTGTGAAC CCCTACAATG TTCATGAGTG
49301 CTTTTTAAAA AACTCATCTT TTTTGTTTAG CTTTTAAAAT TAACATTTAT
49351 TGAATGCTTT CTGTGCCAGA CACTAAGCTA AATCTTCTAC ATACATTATT
49401 TTATTTAATC TTCATAACCA CCATGTGGAG CAGGTACTAT TACTATATGC
49451 AATTTGCAAT GAGGAAACAG AGGTAAAATA AAGGGACTTG CTCAAGTAGC
49501 AGATCCCTGC AAGGTATCAG GTAGGCCGGA GCCTACCGCC AAAGCTCTTA
49551 GTTTGCGGCT ACCCCTCTGG AGGACTAGTC AGGATGAGCG AGCAGGAGGT
49601 AGAGGATAGC GCCACCTATG GGCAAGAGCT CACAACTGTG ATATTAAGTT
49651 GAAAGGGACG GATTGCGTAT GCTCTGACAG ATAGCTAGGT CTGGCACATT
49701 TAGAAGTGAA GACTATACCG AGGGACACAG GAGCAGGCAT GATCTGATCC
49751 CATAGCATTT CGGGAAGAAA GCCTAAGAGT CTGTTGGCAC CTGTTCTCCC
49801 AGTTCCTTGA CTGCTGGTCC CAGGCAGGGA TGTGTGGGCC TGACCTTAGC
49851 TTGAACTTTC TTGTAGAGGA CTGAGGGTTA GCGGATATAG GCCTGCTATC
49901 TGGTGGGCAG GAGGTGAAGC TCTGGGACAT TGCATTCAAG TCCTCTCCAA
49951 GAGAGCTGTA GCAGCTAGAA TAATGCCCAT GTCCTAATCC TCAGAAGCTG
50001 TGAATATGTT TCCTTACATG TCAAAAGGGA CTTTGCAGGT GGGATTAAAT
50051 TGAGGTTCTT GAGATGGGAG TTTATCCTGC ATTATCTAGG TGGGCCCAAT
50101 ATAATCACAA TAATCCTTAT AAAAGGAGGA AGGAGGGTCA GAGTCAGAAA
50151 AGAAGATGTG ATGGTGGAGG CAAGAGTCAG AGTGATGCAG CCACAAACCA
50201 AGGAATGCAA GCAGACCCTA GAAGCTGGAG AAGACAAGAA GAGATTCCGC
50251 CATAGCACCT CTAGAAGGAA TGCAACTCTG TAGGCTGCTG CCTTGACTTT
50301 AGCCCTGTAC CATTTTGGAT TTTTGGCCTC CAGAACTGTA CAATAGTGCA
50351 GAGAGTATTT TAGAGGTGAC ATCTAATCAT TGGAATAGAT CTTAAAGACC
50401 CCTAAGTCTA TCCCTCAGCA GATACTTGAT ATTTGTGTTG TTTTGAGCCA
50451 CTGAGTTTGT GGTAATTTAT TACAGCAGCA AATGAAAACT AACACAGCGG
50501 TAGGCAGGGT GCAGTGGCTC ACTCCTGCAA TCCTAGCACT TTGGGAGGTT
50551 GAGGCGGGCA GACCACTTGA GCTCAGGAGT TCGAAATCAG TCAGGGCAAT
50601 AGTGAGAACT TTTCTCTATT AAAAAATAAA ACATTTATAA AATGAAAACT
50651 AATACAGTAG CCAAAGCCTC ACCCTTCTAA TGATAAAATT CTGCTCCAGC
50701 TGAACAGCCC TCACCCAAGC CCTGAACATA TCTTTCTGTC TCTGACTTTG
50751 CCCACTCCCT TTCTCTTTCC CTGTGAGTTC TCACCTTCAC CTCTCAATCC
50801 AGTCCTCTCT ATACATCCAG CTCAATTCTT CTCCTCTTAT GTTTCCTTAA
50851 AGCCATGCCA TTCTCCAGTG ATCCCCTCTGA ATATGTCCAC ATGGCTAGAT
50901 TGGCAACTCA TCATGTGGTG CCTTATTGCA GCTCTCTCAG GAAAAGATTT
50951 TAGGCAGAGG GAATAGTATG TGCAATGACC CTGGGGCAGG CAGGAATGTG
51001 GCCTGTGTGA GAATAGAAGG AAGGGGAGTC AGAATGGCTG AGTGACGGGA
51051 GACGGGATCG GGATGTTTTT CTAGGGTCAG ATCATGGCAG GCCTTGTCGG
51101 CGTATGCAGA GCTTGGGTTT TATTTGAAGT ACATTGAGAT GCAGATGATT
51151 TAAAGCACGG AATGGATATG ATCTCATTTT TTTTTTTTTT TGAGACAGAG
51201 TCTCGCTCTG TTACCCAGGC TGGAGTGCAG TGGTGCAATC TCAGCTCACT
51251 GCAACCTCCG CCTCTTGGGT TCAAGTGATT CTCCTGCCTC AGCTTCCTGA
51301 GTAGCTGGGA TTACAGGCAT GGGCCACCAT GCCTGGCTAA TCTTTTGTAT
51351 TTTTGTAGAG ACAGGGTTTC ACTATATTGG CCAGGCTGGT CTCAAACTCC
51401 TGACCTCAAG TAATCCGCCC GCCTCGGCCT TCCAAAGTGC TGGGATTACA
51451 GGCATGAGCC ACCTCGCCTG GCCTTGCTTA TTTATTTTTA ATCTGGGGAA
51501 TTATGCAGGG TACAAGAGTA AAAGAAGGGA GACCAGGTAG GAGGTGATTT
51551 CAGTTGTCCT GTCTAGAGAA GATGGTGGCT TAGACAAATG AGGTGGCAAT
51601 GGAGATGGAG AGAGGGGGGT CAATTTCTAA ATTCTCAGAG CCAACAGTTC
51651 TCATCTTTAA ATTACATAAT AATATTTACT TCAGAGGATA GTTATGAGAG
51701 TTAAATGATA CAACGTATGA ATGCACCTAG TGCGGTGTTC AACCTATAAA
```

FIGURE 3O

```
51751 AAGTTCTCAA CAAATGTTAA TGCTGCTTTT TTTCTCCTAT GTTCAAGACA
51801 CAAAAAACAC AGAAGTTTTT CAAAGAGTTC TTTAACAAAT ATCTGTGATT
51851 GTATTTCCTT TGGACAAAAA AATGTACTTC TAAACTGGCA ACTTTAAATA
51901 AGTTTCTGGA TTTTAAACAC TATTTGCACA ACCTCTTCTA AACCCAGATG
51951 CATTGGATAT TCTTGAGCAT ATTTTGTGGG AATGTCTTGT TCCTATTTAA
52001 TTCTGCCCCA GTACCTCTGC TGTTTCTCCA TAATTGGTGG TGATTATGTT
52051 ATGTTGTGGT GATGAGAACT TTCAAAGATG TTTAATTGCT AACAAAGTGC
52101 CTGTTGAGAG GAAATAGTTT TTTTTCTGCA GAAACTAGAA GGCATATGTG
52151 GAATCTTTCT GCCTCATCTC CCATCTTTAA AAAATACCTC TTCACATGGC
52201 TTTTCATGTT CATATATATA TATATTTTTT TTGTTTGTTT GTTTTGTTTT
52251 GTTTTGTTTT TGAGATGGAG TCTCGCTCTG TCACCCAGGC TGGAGTGCAG
52301 TGGCGTGATC TCAGCTCACT GCAAGTTCCG CCTCCCAGGT TCACACCATT
52351 CTCCTGCCTC AGCCTCCCGA GTAGCTGGGA CTACAGGCAC CCGCCACCAC
52401 ACCCGGCTAA TTTTTTGTAT TTTTTAGTAG AGGCGGGGTT TCACCGTGTT
52451 AGCCAGGGTA GTCTCGATCT CCTGACCTTG TGATCCACCC ACCTCGGCCT
52501 CCCAAAGTGC TGGGATTACA GGCATGAGCC ACCGTGCCCG GCCATTCTTT
52551 TATATTTTGA CATAGTAGGA CCAGTGAGTT ATATATAGAA AATAAAATTT
52601 TTAAAAAGAC CATAATGGTC CCACTTTTTC TGCTTAAATA CAGAGATGCT
52651 AGAGCAGAGA TAACTACATG AAAACAAAGT TTTGTGCCAT CAGTGAAGAA
52701 TGCAGGTTGA TTTGGAAATG ATGAAGCACT GGTATGATCT TCCAGAGAAT
52751 TTTGGTTGGC TTTTTGGTTT CCTACTAAGA AATATAGAAG GCATTTCTCA
52801 TCTGAGAAGG ATCACACATA TCTTGGAGCC TGTCATCTTT TATTTCCATA
52851 GATTTTAATA TGCCATTAAA ATCATTTAAA GCAAAACAGA TCACTTAAGA
52901 CATGATGTTC AATTCATTCT GAATCAGGGT CTACGTCTAT GATGCTTAAA
52951 GACAGATGCC AAATTCTTGT CCTGCCCCCT CTATAGAACA TGCAAAGTGT
53001 AACTGAGGTC AAAAATTCTA TTCTGGCTGA ATCAGTTGCA AGTGTGAACT
53051 TCAGATTATT TTAATATGAA ATAAAATATT CTTAGGCCT TTAAGTCCTA
53101 GTTTTGTTTT TCTTGTCAAC TCTAAATAGG TTCAATTTTA AGGATCTCCT
53151 GATTACCCCT AAAGTTGAAA TTTTATCCTT AAGCTCCTGA ACATGCAGC
53201 CCTGTCTCTA GTATTTTAAC TGTCAGTAGA AACCATTTAG GCTCTTAAAT
53251 GCTTTTTTTT CCACTGGCAA TCTGCTATTT GGCCAAAATT TTTTTTCTTA
53301 CAGATGAACT GATGTATCAT TTGTAAGTTT TATTCTTTAT ACAATGTCAT
53351 CATTCTAATT CTTTGGGGGA ATTGACTTTC TGCATGCTTC TGTTCAGAGT
53401 GTAAAAATAA AAGAAGTTTC AGCCAGATGC CTTGTTATTT AGGATAGGCA
53451 CTTCTAAGAC ACATATAGTT AGTATATGAA ACACTAGCTA TTTTTCCCTA
53501 TGTGTAGTCT TAAATGTTGA AACAAAATTA AGAACAAGTA GCAATGATAT
53551 AAAGCCTATA GTTTTAAAAG TAAGACTTCC CTAATTACAT TTCATCCTCT
53601 TTAGAAGCCA TTTAAAACAA TTATTAGTTC TTGCCCTTCT TTATAGTAGT
53651 GTTGAAGAAA TAGGTTCAAA AAGGTAAATA TTAATAACTT AACCATCATT
53701 TACGGTAAGT ACTTCAGCTT GTGAATCTTA TTTTCTTCTT TCTGGGTCCC
53751 ATTTCCTTTC CTTTGCATTA ATTCATTAAA CGTTATGTAT GTATGTATGT
53801 ATGTATGTAT GTATGTATGT ATGTATGTAT GTATTTAGAG ACAGAGTCTC
53851 ACTCTGTTGC CCAGGCTGGA GTGCAGTGGT GCAATCTTGG CTCACTGCAA
53901 CCTCCACCTC CCGGTTTCAA GTGATTCTCC CGCCTCAGCC TCCTGAGTAG
53951 CTGGGATTAC AGGCACATGC AACCATGCCT GGCTAACTTT CATATGTTTA
54001 GTAGAGAAGG GGTTTTGCCA TGTTGCCCAG GCTGGTCTTG AACTCCTGAC
54051 GTCAGGTGAT CCGCCTGCCT CGTCCTCCCA AAGAGCTGGA ATTATAGGTG
54101 TGCACCACCA TGCCTGGCCA AACGTTATTT ATTGAGTGCA TACTACATGC
54151 TAGACAGACT CTGTGTTAAA TATACAGTTT TGTGGGAGAG GCAGAAACAC
54201 AAATGAAAAG TTACAAAGCA ATATTGAAAA GTTCTATAAA ATGATGAGAA
54251 GGTGATGTCA GCTTCATTGG TTGAGGGTAG GGAGAGGGTT GTTAGGGAAG
54301 CTTTCTAGAG GAGGCACTAT TTAATCTGGA CTTTAAAAAT AGTAAGATTT
54351 ATCCAGAAAA AGAGAAAATG ATGAGAGAAG AGTATCCCAG GTAAAGAAAC
54401 AATGTGTGAA AATATGTACA GGCATGAGAT AGTATTGTGT GGTTAGAAAA
54451 CAGCTAATAG AGGAGTATGT CTGTGGCACA GAGGGCTATC CACAGAATGG
54501 GGGCAGTAAG CAAAGAGATG AGGGCTGGAA GAAGATGAAA CTGGAACAGC
54551 AGGAGGTATT CATTATAGAA CACTATACTC ATGATATGGA GCTCATGACA
54601 AACACGTTAA GCACAGGAGC AAATAATGAG GTGTGTGGCT TAGAAAGACA
54651 GTGGTATTGA GAATGCATCA GAGGAGGACG AGTTGGGAAG ACTACCAAAG
54701 TGGCTTATTG TGGCTGAGCA TGGTGGCTTA GGCCTGTAAT CCCAGCACTT
54751 TGGGAGGCCA AGGCAGGCAG ATCACCTGAG GTCAGAAGTT GGAGACCAGC
54801 CTGGCCAACA TGGGGAAACC CGGCCTCTAC TAAAAATACA AAAATTAGAC
54851 TGGGCGTGGT GGCTCACGCC TGTAATCCCA GCACTTTGGG AGGCTGAGGT
54901 GGGTGGATCA CGAGGTCAGG AGACTGAGAC CATCCTGGCT AACACGGTGA
54951 AACCCCATCT CTACTAAATA TATAAACAAT AGCTGGGCA TGGTGGTGGG
55001 TGCCTATAGT CCCAGCTACT CAGGAGGCTG AGGCAGGAGA AGGGCACGAA
55051 CCCGGGAGGC AGAGCTTGCA GTGAGCCAAG ATCGCGCTGC TGCCCTCCAG
55101 CCTGGGTGAC AGAGCAGGAC TCCATCTCAA AAAAAAAAAA AAGTTAGCCG
55151 GGCGTGGTGG TGGACTATAA TCCCAGCGAC GGGGAGGCT GAGTCAGGAG
```

```
55201 AACCACTTGC ACCCGGGAGG CAGAGGTTGT AATGAGCTGA GATTGCACCA
55251 CTGCACTCCA GTCTGGGTGA CAGAGCACGA CTCCATCTCA AACAAAAGAA
55301 GAAAAAAAGG TGGCTTATTG CAGTTTTCCT GGTAAGAGGT CACGGGGCCT
55351 GGAACTAAAG CAGTGACAGG GGAGGGGAAA GTGGCAGTTG CACTGGACAG
55401 ATGTTTCCGA GGCCAAACCT GCAGATTTGT ATATGAAAGC TCAGGCAGGA
55451 GGAGAAGTCC AAGGTAGTTC TGAAGTTTCT GCATCGGACT TCTGGCTATC
55501 ATTTGTTGAG CTGTGCCCAT GTGCCACACT CAGTACCTCA TATACCAATT
55551 TCATTTACTT TTCCGATACC TCACAAGGCT GTGGTACTAT CTCCAGCTTT
55601 TGGATGAGGA ATCTAAGAGG TGTAGTAACT TGTTCAAGGT CACAAAATTA
55651 GTGATTTTGA AGTGGAAAGT GAACCCATAC CAGTTTGACT CTAAAGATTG
55701 GGTTCTAAAC ACAGAATATG GAAGATTAAT TTAGAGGAGA AGAAAGCACG
55751 TGGTGGCGAT GGTTTGGTGA TGGTTTGCTT GTTTGTTTAG GAGTAAAAAA
55801 ATAGGGGAAG AGGCCAGGGG TGGTGGCTCA TGCCTGTAAT CCCAGCACTT
55851 TGGGAGGCTG AAGTGGGCGG ACCACCTGAG GTCAGGAGTG GCCAGCCTGG
55901 CCAACATGGT GAAACCAGCC TGGCCAACAT GGTGAAACCC CAACTCTACT
55951 AAAAATACAA AATTAGCTGG GCGTGGTAGC ACATGCCCAT AATCCCAGCT
56001 ACTTGGGAGG CTGAGGCAGG AGAATCATTT GAACTTGGGA GGCAGAAGTT
56051 GCAGTGAGCC AAGATCATGC CGTTGCACTC CAGCCTGGGT GATAAGAGCA
56101 AGACTCTGTC TCAAAGAAAA AATAAATAAA TAAATAAATA AAAATAGGGG
56151 ATGAGAGAAT TGATTTGGGC ATGTTGCCTT TGAGGTACTG TAGAACAATT
56201 GTGTGGAGAT GTCTGGAATC AGCAGACAGT CTCCAAATGA AGCACCACTA
56251 ATTGTCTCTT CCCCCTCCTA AGGCACTCTA TATACTTGGA AATGATATTT
56301 ATATCATTTT TCTGTCTGTT GTCAGCTGAA CTTTTTTTTC GGGTGAGAAG
56351 GAACTTCTTC ATAATTTCCT CATTCTTTTT ATTTTTTATT GTGCTAGACT
56401 CACTTATTCT GAATGAAAGG AACAGAAAGT ACTTTTGTTC TGCAATATTT
56451 TCTGTGCAAA ATTCTCATGT ATTGTTGTT TTTTTTTTTT TTAAGAGGCC
56501 TGAGAGCTTG GTGAACTTTG AAATAGAAAA ATTTTGACTT TTGCTTTACA
56551 AGGGGTGAAG TGCTGTTTTT GTTTGTTTCT TTGTTTGTTT TTGTTTCAGA
56601 TATTTGCTAC AGTTTTCTGG TTGCTTTTGG CAATAAATAT TAGAGTGTTG
56651 TCATTTTACT TTTAAGGGAA AGGCCATAAC TAGTCAAAGG GGAATCATTA
56701 CCACAGTTAT ATAGTAGAGT TTTAGTATTT AACAATGGCA GGGACAGCTA
56751 CCCATGAAGC AACTAATAAT TAACATCCCT CATCTCAGGA GCATCATTGG
56801 AACCTATTGG GACCGTGTGG TGTTCAAGGT GCACCGCGAT AATGTTAGAA
56851 AGTTTGTGAA CACCCAGGGA ATATTAGCAA AGTCATGTAG TCATGAAAGT
56901 CCTGGGTGGC ATTGTAAGCA CTGTACCAGA ATGTAGGTCT GTGGAGGAAC
56951 AGAAAACCAA ACACTGCATT TCCCCACTCA TAAGTGGGAG ATGAACAATG
57001 AGAACACATG GATACAGGGA GGGGATCATC ACACACTGGG GCCTGCTAGG
57051 GGGCAAGGGG AGGGACAGCA TTAGGGCAAA TACCTAATGC ATGTGGGGCC
57101 CAAAACCTAG ATGATGGGTT GATAGGTGGA GCAAACCATC ATGGCACATG
57151 TATACCTATG TAATAAACCT GCACATTCTG CACATGTATC CCTGAACTTA
57201 AATCCCAGAA CTTCAAGTAA AGTTAAAAAA AAAAAAAAAA AAACTTAAAT
57251 TCCAGAACTT AAAGTAAAAA AAAAACATAG ACACAAACAA AATAAACTTA
57301 GGTCTGTGGA ATTATAGGTT AGTTCTTATT TGATAAATAA ATGAACTTGG
57351 GTTGACCGAT ATGAAAATGA CATTTTTTTC CCTTGCTGTT TCCATTTGCA
57401 GGTTTTGGCA TGGAGGCAAC CTTACTCCTG GTGGTTGGCT TTTCGCATAC
57451 CAAAGGGGTG GCTATCTCCT TTCTGGTACT TGCTGTAGGA TTTAGTGGCT
57501 TCGCTATTTC AGGTAATGTG TCCTTTGGGT TTCCAGATCT TGACTATAGA
57551 TTCAACAAGT CCCAGGAAGA AGGAAGGACA AGGATATTGT AGCACCTTCT
57601 TTCAGTAGCC AGTCCATTCT CAGAGAGCAG GACCACCGTC CAGAGAATGT
57651 GATCTAGTGG GGGTGATTTT GTAAGATCAC TGAGAACTGG GCTTGGGAGC
57701 TCAGTTAAGG TGGAATTTTT CCTACTTACT TTGTTACGGG AAAAGACACA
57751 AAGTGCAGAT GACCCTTCTG AGACACGAGC AGAGGCCCAA GCATATGTCC
57801 TGGGTGAAGT GGACTTTCAT ACTTTAGCAC CATGTCACCC TACCTGACAG
57851 AGGCTCCTGT GACTTTTTCA AGCCTCGCCC TCTTGCTAGA GAACTGCGAG
57901 TGTCATTACA GTCATAGGAT CAGAAGTTTT TTTAAGAGTG AAAACCTTCT
57951 TTAGATTTTT GTCTACTCCA TTGCTTTCAT TTTCCAAACA AGAAAATGCG
58001 GGTCCATAGA GGGGAAGTGA CTTTCTGAAC AGGGTAAAGA ATAATGACAA
58051 TGATGATGTG AGCTAGCGAT GACCAAGCAC AGATTCTGTG CCAGGGAATA
58101 TTCCATGAGA TCTGCATATA TTAAGCCCTG TCTCTCTCAC AACTACCCTG
58151 CTGGGTATCA GTGCTATTAC GGTCCCCATT TTACAGGAGC AGAAACCAGT
58201 CTACTATATG TGAGAGAAAG GCCAGAGTGC AATCATATCA GAAGCTTCCT
58251 ATGCAAAACT GGGTCAAAGA GTGAAATTTA GTTGTTTGTC TATCTTTAAA
58301 ACATCGTAAT AAGAATATGG TTACTGGCCG GGTGCGCTGG CTTACGCGTG
58351 TAATCGCAGC ACTTTGGGAG ACCGAGACGA ATGGATCACT TGAGCCCAGG
58401 AGTTCAAGAC CAGCCTGGGC AACATGGCAA AACCCCATCT CTACAAAAAA
58451 TACAAAAAGT TAGCTAAGTG TAATGGCGCA CACCTGCAGT CCCAGTTAGT
58501 CAGGAGGTTG AGGTGAGAGG ATGGCTTGAG CCTGGGAGTT GGAGGTTGCG
58551 GTGAGCTGAG TTCGTGCCAC TGCATTCCAG CCTGGATGAC AAAGCGAGAC
58601 CCCTTCTCAA GAAAAAAATA AATAAATAAA ATAAAAATAA AAATGGTTA
```

FIGURE 3Q

```
58651 CTTAAAGAAA ATTTCACATA TATTGTATAT ATATCATAAC ATTGTGAAGC
58701 AAGTAGTAGT ATATCACTAT GCTACTGGGT TTTTCACTAT TTTACTAAAG
58751 CTCAGAAAAA TTTGATACTT TCTTAATATC ACACAGTTAG TGGCAAAGGA
58801 AGGATGACAG AACAGTTCTG CCTGGCCCAA AGGCCGTGCT CCTTCCATTA
58851 TTCCAGGTTG CCTTAAATAT CAAACAGTGT TAGTGTCCCA GAATAGAAAA
58901 ATATGGAACC TCTGGTCTAA ACTGCCCTAA GACAGGGGCT TGTATCTTTC
58951 AAAATAAATA GAGTTGATGA ATAAATTAGA AAATAAAGTA AAAGTCTAAA
59001 TTAAAAGTAA CTTGCAGCTA AGTAATTTGG TTTAGAGATG CATAGACCTG
59051 GGTTTGAGGC CCTCTTTACT ATTTACTATT TATAAAATAA AAAATTTGCT
59101 AAATTATGAA AACTCTCAAG CTTCAGTTTT CTCATCTAGA GATTGGAGAG
59151 ATGAAACAGC AACCTCATAG GGTTGTTGGG AGGATAAACT TAGATAATTC
59201 ATGTATTTCC CCGCACTTCT TGTGGGCTGG GCATTATTCT TAGCACTGGG
59251 GATATTGCAG TGAATAAATG AAAGTGTCCA TCCCCATAAA GTTTACATTC
59301 TAGTGGAAAT ACTTATTCAA ATAAAAACCT TAGCTGTATT TATTTGAAGT
59351 CCTTAGCACA GTGCCAGATG CATAACAAAA TTAATGAGTG TTCACCATTA
59401 TTGTTCTATT AGTACACACA CCAGCCCAGT GCCTCTCAAA GTGTTATGTG
59451 AAATCACCAT AAGATATTTC AGAATGCAGA TTCTGATTTG GTAGCTCTAG
59501 GGTGGAGCCT GAGATTCTGC AGTTTTAGCA AGTTCCCCAG AGCTGCTGCT
59551 GCTGCAGGGC AGTCCACACT TTGAGTAGCA AGGGCAGAGC AATCACGATT
59601 TGCTTCCAGT AGGAAGCGGA GGAACGCCTT CCCTTGATAA CTTTGTGATG
59651 CAAAAGAGAT CCATATCCTG TTCCCAGAGA TACTGAAATG TTCAAGTTCA
59701 TATTGCTTCC TTTCCCCCGA TTGCCAATTA AGTCACAATC TGAAGGAGAG
59751 AAACCCAATA CTCCAAATCA CATAAACTGC TTTTTTGTTT TCCTTTTTTT
59801 TTAGACAGGG TCTCTTGCCT TGTGCAGTGT CTCATGACTA TAATCCCAGC
59851 ACTTTGGGAG GCCGAGGCAG ATGGATCACC TGAGATCCAG GAGTTCGAGA
59901 CCAACCTGGC CAACATGGTG AAACCGCATG TCTACTAAAA ATACAAAAAC
59951 TAGTTGGTTG TGGTGGTATG TGCCTGTAGT CCCAGCTACT GGGGAGGCTG
60001 AGGTTGCAGT GAGCCAAGAT TGCACCACTG CACTCCAGCC TGGGTGACAA
60051 AGAGAGATTC TGTCTCAAAA AAAAAAAAAA AATAGACAGG GTCTCGCTCT
60101 GACACACAGG CTGGTGTGCA GTGGCATGAT CGCGGATCAT TGCAGCCTCT
60151 ACCTCCCATG CTCAACTGAT TCTCCTGCCT CAGCCTCCTG AGTAGCTGGG
60201 GCTACAGGCA TGTGCCACCA CTTCCAGATA TATATATATT TTTTCGAGAC
60251 AGGGTCTCAC GATGTTGCCC AAGCTGGTCT CGAACTCCTG GCCTCAAGTG
60301 ATTCTCCTGC CTTGGCCTCT CAAAGTATTG AGATTACAGG CATGAGCCAC
60351 CACACCTGGC CTTCTTGCCA CTTTTTAAAC ATGATTTCAT TTAATCCTCA
60401 TTGCAACCTT GATGAGAAAG GTATTGCTAT ATTCACTTTA TTGGTGGGGA
60451 AACCAAAGTG TGGTTTAACT TGCCGAGTGA AGTGGCTGGG AGTGTGGAAT
60501 AAAGGTCTGT TGGTCCCAGC AATGACACTG TGGGAGGGAT TGCAGCCACA
60551 GGGGCAATAA TTCCTCAGAA TCTACTGTCT GCCAACTTTT AAAGGAATAA
60601 ACATAGATGT CAGGGAAGAC TGACTGGCAC AATTTAGGAG CTGATTATAG
60651 ACAAGACTGC TGAGATAGAT GAAGTTAAAA ATAGGCAAGA GATGAGTGAT
60701 GCCTGTTTTG GGAAATGTCC TATACAGAAG ATAGTTCTC TCAGTTTATG
60751 TGTAATTTTT TTATCTGCTA TAAAAATCTA TCAATATCTC AATTTCTCAG
60801 TGATTTTCCC CCCTCCCCAA ATGTCAGGAT TGTGCAGCTA GAAACCTAAA
60851 TGGCTTTTCC CACATTATCT TTAGCTGAAT GCAGATGCCC AGGCTTTGTA
60901 TCAGAGCATA ATACTCAACA ATCATATTAA TTGCTTCTTA TCTCTGGATT
60951 CTTTTCTAAT AAAGTGTTTA TCACATTCAA ATCCATGGTA AGATTAATGA
61001 ACTTGCAGCT GTTTTATATT CTGATCATTT GGCACATTGA CCTGAAAGAT
61051 AAGGTATGTT TATTATTACC AAAAAGTTTT CTCAAAATTT CTCCCTGAAG
61101 GGAAGTAGGA AAGACAACCA ACCAGTGTGC CAGATTAGAA CAAAAAAATG
61151 TTTTAAGTCC TATTTCAGT TTTTTTTTTT GCACAGAATA GAGAAATAAA
61201 AAGCAAAGCA AAGGAAGACA AAAAGATGAA TAAAGCCTAC AACCCCTTGC
61251 TATAATTTCA GTAGCTGAAG CTGGTAATTA ATTTAGCAAC TATTTATTGA
61301 GTGACTACAA TGTGCCAGGC ACTTTGCTAG TTCAGGGGAG ATGGTGGTAA
61351 ACAAGACGGA TGGCTAACCA CCTGTAAAGA GCATGCATGT TGGTTTACAC
61401 GTCTATGCAC CATGTAGTTA ACATACATTA TTTAACTTAA TTCCTACATC
61451 AATTTTATAA GAATCATTAT CCCGTTATGT AGATGAAACT AAGGTTCAGG
61501 AAGTTTAAAT CCTTGGTCTA GGCTTGCATC TCAACTAAGC TGCCAGAACT
61551 GAGGTCTGTC TGATTTGAAC ATGCACCCCT GCAATATATT GACAAAGTCA
61601 GATCTCAGCT CGCTGTAACC TCCAACTCCT GGGTTCAAGT GATTCTCCTG
61651 TCTCAGCCTC CCAAGTAGCT GGGATTACAG GCATGTGCCA CCATGCCTGG
61701 CTAATTTTTG TATTTTTAGT AGAGGTGAGG TTTTGCCATG TTGGCCAGGC
61751 TGGTCTTGAA CTTCTGACCT CAGGTGATCC ACCCGCCTCA GCCTCCCAAA
61801 GTGCTGAGAT TATAGGCGTG AGCAACCATG CCCGGCCAGC AGCATTATCT
61851 TTTGATAGAA GACCTCAAAG AGAGGGAGTT ACTTTGCAAT GGCAGCAGAA
61901 GGTAGCAGTA GTAGTAGTGG TAGTTAGCAT AGCTTTGATA TTTGCCAAGG
61951 GCTTCACATA CCTATTTCCC CTGAGTCTCT ATCACAGCAC CTCTGTGAAG
62001 TGAATAGTAA TATTATCCTC ATATTGGAGA TGAAGAAACA AAGGCCCCCA
62051 AATTACTTGT TTACATAGTA GAAATAAGAT TCAAGTCCAG ATTTACAGAC
```

FIGURE 3R

```
62101  TCCAAATCAA GTAGGTGTGT GAAAGTGTTT CATAAATTAC AGAAGGTTCT
62151  CCCAATGTTT GTGCAAATGT TTCATTAAAA AGCACCCTTT TCATTGTGTG
62201  AAAATGTGGC CATGTGGCCA ATAAAGTAGG CTTACCCTTG GCTGCCTTTT
62251  AAGAGTAAGT CAGGGGTAGG AGTGGGAATA TTATAAAGCA AGGTTTGGTC
62301  TAGTCATACT GTATGTGATT GTATGATTAT TTACTCTGAA TAAATGTGAT
62351  TCAGGCTTTA GGCTTTTCAA TATTGTGCCA AACACCGTAT TTTGGAATTC
62401  AGAACCTACA AGGTAGAGAT GCCATAATTC TCTTTATAGA GAGAGCCCTT
62451  GATAGATATC CATAATCAAT TCCAGCATTG TCTACCAGTG CTGCTTTGTG
62501  CAGACACAGC CTCTTGAACC CAGTCCTCTT GGTCTGGAAA CTAGTCATAT
62551  ACTAGAGGAA ACCAAACAGA TTGGTAAAGG CTGGGGCAAC TGAGTATTTT
62601  CCAAAGCATA TTTGAAATTC TGTTCTTGAC TCTGATTTTG AGGTTTTGGC
62651  TTCACTGTAG GTTTTAATGT CAACCACCTG GACATTGCCC CACGCTATGC
62701  CAGCATTCTC ATGGGGATCT CAAACGGAGT GGGAACCCTC TCTGGAATGG
62751  TCTGTCCCCT CATTGTCGGT GCAATGACCA GGCACAAGGT AAAGGTCTCC
62801  TTTGTGGCTA TGGGTTACAA TATCAGAGGA CTGGAGCTCT ACACAAACTT
62851  GAGATTTCAA GGCTCTACTG CAGTCTGTAA ATGTGTATGT CCTTGACCTT
62901  GACTGAGTCA GCTGAACTTC TTTTTTTTTT CTTCCTTCTT CTGATTTTCA
62951  AATCATTGCT TATCAATGGC ACCAAGGCTA GTTGTTGTTT TGTTCTATGT
63001  TTTCTCAATT GAGGAATAAT AGTCTGGGGA GAGGGGATGG GCCATAGAAA
63051  CTGTTTAGAG ACCCAAAGAA GAAACTGAGG CAGTCAACTT GGGATAAATG
63101  AGTTACTGAA GATTGTTTTC TCATTCTCAG TGATTAAACC TTATAGCCTA
63151  TTTCCATCCA TTGCTTAGCA TGTTTCAGCA TAAAAGATG AGTGCTATTC
63201  TACTTCCTTG TTAAGAATAA AATAAACAGG ACATTGATAA CCTACCCAGT
63251  TGTTACTGAG CCTTTGTGAA TTTAGACAAG GGTGGATGGT AGAGGCAGAT
63301  CCATCCAGAG TTCAACCACA GCCCACATGA TTTCTTTATC TTTGTCACTG
63351  AAACGTCTCA AGATGCTGCT TTCTGCAAAT AAGAATTCTT TGATACCATG
63401  GGATTTTTTT CCCCCATCTA TTTTCTTAGT TGGATTGCCT ATTACAAATA
63451  TAACTTCAGA AGTTTTGCA GCTTCCTGCA GAAGAAAGTG TGAGATAAAT
63501  TTTCTTACTT TTTGACAGAA AAGGTAGGAT TTTATAGGCA GAGAATTCAT
63551  GTTTTCCATC TCTGTTCATG AAATGATAGG ATTGATAACC TGACTATTAA
63601  ATCCAAGATA TCTTCCCCCA ACCTTAGACA CAAATTCCCA TTATTTTTTG
63651  ACATACTTTT TTTTACACTG AAAATATTAT AAAGTTCTTG TCAGTCAAGG
63701  GTGAGAACTT TAATGGCTCA AATATTGTTA TGTATCCAAC AACAAGCAAG
63751  AAGGAGACTT CTGATATTTA AAACGGTGGG TTCCTAAAAC AATTTTAATT
63801  TAGCTGACTA TGTGAAGGGA AACCCCATTT GAGTATTCAA AAAGCTATGC
63851  AATGGTGCTG CAGGTATTAA TATTTGTATA TGTTGTTTAT TTTAAAATGT
63901  ATTTTCTTGT AATCCCAGCA CTTTGGGAGG CCAAGGCGGG TGGATCATGA
63951  GGTCAGGAGA TCGAGACCAT CCTGGCTAAC ACAGTGAAAC CCCGCCTCTA
64001  CTAAAAATAC AAAAAATTAG CCAGGCGTGG TGGCGGGCAC CTGTAGTCCC
64051  AGCTACTCAG AGGCTGAGGC AGGAGAATGG TGTGAACCCA GGAGGCGGAG
64101  CTTGCAGTGA GCCGAGATCG CGCCACTGCA CTCTAGCCTG GGTGACAGAG
64151  CGAGACTCCA TCTCAAAAAA AAAAAAAAGA ATTTTCTAAA TTAAAAAAAT
64201  ACGTATTTAT TGTTTTGTCT AACTTTCATA TTCATTGTTG TCTTAACTTT
64251  CATTTTTTAA GTTTTTCTTT TAAATTTGGT TTGAATCCCG GATGGTGCTT
64301  CTGACACACG TCCTCCCGCC CAAGGAGCCT CTAGAGCATC GCCTTCCAAA
64351  TGGGCAGGTG CTTTTTCACA GTGGAGGCCT CCAGGACATA CTGGTAATCT
64401  CTAGTTTTAG TTAAAACATT AATTGGCACT TTATTTCCTT ATTTAGACCC
64451  GTGAAGAATG TCAGAATGTG TTCCTCATAG CTGCCCTGGT GCATTACAGT
64501  GGTGTGATCT TCTATGGGGT CTTTGCTTCT GGGGAGAAAC AGGAGTGGGC
64551  TGACCCAGAG AATCTCTCTG AGGAGAAATG TGGAATCATT GACCAGGACG
64601  AATTAGCTGA GGAGATAGAA CTCAACCATG AGAGTTTTGC GAGTCCCAAA
64651  AAGAAGATGT CTTATGGAGC CACCTCCCAG AATTGTGAAG TCCAGAAGAA
64701  GGAATGGAAA GGACAGAGGA GAGCGACCCT TGATGAGGAA GAGCTGACAT
64751  CCTACCAGAA TGAAGAGAGA AACTTCTCAA CTATATCCTA ATGTCTGAGA
64801  GGCACTTCTG TCTTCTCCTT ACTTTAGAAA CAGAAAGTAT CCATACCTAT
64851  TGCCTTTCTT GTAGCCCAGC TTGCCAGAGG TCCAAATATT GGGAGGGGAG
64901  AAGATCTAAC CAGCAACAGG GAAAAGAGAA ATATTATCTT TCAATGACAT
64951  GTATAGGTAA GGAGCTGCGC TCAGTTGATA ACATAGTTGA TAATACATAT
65001  TTTTTGAATT GACAGTTGAC CCTTCTCTCA AAGAGCTAAA CTTATTCAGA
65051  AAGGAATGAC TAGAAGAAAA AGGAGACAAT ACCATGTTGT TCAAAGAAAC
65101  ATTGAAGGAA ATTGGGATGT TTGGCCAGAA GGAATGTAAA CAGTAGTAGT
65151  AGCTGCCACC ACATCTCTAG GGTAGCCATG CAGAGGAGGG CTTCATATTC
65201  CCAATAAACC CCACGTTGTG GCAGGTGCTT TATAAACACT CTTATTTAAT
65251  CTCCACACCT TTATGACACA CATTTCTTAT CCCCATTTTA CAACCAAGGC
65301  ATCTAAAGCA ACAAGAAATG AACTTGCCCA AGGTCATCTG CCAGGGTCAG
65351  TGCTGAGACT GTTGAAGCTC TCAATAGGTG GCAGTTTTAG GGAAGATTTC
65401  CATTCAGTGT AGGGAAGACA TTTGTAATAA TGAAAACTGA AAATGGAGTA
65451  ATTGTGAGTA ACTCACCACT TTAGCAGGTG TTGGGGAAGG GAAACATTTG
65501  GGTTGATGAG GCAGAGGGGA TTCAAATGTG TGAGAGGCTA GATTCAAAGA
```

FIGURE 3S

```
65551 CCCTCAGTGT TCTATGTTAT CTGAAGAGTC AAATGGTTTT GTGACTCCAT
65601 AGTTTTTAAA GTAATAAGGG TCAAAGACTA CATCAGAGAT TCAAATAGGT
65651 TTTTAAAGAA AAGCTAAGCA AGAGAGCCAA ATTTTTAGAA ATCTGATGGT
65701 CAAAATAGCT GAAAGCAGTA AACAAGAGAT TGGCTATTAA ATTTCAACTT
65751 TCCATAATAT TAAGAATGTA GCTAAATGAT GTCCCAAACT ACTTACAAAC
65801 TTTTAAGACA TTTAATAATT TAAGAAGTAG GTTCATGTGT TTTCTTAGGT
65851 AAAGTTCTTC TGAAAGAATT TTCTATTTTT AAAAAATGTA TCTCTTTAGC
65901 CTTTTCTGCT GGAGATTATA TTAGGAAGTT TCATCAGATT GTATAAAATT
65951 ATGATTTTGT ATCAAAAGTA TTCATGATGA CTCTATTTGG AATGATATTC
66001 AGGGAAATCA CAATAATATA GCAGTAGTTA TACAGAGAAA TACTACAATG
66051 AAAACATTTG GGGCAATTAG ACCTACAGTT ACTGTTGAAA AATTCACCTT
66101 TGATTGCATA AGGCAATTAC ATGGATACTT TTAGATATAT TTAAAATTTT
66151 AACATTGGCA TCTAAAGTGT TATTTGAAAA TAAAATTATT TTCCTGTTCA
66201 TTGATTTTAA ACATTTTATT CCTACTTTCA GAAGAAAAAT ATAATACGGA
66251 AAAAATTATA GATTTACTTG TAGCTTATTA TTGTAAAGTG GTTTTTTTTT
66301 TTTTTTTTTT TTTTCTAATT TCTCCCACAT GTATTTCTGG TCCCCAGTGA
66351 TACTAGCTGA GTTGTAGTGT ATTTTATAAA TGGAATAATC TTGGGGAAAA
66401 ATTGCGATTC TTCATTAAAT AATATTCTTT ATGTCACTAG CATACAATTT
66451 ATGTTAGTAG ACATCTTTAA ATCTCTTTAA TGAGTGAATC CATGCAAGCC
66501 CCATAAAACA GTTCCTAGCA TGCAGAAAAT GCCCACGTAA ATAGCTGTCA
66551 TCATCATTAT CTTTTAACAT TTTGGGGGAC TTTCCAGTTG AAAAGAAAAC
66601 ATGCTATGTC ATTTTTATCC ATTATCCCTG GAACTTATTG TGAAAGTTGT
66651 GCTGTTTTCT AAGTAAAATA AAAAATAAAA AATTAGCAAT TTATGATAGC
66701 CAGTGTTTTA TTTTGTGTGT GTGTTAGTAA AGTCAAATAA TTGTATTTTA
66751 AAAACTCACG ATAATCCTTA AGGTAGTATT GTATATTGTG ACACAAAGTT
66801 GTAT (SEQ ID NO:3)
```

FEATURES:
Start: 2029
Exon: 2029-2129
Intron: 2130-25338
Exon: 25339-25591
Intron: 25592-35639
Exon: 35640-35758
Intron: 35759-38007
Exon: 38008-38122
Intron: 38123-40966
Exon: 40967-41054
Intron: 41055-46414
Exon: 46415-46501
Intron: 46502-46977
Exon: 46978-47117
Intron: 47118-47233
Exon: 47234-47383
Intron: 47384-48675
Exon: 48676-48808
Intron: 48809-57401
Exon: 57402-57512
Intron: 57513-62660
Exon: 62661-62788
Intron: 62789-64446
Exon: 64447-64788
Stop: 64789

SNPs:

| DNA Position | Major | Minor | Domain | Protein Position | Major | Minor |
|---|---|---|---|---|---|---|
| 899 | C | G | Beyond ORF(5') | | | |
| 3052 | C | T | Intron | | | |
| 4813 | A | G | Intron | | | |
| 5882 | A | T | Intron | | | |
| 5962 | G | C | Intron | | | |
| 12832 | - | G | Intron | | | |
| 12834 | - | G | Intron | | | |
| 13561 | T | C | Intron | | | |
| 14023 | G | T | Intron | | | |
| 14484 | T | - | Intron | | | |

FIGURE 3T

| | | | | | | | |
|---|---|---|---|---|---|---|---|
| 14975 | C | T | | Intron | | | |
| 18016 | - | G | | Intron | | | |
| 18230 | T | - | | Intron | | | |
| 19104 | T | C | G | Intron | | | |
| 19212 | C | T | A | Intron | | | |
| 19613 | C | T | | Intron | | | |
| 20506 | T | C | | Intron | | | |
| 20530 | G | A | | Intron | | | |
| 21250 | T | C | | Intron | | | |
| 22347 | C | T | | Intron | | | |
| 22757 | A | G | | Intron | | | |
| 23086 | G | A | | Intron | | | |
| 24069 | C | A | | Intron | | | |
| 24086 | - | A | G | Intron | | | |
| 24397 | A | - | | Intron | | | |
| 24435 | G | A | C | Intron | | | |
| 25029 | A | G | | Intron | | | |
| 25297 | A | C | | Intron | | | |
| 25408 | G | A | | Exon | 57 | T | T |
| 26060 | T | C | | Intron | | | |
| 26615 | C | T | | Intron | | | |
| 26816 | T | C | | Intron | | | |
| 28480 | - | A | | Intron | | | |
| 29109 | C | T | | Intron | | | |
| 29754 | C | G | | Intron | | | |
| 29773 | A | T | | Intron | | | |
| 30223 | C | G | | Intron | | | |
| 30356 | G | A | | Intron | | | |
| 32040 | G | A | | Intron | | | |
| 32748 | T | C | | Intron | | | |
| 34248 | T | G | | Intron | | | |
| 34258 | C | G | | Intron | | | |
| 34998 | T | - | | Intron | | | |
| 37708 | A | G | | Intron | | | |
| 37811 | C | T | | Intron | | | |
| 37956 | T | C | | Intron | | | |
| 39038 | - | C | T | Intron | | | |
| 39167 | G | C | | Intron | | | |
| 39965 | - | T | | Intron | | | |
| 40711 | C | T | | Intron | | | |
| 43839 | T | C | | Intron | | | |
| 48345 | A | G | | Intron | | | |
| 49141 | C | - | | Intron | | | |
| 51053 | C | T | | Intron | | | |
| 53010 | C | A | | Intron | | | |
| 53116 | T | G | | Intron | | | |
| 53784 | T | - | | Intron | | | |
| 55309 | G | A | | Intron | | | |
| 56479 | T | - | | Intron | | | |
| 56489 | T | C | | Intron | | | |
| 58172 | G | A | | Intron | | | |
| 58665 | C | T | | Intron | | | |
| 59779 | G | T | | Intron | | | |
| 60360 | C | G | | Intron | | | |
| 61466 | A | G | | Intron | | | |
| 61801 | G | C | | Intron | | | |
| 63124 | T | G | | Intron | | | |
| 64341 | A | G | | Intron | | | |
| 66706 | T | A | | Beyond ORF(3') | | | |

Context:

DNA
Position

899     GGGTGCAGAGAGTTACCCAGGCAGAGGGCATAGCTTGAGTAAAGCCCAGAGGCAATAGGG
        AGCTTGCTGAGTTCAGTGAAATGAGGATGTGGAAAGCAGAGTGACAAGAAGAAAGACTTA
        GGGTCCCAGGGAAAGGCCTTGTGTGCCATGATAAAGAATTGTATTGTAAATAGTGCTGCA

FIGURE 3U

ATAAACATACGTGTGGATGTGTCTTTGTAGTAGAATGATTAGAATACATGGATACAGAGA
GGGGAACATCACACACCGGAGCTGGTCAGGGGTTGGGGGGCAAGGAGAGGGAGAGCATTA
[C,G]
GACAAATACCTAATGCATGTGGGGCTTAAAACCTAGATGATGGGTTGATAGGTGCAGCAA
ACCACCATGGCACATGTATACCTATGTAACAAACCTGCATGTTCTGCACATGTATCCTGG
AACTTAAAGTAAAAAAAAAAAAGTCCATCTAGAGGGAGAAAAGGGGAAAAAACAAAAATA
ATTTTATTTATCCTGAGGACAATGAGGAGTCAGTGGAGAGTTCTAAGCAGGTTCTAGATA
TCTTCCGGCTCAGAAATCTTCAATTAGATGGTCCCAAATGGCATCTACGTATCATACTTT

3052    AGTAAAATATATTAATGGAAGGAGAGTTTGCTATAAATGATTGAATTAATGTGACAGTTT
AATTTATGAATTTTTATAGACATAGTAAATGCCTTCTCAAATTATATAAATGATTTCATA
AGTGGTCCTTATGTGCAAGGTAAAATGACTGCTTTATCTCTCTGATATAAATAAATGTGA
AAAATAACTTTGATACACTTTTTATTTGTTTGGATGATTATTTCTAATCCTGGTGAGTGA
AAATGCCATCTGGTGTGTCCTTTTAACTTTTCTATTATCTCTTAAATTTAAAAACTTTTT
[C,T]
ATTTAAATGACTATTTCCAGGCAATCTGAGATTCATCCCATTTCTTGTGTTTTAAAACAC
ATATGCTCCTGTCAGTGTTAAATTTTCCCATGGTATCACTGTTAATATTAACTTTCCTAA
TAAGAAAAAAGAGTTGGACACCTTATTATTTTAGTAATTAGAAACAAAAAAGCTTCAATC
AGACCTACACTGAATTAGCATGTCTAGATGAAAACCTAGCTCAGTGACAGCAGCATAAAC
CAGCCAAATATAGAAAAAATTACAATAACATTTTTTTCAGAGTGTTTTATCCTTCCGTTG

4813    AAAGAACTGTTTTCTGTTTTGTAGGAGCTTTTGGAAGCTAGAAGCCCCTACATTGTAACT
TAGAAGGCAATGTAAATCACAGCTGTCTAATAATGTTTGAGGCTGAGGTCATCATCTAAA
TGGAATTCTTGAGATGCTTTTTAATCACAGTGTTCCTCACAGTCAGGGGAGTGGCAATTG
CACAGGGAAGCATTTGAGAGTTCGCACACAGGCTTGATTACAGTCAGGCATGATTAGCTT
TCCTGGAAAACAGTCATTGATAAGAAGCAGCTGAGCAATTAATCAGCTAAAGGTAAAATA
[A,G]
TATTTTAGAAGTGCAGGAAGAAAGAAGATGCACTCATTTATAGTTTAGTATTGAATTATA
TAGATGACATAGAAAGCATTAAACTTGGAAACTAATGTCCAGAAAGTGACATGCAGATTT
GTTCAATTTAAATTACAATTTATGTGTCCTTTAATTGTTCATGTCTAAAAAACATAACAG
TGACAAAACAGTATCTTTCAGACACTGTAAACTCATTTAATTCTATTAAAATCCCCATGA
AGAGGGGATTACTATAATTACAACTTTTCTTTTTTTGGGATAGGGTCTCACTCTGTTGC

5882    GTCTATCTTCCCTTTAAATGAAACTAGTCCCTGCATCGTGTCTGTCTTCAGCATTCAGGA
GTGTGCCAGATATGCACTTCCTGCTCCATCAACAAAGGTGAGTGTGTTAAAGCTTGCTCT
GAGATCAGGTGATCCTGGGTTCCAACTGCTGCAACATCCTTTACTTCCCTGCCTGCATGA
CCTCAGGCAACTTGGCTGCAATGGGGTGACTCTAGGAAACCAAGTCAGATCACATCTCAC
CCCTGCTCAAAACTACCTCACTCAGAGTTAAAGCCAGTGCCCTTTCAATGGCCTTCAAGG
[A,T]
CCTCTGTGATCTAGGACTTTTGGAAGGCTCTCTGAGTTCATCTGTGACATTTTCCTGCCT
CACTCCTACTCTGGATTCACGGGCCTCCTGGCTCTTATTAGAACTCCCCCAGATTCACTCC
TGTCCCGGCTTTCGCCCTGTTTCTTTTGCTTAAATGCTTTCCTCCCAGATAGCCTGATGG
CTCATTCCCTCGCTTTCTTCAAGTATGTGCTCAAAGATCCCCACTTTCCTGGCCATTCTA
TTTAAACATGAAGCTCACCTGCCCTCCTCCTCCTGCCCTCTTCTCTGTCCCTCTTTCCTG

5962    CTGCTCCATCAACAAAGGTGAGTGTGTTAAAGCTTGCTCTGAGATCAGGTGATCCTGGGT
TCCAACTGCTGCAACATCCTTTACTTCCCTGCCTGCATGACCTCAGGCAACTTGGCTGCA
ATGGGGTGACTCTAGGAAACCAAGTCAGATCACATCTCACCCCTGCTCAAAACTACCTCA
CTCAGAGTTAAAGCCAGTGCCCTTTCAATGGCCTTCAAGGACCTCTGTGATCTAGGACTT
TTGGAAGGCTCTCTGAGTTCATCTGTGACATTTTCCTGCCTCACTCTACTCTGGATTCAC
[G,C]
GGCCTCCTGGCTCTTATTAGAACTCCCCCAGATTCACTCCTGTCCCGGCTTTCGCCCTGT
TTCTTTTGCTTAAATGCTTTCCTCCCAGATAGCCTGATGGCTCATTCCCTCGCTTTCTTC
AAGTATGTGCTCAAAGATCCCCACTTTCCTGGCCATTCTATTTAAACATGAAGCTCACCT
GCCCTCCTCCTCCTGCCCTCTTCTCTGTCCCTCTTTCCTGCTTTACTTCACCTCTGTCTT
AGGTAGGTTCCCTAAAAAGCACAGCCTGAGACAGGGATTTGGGTGAGCCTAGAATGTGAT

12832   CTCTGTGTATAATGTAATAATGACTAGAAATTAGTACAGAATTATATTTTAAAAGTCACC
AGGCTACTCTGGACATATCTATTTTGTTTAAGTTTCCAAGAACCGTATTAGCAGTTTATC
AGGATCATTTCTCTTAAGGCCTTTGCCGGGATGTTAGACCCTGTGTCATGGGACCATGCC
CCCTTTATTAGTTTCCTAGGGCTGCTGTAACAAAGTACCACAAACTAGGTAGCTTAAAAC
AACAGAAACTTATTCTCTCACAATTCTGGAGACCAGAAGTCCAAACCCAAGGTGTTGGCA
[-,G]
GGCCAAGCTCCTCCTGAAGGCTCTTAAGGAGGCCTCATGCTTGCCTCTTGCTGGCTGCTG
GTAGCTGCTGGGAATCCCAGGCGTGCCTTGGCTTGTGGATGCATTGCTCCAATTGCTGCA
TTTGTTGTCACATGGTCTTCTCCCCTGGTGTCTGTGTCTATGATTTCAAATTCCCCTCTT
CTTATAAGGACACCAGTCATGAAATCAATCTATTATGACCTCATGTTAACTTGATTACAT
CTGTGAAGACTCCATTTCCAAATAAGGCTACATTCACAGGTATCGGGGGTTAGAACATCA

FIGURE 3V

| | |
|---|---|
| 12834 | CTGTGTATAATGTAATAATGACTAGAAATTAGTACAGAATTATATTTTAAAAGTCACCAG |
| | GCTACTCTGGACATATCTATTTTGTTTAAGTTTCCAAGAACCGTATTAGCAGTTTATCAG |
| | GATCATTTCTCTTAAGGCCTTTGCCGGGATGTTAGACCCTGTGTCATGGGACCATGCCCC |
| | CTTTATTAGTTTCCTAGGGCTGCTGTAACAAAGTACCACAAACTAGGTAGCTTAAAACAA |
| | CAGAAACTTATTCTCTCACAATTCTGGAGACCAGAAGTCCAAACCCAAGGTGTTGGCAGG |
| | [-,G] |
| | CCAAGCTCCTCCTGAAGGCTCTTAAGGAGGCCTCATGCTTGCCTCTTGCTGGCTGCTGGT |
| | AGCTGCTGGGAATCCCAGGCGTGCCTTGGCTTGTGGATGCATTGCTCCAATTGCTGCATT |
| | TGTTGTCACATGGTCTTCTCCCCTGGTGTCTGTGTCTATGATTTCAAATTCCCCTCTTCT |
| | TATAAGGACACCAGTCATGAAATCAATCTATTATGACCTCATGTTAACTTGATTACATCT |
| | GTGAAGACTCCATTTCCAAATAAGGCTACATTCACAGGTATCGGGGGTTAGAACATCAAC |
| 13561 | GCTTCTTGATGTAAATGTTCATCAGATTCTACGACTCCTGCTCCCAGTATCTTTTCTTAG |
| | CTCAAAAGTGTATTTTCTCATCTAAAGTTTATATTCTCCTTTTACAACTTCTCCCAAG |
| | TACTTTTACAACAATCAAATTTTCTAAGTGCTTCTTAAAGGTTAGTAAGGCCTATAGATT |
| | CAATACCTACAGAGTAAAGCAACCATATTATATATTTTGACATAGACACACTACATATTA |
| | ACACATAGAAATAGGCTCCACTTCTGCAAGGAAATATGTTGTATCATTCAAAGTTCTTAG |
| | [T,C] |
| | TGCAATCAACAGAATACACTCTAGCTAAAGTGGAATGAAATTTCGTAAAGAATGTTAAGA |
| | ATTGGGCTGGGGGCAATGGCTCATCCCTGTAATCCCAGCACTTTGGGAGGCCAAGGCAGG |
| | GAGAGGATCACCTGAGGTCTGGAGTTTGAGACCAGCCTGGCCAACATGGTGAAATCCCAT |
| | CTCTACTAAAACTACAAAAATTAGCCAGGCATGGTGGTACGTGCCTGTAATCCCAGCTAC |
| | TCAGGAGGCTGAGGCAGGAGAACTGCTTGAACCCAGGAGGCAGACGTTGCAGTGAGCCGA |
| 14023 | CAACATGGTGAAATCCCATCTCTACTAAAACTACAAAAATTAGCCAGGCATGGTGGTACG |
| | TGCCTGTAATCCCAGCTACTCAGGAGGCTGAGGCAGGAGAACTGCTTGAACCCAGGAGGC |
| | AGACGTTGCAGTGAGCCGAAATCCCACCACTGCACTCCAGCCTGGGCAACAGAGCAAGAC |
| | TCCATCTCAAAACCATAAATTAATAAAAAATAAAAGAATGTTAGGAATTGTTCAGACTTC |
| | CTGGAAGGATCAGGTCTGGATGCTGTATTCTCCAGGAAAAAGCAGCAGAGAACATATACT |
| | [G,T] |
| | CTAGACTGTTCTGGATAAAACACAGCTGCCACCACTGCCTGCTTCTAAGTGTTGATTATA |
| | TTGATGACTTGTTCCAGAAATTCTGCCACAGCAGTCACAGAGGAGCCAGTTGCCTCTGTT |
| | GCATTTGAAACCATCTGCACTGCCATTCCCCTGCATGCTGTATCCTCTTCTTGTTCTGTC |
| | CCGTATCTAAATCTCATTCAAGTGCTTTGGATTTAGCAGAGTCCACCTCTCATGCCTGCA |
| | TTGTAGCTGCAAGAGAGCCTAGGAAAAGTAGGTGTTTTTTTTGTTTTTGTTTTTGTTGTT |
| 14484 | TATCCTCTTCTTGTTCTGTCCCGTATCTAAATCTCATTCAAGTGCTTTGGATTTAGCAGA |
| | GTCCACCTCTCATGCCTGCATTGTAGCTGCAAGAGAGCCTAGGAAAAGTAGGTGTTTTTT |
| | TTGTTTTTGTTTTTGTTGTTTTTTATTTTGTTTTGTTTTTGCTGCTCCAGCAAGATTCAA |
| | AATATCAAGAATTCATTAAGATATTGGACAGCTATAAATGATGGTTGTCTGCTACATATG |
| | TGTGCTACTAGTCTAATTTTTATTTTTCAACTTTTGATACAGACATGGGTACAAAACATA |
| | [T,-] |
| | TTTTCTAATGTCTTGATTTTAACTACTAGAAAAGTAACAGTGCAAGTATAACGTTAAATG |
| | GCAACTGAGCTCACTATGGAAGTGACAATAGGGAGTGGTGGGGACTGTGGTAAATTGAGA |
| | GCCAATTGTAGCCATGACAGAGTGAGAGCTTGATTATTTCAGGTCTTCAGATTTTTCAAA |
| | ATGAACAAGAAATCCAAAGTTTTATATGTTTGCTTGTTTCTGCTTTTTTGAGCTATCTCC |
| | TGATATTTATTTATTTTTTATTTATTTAATACAATTTTTAAAAGTAGAGATGGGGGTCT |
| 14975 | AATCCAAAGTTTTATATGTTTGCTTGTTTCTGCTTTTTTGAGCTATCTCCTGATATTTAT |
| | TTATTTTTTATTTATTTAATACAATTTTTAAAAGTAGAGATGGGGGTCTTACTATGTTG |
| | CCCAGGCTGGTCTCAAACTCCTGGCCTCAAGCAATCCTCTCACCTTGGCCTCCCAAAGTT |
| | CCAGGATTACAGGTGTGAGCCACTGTGCTGGGCCTTGGTTTTTAAACTCTGTCAATTAAT |
| | CTAAATTTATTTTTTATTTTTTATTTTTTATTTTTGAGATGGAGTTTTGCTCTTGTCACC |
| | [C,T] |
| | AGGCTGGAGTGCAAAGGCACAATCTCAGCTCACTACAACCTCTGCCTCCTGGGTTCAGGC |
| | GATTCTCCTGCCTCAGCCTTCTGGGTAGCTGGGATTACAGGCATGCACCACCATGTCCAG |
| | CTAATTTTGTATTTATAATAGAGATGGAGTTTTGCCATGTTGGCCAGGCTGGTCTTGAAC |
| | TCCTGACCTCAAGTGATCTGCATGCCTTGGCCTACCAAAGTGCTGGGGTTACAGGCATGA |
| | GCCACCGTGCCCAGCCAATTAATCTAAATTCTAAAAAAAAAAAAAAAAAAAAAAGCAAAG |
| 18016 | AACTGTGCCTGAGAACAGAGAGCAGGCACCTCCCTAGTGTGCAGAGGGCCAGCAGTCTGC |
| | AGACCGCGGCTGTCTATATTTGGAGAAACAACAATGAGAATGTCACTCTAGAAAGAATGA |
| | AGATTCTCTGATCTAAAAGACCAACTGCAGTCAAGCAGGGAAGGAAAACGAAATGGGATA |
| | AATAGCTATTATGGATAATTAAAGTCCTCCAACTCCTAAGAAATGAGTTCGTTTTTCTTC |
| | TCTTATTCTTAAATAACTTTCTCGTCTCCTCCCCTTTTTATAAAGCCTTTTTTCTGGGCA |
| | [-,G] |
| | GATGAATAGATCCTTAACCCTGTCTGTAAGTGCTTCAAGCCAGGAGTGATGTCTGGAATT |
| | GATCCACCAATTCCATTCAGTTGGACAAGGATTCATTGCTTCCAGGCACGATGCTGAACA |
| | TGGAGAATAAAGATGAGTTGGAAATGGTCCTGGGATCAGGGAGACCTTCATTCATATATG |

FIGURE 3W

```
         GACACAAATCAGTGACTTTTTTTTTTTTTTTTTTTCCGAGACAGAGTCTCGCTCTG
         TCACCCAGGCTGGAGTGCAATGGCACCATCTCGGCTCACTGCAACCTCCGCCTCCTAGGT

18230    CCTAAGAAATGAGTTCGTTTTCTTCTCTTATTCTTAAATAACTTTCTCGTCTCCTCCCC
         TTTTTATAAAGCCTTTTTTCTGGGCAGGATGAATAGATCCTTAACCCTGTCTGTAAGTGC
         TTCAAGCCAGGAGTGATGTCTGGAATTGATCCACCAATTCCATTCAGTTGGACAAGGATT
         CATTGCTTCCAGGCACGATGCTGAACATGGAGAATAAAGATGAGTTGGAAATGGTCCTGG
         GATCAGGGAGACCTTCATTCATATATGGACACAAATCAGTGACTTTTTTTTTTTTTTT
         [T,-]
         TTTTTCCGAGACAGAGTCTCGCTCTGTCACCCAGGCTGGAGTGCAATGGCACCATCTCGG
         CTCACTGCAACCTCCGCCTCCTAGGTTCAAGAGATTCTCCTGCCTCAGCCTCCCGAGTAG
         CTGGGATTACAGGTGCCAGCCACTATGCCCAGCTGATTTTTGTATTTTTAGTAGAGACGG
         GGTTTCATTCACCATGTTGGTTAGGCTGGTCTCGAACCCCTAATTTCAGGTGATCCTCTC
         GCCTCAGCCTTCCAAAGTGCTCAGATTACAGGCATGAGCCACTGTGCCTGGCCCAAATCA

19104    GCGTATCAGTGGCAGAGCTGGAAATCAAATCCAGGTTATCTGACTGCCCAGAAGCCTGGT
         GTGTTCCATGATACAGGGTGAGGGGGTTCTGTCTTCCTCTGTGAGCTAGGCTATACAAGA
         AATGGCCTGCTATTTGAATGCTTTTAAAACAAATCAAATCTGGTCAGGCATAGTGGTTCA
         CACCTATAATCCCAACACTCTGGGAGACTGAGATGGGTGGATTGCTTGAGGCCAGAAGTT
         CCACACCAGCCTGGCCAACACGCTGAAACCCTGTCTCTACTAAAAATACAAAAATTAGCC
         [T,C,G]
         GGCGTGGTGGCCTACGCCTGTAATCCCAGCTACTCGGGAGGCTGAGGCACAAGAATTGCT
         TGAACCTGGGAGGCGGAAGTTGCAGTGAGCCAAGATTGCGCCACTGCACTCCAACCTGGG
         TGACAGTGCAAGACTCCGTCTCAAAAAAATAAATAAAACAAAACAAATCAAATCTGACTC
         TGAGCCCCCTGCCTGGGGGAAGTTAGATTTCTGTTCATTTTGATGCTCCCCTTTTGCCAC
         AGCAATATTATGCAAAGGACTCACAAACAACTCAGGAGGTCCTGCTAATTATTGATCCTC

19212    GGCTATACAAGAAATGGCCTGCTATTTGAATGCTTTTAAAACAAATCAAATCTGGTCAGG
         CATAGTGGTTCACACCTATAATCCCAACACTCTGGGAGACTGAGATGGGTGGATTGCTTG
         AGGCCAGAAGTTCCACACCAGCCTGGCCAACACGCTGAAACCCTGTCTCTACTAAAAATA
         CAAAAATTAGCCGGGCGTGGTGGCCTACGCCTGTAATCCCAGCTACTCGGGAGGCTGAGG
         CACAAGAATTGCTTGAACCTGGGAGGCGGAAGTTGCAGTGAGCCAAGATTGCGCCACTGC
         [C,T,A]
         CTCCAACCTGGGTGACAGTGCAAGACTCCGTCTCAAAAAAATAAATAAAACAAAACAAAT
         CAAATCTGACTCTGAGCCCCCTGCCTGGGGGAAGTTAGATTTCTGTTCATTTTGATGCTC
         CCCTTTTGCCACAGCAATATTATGCAAAGGACTCACAAACAACTCAGGAGGTCCTGCTAA
         TTATTGATCCTCATTTGCTCCTGAGCCCATGATCCCTTGAAGTGGTGGCTCAGCTGCCAC
         TTTGGGCAAAGAAAAGTGAGATCCTGTGCTCAGACCCCTCCCCACAGCTCCTGATATCCC

19613    TTCTGTTCATTTTGATGCTCCCCTTTTGCCACAGCAATATTATGCAAAGGACTCACAAAC
         AACTCAGGAGGTCCTGCTAATTATTGATCCTCATTTGCTCCTGAGCCCATGATCCCTTGA
         AGTGGTGGCTCAGCTGCCACTTTGGGCAAAGAAAAGTGAGATCCTGTGCTCAGACCCCTC
         CCCACAGCTCCTGATATCCCCATCTCCAACTGGAGAGCTGCTGTGAGGGGCTGGCTTCAGG
         TCAGCCAGCTGTAGGTCCTGCTTCTTGTGGAGCCCACAGCTCCTTCTTTCAGGGCTTTCC
         [C,T]
         TTTGATCGTTACTTTCCCCTTCTTTCTCCCCATCTCCCATACTGTATGTCTTCCCTCTGG
         AAAGTCTCGGGATGTCTAAGATGACACTGTGCACACAGAGGGTGCTTGTGTTGGTTCAGG
         TCTTCCAAGAAAGCAGATACCAAGACAGGACTCGGCACATACGAGATATGGTCTCGCTCT
         GTTTTCCAGGCTGGAGTGCAGTGGCACAATCACAGCTCACTGCAGCCTCAAACTCTTGAG
         CTCAAGTGATCTTCCTGCCTCCGCCTCCCAAAGTACTTGGATTACAGGCATGAGTTACTA

20506    AATGGGTGGTTGATTCAGAGCACAGCAGCTGGGGCTGTCTGCAATTAAGCAGTGCAAAGC
         TCCACAGCGCTTTCAGTTTTCATTAGCCTTCATCTAAAGCATCTGCATGTATATAGAGAG
         CGCTAAGCTTATGACTGGTGACACTTTATTAATAGCAATAGTGATAGTACTTACCACTTA
         TTAAATATAAAGCACTTTTTACGTACCAGGCACTGCCGTGAATCATTTACATGCATCAATC
         ATTGAACAACCCTATGAGATACCCATTACGATTAGCCCAGTTTAGAGATAGGGATTCTTA
         [T,C]
         GGGCTGAATTGTGTCTTCATATGGATCTGCCCAAATTCATTATGGTGAAATTCTAACCCT
         CAGTACCTCAGAATATGAGTATATTTGGAGATAGGGTCTTTAAAAAGGTAATTAAGGTTA
         AATGAGGTCCTTACGGTAGGCCCTAATCGAATATGACTGATGTCCTTATATGAAGAAAAA
         ATTGGGACACACGGATACATAGAAGGAAGACTATGTGAAGGCACAGGGAGAAGAGAGCCA
         TCTGCAAGCCAAAAAGAAAGGCCTCAGAAGAAACCAAGGCCTGCTGAAACCTGGATCTCA

20530    GCAGCTGGGGCTGTCTGCAATTAAGCAGTGCAAAGCTCCACAGCGCTTTCAGTTTTCATT
         AGCCTTCATCTAAAGCATCTGCATGTATATAGAGAGCGCTAAGCTTATGACTGGTGACAC
         TTTATTAATAGCAATAGTGATAGTACTTACCACTTATTAATATAAAGCACTTTTTACGTA
         CCAGGCACTGCCGTGAATCATTTACATGCATCAATCATTGAACAACCCTATGAGATACCC
         ATTACGATTAGCCCAGTTTAGAGATAGGGATTCTTATGGGCTGAATTGTGTCTTCATATG
         [G,A]
```

FIGURE 3X

```
         ATCTGCCCAAATTCATTATGGTGAAATTCTAACCCTCAGTACCTCAGAATATGAGTATAT
         TTGGAGATAGGGTCTTTAAAAAGGTAATTAAGGTTAAATGAGGTCCTTACGGTAGGCCCT
         AATCGAATATGACTGATGTCCTTATATGAAGAAAAAATTGGGACACACGGATACATAGAA
         GGAAGACTATGTGAAGGCACAGGGAGAAGAGAGCCATCTGCAAGCCAAAAAGAAAGGCCT
         CAGAAGAAACCAAGGCCTGCTGAAACCTGGATCTCAGATTTCTGGCTCTAGAATTGTAGG

21250    TAGCACTGGGCATCTCTCAGTCCAGAGTCCATTCTCTTCCCCTGCTCTTCTGAGTCATGA
         TGGCTGCGCAAGGACTACAAAGTAACAGGTACAGATGACAAAGTGACTCAGGAAGATCAT
         TGAGAAGGAGCATGGCCTGGTGTGCTGGGAACACACAGGAAAGTGGTCCAAGGAACCTAG
         ACAGCAAAGGAGAAGGGTTTCATATCTTGCCTCTACCCACTAAGGGCTGTGTGACCTTGG
         CCAATTTGTTCTTGCTTTCTGAACTACAGTTGTATTTTGTGTCAAATGGGAGTATTAGAT
         [T,C]
         TCCCATGTCTCACTGAGCTGTATTAATGATCAAATAAGAGAATTACATGAAAGTATCTGT
         AGAGGAGGGCAGAGGGAGAGAACTGAATTTGCCTCATACAATATTACTGTGGTTGTTACA
         TATTATCCTTGTTTTAGCTGCTAGGAATATACTATTATAGTAATGTGTCAATATTAGAGC
         ATCAGTTTTCTTTCTTTTCTTTTCTTTTTTTTGAGATGGAGTCTCACTCTGTTACCCAGG
         CTGGAGTGCAGCAGTGCAATCTCAGCTCACTGTAACCTCTGCCTCCAAGGTTCAAGTGAT

22347    TAGCTTACAGATGAAGAAACTGAAGTCCAGGGAGTTTAAGTAATTAGGCTAAAGTCACAC
         AGCTGAGTAAGTGGGCGACTCAACATTCAAAGTAAGGTACATGAGCTCCTCAGTTGGACA
         TAGATTGGAGAAGTGAGGCATCCAAGATGGCTTCAAGATATATATATATATATTTTTT
         TTTTTTTTTTTTTTGAGACGGAGTCTCACTGTCATGAAGACTGGAATGCAATGCCGCT
         ATATCAGCTCACTGCAGCCTCCGCCTCCCAGATTCAAGTGATTCTCCTGCCTCAGTCTCC
         [C,T]
         GAGTAGCTGGGACTACAGGCGCGTGCCACCACGGCCAGCTAATTTTTGTATTTTTAGTAG
         AGACGGAGTTTGCCATGTTGGCCAGGCTGGTCTCGAACTCCTGACCTCAGGTGATCTACC
         TGCCTTGGCCTCCCAAAGTGCTGGGATTACAGGCGTGAGCCACCGCGCCCAGCCTGATGG
         CTTCAAGATTTTTGCTGGAGCAACCAAAGTAGCAAAATTGTCATTACTTATGATGAGAAT
         AACTTCAGGAATTAATTTTTTTTAGGGGAAGTCAGTTTGGACATGTTAAGTTTAAGCTG

22757    GGTGATCTACCTGCCTTGGCCTCCCAAAGTGCTGGGATTACAGGCGTGAGCCACCGCGCC
         CAGCCTGATGGCTTCAAGATTTTTGCTGGAGCAACCAAAGTAGCAAAATTGTCATTACTT
         ATGATGAGAATAACTTCAGGAATTAATTTTTTTTAGGGGAAGTCAGTTTGGACATGTTA
         AGTTTAAGCTGCCTTTTAGGTGTCCAAGGAGATGTCAGATAAGTCTAGTTATAAAGATTG
         GGAGCTGTTAGCATATACATGGTATCTAAAGCCCAGAGCCTGCTTAGATGTCCAGAGGGC
         [A,G]
         TAGACAGAAAGCAAGAGACCCGAGAATGGAGTCCTAGGCATTCTAGTGTATATAGGTTGA
         GGTAAGAAGGAATCAGCTATAAGAGATAAAACAGAAGAATTAGGAGGATGACCAAGTGTT
         TTCCTGGAAAAACATAAAATGGCCAAGAAAGAGAAAGTGGTCAATTGTATCAAATGCTGC
         TGCTAGGTTGATTAAATCAGATGAGGACTGAAAATGACCTTTGGACTGAGCCATGAGGAG
         GGCATTGATAACCTTAAGTAGGGCAGTTTTGGGGGCTCAGGTTGGGAATACCTGGCTGGA

23086    GAGTCCTAGGCATTCTAGTGTATATAGGTTGAGGTAAGAAGGAATCAGCTATAAGAGATA
         AAACAGAAGAATTAGGAGGATGACCAAGTGTTTTCCTGGAAAAACATAAAATGGCCAAGA
         AAGAGAAAGTGGTCAATTGTATCAAATGCTGCTGCTAGGTTGATTAAATCAGATGAGGAC
         TGAAAATGACCTTTGGACTGAGCCATGAGGAGGGCATTGATAACCTTAAGTAGGGCAGTT
         TTGGGGGCTCAGGTTGGGAATACCTGGCTGGAGTGGGTCCAGGAGAGAACAGGAGGAGAG
         [G,A]
         AATTGAAGACAGTCATTTCTTTCTTAAAAAAAGGAAAATGAGAAATAGGAGGATAACTGA
         AAGAGAAAATGTCTTTTATTTTAGATTCTAATATGGGAGGAATAAAAGCTTATTTATAGG
         CAACAGGAATGATCTATTATACTAGGGAGGAGAACATAATGAATGAAGCGTGGGGGTGGG
         GATTTCTGGAGCAATATTCGTGAGGGGATAAAAGGGGACAAGATCTAGTGTCCAGGGAAA
         GGGGCTGGACTTAGCTAGAAGCATGGACAACTGCATAGACCCCATCAGTATAAATGCAGG

24069    GTCATAAGAACCTGCCAAGGTGCCGGGGCGGTGGCTCACGCCTGTAATCCCAGCACTTT
         GGGAGGCCAAGGTGGGCGGATCACGAGGTCAGGAGATCGAAACCATCCTGGCCAACATGT
         TGAAACCCCGTCTCTACTAAAAATACAAAAATTATCTGGGTGTGGTGGCGCATGGCTGTA
         ATCCCAGCTACTCAGGAAGTTGAGGCAGGAGAATTGCTTGAGCTAGGGAGTCAGAGATTG
         CAGTGAGCCGAGAATCGTGCCACTGCACTCCAGCCTGGCAACAGACCGAGATTCCGTCCC
         [C,A]
         AAAAAAAAAAAAAAAAGAACCTGCCAAGGTTATCTTTCATATGAACTTGTGGGCAAATGA
         CTTGTGTTTTATCCAAACTATTGGGTTAACCATTATATTAGCTATTTATCACTGCATTTA
         ATATTTATGAAAACTTGCAAGCTTTAATTATTTTTAAAAAGACTTGGACCTTAAGTGGGC
         CATGACAGTATCCTCAGAAAGATGACAATAAGTAAGAGGATACAACTTCCTTTATAATTG
         ACAGATAGGGTTCCGTTTGTCCAATTACTTTTTTTTAAAAGAAGAGATAAATTCACTGT

24086    AGGTGCCGGGGGCGGTGGCTCACGCCTGTAATCCCAGCACTTTGGGAGGCCAAGGTGGGC
         GGATCACGAGGTCAGGAGATCGAAACCATCCTGGCCAACATGTTGAAACCCCGTCTCTAC
         TAAAAATACAAAAATTATCTGGGTGTGGTGGCGCATGGCTGTAATCCCAGCTACTCAGGA
```

FIGURE 3Y

```
              AGTTGAGGCAGGAGAATTGCTTGAGCTAGGGAGTCAGAGATTGCAGTGAGCCGAGAATCG
              TGCCACTGCACTCCAGCCTGGCAACAGACCGAGATTCCGTCCCCAAAAAAAAAAAAAAAA
              [-,A,G]
              AACCTGCCAAGGTTATCTTTCATATGAACTTGTGGGCAAATGACTTGTGTTTTATCCAAA
              CTATTGGGTTAACCATTATATTAGCTATTTATCACTGCATTTAATATTTATGAAAACTTG
              CAAGCTTTAATTATTTTTAAAAAGACTTGGACCTTAAGTGGGCCATGACAGTATCCTCAG
              AAAGATGACAATAAGTAAGAGGATACAACTTCCTTTATAATTGACAGATAGGGTTCCGTT
              TGTCCAATTACTTTTTTTTAAAAGAAGAGATAAATTCACTGTAATGAATGTGCCATAAT

24397      GGTTATCTTTCATATGAACTTGTGGGCAAATGACTTGTGTTTTATCCAAACTATTGGGTT
              AACCATTATATTAGCTATTTATCACTGCATTTAATATTTATGAAAACTTGCAAGCTTTAA
              TTATTTTTAAAAAGACTTGGACCTTAAGTGGGCCATGACAGTATCCTCAGAAAGATGACA
              ATAAGTAAGAGGATACAACTTCCTTTATAATTGACAGATAGGGTTCCGTTTGTCCAATTA
              CTTTTTTTTAAAAGAAGAGATAAATTCACTGTAATGAATGTGCCATAATTGGAATCTAT
              [A,-]
              GAGGTCTACCATTTGAATAAAAGGTGCTGGATGATCACCTCCTTAGAGGAACCATCTAAG
              GAGAAAAGGATATACAACCAAATGGGTGTGCATTGTGATAGAAAATGTCCCTCTCCACCT
              CCACTTAGTATTTTATTAAGACTTAGAAAAATTAGGCCGGGCACAGTGCCTCACACCTAT
              AATCCCAGCACTTTGGGAGGCTGAGGCGGGCGGATCATCTGAGTCGGGAGTTTGAGACCA
              GCCTGACCAACATGGAGAAACCCCGTCTCTACTGAAAATACAAAAATTAGCCTGGCATGG

24435      GTTTTATCCAAACTATTGGGTTAACCATTATATTAGCTATTTATCACTGCATTTAATATT
              TATGAAAACTTGCAAGCTTTAATTATTTTTAAAAAGACTTGGACCTTAAGTGGGCCATGA
              CAGTATCCTCAGAAAGATGACAATAAGTAAGAGGATACAACTTCCTTTATAATTGACAGA
              TAGGGTTCCGTTTGTCCAATTACTTTTTTTTAAAAGAAGAGATAAATTCACTGTAATGA
              ATGTGCCATAATTGGAATCTATAGAGGTCTACCATTTGAATAAAAGGTGCTGGATGATCA
              [G,A,C]
              CTCCTTAGAGGAACCATCTAAGGAGAAAAGGATATACAACCAAATGGGTGTGCATTGTGA
              TAGAAAATGTCCCTCTCCACCTCCACTTAGTATTTTATTAAGACTTAGAAAAATTAGGCC
              GGGCACAGTGCCTCACACCTATAATCCCAGCACTTTGGGAGGCTGAGGCGGGCGGATCAT
              CTGAGTCGGGAGTTTGAGACCAGCCTGACCAACATGGAGAAACCCCGTCTCTACTGAAAA
              TACAAAAATTAGCCTGGCATGGTGGTGCAGACCTGTAATCCCAGCTACTCAGGAGGCTGA

25029      AGGCTGATGTGAGAGAATCGCTTGAACCTGGGAAGCAGAGGTTGCGGGGAGCCGAGATCG
              TGCCATTGCATTCCAGCCTGGGCAACGGGCAACAAAAGCAAAACTCCGTCTCAAAAAAAA
              AAAAAAAAAAAAGACTTAGAAAGGTTAAGGTCAACTGTATCAGCTGGGTCGAGCAATGTGA
              ACAAAGTCTGTCAATGCTCTTTCAGCAGGAAATGCAGTATAGCATATTGTTTTAGACATA
              GACTCTGGACTTGGGCCTCTATCCTACCTCAAATGACTTAGTTTCCTCATCTATAAAATG
              [A,G]
              CATGATGACACTGTCTACCTCATGGGGTTGTTATAAAATTTAAATGATTGATTGAATGTT
              TATAAAAGTCCCACACAATACCCAGAACATCAGTAGTTTTAGCCACTATAACTTACTTTA
              ATAATAATAATATTTAATAATAATAATAACTTACTTTAATAATAATAGTAATACCTC
              CATAGTATTCTACTATGGGTCTTCCTTTTTGTTTTTCATCTGCTGGTACCTTTTTTCTTT
              TTGCTTAGTATACTTTCTTTTTCCTTTAATCCTGGCTTTTATTTTCTGCCTATCCTTTTT

25297      TCAAATGACTTAGTTTCCTCATCTATAAAATGACATGATGACACTGTCTACCTCATGGGG
              TTGTTATAAAATTTAAATGATTGATTGAATGTTTATAAAAGTCCCACACAATACCCAGAA
              CATCAGTAGTTTTAGCCACTATAACTTACTTTAATAATAATAATAATATTTAATAATAAT
              AATAACTTACTTTAATAATAATAGTAATACCTCCATAGTATTCTACTATGGGTCTTCCTT
              TTTGTTTTTCATCTGCTGGTACCTTTTTCTTTTTGCTTAGTATACTTTCTTTTTCCTTT
              [A,C]
              ATCCTGGCTTTTATTTTCTGCCTATCCTTTTTCCCATGTAGAAAAATCGATGGGACAACT
              GAGGAAGAAGATAACATTGAGCTGAATGAAGAAGGAAGGCCGGTGCAGACGTCCAGGCCA
              AGCCCCCCACTCTGCGACTGCCACTGCTGCGGCCTCCCCAAGCGTTACATCATTGCTATC
              ATGAGTGGGCTGGGATTCTGCATTTCCTTTGGGATCCGGTGCAATCTTGGAGTTGCCATT
              GTGGAAATGGTCAACAATAGCACCGTATATGTTGATGGAAAACCGGAAATTCAGGTTGGT

25408      TACCCAGAACATCAGTAGTTTTAGCCACTATAACTTACTTTAATAATAATAATAATATTT
              AATAATAATAATAACTTACTTTAATAATAATAGTAATACCTCCATAGTATTCTACTATGG
              GTCTTCCTTTTTGTTTTTCATCTGCTGGTACCTTTTTCTTTTTGCTTAGTATACTTTCT
              TTTTCCTTTAATCCTGGCTTTTATTTTCTGCCTATCCTTTTTCCCATGTAGAAAAATCGA
              TGGGACAACTGAGGAAGAAGATAACATTGAGCTGAATGAAGAAGGAAGGCCGGTGCAGAC
              [G,A]
              TCCAGGCCAAGCCCCCCACTCTGCGACTGCCACTGCTGCGGCCTCCCCAAGCGTTACATC
              ATTGCTATCATGAGTGGGCTGGGATTCTGCATTTCCTTTGGGATCCGGTGCAATCTTGGA
              GTTGCCATTGTGGAAATGGTCAACAATAGCACCGTATATGTTGATGGAAAACCGGAAATT
              CAGGTTGGTATCAGTCCATGGTGGAAGACTTTTCTTTTTGAGACAGGGTCTCGCTCGGTC
              TCCCAGGCTAGAGTACAGTGGCACGATCTTGGCTTACTGCAGCCCCAACCTGCCAGGTTG
```

FIGURE 3Z

| | |
|---|---|
| 26060 | GCTCCTCCCATCTCAGCATCTCAGCATCTCAGCATCTCAGCATCTCAGATCAGTAGCTGA
GACTACAATCCTGAGGAAACTGTTGACTGCAGCTGTGTCAATACTTTGCTCCTTGAGAGA
AAGCCCTGCAATTCCTTCAGTGATATGACAAAAATGGAGAGTGGCTACTTGTGCTGGGCA
TTGTGCAGAATGATGGGGATAGAAAGGTGAATGACCTAGACTGAGCCCTGTCCTCATGGA
GACAAGTAAGTGATGACAGTTTGAGGGGGTAGGTGCCACGTTGGAGGTACACAGGATTCT
[T,C]
GGGCTCATAGGAGAGGGCACAGCCCAGACTTCCCTATTGTGAACAAATTCCCAAAGTGAT
GGCTGGACCAGGCAAAGAGGGTGTGGTGTGGTGGGAAGAAGAATGTTTGAAGAAAAAGGT
ACTGTGAAGGACTGTAAGAAAGAGACAGAGAGAGAGAGAGAGAGAGAGAACGTACACATG
CTATGTAGGTATATTTTAGGAACTGAAACAGGAGCTCATCATCTTTTCTGTGTCATGGAC
TCCTGGAGATGACTAATGAACCTTTGCCAAAGTAATGTTTTAAGTTCTTAAAATAAAACA |
| 26615 | AATGAACCTTTGCCAAAGTAATGTTTTAAGTTCTTAAAATAAAACACAAAGGATGACAAA
AGAAGCCAATTATATTAAAATATAAATACCAAAACATTTAAAAATCACATTTGTGACATA
GAAACATATGGGCTTCTTTAGTAGTACATCAGTGACAAAATCTAGTATTGGGTCTAACAT
TTACTCTGATTTTAAGTTGGAATGTATGCCATTGTTGGAAATAGTGGCCATGACTGTAAT
ACGATTTGAACATATTTGCTATTTCCACGTGGGACACAGTCATAGGTACTAGTCATATGA
[C,T]
GGTGGCTTGTTGCCTACATTCATAATGGCAGAAAATGCTAAATTTTGGTTAAGAGTGAAA
ATAAAGATGCATGTTTTCTTCCCATCCAAGTTCTCAGATGCACAGGATTCCATCCACAGA
CTCCAGGTTGAGAACTCCCAGTGATTGGGTAGAGCACGTTGAGGTGGAGGCAGCGAAGTA
AATAGGGGGCTGATCATCCATAGCCTGGTAGGCATGTAGCAAGGGGCTGCAAGCATGGAA
TGATCACATCTGTGCTCCAGATTGTTCACTGCCCCATTGCAGGGGGCCAGATTGAGGTAA |
| 26816 | ATGTATGCCATTGTTGGAAATAGTGGCCATGACTGTAATACGATTTGAACATATTTGCTA
TTTCCACGTGGGACACAGTCATAGGTACTAGTCATATGACGGTGGCTTGTTGCCTACATT
CATAATGGCAGAAAATGCTAAATTTTGGTTAAGAGTGAAAATAAAGATGCATGTTTTCTT
CCCATCCAAGTTCTCAGATGCACAGGATTCCATCCACAGACTCCAGGTTGAGAACTCCCA
GTGATTGGGTAGAGCACGTTGAGGTGGAGGCAGCGAAGTAAATAGGGGGCTGATCATCCA
[T,C]
AGCCTGGTAGGCATGTAGCAAGGGGCTGCAAGCATGGAATGATCACATCTGTGCTCCAGA
TTGTTCACTGCCCCATTGCAGGGGGCCAGATTGAGGTAAGATAGGAATGGAGGCCACAGG
GCCAGTTCAGAGGCCATCATAGTTATAAGCAAGGATACTTCGAAGTGACTTAAATAGTAT
TGTTTTAGGAATCACTGGAAACATAAAATCGGTTTGCTGCTTAAACGATAGACCTAGAG
AAGTACTGAGGTTATGGGGTAAAAGAAACAAACAAAAATGTCTGCCCAGTGGACACCCCA |
| 28480 | TTGGTTTTTCTGTTTTAAGGGAAAAACTAGATATTTGGCACTGAGATATCTTTAAATCTT
TATTTCAAAAGAAGGAGAGAAATAAGCAGTATGAATAGGTAGATCTTTCAAATATGTGGC
ATATGTTCTACAAGGGGTATGAAGAGTGATTTTAACTAAAGCGTGAACACTTTTTTTTTT
TTTTGAAACGGGATCTCTGTTGCCCAGGCTTTAGTGAAGTGGTGTGATCATAGTTCACCG
CAGCCTTGACCTCCTGGGCTTAAGTGATCCTCCCACTTCAGTTTCCAAGTAGCTGGGTCC
[-,A]
CAGGCTCATGCCACCATTCTTAGCTAATTAAAAAAAAATTTTTTTTAGAGATGGGATCATG
CCATGTTGCCCAGGCTGATCTCAAACCCCTGGCCTCAAGGGATCCTCCTGCCTTGGTCTC
CCAAAGTGCTGGGACAAGCATGCACCACTGTGCCTGGCCCATATTTTAAATTTAATAGTT
ATGAGTTAAAACATGTGAACTCTTAGAAAAGTGTTTGGCATATAGTAAGAAAATAAAATG
ACCGAAGTTTGAGAAACTTGTGATTTTGTTTTCTCATTACTCTCAGGAAAAGTCCAAAGT |
| 29109 | ATTCAGAGCATGGGCTTTGGAACTGGCCAGACCTGGTTTTAATGAGCTCTGGGACCTTGA
ATAAGTTGCCCTTGTGTCCTGGTCAGAGATTGCTGGTTGCAAGAAATGTGCAGTGAAAC
TGGCTCGAGTTAAAAGGGGATTATTGGGGCCCGGCATGGTGGCTCATGCCTGTAATCCCA
GCAATTTGGGAGGCCAAGGTGGGTGGATCACCTGAGGTCAGGAGTTCTAGACTAGCCTGG
CCAACATGGTGAAACCCCATCTCTACTAAAAAATACAAAAAATTTGGCCAGACATGGTGG
[C,T]
GCACACCTGTAGTACCAGCTACTTGGGAAGCTGAGGCAAGAGAATCCTGGCAGTTGGAGG
TTGTAGTGAGTCGAGATGTGTGAGACTCCATCTAAACAAACAAACAAACAAACAAAAAT
GGTAGTGGGGATTATTGTAGGGCTGTAAGAGGATCTCGTGAAAGCCAAGGGCAGAAAGCA
GGTCTGTGGTGTATGTGTGCAGTCTGCACCCAGGACGCAGAAGCCAGCCTGAGGTGGGGC
TGAAACCCAGGCTGTCCTCCACCCTGAGGAGGGAAGGGAGTCTTTATGTAATTCTTTCTG |
| 29754 | CCTCGTGGGAACTAGAGAAGCCTTTGCTAAGGTCTCCAGCTTGCTTGCCCCACAGAGTCT
TTCATTGGCTTTTCTTGGAGTCAGCTCCGTTTTCCCTGGTCCTTCATGGACTGCTTTCTT
TCCTCTTCCCTGGCTTCTCACTGCCCTCACAGTGGAAGTGCCTTGAGCCTTTGTCTTGC
TAGGAAGCTGATTTACTTGGCCCTGACTCTGTGACTCCGTGGGACTTATTTGGGTTCAAG
AGTGCACTATTGTCTAACTAGAATCTCTGTGGGTTTGGGTTGCTGTCTCTCTCTCTCTCT
[C,G]
TGTGTGTGTGTGTGTGTGAGAGAGAGAGAGAGAGAGAGAAAGAGAAAGAGACAGAGACAC
AGAGAGAGGGAGAGGCTGACTGGCTGAGCCTAGCCTATGGCTTTGCTGTCTTAAACATTT
TTTTTTTTTTTTTTTTTGAGACAGAATCTTCCTCTGTTGCCCAGGCTGGAGTGCGGTGA |

FIGURE 3AA

```
         CATGATCTCAGCTCACTGCGACCTCCACCTCCCCGGTTCAAGCGATTCTACTCCTTAGGC
         TATCAAGTAGCTGGGATTACAGGTGCATGCCACAACGCCCAGCTAATTTTCGTATTTTAA

29773    GCCTTTGCTAAGGTCTCCAGCTTGCTTGCCCCACAGAGTCTTTCATTGGCTTTTCTTGGA
         GTCAGCTCCGTTTTCCCTGGTCCTTCATGGACTGCTTTCTTTCCTCTTCCCTGGCTTCTC
         ACTGCCCTCCACAGTGGAAGTGCCTTGAGCCTTTGTCTTGCTAGGAAGCTGATTTACTTG
         GCCCTGACTCTGTGACTCCGTGGGACTTATTTGGGTTCAAGAGTGCACTATTGTCTAACT
         AGAATCTCTGTGGGTTTGGGTTGCTGTCTCTCTCTCTCTCTGTGTGTGTGTGTGTGTGTG
         [A,T]
         GAGAGAGAGAGAGAGAGAGAAAGAGAAAGAGACAGAGACACAGAGAGAGGGAGAGGCTGA
         CTGGCTGAGCCTAGCCTATGGCTTTGCTGTCTTAAACATTTTTTTTTTTTTTTTTTTTTG
         AGACAGAATCTTCCTCTGTTGCCCAGGCTGGAGTGCGGTGACATGATCTCAGCTCACTGC
         GACCTCCACCTCCCCGGTTCAAGCGATTCTACTCCTTAGGCTATCAAGTAGCTGGGATTA
         CAGGTGCATGCCACAACGCCCAGCTAATTTTCGTATTTTAAAAATAGAGACGAGGTTTCA

30223    GGAGTGCGGTGACATGATCTCAGCTCACTGCGACCTCCACCTCCCCGGTTCAAGCGATTC
         TACTCCTTAGGCTATCAAGTAGCTGGGATTACAGGTGCATGCCACAACGCCCAGCTAATT
         TTCGTATTTTAAAAATAGAGACGAGGTTTCACCATGTTGGCCAGGCTGGTCTTGAACTCC
         TGACTTCAGGTGATCTGTCCACCCCGGCCTCCCAAAGTGCTGGGATTACAGGCGTGAGCC
         ACCACACCTGACTGGCTTGGCTGTCTCTACTCAGGTGTCCAGTCAGCTGTGGTAGTCAGT
         [C,G]
         GGGGAGAATCCCATGTTGCGGGGAAGGTGCAATCCTCTCAGAAGTGTGAGCAGACAGGA
         ACTGACATTTCTAGAAGTTCCTTGCTAACCCTCATTGCCCTTATTGTGAAATGGGAATAA
         AAGGACTGCTTTGAAGATCAAATAAGCTAACCTATATTAAATACCTATATTAGTTCCCTA
         AGGCTGCCGTAACATATTACCACAAACTTGATGGCTTAAAACAATAGAAATTTATTCTCT
         CAGAGCTGTGGAGACCGGAAGTCTAAATCAAGGTGTTGGCAGCACCTCATGCCCTCTGAA

30356    AATAGAGACGAGGTTTCACCATGTTGGCCAGGCTGGTCTTGAACTCCTGACTTCAGGTGA
         TCTGTCCACCCCGGCCTCCCAAAGTGCTGGGATTACAGGCGTGAGCCACCACACCTGACT
         GGCTTGGCTGTCTCTACTCAGGTGTCCAGTCAGCTGTGGTAGTCAGTCGGGGAGAATCCC
         ATGTTGCGGGGAAGGTGCAATCCTCTCAGAAGTGTGAGCAGACAGGAACTGACATTTCT
         AGAAGTTCCTTGCTAACCCTCATTGCCCTTATTGTGAAATGGGAATAAAAGGACTGCTTT
         [G,A]
         AAGATCAAATAAGCTAACCTATATTAAATACCTATATTAGTTCCCTAAGGCTGCCGTAAC
         ATATTACCACAAACTTGATGGCTTAAAACAATAGAAATTTATTCTCTCAGAGCTGTGGAG
         ACCGGAAGTCTAAATCAAGGTGTTGGCAGCACCTCATGCCCTCTGAAGACTCTAGCAGAG
         AATCTTTCCTTGACTCTTCTAGCTTCTAGTGGCTGCAGCAGATCCTCGGTGTGCGACAAT
         GTCACTCTCATGTCTGCCTCCATCTTCACGTGGACATCTTTCTGCGTGTCTCCTCTTTTG

32040    CAACTCTTTTGGATAAATACCCAGAAGTGGGATTGCTAAGTCATACATTCGTTCTGTTTT
         TAAGTTTTGGAGGAACCTCTGTACTGTTTCCATGGTGGCTGCACCCATTCCCACCAACAG
         TATATAAGGGCTTTATTTTCTCTTCATCCGCACCAACACTTCTGTCTTTTGTTTTTGAT
         AATGGTCATCCTAACAGGTATAAAGTGACGTCTTATGGTGGTTTTGATTTGCATTTCCCT
         GATGGTTAGTGACATTGACCGCCTCTTCATGTAGATATTGGCCATTTATTGGTCTTCTTT
         [G,A]
         GAGAAATGTCTATTCAAGTCTTTAGTCCACTATTATGGTTTTAATGGGTCTCAAATGACA
         ATGAAAGTCAGTTCTCAGCAGCCTAGGGGCTCTTCTTCATGTATTATTTCTTTCAGAGAT
         TGACAGAAGCACTATTTCCCCAGAGAGAAAGGCATGAGAAAGGGATGTTGTGATTGACAA
         TTAGCAGCTGGTTGAAGTGGGAGTTAGAGAAAGGGTCTAGTTCTCCCTCTGTCTTGGATC
         CTCAGGTAATTCTGTGGATCTGGGCAAAGAAGTCTTGTCTCTCCTTAGTGAGAAAATTAA

32748    AATCTCTCTAAGCCTTAGTTTCCTCATTTGCAATTACCTCTAGGTGTTTTAAAGATTAAA
         GGAGGAAATCTGTAGAAAGCACCTTAGTGAAATCATATTCCACCTCTGCTCAAATTTTCC
         AATGGTTTTCATTTCTCTTTGTTTAAAAGCCAGAGTTCCGGTGATGTCTTAAAGAACCCT
         TCATCATTGTAACCTCTCTTGCATTAACACCTATTCTCTTCCTCCTCATTCATTACCCTC
         CAGCTGTACTGACATACTGCTTTTCCTCTAACACGCAAGCACAACCCTACCTTGGGTCC
         [T,C]
         TTGTACTTGCTGTTTCTCTGCCTGGAAAGCTCACATCTCAAATGACCATATGACTTGCTC
         CCTTCCTTTCTTTAGGTCTTTACTTAAAACTCATCTTCTCAGTGAAGACTTCCCTGGCCG
         TTCTATCTAAAATTTACCCCACCAACTGCCATCCAACACTTCATATTCCCTTCCCTTCT
         TTATTTTTTCATCTTATTGCTGGTTACCATCTAACTCTGCCTGTAATTGTTTATCACCTG
         CTATCTCCACTGGCATCTTCAAAATGGCAGGAGTCACTACAGCTGTTCACTGCTGTACCC

34248    GCAGAGAGATAACCTACTAGAAATATTCATGCCATTTATCCCCACACATCCTATGGATAG
         GTAGAATGGGCTTTATTGTCCTCATTAAGAAATGAGAGACTTAAGACTCTAATTCTCTTT
         GTGCTATCACAAAACTGGCATCTGAATAATGTAGTAAATAACTTAGTAGCCCCCCAAAAC
         CCCATTTTTTGTTTTATTCACAAGCTATTTTATTTTCTCCTTAGCATTCATTGCTATTTT
         GTGTTTTTTCTCTCTGTGTATATACATATATACACACACATTATATATATTATATATATA
         [T,G]
```

FIGURE 3BB

```
              AGAGAGAGACACACACACATTAGATATATGTATTTTTAGAGACAGGAGCTTGCTCTGTCA
              CTCCCACTGGAGTGCAGTGTGTGTTTGTAGCTTACCTTAACCTTGACCAACTCCTGGGTT
              CCAGGGATCCTCCCATCTCAACCTCCTGAGTAGCTAGGACTACAGGCACACACCACCACA
              CCTGGCTAGATTTGTATTATTATTATTATTATTATTATTATTACTATTGAGATGGAGTCT
              CTCTCAGTCACCCAGGCTGGAGTGTAGTGGTGTGATCTTGGCTCACTACAACCTCTGCCT

34258    AACCTACTAGAAATATTCATGCCATTTATCCCCACACATCCTATGGATAGGTAGAATGGG
              CTTTATTGTCCTCATTAAGAAATGAGAGACTTAAGACTCTAATTCTCTTTGTGCTATCAC
              AAAACTGGCATCTGAATAATGTAGTAAATAACTTAGTAGCCCCCCAAAACCCCATTTTTT
              GTTTTATTCACAAGCTATTTTATTTTCTCCTTAGCATTCATTGCTATTTTGTGTTTTTTC
              TCTCTGTGTATATACATATATACACACACATTATATATATTATATATATATAGAGAGAGA
              [C,G]
              ACACACACATTAGATATATGTATTTTTAGAGACAGGAGCTTGCTCTGTCACTCCCACTGG
              AGTGCAGTGTGTGTTTGTAGCTTACCTTAACCTTGACCAACTCCTGGGTTCCAGGGATCC
              TCCCATCTCAACCTCCTGAGTAGCTAGGACTACAGGCACACACCACCACACCTGGCTAGA
              TTTGTATTATTATTATTATTATTATTATTATTACTATTGAGATGGAGTCTCTCTCAGTCA
              CCCAGGCTGGAGTGTAGTGGTGTGATCTTGGCTCACTACAACCTCTGCCTCTTGGGTTCA

34998    ATCCACCCACCTCTATCTCCCAAAGTGCTGGGATTACAGGCGTGAGCCATTGCACCTGGC
              CTAGCTGGCTAGATTTTTGATTTTTTGTAGAGATGGGGTCTCGCCACGTTGCCCAGGCTG
              GTCTTGAGCTCCTGGCCTCAAGTAATCCTCTTGCCTAGGCCTTCCAAAGCATTGGGATTA
              CAGGTGTGAGTCACCATGACCATTAATATAAATACATATATATTTAAATTTGTACATAAT
              CTCTTATTACAAGGTGAAATCTATGAGAGCAGGGACTTTTGTTTGTTTGTTTCATTTTTT
              [T,-]
              TTTTTGAGATGGAGTCTCACTCTGTTGCCCAAGCTGGAATGCAGTGGTGCAATCTCAGCT
              CACTGCAAATTCCATCTCCCAGGTTCATGCCATTCTCCTGCCTCAGCTTCCTGAGTAGCT
              GGGAGTACAGGTGCCCGCCACCACGCCCGGCTAATTTTTTTTGTATTTTTAGTAGAGATG
              GGGTTTCACCGTGTTAGCCAGGATGGTCTGGATCTCCTGACCTCGTGATCCACCCGCCTC
              AGCCTCCCAAAGTGCTGGGATTACAGGTGTGAGCCACCGCACCCGGCCGGTTTTGTTTTT

37708    ACACAACCTGTCTTGTGCTTGGCTGGTCCCAGGACATACAATGCTTCTTGGATAGTCAGT
              GTTTCTGACTCTGGGAAGCAGGAAACAACCTCAAACATACAGTAACAGTCAGAAAAGATC
              AGTCGGTGGGGAACCAGGCAGGATGGTAGGTCTCTAGCAAGCTTACCTGAACCTGGCCAA
              TCTCCAACTTTTCAGGACATCATCCAGGCAGGACATCCCTGTGCCACCAAAAATTTGTTC
              ATAGTTGGTCCAGGGGCCAGAGCTTGGGAATCAAAGAAGCCCAAGAGTCTAGCTTGGGGT
              [A,G]
              CACTAGACCCTAACACATCTATTTCTCCAAATTACAGGTGCCAGCCGCCATGCCTGGCTA
              ATTTTTTGTATTTTTAGTAGAGATGGGGTTCACCATGTTGGCCAGGCTGGTCTCAAACTC
              CTGACCTCAGGTGATCCACCCACCTCAGCCTCCCAAAGTGCTGGGATTACAGGTACGATC
              TTTCCACAGGGATTTCCACAGGGATCTTTCATGAACTGTTAGGTTTGTTTCTGGTGCTTA
              GCTGAAGTAGCACATCCATCAGCAGACCTGCCGAATAACACAATGCTTTGGTCCCCCAGG

37811    AACAGTCAGAAAAGATCAGTCGGTGGGGAACCAGGCAGGATGGTAGGTCTCTAGCAAGCT
              TACCTGAACCTGGCCAATCTCCAACTTTTCAGGACATCATCCAGGCAGGACATCCCTGTG
              CCACCAAAAATTTGTTCATAGTTGGTCCAGGGGCCAGAGCTTGGGAATCAAAGAAGCCCA
              AGAGTCTAGCTTGGGGTGCACTAGACCCTAACACATCTATTTCTCCAAATTACAGGTGCC
              AGCCGCCATGCCTGGCTAATTTTTTGTATTTTTAGTAGAGATGGGGTTCACCATGTTGGC
              [C,T]
              AGGCTGGTCTCAAACTCCTGACCTCAGGTGATCCACCCACCTCAGCCTCCCAAAGTGCTG
              GGATTACAGGTACGATCTTTCCACAGGGATTTCCACAGGGATCTTTCATGAACTGTTAGG
              TTTGTTTCTGGTGCTTAGCTGAAGTAGCACATCCATCAGCAGACCTGCCGAATAACACAA
              TGCTTTGGTCCCCCAGGGTCTTTGGAGCTGCCATCTTCTTAACATCGACTCTGAACATGT
              TTATTCCCTCTGCAGCCAGAGTGCATTACGGATGCGTCATGTGTGTCAGAATTCTGCAAG

37956    TCCAGGGGCCAGAGCTTGGGAATCAAAGAAGCCCAAGAGTCTAGCTTGGGGTGCACTAGA
              CCCTAACACATCTATTTCTCCAAATTACAGGTGCCAGCCGCCATGCCTGGCTAATTTTTT
              GTATTTTTAGTAGAGATGGGGTTCACCATGTTGGCCAGGCTGGTCTCAAACTCCTGACCT
              CAGGTGATCCACCCACCTCAGCCTCCCAAAGTGCTGGGATTACAGGTACGATCTTTCCAC
              AGGGATTTCCACAGGGATCTTTCATGAACTGTTAGGTTTGTTTCTGGTGCTTAGCTGAAG
              [T,C]
              AGCACATCCATCAGCAGACCTGCCGAATAACACAATGCTTTGGTCCCCCAGGGTCTTTGG
              AGCTGCCATCTTCTTAACATCGACTCTGAACATGTTTATTCCCTCTGCAGCCAGAGTGCA
              TTACGGATGCGTCATGTGTGTCAGAATTCTGCAAGGTTTAGTGGAGGTAGGAGATACTTT
              CCTTACAGTTTTTGATATTGCTAGAGACAGCGCAGTCCTTTAGAAAATTCACCTTCTGAA
              GAAAATCCCCTTTACTCAGTTTTTTTCTATATTTTCTTCCTTTTCCTGCTGTTTCCATTC

39038    TTTTTTTCTCACCATTTTAAAATGTAAAAAAGATTCTTAGCTTGTGGGCTATACAAAAAC
              AGATGGTGAACCAATTGGCCCATAGTTTGCCAACCCTCGATATACAGCAATGTTTCCCAA
              ACACAGTCATTCACCTCTGACCTTCGCCAGTTTGTTATGCCCATGTACAACTTGTACTAT
```

FIGURE 3CC

```
         TATTTGCCTATTGTTTTCCCCTAGATCGACTCATTTAAAACAAAAAACAAAAGATACCTA
         TTACTCTAAGCAATACCATCTTTGAAATCATGGGTTTGATGTGTTAGTTACATCTTTTCC
         [-,C,T]
         TTTTTTTTTTTTTTTTTTTGAGATAGAGTCTCGCTCTGTAGCCCAGGCTGAAGTGCGGTG
         GCATGATCTCGGCCCGTTGCAACATCTGCCTCCCAGGTTCAAGCGATTCTCCTGCCTCAG
         CCTCCTGAGTAGCTGGGACTACAGGTGCCAGTTACCACACCCGGCTAATTTTTTGTATTT
         TTAGTAGAGATGGGGTTTTACCATGTTGGCCAGGCTGGTCTTGAACTCCTGACCTCAGGT
         GATCCGCCCACCTCAGCCTCCCAAAATGCTGGGATTACAGGTGTTAGCCACCACACCCAG

39167   TTCACCTCTGACCTTCGCCAGTTTGTTATGCCCATGTACAACTTGTACTATTATTTGCCT
         ATTGTTTTCCCCTAGATCGACTCATTTAAAACAAAAAACAAAAGATACCTATTACTCTAA
         GCAATACCATCTTTGAAATCATGGGTTTGATGTGTTAGTTACATCTTTTCCTTTTTTTTT
         TTTTTTTTTTTGAGATAGAGTCTCGCTCTGTAGCCCAGGCTGAAGTGCGGTGGCATGATC
         TCGGCCCGTTGCAACATCTGCCTCCCAGGTTCAAGCGATTCTCCTGCCTCAGCCTCCTGA
         [G,C]
         TAGCTGGGACTACAGGTGCCAGTTACCACACCCGGCTAATTTTTTGTATTTTTAGTAGAG
         ATGGGGTTTTACCATGTTGGCCAGGCTGGTCTTGAACTCCTGACCTCAGGTGATCCGCCC
         ACCTCAGCCTCCCAAAATGCTGGGATTACAGGTGTTAGCCACCACACCCAGCCACTAGTT
         ACATCTTTTTCAAAGCATACATATATATAGTAGAATTATATATAAATTTAATTATATATA
         GATTAATTATAACATATATACTAGTGTATATATGTATATATAATATATACATATATAGTA

39965   CCATGAAGACTAAATTTTAGTCACTTAACAGCCCTGAGTCTCAGGTTCTGTATCTTGAAA
         TGAGTGGATGGACCAACTGATTGTGGAAGGCTCTTCCTACACTGATAGTCTATGATAATA
         TGAAATATAAATATAAAGACCTTTTCCCCCATCTCCTACCATGCTTACATGTGAAGTGTA
         TTTGAATTTCAGCATCTGTACTGTGAGTCAAAATAGCTCAATCATGCTGTTTAGTGTCTG
         TTTTAGTCCATTTGGGCTTCTACAGAATACCATAAACTAGGTAGGTTATAAACAAAAGAA
         [-,T]
         TTTTTTTTTTTTTTTTGAGACAGAGTCTCACTGTGTCACCGAGGCTGGAGGCAGTGGTGT
         GATCTCAGCTCACTGCAACCTCTGCCTCCCAGGTTCAAGCGATTCTTCTGCTTCAGCCTC
         CTGCATAGCTGGGATAACAGGCACATGCCACTGCACCCGGCTAATTTTTGTATTTTTGGT
         AGAGATAGGATTTTGCCATGTTGGCCAGGCTGGTCTCGAACTCCTGACTTAGGTGATCCG
         CCCACCTCGGCCTCCCAAACTGTTGGGATTACAAGCATAAGCCACTGTGCCTGGCCTTTT

40711   AACTAGTTTTTGTATTTTTAGTAGAGATGGGGTTTCATCACGTTGGCTAGGCTGGTCTTG
         AACTCCTGGCTTCAAGTGATCCACCCACCTCGGCCTCTCAAAGTGCTGGGACTACAGGCG
         TGAGCCACCGCTCCTGGCCTAGAAATGTATTTCTTACAGTTCTGGAGGCTGAGGAGTCAA
         AGATCAAGGTGCTGGCAGATCGGTGACTTGGGAGAGCTAGCTTCCTGGTTCATAAACAAC
         TACCTTCTCTTTGTCTGCCCATGGCAGAACGGATGAGGGAGCTCTCTGGAGTTTCTTTTA
         [C,T]
         AAGGCACTAATCTCATTCATGAGGGCTACACCCTTATTACTTAGTCACTTCCCAAAGGTC
         CATCTCCAAATACCATCACATTGGGAATTAGGTTTTAACATAGGAATTTGGTGGGACAC
         AAACATTCAACCTACAACAGTGTCTGTAAATTGGGCTTTTATATTGTAGCCTGTGTGAAG
         AAGCAGCATCCATATTTTAAACACAAGCAGAAACTACAGTCAAATCAACTAATCTATTTT
         CAACTCTTCTGCCAGGGTGTGACCTACCCAGCCTGCCATGGGATGTGGAGTAAGTGGGCA

43839   TTTGCTTGCCGCCATCCACGTAAGATGTGACTTGCTCTTCTATGCCTTCCGCCATGATTG
         TGAGGCCTCCCCCGCCACGTGGAACTGTGAGTCCAATTAAACCTCTTTCTTTTGTAAATT
         GCTCACACTTGGGTTTGTCTTTATCAGCAGCATGAAATCAGACTAATACATCCAGTTACA
         ACCCATTGTTTTATAGTTGAGGAAACTGAGGCTGAGGGAGGAAAAAAGATTTAAATTCTT
         ACAGCTAGTGAGGGCCGAACCGGGGGCTCTTTCTCACCCCCAGTTCTGTTCTTCCTTCTT
         [T,C]
         GCATACCATTCAACAATCATCTGAGGCCCAGGGGACTGAGCTGCAGTCTGCTCCCCAGGG
         CAGTCTGGGAGCAGCTGGGGCAGCTGCAGTAAGGGCTGAGTGCCCTGTTGTTTGCTCAA
         GGGGCTGTGTCTAATAGGAACTGACATTGGGAAGAATGTCTAAAAGGATGAGGAAGATTTTT
         TCTGATAGAAAAGAAGGGTAGTTTAGGTCACATTGTGTATTAGTCTGTTTTCACATAACT
         ATAAAGAACCACCTGAGACTGGGTAATTTATAAAAGAAAGAGGTTTAATCAACTCACAGT

48345   TGCAGTGAGGCGAGATTGCACCACTGCACTCCAGCCTGGGCAACAGAGCAAGACTCTGTC
         TAAAAAAAAAAAAGAAGAAGAAAAAATAAACAGAAAAAAAAGAAAGAACCTCTTTCAATG
         CTCCCAGACATTATCATCAAGCCAATTGTGTTTAGGGAGGAAGGGTGTGGATAGTGAAT
         CATCAACCATCATCATAAGATAAACCTCTTTCCTACAAGGGAAAGAACAGCAGCCGAGCA
         AACACAAATGTCTGCCTAGCTACAGATACTGTCAGAAGTGACCATGGAAGAGCTGGCATA
         [A,G]
         TCATGAAATGGTGGCTGTCATCAGTCATCAGTGCTCACTGGGTGCCAAGTGCTTTATCTC
         CCATGTGCCATGCCCTCTGTGATGAATAAAGTCATCGCTGCCCTCAAGGAGCTTCCAAT
         CTGGTAGAGGACACAGATAGGTCTAAAATCATTCGCTCATTCATCATTTATTTATTATGA
         AATTCAGGCCTACCCAGCTCCCACATAATTAGATGCTTAAATTTGGTGGTGGTAGGTAGG
         GGGGCTGTGGAGTGGAGGTGGGCAAGGGAATTAGGGAGGCCCCTCTCTCAGAAATAATGA
```

FIGURE 3DD

| | |
|---|---|
| 49141 | TTTTGTAGAATTAGGGTAAACTGAACTGCAGAGCATATATTAAGAAGTGACATTTAGTCA<br>TTGGAGTGGATCTTAAAGACCTCTAAGTCTGTCCCTCAGCAGACACTTGAGTGTTGTCCA<br>TCACAGTGCTGCCAAGAGGTCATCCAGCTGGGACCTTTCCATACATCCTTCCACATTTAT<br>TGTTTGCTTATGTAGTTTATTCCCTTCTCTGCTTACCTTTCTACCTATCCATATGTTTTG<br>GTAAGAAACAGAAGAAAAGTAGTCTTTCCTCCTAGCCTATGCTTGTGCATGGGACACACA<br>[C,-]<br>ACACACACACACACACACACACACACACACCATTTTCTTTCTTGATTTTATTTAGCTCCT<br>GCTTTATGTTTTAATTTTGTAAAGACAAAGTGAATGTTAGGTGATTTCCCAAAAGAGGTA<br>GGCGAAAGTAATTGTGAACCCCTACAATGTTCATGAGTGCTTTTTAAAAAAACTCATCTTT<br>TTTGTTTAGCTTTTAAAATTAACATTTATTGAATGCTTTCTGTGCCAGACACTAAGCTAA<br>ATCTTCTACATACATTATTTTATTTAATCTTCATAACCACCATGTGGAGCAGGTACTATT |
| 51053 | CACTCCCTTTCTCTTTCCCTGTGAGTTCTCACCTTCACCTCTCAATCCAGTCCTCTCTAT<br>ACATCCAGCTCAATTCTTCTCCTCTTATGTTTCCTTAAAGCCATGCCATTCTCCAGTGAT<br>CCCTCTGAATATGTCCACATGGCTAGATTGGCAACTCATCATGTGGTGCCTTATTGCAGC<br>TCTCTCAGGAAAAGATTTTAGGCAGAGGGAATAGTATGTGCAATGACCCTGGGGCAGGCA<br>GGAATGTGGCCTGTGTGAGAATAGAAGGAAGGGGAGTCAGAATGGCTGAGTGACGGGAGA<br>[C,T]<br>GGGATCGGGATGTTTTTCTAGGGTCAGATCATGGCAGGCCTTGTCGGCGTATGCAGAGCT<br>TGGGTTTTATTTGAAGTACATTGAGATGCAGATGATTTAAAGCACGGAATGGATATGATC<br>TCATTTTTTTTTTTTTTTGAGACAGAGTCTCGCTCTGTTACCCAGGCTGGAGTGCAGTGG<br>TGCAATCTCAGCTCACTGCAACCTCCGCCTCTTGGGTTCAAGTGATTCTCCTGCCTCAGC<br>TTCCTGAGTAGCTGGGATTACAGGCATGGGCCACCATGCCTGGCTAATCTTTTGTATTTT |
| 53010 | ATTTGGAAATGATGAAGCACTGGTATGATCTTCCAGAGAATTTTGGTTGGCTTTTTGGTT<br>TCCTACTAAGAAATATAGAAGGCATTTCTCATCTGAGAAGGATCACACATATCTTGGAGC<br>CTGTCATCTTTTATTTCCATAGATTTTAATATGCCATTAAAATCATTTAAAGCAAAACAG<br>ATCACTTAAGACATGATGTTCAATTCATTCTGAATCAGGGTCTACGTCTATGATGCTTAA<br>AGACAGATGCCAAATTCTTGTCCTGCCCCCTCTATAGAACATGCAAAGTGTAACTGAGGT<br>[C,A]<br>AAAAATTCTATTCTGGCTGAATCAGTTGCAAGTGTGAACTTCAGATTATTTTAATATGAA<br>ATAAAATATTTCTTAGGCCTTTAAGTCCTAGTTTTGTTTTCTTGTCAACTCTAAATAGG<br>TTCAATTTTAAGGATCTCCTGATTACCCCTAAAGTTGAAATTTTATCCTTAAGCTCCTGA<br>AACATGCAGCCCTGTCTCTAGTATTTTAACTGTCAGTAGAAACCATTAGGCTCTTAAAT<br>GCTTTTTTTTCCACTGGCAATCTGCTATTTGGCCAAAATTTTTTTCTTACAGATGAACT |
| 53116 | ACATATCTTGGAGCCTGTCATCTTTTATTTCCATAGATTTTAATATGCCATTAAAATCAT<br>TTAAAGCAAAACAGATCACTTAAGACATGATGTTCAATTCATTCTGAATCAGGGTCTACG<br>TCTATGATGCTTAAAGACAGATGCCAAATTCTTGTCCTGCCCCCTCTATAGAACATGCAA<br>AGTGTAACTGAGGTCAAAAATTCTATTCTGGCTGAATCAGTTGCAAGTGTGAACTTCAGA<br>TTATTTTAATATGAAATAAAATATTTCTTAGGCCTTTAAGTCCTAGTTTTGTTTTCTTG<br>[T,G]<br>CAACTCTAAATAGGTTCAATTTTAAGGATCTCCTGATTACCCCTAAAGTTGAAATTTTAT<br>CCTTAAGCTCCTGAAACATGCAGCCCTGTCTCTAGTATTTTAACTGTCAGTAGAAACCAT<br>TTAGGCTCTTAAATGCTTTTTTTTCCACTGGCAATCTGCTATTTGGCCAAAATTTTTTTT<br>CTTACAGATGAACTGATGTATCATTTGTAAGTTTTATTCTTTATACAATGTCATCATTCT<br>AATTCTTTGGGGGAATTGACTTTCTGCATGCTTCTGTTCAGAGTGTAAAAATAAAAGAAG |
| 53784 | CTAGCTATTTTTCCCTATGTGTAGTCTTAAATGTTGAAACAAAATTAAGAACAAGTAGCA<br>ATGATATAAAGCCTATAGTTTTAAAAGTAAGACTTCCCTAATTACATTTCATCCTCTTTA<br>GAAGCCATTTAAAACAATTATTAGTTCTTGCCCTTCTTTATAGTAGTGTTGAAGAAATAG<br>GTTCAAAAAGGTAAATATTAATAACTTAACCATCATTTACGGTAAGTACTTCAGCTTGTG<br>AATCTTATTTTCTTCTTTCTGGGTCCCATTTCCTTTCCTTTGCATTAATTCATTAAACGT<br>[T,-]<br>ATGTATGTATGTATGTATGTATGTATGTATGTATGTATGTATGTATGTATTTAGAGACAG<br>AGTCTCACTCTGTTGCCCAGGCTGGAGTGCAGTGGTGCAATCTTGGCTCACTGCAACCTC<br>CACCTCCCGGTTTCAAGTGATTCTCCCGCCTCAGCCTCCTGAGTAGCTGGGATTACAGGC<br>ACATGCAACCATGCCTGGCTAACTTTCATATGTTTAGTAGAGAAGGGGTTTTGCCATGTT<br>GCCCAGGCTGGTCTTGAACTCCTGACGTCAGGTGATCCGCCTGCCTCGTCCTCCCAAAGA |
| 55309 | GTCCCAGCTACTCAGGAGGCTGAGGCAGGAGAAGGGCACGAACCCGGGAGGCAGAGCTTG<br>CAGTGAGCCAAGATCGCGCTGCTGCCCTCCAGCCTGGGTGACAGAGCAGGACTCCATCTC<br>AAAAAAAAAAAAAAGTTAGCCGGGCGTGGTGGTGGACTATAATCCCAGCGACGGGGGAGG<br>CTGAGTCAGGAGAACCACTTGCACCCGGGAGGCAGAGGTTGTAATGAGCTGAGATTGCAC<br>CACTGCACTCCAGTCTGGGTGACAGAGCACGACTCCATCTCAAACAAAAGAAGAAAAAAA<br>[G,A]<br>GTGGCTTATTGCAGTTTTCCTGGTAAGAGGTCACGGGGCCTGGAACTAAAGCAGTGACAG<br>GGGAGGGGAAAGTGGCAGTTGCACTGGACAGATGTTTCCGAGGCCAAACCTGCAGATTTG<br>TATATGAAAGCTCAGGCAGGAGGAGAAGTCCAAGGTAGTTCTGAAGTTTCTGCATCGGAC |

FIGURE 3EE

```
          TTCTGGCTATCATTTGTTGAGCTGTGCCCATGTGCCACACTCAGTACCTCATATACCAAT
          TTCATTTACTTTTCCGATACCTCACAAGGCTGTGGTACTATCTCCAGCTTTTGGATGAGG

56479     TTTGAGGTACTGTAGAACAATTGTGTGGAGATGTCTGGAATCAGCAGACAGTCTCCAAAT
          GAAGCACCACTAATTGTCTCTTCCCCCTCCTAAGGCACTCTATATACTTGGAAATGATAT
          TTATATCATTTTTCTGTCTGTTGTCAGCTGAACTTTTTTTTCGGGTGAGAAGGAACTTCT
          TCATAATTTCCTCATTCTTTTTATTTTTTATTGTGCTAGACTCACTTATTCTGAATGAAA
          GGAACAGAAAGTACTTTTGTTCTGCAATATTTTCTGTGCAAAATTCTCATGTATTGTTTG
          [T,-]
          TTTTTTTTTTTTTAAGAGGCCTGAGAGCTTGGTGAACTTTGAAATAGAAAAATTTTGACT
          TTTGCTTTACAAGGGGTGAAGTGCTGTTTTTGTTTGTTTCTTTGTTTGTTTTGTTTCAG
          ATATTTGCTACAGTTTTCTGGTTGCTTTTGGCAATAAATATTAGAGTGTTGTCATTTTAC
          TTTTAAGGGAAAGGCCATAACTAGTCAAAGGGGAATCATTACCACAGTTATATAGTAGAG
          TTTTAGTATTTAACAATGGCAGGGACAGCTACCCATGAAGCAACTAATAATTAACATCCC

56489     TGTAGAACAATTGTGTGGAGATGTCTGGAATCAGCAGACAGTCTCCAAATGAAGCACCAC
          TAATTGTCTCTTCCCCCTCCTAAGGCACTCTATATACTTGGAAATGATATTTATATCATT
          TTTCTGTCTGTTGTCAGCTGAACTTTTTTTCGGGTGAGAAGGAACTTCTTCATAATTTC
          CTCATTCTTTTTATTTTTTATTGTGCTAGACTCACTTATTCTGAATGAAAGGAACAGAAA
          GTACTTTTGTTCTGCAATATTTTCTGTGCAAAATTCTCATGTATTGTTTGTTTTTTTTTT
          [T,C]
          TTTAAGAGGCCTGAGAGCTTGGTGAACTTTGAAATAGAAAAATTTTGACTTTTGCTTTAC
          AAGGGGTGAAGTGCTGTTTTTGTTTGTTTCTTTGTTTGTTTTTGTTTCAGATATTTGCTA
          CAGTTTTCTGGTTGCTTTTGGCAATAAATATTAGAGTGTTGTCATTTTACTTTTAAGGGA
          AAGGCCATAACTAGTCAAAGGGGAATCATTACCACAGTTATATAGTAGAGTTTTAGTATT
          TAACAATGGCAGGGACAGCTACCCATGAAGCAACTAATAATTAACATCCCTCATCTCAGG

58172     GCCTCGCCCTCTTGCTAGAGAACTGCGAGTGTCATTACAGTCATAGGATCAGAAGTTTTT
          TTAAGAGTGAAAACCTTCTTTAGATTTTTGTCTACTCCATTGCTTTCATTTTCCAAACAA
          GAAAATGCGGGTCCATAGAGGGGAAGTGACTTTCTGAACAGGGTAAAGAATAATGACAAT
          GATGATGTGAGCTAGCGATGACCAAGCACAGATTCTGTGCCAGGGAATATTCCATGAGAT
          CTGCATATATTAAGCCCTGTCTCTCACAACTACCCTGCTGGGTATCAGTGCTATTACG
          [G,A]
          TCCCCATTTTACAGGAGCAGAAACCAGTCTACTATATGTGAGAGAAAGGCCAGAGTGCAA
          TCATATCAGAAGCTTCCTATGCAAAACTGGGTCAAAGAGTGAAATTTAGTTGTTTGTCTA
          TCTTTAAAACATCGTAATAAGAATATGGTTACTGGCCGGGTGCGCTGGCTTACGCGTGTA
          ATCGCAGCACTTTGGGAGACCGAGACGAATGGATCACTTGAGCCCAGGAGTTCAAGACCA
          GCCTGGGCAACATGGCAAAACCCCATCTCTACAAAAAATACAAAAAGTTAGCTAAGTGTA

58665     TGGGAGACCGAGACGAATGGATCACTTGAGCCCAGGAGTTCAAGACCAGCCTGGGCAACA
          TGGCAAAACCCCATCTCTACAAAAAATACAAAAAGTTAGCTAAGTGTAATGGCGCACACC
          TGCAGTCCCAGTTAGTCAGGAGGTTGAGGTGAGAGGATGGCTTGAGCCTGGGAGTTGGAG
          GTTGCGGTGAGCTGAGTTCGTGCCACTGCATTCCAGCCTGGATGACAAAGCGAGACCCCT
          TCTCAAGAAAAAATAAATAAATAAAATAAAAATAAAAAATGGTTACTTAAAGAAAATTT
          [C,T]
          ACATATATTGTATATATATCATAACATTGTGAAGCAAGTAGTAGTATATCACTATGCTAC
          TGGGTTTTTCACTATTTTACTAAAGCTCAGAAAAATTTGATACTTTCTTAATATCACACA
          GTTAGTGGCAAAGGAAGGATGACAGAACAGTTCTGCCTGGCCCAAAGGCCGTGCTCCTTC
          CATTATTCCAGGTTGCCTTAAATATCAAACAGTGTTAGTGTCCCAGAATAGAAAAATATG
          GAACCTCTGGTCTAAACTGCCCTAAGACAGGGGCTTGTATCTTTCAAAATAAATAGAGTT

59779     GATTCTGATTTGGTAGCTCTAGGGTGGAGCCTGAGATTCTGCAGTTTTAGCAAGTTCCCC
          AGAGCTGCTGCTGCTGCAGGGCAGTCCACACTTTGAGTAGCAAGGGCAGAGCAATCACGA
          TTTGCTTCCAGTAGGAAGCGGAGGAACGCCTTCCCTTGATAACTTTGTGATGCAAAAGAG
          ATCCATATCCTGTTCCCAGAGATACTGAAATGTTCAAGTTCATATTGCTTCCTTTCCCCC
          GATTGCCAATTAAGTCACAATCTGAAGGAGAGAAACCCAATACTCCAAATCACATAAACT
          [G,T]
          CTTTTTTGTTTTCCTTTTTTTTTAGACAGGGTCTCTTGCCTTGTGCAGTGTCTCATGACT
          ATAATCCCAGCACTTTGGGAGGCCGAGGCAGATGGATCACCTGAGATCCAGGAGTTCGAG
          ACCAACCTGGCCAACATGGTGAAACCGCATGTCTACTAAAAATACAAAAACTAGTTGGTT
          GTGGTGGTATGTGCCTGTAGTCCCAGCTACTGGGGAGGCTGAGGTTGCAGTGAGCCAAGA
          TTGCACCACTGCACTCCAGCCTGGGTGACAAAGAGAGATTCTGTCTCAAAAAAAAAAAAA

60360     CTGTCTCAAAAAAAAAAAAAAAAATAGACAGGGTCTCGCTCTGACACACAGGCTGGTGTGC
          AGTGGCATGATCGCGGATCATTGCAGCCTCTACCTCCCATGCTCAACTGATTCTCCTGCC
          TCAGCCTCCTGAGTAGCTGGGCTACAGGCATGTGCCACCACTTCCAGATATATATATAT
          TTTTTCGAGACAGGGTCTCACGATGTTGCCCAAGCTGGTCTCGAACTCCTGGCCTCAAGT
          GATTCTCCTGCCTTGGCCTCTCAAAGTATTGAGATTACAGGCATGAGCCACCACACCTGG
          [C,G]
```

FIGURE 3FF

```
         CTTCTTGCCACTTTTTAAACATGATTTCATTTAATCCTCATTGCAACCTTGATGAGAAAG
         GTATTGCTATATTCACTTTATTGGTGGGGAAACCAAAGTGTGGTTTAACTTGCCGAGTGA
         AGTGGCTGGGAGTGTGGAATAAAGGTCTGTTGGTCCCAGCAATGACACTGTGGGAGGGAT
         TGCAGCCACAGGGGCAATAATTCCTCAGAATCTACTGTCTGCCAACTTTTAAAGGAATAA
         ACATAGATGTCAGGGAAGACTGACTGGCACAATTTAGGAGCTGATTATAGACAAGACTGC

61466    TCAGTTTTTTTTTTGCACAGAATAGAGAAATAAAAAGCAAAGCAAAGGAAGACAAAAAG
         ATGAATAAAGCCTACAACCCCTTGCTATAATTTCAGTAGCTGAAGCTGGTAATTAATTTA
         GCAACTATTTATTGAGTGACTACAATGTGCCAGGCACTTTGCTAGTTCAGGGGAGATGGT
         GGTAAACAAGACGGATGGCTAACCACCTGTAAAGAGCATGCATGTTGGTTTACACGTCTA
         TGCACCATGTAGTTAACATACATTATTTAACTTAATTCCTACATCAATTTTATAAGAATC
         [A,G]
         TTATCCCGTTATGTAGATGAAACTAAGGTTCAGGAAGTTTAAATCCTTGGTCTAGGCTTG
         CATCTCAACTAAGCTGCCAGAACTGAGGTCTGTCTGATTTGAACATGCACCCCTGCAATA
         TATTGACAAAGTCAGATCTCAGCTCGCTGTAACCTCCAACTCCTGGGTTCAAGTGATTCT
         CCTGTCTCAGCCTCCCAAGTAGCTGGGATTACAGGCATGTGCCACCATGCCTGGCTAATT
         TTTGTATTTTAGTAGAGGTGAGGTTTTGCCATGTTGGCCAGGCTGGTCTTGAACTTCTG

61801    AAGTTTAAATCCTTGGTCTAGGCTTGCATCTCAACTAAGCTGCCAGAACTGAGGTCTGTC
         TGATTTGAACATGCACCCCTGCAATATATTGACAAAGTCAGATCTCAGCTCGCTGTAACC
         TCCAACTCCTGGGTTCAAGTGATTCTCCTGTCTCAGCCTCCCAAGTAGCTGGGATTACAG
         GCATGTGCCACCATGCCTGGCTAATTTTTGTATTTTTAGTAGAGGTGAGGTTTTGCCATG
         TTGGCCAGGCTGGTCTTGAACTTCTGACCTCAGGTGATCCACCCGCCTCAGCCTCCCAAA
         [G,C]
         TGCTGAGATTATAGGCGTGAGCAACCATGCCCGGCCAGCAGCATTATCTTTTGATAGAAG
         ACCTCAAAGAGAGGGAGTTACTTTGCAATGGCAGCAGAAGGTAGCAGTAGTAGTAGTGGT
         AGTTAGCATAGCTTTGATATTTGCCAAGGGCTTCACATACCTATTTCCCCTGAGTCTCTA
         TCACAGCACCTCTGTGAAGTGAATAGTAATATTATCCTCATATTGGAGATGAAGAAACAA
         AGGCCCCCAAATTACTTGTTTACATAGTAGAAATAAGATTCAAGTCCAGATTTACAGACT

63124    CAGAGGACTGGAGCTCTACACAAACTTGAGATTTCAAGGCTCTACTGCAGTCTGTAAATG
         TGTATGTCCTTGACCTTGACTGAGTCAGCTGAACTTCTTTTTTTTTTCTTCCTTCTTCTG
         ATTTTCAAATCATTGCTTATCAATGGCACCAAGGCTAGTTGTTGTTTTGTTCTATGTTTT
         CTCAATTGAGGAATAATAGTCTGGGGAGAGGGGATGGGCCATAGAAACTGTTTAGAGACC
         CAAAGAAGAAACTGAGGCAGTCAACTTGGGATAAATGAGTTACTGAAGATTGTTTTCTCA
         [T,G]
         TCTCAGTGATTAAACCTTATAGCCTATTTCCATCCATTGCTTAGCATGTTTCAGCATAAA
         AAGATGAGTGCTATTCTACTTCCTTGTTAAGAATAAAATAAACAGGACATTGATAACCTA
         CCCAGTTGTTACTGAGCCTTTGTGAATTTAGACAAGGGTGGATGGTAGAGGCAGATCCAT
         CCAGAGTTCAACCACAGCCCACATGATTTCTTTATCTTTGTCACTGAAACGTCTCAAGAT
         GCTGCTTTCTGCAAATAAGAATTCTTTGATACCATGGGATTTTTTCCCCCATCTATTTT

64341    CTGTAGTCCCAGCTACTCAGAGGCTGAGGCAGGAGAATGGTGTGAACCCAGGAGGCGGAG
         CTTGCAGTGAGCCGAGATCGCGCCACTGCACTCTAGCCTGGGTGACAGAGCGAGACTCCA
         TCTCAAAAAAAAAAAAAAAGAATTTTCTAAATTAAAAAAATACGTATTTATTGTTTTGTCT
         AACTTTCATATTCATTGTTGTCTTAACTTTCATTTTTTAAGTTTTTCTTTTAAATTTGGT
         TTGAATCCCGGATGGTGCTTCTGACACACGTCCTCCCGCCCAAGGAGCCTCTAGAGCATC
         [A,G]
         CCTTCCAAATGGGCAGGTGCTTTTTCACAGTGGAGGCCTCCAGGACATACTGGTAATCTC
         TAGTTTTAGTTAAAACATTAATTGGCACTTTATTTCCTTATTTAGACCCGTGAAGAATGG
         CAGAATGTGTTCCTCATAGCTGCCCTGGTGCATTACAGTGGTGTGATCTTCTATGGGGTC
         TTTGCTTCTGGGGAGAAACAGGAGTGGGCTGACCCAGAGAATCTCTCTGAGGAGAAATGT
         GGAATCATTGACCAGGACGAATTAGCTGAGGAGATAGAACTCAACCATGAGAGTTTTGCG
```

FIGURE 3GG

| | |
|---|---|
| 66706 | GATTCTTCATTAAATAATATTCTTTATGTCACTAGCATACAATTTATGTTAGTAGACATC |
| | TTTAAATCTCTTTAATGAGTGAATCCATGCAAGCCCCATAAAACAGTTCCTAGCATGCAG |
| | AAAATGCCCACGTAAATAGCTGTCATCATCATTATCTTTTAACATTTTGGGGACTTTCC |
| | AGTTGAAAAGAAAACATGCTATGTCATTTTTATCCATTATCCCTGGAACTTATTGTGAAA |
| | GTTGTGCTGTTTTCTAAGTAAAATAAAAAATAAAAAATTAGCAATTTATGATAGCCAGTG |
| | [T,A] |
| | TTTATTTTGTGTGTGTGTTAGTAAAGTCAAATAATTGTATTTTAAAAACTCACGATAATC |
| | CTTAAGGTAGTATTGTATATTGTGACACAAAGTTGTAT |

Chromosome map:
Chromosome 12

FIGURE 3HH

SEQUENCE LISTING

<160> NUMBER OF SEQ ID NOS: 4

<210> SEQ ID NO 1
<211> LENGTH: 1811
<212> TYPE: DNA
<213> ORGANISM: Human

-continued

```
<400> SEQUENCE: 1
tcagaggtgc ccctcattca aaatgccttt taaagcattt gataccttca agaaaaaat      60
tctgaaacct gggaaggaag gagtgaagaa cgccgtggga gattctttgg gaattttaca    120
aagaaaaatc gatgggacaa ctgaggaaga agataacatt gagctgaatg aagaaggaag    180
gccggtgcag acgtccaggc caagcccccc actctgcgac tgccactgct gcggcctccc    240
caagcgttac atcattgcta tcatgagtgg gctgggattc tgcatttcct tgggatccg     300
gtgcaatctt ggagttgcca ttgtggaaat ggtcaacaat agcaccgtat atgttgatgg    360
aaaaccggaa attcagacag cacagtttaa ctgggatcca gaaacagtgg gccttatcca    420
tggatctttt ttctggggct atattatgac acaaattcca ggtggtttca tttcaaacaa    480
gtttgctgct aacagggtct ttggagctgc catcttctta acatcgactc tgaacatgtt    540
tattccctct gcagccagag tgcattacgg atgcgtcatg tgtgtcagaa ttctgcaagg    600
tttagtggag ggtgtgacct acccagcctg ccatgggatg tggagtaagt gggcaccacc    660
tttggagaga agccgactgg ccacaacctc tttttgtggt tcctatgcag ggcagtggt     720
tgccatgccc ctggctgggg tgttggtgca gtacattgga tggtcctctg tcttttatat    780
ttatggcatg tttgggatta tttggtacat gttttggctg ttgcaggcct atgagtgccc    840
agcagctcat ccaacaatat ccaatgagga gaagacctat atagagacaa gcataggaga    900
gggggccaac gtggttagtc taagtaaatt tagtacccca tggaaaagat ttttcacatc    960
tttgccggtt tatgcaatca ttgtggcaaa ttttttgcaga agctggacct tttatttgct   1020
cctcataagt cagcctgctt attttgaaga ggtcttttga tttgcaataa gtaaggtggg   1080
tctcttgtca gcagtcccac acatggttat gacaatcgtt gtacctattg gaggacaatt   1140
ggctgattat ttaagaagca gacaaatttt aaccacaact gctgtcagaa aaatcatgaa   1200
ctgtggaggt tttggcatgg aggcaacctt actcctggtg gttggctttt cgcataccaa   1260
aggggtggct atctccttc tggtacttgc tgtaggattt agtggcttcg ctatttcagg   1320
ttttaatgtc aaccacctgg acattgcccc acgctatgcc agcattctca tggggatctc   1380
aaacggagtg ggaaccctct ctggaatggt ctgtcccctc attgtcggtg caatgaccag   1440
gcacaagacc cgtgaagaat ggcagaatgt gttcctcata gctgccctgg tgcattacag   1500
tggtgtgatc ttctatggga tctttgcttc tggggagaaa caggagtggg ctgacccaga   1560
gaatctctct gaggagaaat gtggaatcat tgaccaggac gaattagctg aggagataga   1620
actcaaccat gagagttttg cgagtcccaa aaagaagatg tcttatggag ccacctccca   1680
gaattgtgaa gtccagaaga aggaatggaa aggacagaga ggagcgaccc ttgatgagga   1740
agagctgaca tcctaccaga tgaagagag aaacttctca actatatcct aatgtctgag    1800
aggcacttct g                                                         1811
```

<210> SEQ ID NO 2
<211> LENGTH: 589
<212> TYPE: PRT
<213> ORGANISM: Human

<400> SEQUENCE: 2

```
Met Pro Phe Lys Ala Phe Asp Thr Phe Lys Glu Lys Ile Leu Lys Pro
  1               5                  10                  15

Gly Lys Glu Gly Val Lys Asn Ala Val Gly Asp Ser Leu Gly Ile Leu
             20                  25                  30

Gln Arg Lys Ile Asp Gly Thr Thr Glu Glu Glu Asp Asn Ile Glu Leu
```

```
              35                  40                  45
Asn Glu Gly Arg Pro Val Gln Thr Ser Arg Pro Ser Pro Leu
    50                  55                  60
Cys Asp Cys His Cys Gly Leu Pro Lys Arg Tyr Ile Ile Ala Ile
65                  70                  75                  80
Met Ser Gly Leu Gly Phe Cys Ile Ser Phe Gly Ile Arg Cys Asn Leu
                85                  90                  95
Gly Val Ala Ile Val Glu Met Val Asn Asn Ser Thr Val Tyr Val Asp
            100                 105                 110
Gly Lys Pro Glu Ile Gln Thr Ala Gln Phe Asn Trp Asp Pro Glu Thr
            115                 120                 125
Val Gly Leu Ile His Gly Ser Phe Phe Trp Gly Tyr Ile Met Thr Gln
    130                 135                 140
Ile Pro Gly Gly Phe Ile Ser Asn Lys Phe Ala Ala Asn Arg Val Phe
145                 150                 155                 160
Gly Ala Ala Ile Phe Leu Thr Ser Thr Leu Asn Met Phe Ile Pro Ser
                165                 170                 175
Ala Ala Arg Val His Tyr Gly Cys Val Met Cys Val Arg Ile Leu Gln
            180                 185                 190
Gly Leu Val Glu Gly Val Thr Tyr Pro Ala Cys His Gly Met Trp Ser
            195                 200                 205
Lys Trp Ala Pro Pro Leu Glu Arg Ser Arg Leu Ala Thr Thr Ser Phe
    210                 215                 220
Cys Gly Ser Tyr Ala Gly Ala Val Val Ala Met Pro Leu Ala Gly Val
225                 230                 235                 240
Leu Val Gln Tyr Ile Gly Trp Ser Ser Val Phe Tyr Ile Tyr Gly Met
                245                 250                 255
Phe Gly Ile Ile Trp Tyr Met Phe Trp Leu Leu Gln Ala Tyr Glu Cys
            260                 265                 270
Pro Ala Ala His Pro Thr Ile Ser Asn Glu Glu Lys Thr Tyr Ile Glu
            275                 280                 285
Thr Ser Ile Gly Glu Gly Ala Asn Val Val Ser Leu Ser Lys Phe Ser
    290                 295                 300
Thr Pro Trp Lys Arg Phe Phe Thr Ser Leu Pro Val Tyr Ala Ile Ile
305                 310                 315                 320
Val Ala Asn Phe Cys Arg Ser Trp Thr Phe Tyr Leu Leu Ile Ser
                325                 330                 335
Gln Pro Ala Tyr Phe Glu Glu Val Phe Gly Phe Ala Ile Ser Lys Val
            340                 345                 350
Gly Leu Leu Ser Ala Val Pro His Met Val Met Thr Ile Val Val Pro
    355                 360                 365
Ile Gly Gly Gln Leu Ala Asp Tyr Leu Arg Ser Arg Gln Ile Leu Thr
    370                 375                 380
Thr Thr Ala Val Arg Lys Ile Met Asn Cys Gly Gly Phe Gly Met Glu
385                 390                 395                 400
Ala Thr Leu Leu Leu Val Val Gly Phe Ser His Thr Lys Gly Val Ala
                405                 410                 415
Ile Ser Phe Leu Val Leu Ala Val Gly Phe Ser Gly Phe Ala Ile Ser
            420                 425                 430
Gly Phe Asn Val Asn His Leu Asp Ile Ala Pro Arg Tyr Ala Ser Ile
            435                 440                 445
Leu Met Gly Ile Ser Asn Gly Val Gly Thr Leu Ser Gly Met Val Cys
    450                 455                 460
```

```
Pro Leu Ile Val Gly Ala Met Thr Arg His Lys Thr Arg Glu Glu Trp
465                 470                 475                 480

Gln Asn Val Phe Leu Ile Ala Ala Leu Val His Tyr Ser Gly Val Ile
                485                 490                 495

Phe Tyr Gly Val Phe Ala Ser Gly Glu Lys Gln Glu Trp Ala Asp Pro
                500                 505                 510

Glu Asn Leu Ser Glu Glu Lys Cys Gly Ile Ile Asp Gln Asp Glu Leu
            515                 520                 525

Ala Glu Glu Ile Glu Leu Asn His Glu Ser Phe Ala Ser Pro Lys Lys
        530                 535                 540

Lys Met Ser Tyr Gly Ala Thr Ser Gln Asn Cys Glu Val Gln Lys Lys
545                 550                 555                 560

Glu Trp Lys Gly Gln Arg Gly Ala Thr Leu Asp Glu Glu Leu Thr
                565                 570                 575

Ser Tyr Gln Asn Glu Glu Arg Asn Phe Ser Thr Ile Ser
            580                 585
```

<210> SEQ ID NO 3
<211> LENGTH: 66804
<212> TYPE: DNA
<213> ORGANISM: Human

<400> SEQUENCE: 3

```
aacctctttt tgtctgagtt tcctgccagt aaaattgggg aaaataagaa gttatttacc      60
acagagtctt gctgggaaga ttgtggtgat acttaaagag tgcttaacac agagccagga    120
ccctagaaag aactcaaaag atattagcaa tatttagcct accaaggatt cagcacggac    180
ttagttgaac ttaattcaaa ttttggataa tttggacagt ggcttgcaga ggatattgac    240
tggtcttgtg gaaatgactc ctggggagcc tgagagccta tagcctatga tttgtcagtc    300
gcatgcagac tggaggattg aacacagga gcctcaaaga tgaagagttt ttttccacc     360
gcagcagcat ttacagaggc gtcatcctgc tgcccataaa tgtggccaca acttgcagcg    420
tttcagcccc agttcaacaa gtatttaggt aacgcccact ccctgccagg ctctgctagg    480
gcagaggaca ggtgatttgg aggcacagag gagggacatc tcaccttgcc catgcagttt    540
tctagaggat tgatatctta gcatgacctt agaaccccta gaagttaccc agttgaaggg    600
gtgcagagag ttacccaggc agagggcata gcttgagtaa agcccagagg caatagggag    660
cttgctgagt tcagtgaaat gaggatgtgg aaagcagagt gacaagaaga aagacttagg    720
gtcccaggga aaggccttgt gtgccatgat aaagaattgt attgtaaata gtgctgcaat    780
aaacatacgt gtggatgtgt cttttgtagta gaatgattag aatacatgga tacagagagg    840
ggaacatcac acaccggagc tggtcagggg ttgggggggca aggagaggga gagcattagg    900
acaaatacct aatgcatgtg gggcttaaaa cctagatgat gggttgatag gtgcagcaaa    960
ccaccatggc acatgtatac ctatgtaaca aacctgcatg ttctgcacat gtatcctgga   1020
acttaaagta aaaaaaaaa agtccatcta gagggagaaa aggggaaaaa acaaaaataa   1080
ttttatttat cctgaggaca atgaggagtc agtggagagt tctaagcagg ttctagatat   1140
cttccggctc agaaatcttc aattagatgg tcccaaatgg catctacgta tcatactttg   1200
agagagcctg ctctgttgat taggagcaaa taaatgtcct cctggatgta tgtggcctgg   1260
gttttgcatt tgggctactc aaatgcaagt tcctcgtggg accacatcca tgctagtggc   1320
tggctgaaaa acggcttcat gactctcatg aggggaataa aaggcatgga gtggtggctg   1380
```

-continued

| | | | | |
|---|---|---|---|---|
| tgagcctgtc | tgcagggcca | gacctcagaa | aagcaaaggg | ctgtaaatgt | ttcataaatt | 1440 |
| tctctctggg | tgcctgctct | ggctgagagc | ccattcataa | gcccaggcgg | ctgaggggca | 1500 |
| ggtattgtgc | cggttactat | agcatcacct | tggaaagtct | cacttggtga | gagcggcagg | 1560 |
| cgagctgggg | tggggcagga | gggggacgcg | gctggctgga | ggggctggag | ctaggccacg | 1620 |
| gatactgctg | ctggtctcag | gactcctggt | ggtccggagc | tcatgttagc | gtccccagct | 1680 |
| gcagcccagg | gagggagaga | ggctgcgctc | agtctgagag | tggctgcctg | agacagctgc | 1740 |
| cacaggctgc | tgcagagcgt | gcagcttttg | caagggactg | aattcccagc | cagacacccc | 1800 |
| ttggactctt | ttttggaggg | gtggggagca | gagagaggag | ggagttgtct | tatcttggaa | 1860 |
| gatccgagct | gggtttcatc | tccttttga | ttttgagtag | ttccctccac | gagaactgac | 1920 |
| ttccaggtgt | tcaccaaggg | aaacaaggtg | gttctcacac | tggaaatgag | gaaggatgac | 1980 |
| agtttttgag | actgactgtt | aacggctcag | aggtgcccct | cattcaaaat | gcctttaaaa | 2040 |
| gcatttgata | ccttcaaaga | aaaaattctg | aaacctggga | aggaaggagt | gaagaacgcc | 2100 |
| gtgggagatt | ctttgggaat | tttacaaagg | taaagtttga | atgcgaactt | tagttccttt | 2160 |
| ctgagtagct | tcgtattgcc | aatgtgtgag | agacttggta | tcacgttttt | aaaaccacac | 2220 |
| tttaatgagg | agaggatggg | tcagattaga | tccttctgga | gcccttcta | gctccagtag | 2280 |
| tctatgcctg | gaggaaaaac | agatgcatga | atagtattgg | gttgtattag | gaaaagatca | 2340 |
| agacaaatat | gctgtttata | tagctggatt | agcactttct | ggagatgatg | atattgcata | 2400 |
| tggtatgttt | ggcattgaat | tagaaaatat | ttagggagat | aatatttat | gttaactcat | 2460 |
| tagtaatgac | aaatatgcct | tgaactgaaa | taattttat | gttttcact | gaatccacta | 2520 |
| taaatgaaaa | ttaaatattt | gcaatttta | gcttatttaa | taaatacat | aaagtggttc | 2580 |
| ctgattgtat | agtttgcaaa | gagaaggata | gttacacatt | aatttgaagg | aagtaactta | 2640 |
| aaaaatgtct | ttgaagcaga | aaatctcaca | taattgcagt | gggaaaatgt | taagtactat | 2700 |
| cactgaattg | aatgagattt | tagtccaaac | caaaagtaa | atatttta | aagtaaaata | 2760 |
| tattaatgga | aggagagttt | gctataaatg | attgaattaa | tgtgacagtt | taattatga | 2820 |
| attttatag | acatagtaaa | tgccttctca | aattatataa | atgatttcat | aagtggtcct | 2880 |
| tatgtgcaag | gtaaaatgac | tgctttatct | ctctgatata | aataaatgtg | aaaaataact | 2940 |
| ttgatacact | ttttatttgt | ttggatgatt | atttctaatc | ctggtgagtg | aaaatgccat | 3000 |
| ctggtgtgtc | cttttaactt | ttctattatc | tcttaaattt | aaaaacttt | tcatttaaat | 3060 |
| gactatttcc | aggcaatctg | agattcatcc | catttcttgt | gttttaaaac | acatatgctc | 3120 |
| ctgtcagtgt | taaattttcc | catggtatca | ctgttaatat | taacttcct | aataagaaaa | 3180 |
| aagagttgga | caccttatta | ttttagtaat | tagaaacaaa | aaagcttcaa | tcagacctac | 3240 |
| actgaattag | catgtctaga | tgaaaaccta | gctcagtgac | agcagcataa | accagccaaa | 3300 |
| tatagaaaaa | attacaataa | catttttc | agagtgtttt | atccttccgt | tgagcactcc | 3360 |
| ccaggtaacg | tcttattgtg | ttggcgttca | tttgattaga | aacgcaaaaa | taattttgc | 3420 |
| ataataagca | cgatagctta | attggcttat | tcaagtaatg | acaaaggaat | ctggcaaagt | 3480 |
| caagaataaa | aaccataggc | cgggcgcagt | ggctcacgcc | tgtaatccca | gcactttggg | 3540 |
| aggcggaagt | gggaggatcg | cttgaggcca | gaagttcgag | actagcctgg | ggaacataga | 3600 |
| gagaccatgt | ctctacagaa | atacaaaaaa | ttagccagca | tgatggtgca | tgcctgtcat | 3660 |
| ctcagcttcc | caagaagtgg | gagtattgct | tgagcccaga | cattcaaggt | tgcagcgagc | 3720 |
| caagattgcg | tctctgcact | ccagctaggg | tgacagagtc | agactctgtc | tcaaaaaata | 3780 |

```
aaaaaataaa ataaatttaa aaacctatga cgttgggcca tagtcaccat tataaacagc    3840
aaactctgcc ttcatttata aaatatttga tataaaaata cttaggaatt ttcttttcaa    3900
ccttaagttt aattgctttt tgtgaaattt gattgctttt ttcaatagga attattgatc    3960
gaagagccgg ttttgctatg tttgattgga ggagctacat ggagatcttt ttgtttacaa    4020
aattgatttg cttagggata taacaaaatt ggcgattttc caaattgtgt gacctcaacc    4080
agaaattggg ctatgtgtct aggactgttt gaatagtttc ctcagaacaa tagaaaaaca    4140
gctagcacag tactagggac agagaatgca ctaaacaaat gctagatatt gtcatggttg    4200
tcctaattgt agaatggctt tagaaaaaat aaagccaagg tcaaatccct tttttcagtg    4260
atctatagag agaaattatt ggcagaagaa acgaaaacag acattgcttg agcggtgatc    4320
caagttgatc ctcagttcta gtgaggaatt atcaagacca gctctgccac gtgtttggca    4380
ttaatcacag gtgtataagg taattgtatg taaatgaccc tgcccagagc ctggcacata    4440
ctggcatttt ccctctcatt tcactgcttt tcacgtaaaa ccagttgaca gaatcccatg    4500
taaaaaaatc acaagaact gttttctgtt ttgtaggagc ttttggaagc tagaagcccc    4560
tacattgtaa cttagaaggc aatgtaaatc acagctgtct aataatgttt gaggctgagg    4620
tcatcatcta aatggaattc ttgagatgct ttttaatcac agtgttcctc acagtcaggg    4680
gagtggcaat tgcacaggga agcatttgag agttcgcaca caggcttgat tacagtcagg    4740
catgattagc tttcctggaa aacagtcatt gataagaagc agctgagcaa ttaatcagct    4800
aaaggtaaaa taatatttta gaagtgcagg aagaaagaag atgcactcat ttatagttta    4860
gtattgaatt atatagatga catagaaagc attaaacttg gaaactaatg tccagaaagt    4920
gacatgcaga tttgttcaat ttaaattaca atttatgtgt cctttaattg ttcatgtcta    4980
aaaaacataa cagtgacaaa acagtatctt tcagacactg taaactcatt taattctatt    5040
aaaatcccca tgaagagggg attactataa ttacaacttt tcttttttt gggatagggt    5100 ctcactctgt tgcctaggct ggagtgcagt gatgtgatca tagctcactg cagcctcaaa    5160
ctcctggcct caagccatac tgcctccttg gcctcccaaa gtgctaggat tacaggcatg    5220
agccacagca tctagcaata attttacaga tgagaaaact gaggcacaga gaggttaagt    5280
agcttgccca aggtcacaca gctataaatg gaagagctag gtttcaaacc agatgttcta    5340
tgcccatcat tcttaatcac tacattatgt taccctgta atcaagtgtc tttcctcttc    5400
ccactcactg tcttgatatt gggccactta tttaggttta gggaggtcta cttggactgc    5460
aatgtagcca gcaacttctg gatctgctgt caagtgtggg ctattctcct aatcagttgc    5520
atctttattg aaggctttct ccaagggagg cttaagggga gtctggtctc cttacaagta    5580
tgtctatctt cccctttaaat gaaactagtc cctgcatcgt gtctgtcttc agcattcagg    5640
agtgtgccag atatgcactt cctgctccat caacaaaggt gagtgtgtta aagcttgctc    5700
tgagatcagg tgatcctggg ttccaactgc tgcaacatcc tttacttccc tgcctgcatg    5760
acctcaggca acttggctgc aatggggtga ctctaggaaa ccaagtcaga tcacatctca    5820
cccctgctca aaactacctc actcagagtt aaagccagtg ccctttcaat ggccttcaag    5880
gacctctgtg atctaggact tttggaaggc tctctgagtt catctgtgac attttcctgc    5940
ctcactctac tctggattca cgggcctcct ggctcttatt agaactcccc cagattcact    6000
cctgtcccgg ctttcgccct gtttcttttg cttaaatgct ttcctcccag atagcctgat    6060
ggctcattcc ctcgctttct tcaagtatgt gctcaaagat ccccactttc ctggccattc    6120
```

-continued

```
tatttaaaca tgaagctcac ctgccctcct cctcctgccc tcttctctgt ccctctttcc      6180
tgctttactt cacctctgtc ttaggtaggt tccctaaaaa gcacagcctg agacagggat      6240
ttgggtgagc ctagaatgtg atttaatgag ctcttcctga aaaactggg agggagtaaa      6300 acaagaaggg aaaggagagg ctgggtgtgg tggctcacgc ctataatcct agcattttgg      6360
gagtccgagg caggcagatt gcctgagctc aggagtttga ccagcctg ggcaacatgg       6420 tgaaacctgt ctctactaaa agacaaaaaa tgagccaggc atagaggcat gtgcctatag      6480
tcgtagctac tcaggaggct gaggcaggag aattgcttga atccgggagg cagaggttgc      6540
agtgagccga gatcacacca ctgcactcca gcctggacga cagagggaga ctccatctcc      6600
aaaaaaaaca aaacaaaaaa aaacagaaag gagaaagagc caagcaagga tgcatgctca      6660
caatgcccag tggccagatc caaagggaa ggctctggag cacaagcgat gtgctgagtc       6720
cttcctttgg ggcaagtggg gcagccttt atatctctgc ctcagtcagt catcagctct       6780
gggctgatgg gggtgggtga ggggtttatt tggaggccac tgagcagtgg gaagttctcc      6840
agggttcctc atgccaggac tagaagccca ggcaaggagt caccatggtg gcaagggtca      6900
tgggtcctga tcctcaggag gaaccagaac tgtcacctca tcacgggagc aggaagagat      6960
gtgtttggca ctgaggtggt ccactcggac atctcctgat actgcctggg ctagttttat      7020 ttatttttt attttaattt ttaaaataat agagatgggg gtctcaccat gttgattagg        7080
ctggtcttaa actcctgggc tcaggagatc ttcctgcctt ggcctcccaa gtgctagaat      7140
tacaggcatg agccaccgca ccctgcctag ttttaactgc aaatgggaaa atacagcaac      7200
cgtgacctgc tagcagctct ggaagtagaa gtgtgcttgc ccatcaaggg gaactgggga      7260
gtgtgctatg gtgtctatga cagcccaccc actgcaccgc tcagatcaac ttgcttctca      7320
catgaagttc actccatcca ggtacagctt ctccaagact ctatggttgt aattcctgag      7380
gagccttcca aagaagagtt attaagacag actccaggcc ccactgtgat gactggtccc      7440
tcctctccac ccctttttga tttccctcac ttctgtttgc ttgtctgatg ggttgcccca      7500
gatcttcatc cctgagaggt ctaaatccct ggttaacata acctcaccag gtcatggttg      7560
ctgtatttgc ccactgacag ttaaaaacta gccaaggcag tatcaggaga tgtcccagca      7620
gatcatctgt gtgccaaaca tatttcttcc tgctcccatg atgaagcgac agttctgatt      7680
cctcctgaag attaggatcc atgacccctta tcactgtagt gacttcttac catgtcttct      7740
ggtcttggca cgaggacccc aaagtgactg agcagcagtc gtaaccatat gttgactagg      7800
atttccattg tgttcctaaa tggaagaatt cttccttgtg aatcgggatt tctagctcct      7860
cagagcctaa gctgaagaga tgagatattc ctcaggtggg ttactgggaa tgatggcgag      7920
tggggccact ccttctctca tgccttgttt ctttgacctg tgtgttctgc ccactgggca      7980
cacagcacca tatcataact gttgggtttt ttgtttgttt gtttgggatg gagtcccact      8040
ctgtcgccca ggctggatgc agcggcttga tctcagctca ctgcaacctc tgcctcctgg      8100
gttcaagcaa ttcctgtcc tcagcctcct gaatagtggg attacgggca cccaccacca       8160
tgcccggcta atttttgtatt tttagtagag atgggggtttc ggtatgttgg tcaggctggt      8220
ttcaaacacc tgacttcaaa tgatccaccc gccttggcct cccaaaatgc tggcgttaca      8280
ggtgcataac tgttgattta tggaatatac tgcatcctgg aagatagcac cttaccctcc      8340
cagggtttca tctccaagct gatgtcgcag ctgcatctttt aagaagcttc ttcagaggcc      8400
aggtgccatg gctcacacct gtaatcccag cactttggga ggccaacgca gatggatcat      8460
ttgaggtcag gagttggaga ccagcctggt caacatggtg aaacatatat tttctactaa      8520
```

```
aaatacaaaa aattgccagg cgtggtggtg ggcacctgta atcccaacta ctcaggaggc    8580
tgaggcagga gaattgcttg attaaaccca aggggggaaga ggttgcagtg agctgagata    8640
gagccactgc actccagcct gggtgataga acaagattcc atctcaaaaa aaaaaaaaaa    8700
aaaaaaagct tctttagctc tggcaggctg tcagcttctg gatggtgtgg tatatggtgg    8760
ggcttgtgca tcccattgtc atgtgcccac tgctatgcca tcttcaccat aaattgggtg    8820
ttttggtctg aaaaaatgtg atgtgagatc ccatgttgag aaatcagaca ctgaatcctc    8880
agatagtgat gttggctgag acttgtagtc tgaataggca aactcataca tggaatattt    8940 caacccccagt caggatgaat tgctacccct tccaggatgg aagggtctg ttacaaacaa    9000 cttctgacca agagactggt ttgtcccctc aggaattgtg ccatctcagg ggctcagcat    9060
tagtcttgtt gctgaccgca gcaggagcta gctcagtcct ggtgagtggg agctccgaca    9120
tagcctccat ccctgctgcc atggttactc tgttcataag tgcactgctc tagcactggg    9180
tggctgagga cggaagctag ctgacatcaa ctggccaagt cagcctgcct atcgtctgtt    9240
ttgtgcctct tccaagtggc atgtgataat gtgcaatcag gagagctcat actaggcatc    9300
cactcataga ttgatccaca tctcttcccc agatcttttt cccagtcctc caatattgct    9360
ttaaatgtcc cctgacctcc agtgaggtca ttcaccactg cctatgagtc catgtatatc    9420
cttacctttg aatgtttctc ttttcataca aaatgtgtgg ccaggagact gctcaaaact    9480
ctgcctattg ggaggctttc cccctcactg tccttcaggg ccatccctgg gtgggctgaa    9540
gtatagcagc agtccatttg caacatgctc taacatacca aattgaccag ctctggacca    9600
aactaagttt ttttttcctcc tgtaatttgt tcacaggtgt gagctcatgg agaggcattg    9660
gtatagtaga tataggtcag gtggaaaact ggcccctctg acatgggatt acttgtgtcc    9720
tgtggccctg ctggtgttag attccagatg gaccacttcc gtcttatgat ggacagttgg    9780
acttctcagg tctgatagaa cctagctcct gatgggtcgt tttggctgca tggtctcttg    9840
atattccatg gtcagatgct gtgtctccac caggactcag taacatgcca tgagatgttt    9900
tttgtctgtt gtatatttct ctactataga tgacaaggcc ttgtcccaga atcctaaggc    9960
tctatgctat atttctccta ttgagttttg ccagaaacct catatagtgt cttttcctat   10020
tcagatgact ttagtaccaa gggtatgctg gagaatacag ccctagtggc aagatcaccc   10080
ttattgcagc ctagacttgc tacagaacat tttcttgttt ttggatttca ttaaaaacca   10140
gcagcctttt atgtcatgga ataagtgggt tagaacaata ttcccaagtg ttgaatacac   10200
tgcctcaaaa acccaaagag gtctgccaac cattgtgctt cttccttagt ggcaggaagt   10260
tcaaagcaca ataactttc cttcactttg aagggaatgt tctggaatgt ctcaaacact   10320
agactcctgt gaacttcgcc cacgtgatgg acctgtgatc tttgtagcaa ttatttctgg   10380
agcacacatg tcttactgag gcatccagag tacttgtcaa ttcttgctcc tgaggtctaa   10440
ataacataat gtcatctatt ggtcataata gatcaatgtg atgttctgca gcaggtccag   10500
aaggtctctc tgactatatt atgagagaga acaatccacg gatatatact gtcattcatc   10560
tcatgtcatt gtgaatttct tagcctcctt tctaatggat atggaaagaa tgcaccagat   10620
caagacaggc aagctatgta catgagttaa gagtgtggta gttccctgtc atccaccgtg   10680 atccccttctt tttttttttt tttttttttt caggggggtag gctggtgaat taccttggga   10740
tccaatgggg gctaccaccc ctgcatcctt taaatctctg aaggtgcaat aatctctgtc   10800
attctgcata atataatact gttttttgatt tatcttctta cacagggatg acagttttaa   10860
```

-continued

```
ggacttccat ttgactttt  tctattacaa tagcttttat tctacaagtc aaggaaccac   10920
ggaaagcgtt ttccaaatgc taggtgtctc tcttccaatt atacatgtgg gaattataca   10980
tgggggaatg accactggat gggtccatgg acatgaactc actatgagac gatcctgtgc   11040
caggactcca cttattacct gacccttata agccccactc taatggagga agaatagtgc   11100
tataaatctc tgagtatcaa catcaatttg cccctttatc caaagtctg  caaaagatag   11160
aggtatttct ctttcttcag tgtatgttta cccaaattaa tggtggtaga gtcctttggg   11220
gaaggactgt gggcatcatg actgcatttc cttctgtggt gttgcaggtt ccttagtcac   11280
ggaaccttcg gtcttctcct tcagtctttg gattctggcc tagaaactgg gcaagagagt   11340
gtgactttcc actggggtgg ccagcctcag cctactgccc attcatcagc tctttatctt   11400
ttctggtttt atgtatatga agcaataccc ttattggctg cccatttat  ttttgttcct   11460
tggagcacca tgttctgtga gtcatctctg agattcctat gggctgattc cctaactgta   11520
gttctgaatt ttctgccctt acctatgatg gttaagtgct cccaatcatc ccaattgcca   11580
ctggttctgg agcagcacct tctactgtga gcctcagcca gaagaggaca gcagcttctg   11640
agcatcagtg gtgcctgtgg ccccatcacc actgcattcc ttattatctt aagagcagga   11700
gtattcctca ggcctcctga gaaatatagt tcgtttgtgg gttttctggt cttatataga   11760
aaatccattc ctgcatagtc atttatttga ggcttttgat ctttctttat aatctgctgt   11820
aacagttccc aacatttctc atttttaaag aaaataagtt aaagagagac cttttaattg   11880
atcaagagtg tgatcaacat taaagatata acaattatga aattcttata ttccaaataa   11940
tagagatcaa aactttactt aaaggaatag aagatagcca atttaattat cagtaattca   12000
tcgctatgac tggttcaaat tcagcaattt ttataccagg cattaaaaaa tgaaataggc   12060
ttgtaaatta ggtttatata acaatgaagg aaaagagagg atgtagacct ggaccaacca   12120
aaataaggac actcttgtgg ccttaggcat tctctcctgg aatggataat ttttattct   12180
tttatttatt tatttattta tttgagacag ggtctcactc tgtcacctag gctggagtgc   12240
agtggcacaa tcatacctca cggcagcctc aacctcccag gctcaagtga tcctcccacc   12300
tcagcctcct gagtagctga gactacagtt gcgagccacc atgcttggct aattttaaa   12360
atattctgta gagacgaagg tctcgctatg ttgcctagaa tggtctcgaa ctcctgggct   12420
caagccatcc tcccacctca gcctgccaaa ttgctgggat tacaggcgtg aaccctgtg   12480
cccagctttc aagttatttt ttttaaaagt catggtggcc atatcctgta tctctgtgta   12540
taatgtaata atgactagaa attagtacag aattatattt taaaagtcac caggctactc   12600
tggacatatc tatttgttt  aagtttccaa gaaccgtatt agcagtttat caggatcatt   12660
tctcttaagg cctttgccgg gatgttagac cctgtgtcat gggaccatgc ccctttatt   12720
agtttcctag ggctgctgta acaaagtacc acaaactagg tagcttaaaa caacagaaac   12780
ttattctctc acaattctgg agaccagaag tccaaaccca aggtgttggc agggccaagc   12840
tcctcctgaa ggctcttaag gaggcctcat gcttgcctct tgctggctgc tggtagctgc   12900
tgggaatccc aggcgtgcct tggcttgtgg atgcattgct ccaattgctg catttgttgt   12960
cacatggtct tctcccctgg tgtctgtgtc tatgatttca aattcccctc ttcttataag   13020
gacaccagtc atgaaatcaa tctattatga cctcatgtta acttgattac atctgtgaag   13080
actccatttc caaataaggc tacattcaca ggtatcgggg gttagaacat caacatatct   13140
attttggagg acagaattca atctacctcc catattgatg aactctccct tatccaactt   13200
tattacccta ctccctccaa atctagtaca ttcaggatcc attcccgggc atactttcct   13260
```

```
gcttcttgat gtaaatgttc atcagattct acgactcctg ctcccagtat cttttcttag   13320
ctcaaaagtg tattttctca tctaaagttt atattctctc cttttacaac ttctcccaag   13380 tactttaca  acaatcaaat tttctaagtg cttcttaaag gttagtaagg cctatagatt   13440
caatacctac agagtaaagc aaccatatta tatattttga catagacaca ctacatatta   13500
acacatagaa ataggctcca cttctgcaag gaaatatgtt gtatcattca aagttcttag   13560
ttgcaatcaa cagaatacac tctagctaaa gtggaatgaa atttcgtaaa gaatgttaag   13620
aattgggctg ggggcaatgg ctcatccctg taatcccagc actttgggag gccaaggcag   13680
ggagaggatc acctgaggtc tggagtttga gaccagcctg gccaacatgg tgaaatccca   13740
tctctactaa aactacaaaa attagccagg catggtggta cgtgcctgta atcccagcta   13800
ctcaggaggc tgaggcagga gaactgcttg aacccaggag gcagacgttg cagtgagccg   13860
aaatcccacc actgcactcc agcctgggca acagagcaag actccatctc aaaaccataa   13920
attaataaaa aataaaagaa tgttaggaat tgttcagact tcctggaagg atcaggtctg   13980
gatgctgtat tctccaggaa aaagcagcag agaacatata ctgctagact gttctggata   14040
aaacacagct gccaccactg cctgcttcta agtgttgatt atattgatga cttgttccag   14100
aaattctgcc acagcagtca cagaggagcc agttgcctct gttgcatttg aaaccatctg   14160
cactgccatt cccctgcatg ctgtatcctc ttcttgttct gtcccgtatc taaatctcat   14220
tcaagtgctt tggatttagc agagtccacc tctcatgcct gcattgtagc tgcaagagag   14280
cctaggaaaa gtaggtgttt ttttttgtttt tgttttttgtt gttttttatt ttgttttgtt   14340
tttgctgctc cagcaagatt caaaatatca agaattcatt aagatattgg acagctataa   14400
atgatggttg tctgctacat atgtgtgcta ctagtctaat ttttatttt caacttttga    14460 tacagacatg ggtacaaaac atattttct aatgtcttga ttttaactac tagaaaagta    14520
acagtgcaag tataacgtta aatggcaact gagctcacta tggaagtgac aatagggagt   14580 ggtgggact gtggtaaatt gagagccaat tgtagccatg acagagtgag agcttgatta    14640
tttcaggtct tcagattttt caaaatgaac aagaaatcca aagttttata tgtttgcttg   14700
tttctgcttt tttgagctat ctcctgatat ttatttattt ttttatttat ttaatacaat   14760
ttttaaaagt agagatgggg gtcttactat gttgcccagg ctggtctcaa actcctggcc   14820
tcaagcaatc ctctcacctt ggcctcccaa agttccagga ttacaggtgt gagccactgt   14880
gctgggcctt ggttttaaa  ctctgtcaat taatctaaat ttatttttta tttttattt    14940 tttattttg  agatggagtt ttgctcttgt cacccaggct ggagtgcaaa ggcacaatct   15000
cagctcacta caacctctgc ctcctgggtt caggcgattc tcctgcctca gccttctggg   15060
tagctgggat tacaggcatg caccaccatg tccagctaat tttgtattta taatagagat   15120
ggagttttgc catgttggcc aggctggtct tgaactcctg acctcaagtg atctgcatgc   15180
cttggcctac caaagtgctg gggttacagg catgagccac cgtgcccagc caattaatct   15240
aaattctaaa aaaaaaaaa  aaaaaaaag  caaagaccca tacacacatt ataccagata   15300
aacaaaacat ggctatgggc cacatatggc cattgggctt tcagcttgtc atctgtgact   15360 taggcttta  aagccataga gactatcttt ttttcctctt gttcatctaa tgatccctgc   15420
tgaggtaaga agcagtgagt ctctgcttaa atgggggat  aggaaagggt caaattacca   15480
ggaggaaaca aaaacagcat aggttaatac ctcaaaatct atgaagctgg gctgagtgct   15540
agggattttt ggttcctgac tttctgaaat tataatctac tggaagaggc aaatattaat   15600
```

```
ttaaaaatga gagacataga tactgggga gcattgactg ggctggcgtt ggccaggtgc   15660
actttattga gctccttttg aatgtggtgt gctgaaatcc atgctgataa gatcctattt   15720
caaatctcaa actagctctg gggatcgtat tttaaattct ccttcctttc tttaaaattt   15780
accatttatt gattatttat caagtgccag gaattatgct aagcattttg taactcggtc   15840
tcatttaacg ttcacagtag tcccatcttc ctttcataaa tgagggaact caggttgagg   15900
gaagttaggt aatttgctca aggccacata cctaataaat accacagtca gcattgaacc   15960
cagtactgtc tgtctccagg gcatgttctc tgaatcccac tgcaatactc ctccagaacc   16020
tttaaaaaaa agtctctgta ggtaaagcac tcgccattcg tcaggcgctt tctgattagt   16080
tcgtgtggca cactggtagc aataggctgg atagcaaatc tcagttgtgt tctcccttca   16140
ccagctgcag ctggatgatc cttgggcaag ttttttttgt ttgtttgttt tcttttcttt   16200
tgttttgttt tttaagtcag agttctcact ctgtcaccca ggctggagtg cagttcactg   16260
caaccgccac ctcccaggtt caagtgattc tcctgcttca gcctcctgag tagctgggat   16320
tacaggtgct tgccagcaca cccggctaac ttttttgtat tttagtaga gatgggtttt   16380 caccatgttg gccaggctgg tcttgaactc tgagctcagg tgatccacct gccttggcct   16440
tccaaattgt tgggattaca gccgtgagcc accgtgccca gctgggcaag ttttaaata   16500 ttctgagtgt ctcagtcttc tgagcgtctc agtcttctga gcagtaagat ggggatatct   16560
cctatttgtc aagactattt tgagaattaa gggagataat atatatttta tagaaacctc   16620
gtggagtccc tagagtgtag caagtagtca acgtccttca gttaattttc ttcttccagt   16680
agaatagcaa ctcaaggatc gtgtaaaaga caacatgagc taaatgggac cttttcagag   16740
ggcaaatttg aatgctgtat ttgtttgcta gggctgccac aacaaaatac tacagaatgg   16800
gtggcttaac aaacagaaat ttattttctc acagttctgg aagctagaag tccaagatca   16860
aggtttgatt tctcctgagg cctttgtcct tggcttgcag atattgcctt cttgctatgt   16920
cctcagatgg ctttcctcta tgcatatgca tccctggtgt ctctgtgtgt ccaagtctct   16980 ttttattat gtattttttt gaaacagggt ctcactctgt cacccagcct ggagtgcagt   17040
ggcgagatca tagttcactg cagtgtccaa ctcctgggct taagtgatcc tctcccctca   17100
gcctcccaag tagctgggac cacaggcatc catgccacca cacctggctc aaatgtcctc   17160
ttcttataag gacattattc atattagatg agggcccacc ctaagggcct catttaacca   17220
taattacgtc cttaagcacc tcatcctaaa tatagccaca tttggtggta ctgggggtta   17280
agacttcaac acatgaattt tgggtcacac atttcagttc ataccaaata cagtgagcaa   17340
gtaaattgat ttaaaaatac tgttttatat atatatttaa ctttagatag gctctctcta   17400
tattgcccat gctggtctcg aactcctggg ctcaagggat cctcctgcct cagcgtccca   17460
aactgctagg attgcaggcg tgagccacca cgcccagcca gtaaatggat ttttaaaata   17520
cgtaaaatta tctgcaagtt ctctcacttt gtgctccaaa tgttgatctt attacctatg   17580
aaacaaaaca aaacaaaacc ttttccgcaa ttagtgggaa catttgaatt gcaaagaaat   17640
agttctttaa gtgcctaagg actagttagc atatcttagg caattagacc cctggggctt   17700
ggatgtttgc tggacaactg tgcctgagaa cagagagcag gcacctccct agtgtgcaga   17760
gggccagcag tctgcagacc gcggctgtct atatttggag aaacaacaat gagaatgtca   17820
ctctagaaag aatgaagatt ctctgatcta aagaccaaac tgcagtcaag cagggaagga   17880
aaacgaaatg ggataaatag ctattatgga taattaaagt cctccaactc ctaagaaatg   17940
agttcgtttt tcttctctta ttcttaaata actttctcgt ctcctcccct ttttataaag   18000
```

```
ccttttttct gggcaggatg aatagatcct taaccctgtc tgtaagtgct tcaagccagg   18060
agtgatgtct ggaattgatc caccaattcc attcagttgg acaaggattc attgcttcca   18120
ggcacgatgc tgaacatgga gaataaagat gagttggaaa tggtcctggg atcagggaga   18180
ccttcattca tatatggaca caaatcagtg acttttttt ttttttttt tttttccgag       18240 acagagtctc gctctgtcac ccaggctgga gtgcaatggc accatctcgg ctcactgcaa   18300
cctccgcctc ctaggttcaa gagattctcc tgcctcagcc tcccgagtag ctgggattac   18360
aggtgccagc cactatgccc agctgatttt tgtatttta gtagagacgg ggtttcattc     18420
accatgttgg ttaggctggt ctcgaacccc taatttcagg tgatcctctc gcctcagcct   18480
tccaaagtgc tcagattaca ggcatgagcc actgtgcctg gcccaaatca gtggctattt   18540
acttagcacc tatgctgctg aatgaaaatg actctaactc catgtgagaa gtgttctaac   18600
agaggaatgt ataaaatgcc aaggaaacac cagggatggc agagaccta acgttcaggc     18660 aatgtctatt catttattgg tgataatgtg ttagtctttg tagggtcggc tcatgtatct   18720
ctgtgagata aatatttatt gtacagaaga ggatatgtga gattcagaga ggccaggtta   18780
tttgccccca agtcacacag ctcgcgtatc agtggcagag ctggaaatca aatccaggtt   18840
atctgactgc ccagaagcct ggtgtgttcc atgatacagg gtgaggggt tctgtcttcc    18900 tctgtgagct aggctataca agaaatggcc tgctatttga atgcttttaa aacaaatcaa   18960
atctggtcag gcatagtggt tcacacctat aatcccaaca ctctgggaga ctgagatggg   19020
tggattgctt gaggccagaa gttccacacc agcctggcca cacgctgaa accctgtctc     19080 tactaaaaat acaaaaatta gccgggcgtg gtggcctacg cctgtaatcc cagctactcg   19140
ggaggctgag gcacaagaat tgcttgaacc tgggaggcgg aagttgcagt gagccaagat   19200
tgcgccactg cactccaacc tgggtgacag tgcaagactc cgtctcaaaa aaataaataa   19260
aacaaaacaa atcaaatctg actctgagcc ccctgcctgg gggaagttag atttctgttc   19320
attttgatgc tccccttttg ccacagcaat attatgcaaa ggactcacaa acaactcagg   19380
aggtcctgct aattattgat cctcatttgc tcctgagccc atgatccctt gaagtggtgg   19440
ctcagctgcc actttgggca agaaaagtg agatcctgtg ctcagacccc tcccacagc    19500 tcctgatatc ccatctccaa ctggagagct gctgtgaggg gctggcttca ggtcagccag   19560
ctgtaggtcc tgcttcttgt ggagcccaca gctccttctt tcagggcttt cccttttgatc    19620 gttactttcc ccttctttct cccatctccc catactgtat gtcttccctc tggaaagtct    19680
cgggatgtct aagatgacac tgtgcacaca gagggtgctt gtgttggttc aggtcttcca   19740
agaaagcaga taccaagaca ggactcggca catacgagat atggtctcgc tctgttttcc   19800
aggctggagt gcagtggcac aatcacagct cactgcagcc tcaaactctt gagctcaagt   19860
gatcttcctg cctccgcctc ccaaagtact tggattacag gcatgagtta ctacacctgg   19920
ccaagagatt tattgaggga aaatggggaa ggagctggag gaggctgggg gagcattcaa   19980
actgctacct gtgtaggaga gagggaagga agaaaagcta ggtgggaaga ctttcagact   20040
atattacaat actgggacat tttggcatgg ccagtgcaga gtcctagagc cagtcgctgt   20100
cagaggagtc ctgcctctgg caggaaagaa cggcctcaca tccctgcggt gctcagttct   20160
tggcagaata acagcctgtg agaaagaggc gctgtcccca cgccaaatgg gtggttgatt   20220
cagagcacag cagctgggc tgtctgcaat taagcagtgc aaagctccac agcgctttca    20280
gttttcatta gccttcatct aaagcatctg catgtatata gagagcgcta agcttatgac   20340
```

-continued

```
tggtgacact ttattaatag caatagtgat agtacttacc acttattaat ataaagcact    20400
ttttacgtac caggcactgc cgtgaatcat ttacatgcat caatcattga acaaccctat    20460
gagataccca ttacgattag cccagtttag agatagggat tcttatgggc tgaattgtgt    20520
cttcatatgg atctgcccaa attcattatg gtgaaattct aaccctcagt acctcagaat    20580
atgagtatat ttggagatag ggtctttaaa aaggtaatta aggttaaatg aggtccttac    20640
ggtaggccct aatcgaatat gactgatgtc cttatatgaa gaaaaaattg ggacacacgg    20700
atacatagaa ggaagactat gtgaaggcac agggagaaga gagccatctg caagccaaaa    20760
agaaaggcct cagaagaaac caaggcctgc tgaaacctgg atctcagatt tctggctcta    20820
gaattgtagg aaaatacatt tctgttgttt aggccaccta gtttgtggtg ctttgttaca    20880
gcatccctgg aagactagta aaggtcaag taacttagcc aaagtcacag agctagcaca    20940
agggagagat agcactgggc atctctcagt ccagagtcca ttctcttccc ctgctcttct    21000
gagtcatgat ggctgcgcaa ggactacaaa gtaacaggta cagatgacaa agtgactcag    21060
gaagatcatt gagaaggagc atggcctggt gtgctgggaa cacacaggaa agtggtccaa    21120
ggaacctaga cagcaaagga gaagggtttc atatcttgcc tctacccact aagggctgtg    21180
tgaccttggc caatttgttc ttgctttctg aactacagtt gtattttgtg tcaaatggga    21240
gtattagatt tcccatgtct cactgagctg tattaatgat caaataagag aattacatga    21300
aagtatctgt agaggagggc agagggagag aactgaattt gcctcataca atattactgt    21360
ggttgttaca tattatcctt gttttagctg ctaggaatat actattatag taatgtgtca    21420
atattagagc atcagttttc tttcttttct tttcttttt ttgagatgga gtctcactct    21480
gttacccagg ctggagtgca gcagtgcaat ctcagctcac tgtaacctct gcctccaagg    21540
ttcaagtgat tctcatgcct cagcctccgg agtagctggg actacaggtg ctcgccacca    21600
tgcctggcta attttgcat ttttagtaga cgggggttt gccgtgttg gtcagtctgg    21660 tctcgaactc ctgacctcag gtgatctgcc cacctcagct tctcaaagtg ctgggattac    21720
aggcgtgagc taccacgcca ggcctagagc atcagttttc catcctactt aagttacacg    21780
tatttggttg ccagaaattc atggagacta ctagggcagc ccattataaa gtcctatcat    21840
ccaactgcct ctcagagcta atggcatcaa tgctaagtct agcatcatag actcattaag    21900
tgacggtgag gattaacgta ataaaaatag ctggtatatg ttgctttta ttatgtggca    21960 agttctgttc taaattacct aagtttgata actcatttat gacaatccta agaacaaccc    22020
tatgaagaag aaactattat aattcctagc ttacagatga agaaactgaa gtccagggag    22080
tttaagtaat taggctaaag tcacacagct gagtaagtgg gcgactcaac attcaaagta    22140
aggtacatga gctcctcagt tggacataga ttggagaagt gaggcatcca agatggcttc    22200
aagatatata tatatatata tttttttttt tttttttttt ttgagacgga gtctcactgt    22260
catgaagact ggaatgcaat gccgctatat cagctcactg cagcctccgc ctcccagatt    22320
caagtgattc tcctgcctca gtctcccgag tagctgggac tacaggcgcg tgccaccacg    22380
gccagctaat ttttgtattt ttagtagaga cggagtttgc catgttggcc aggctggtct    22440
cgaactcctg acctcaggtg atctacctgc cttggcctcc caaagtgctg ggattacagg    22500
cgtgagccac cgcgcccagc ctgatggctt caagattttt gctggagcaa ccaaagtagc    22560
aaaattgtca ttacttatga tgagaataac ttcaggaatt aatttttttt taggggaagt    22620
cagtttggac atgttaagtt taagctgcct tttaggtgtc caaggagatg tcagataagt    22680
ctagttataa agattgggag ctgttagcat atacatggta tctaaagccc agagcctgct    22740
```

```
tagatgtcca gagggcatag acagaaagca agagacccga gaatggagtc ctaggcattc  22800
tagtgtatat aggttgaggt aagaaggaat cagctataag agataaaaca gaagaattag  22860
gaggatgacc aagtgttttc ctggaaaaac ataaaatggc caagaaagag aaagtggtca  22920
attgtatcaa atgctgctgc taggttgatt aaatcagatg aggactgaaa atgacctttg  22980
gactgagcca tgaggagggc attgataacc ttaagtaggg cagttttggg ggctcaggtt  23040
gggaatacct ggctggagtg ggtccaggag agaacaggag gagaggaatt gaagacagtc  23100
atttctttct taaaaaaagg aaaatgagaa ataggaggat aactgaaaga gaaatgtctt  23160
tttattttag attctaatat gggaggaata aaagcttatt tataggcaac aggaatgatc  23220
tattatacta gggaggagaa cataatgaat gaagcgtggg ggtggggatt tctggagcaa  23280
tattcgtgag gggataaaag gggacaagat ctagtgtcca gggaaagggg ctggacttag  23340
ctagaagcat ggacaactgc atagacccca tcagtataaa tgcaggccgg caggtaggta  23400
ggtacattgg tagggaaatg gttaggttct tttccaattg ctttaatgtt ctggcacatt  23460
tactaagctt ctactctggg ctcaccggtt gaaattcaaa gctccttccc ttgttctacc  23520
attgcttttc actttgattt caataaaacc cacatcatcc agtaattata gctgcttgta  23580
tatgtgtctt tcttccccat cagcctaaga gctggaagaa ggcagataat atgtcacgtt  23640
gtctattgct ccccaatact tagcccagta cctgagacac agtaggcgct caatatatat  23700
ctgatgaact gaattgaatc cagtgtattt gtttctctat acttgtgccg gaaatttgat  23760
ttccttgagt cataagaacc tgccaaggtg ccgggggcgg tggctcacgc ctgtaatccc  23820
agcactttgg gaggccaagg tgggcggatc acgaggtcag gagatcgaaa ccatcctggc  23880
caacatgttg aaaccccgtc tctactaaaa atacaaaaat tatctgggtg tggtggcgca  23940
tggctgtaat cccagctact caggaagttg aggcaggaga attgcttgag ctagggagtc  24000
agagattgca gtgagccgag aatcgtgcca ctgcactcca gcctggcaac agaccgagat  24060
tccgtcccca aaaaaaaaaa aaaaagaacc tgccaaggtt atctttcata tgaacttgtg  24120
ggcaaatgac ttgtgttta tccaaactat tgggttaacc attatattag ctatttatca  24180
ctgcatttaa tatttatgaa aacttgcaag ctttaattat ttttaaaaag acttggacct  24240
taagtgggcc atgacagtat cctcagaaag atgacaataa gtaagaggat acaacttcct  24300
ttataattga cagatagggt tccgtttgtc caattacttt tttttttaaaa gaagagataa  24360 attcactgta atgaatgtgc cataattgga atctatagag gtctaccatt tgaataaaag  24420
gtgctggatg atcacctcct tagaggaacc atctaaggag aaaaggatat acaaccaaat  24480
gggtgtgcat tgtgatagaa aatgtccctc tccacctcca cttagtatt tattaagact  24540 tagaaaaatt aggccgggca cagtgcctca cacctataat cccagcactt gggaggctg  24600 aggcgggcgg atcatctgag tcgggagttt gagaccagcc tgaccaacat ggagaaaccc  24660
cgtctctact gaaaatacaa aaattagcct ggcatggtgg tgcagacctg taatcccagc  24720
tactcaggag gctgatgtga gagaatcgct tgaacctggg aagcagaggt tgcggggagc  24780
cgagatcgtg ccattgcatt ccagcctggg caacgggcaa caaaagcaaa actccgtctc  24840
aaaaaaaaaa aaaaaaaag acttagaaag gttaaggtca actgtatcag ctgggtcgag  24900
caatgtgaac aaagtctgtc aatgctcttt cagcaggaaa tgcagtatag catattgttt  24960
tagacataga ctctggactt gggcctctat cctacctcaa atgacttagt ttcctcatct  25020
ataaaatgac atgatgacac tgtctacctc atggggttgt tataaaattt aaatgattga  25080
```

```
ttgaatgttt ataaaagtcc cacacaatac ccagaacatc agtagtttta gccactataa   25140
cttactttaa taataataat aatatttaat aataataata acttacttta ataataatag   25200
taatacctcc atagtattct actatgggtc ttccttttg tttttcatct gctggtacct    25260
tttttctttt tgcttagtat actttctttt tcctttaatc ctggctttta ttttctgcct   25320 atccttttc ccatgtagaa aaatcgatgg gacaactgag gaagaagata acattgagct     25380
gaatgaagaa ggaaggccgg tgcagacgtc caggccaagc cccccactct gcgactgcca   25440
ctgctgcggc ctccccaagc gttacatcat tgctatcatg agtgggctgg gattctgcat   25500 ttccttggg atccggtgca atcttggagt tgccattgtg gaaatggtca acaatagcac     25560
cgtatatgtt gatggaaaac cggaaattca ggttggtatc agtccatggt ggaagacttt   25620
tctttttgag acagggtctc gctcggtctc ccaggctaga gtacagtggc acgatcttgg   25680
cttactgcag ccccaacctg ccaggttgaa attaacctcc catctcagca tcctcccatt   25740
tcagcatctc agataagtag ctcctcccat ctcagcatct cagcatctca gcatctcagc   25800
atctcagatc agtagctgag actacaatcc tgaggaaact gttgactgca gctgtgtcaa   25860
tactttgctc cttgagagaa agccctgcaa ttccttcagt gatatgacaa aaatggagag   25920
tggctacttg tgctgggcat tgtgcagaat gatggggata gaaaggtgaa tgacctagac   25980
tgagccctgt cctcatggag acaagtaagt gatgacagtt tgagggggta ggtgccacgt   26040
tggaggtaca caggattctt gggctcatag gagagggcac agcccagact tccctattgt   26100
gaacaaattc ccaaagtgat ggctggacca ggcaaagagg gtgtggtgtg gtgggaagaa   26160
gaatgtttga agaaaaggt actgtgaagg actgtaagaa agagacagag agagagagag     26220
agagagagaa cgtacacatg ctatgtaggt atattttagg aactgaaaca ggagctcatc   26280
atcttttctg tgtcatggac tcctggagat gactaatgaa cctttgccaa agtaatgttt   26340
taagttctta aaataaaaca caaggatga caaaagaagc caattatatt aaaatataaa     26400
taccaaaaca tttaaaaatc acatttgtga catagaaaca tatgggcttc tttagtagta   26460
catcagtgac aaaatctagt attgggtcta acatttactc tgattttaag ttggaatgta   26520
tgccattgtt ggaaatagtg gccatgactg taatacgatt tgaacatatt gctatttcc    26580 acgtgggaca cagtcatagg tactagtcat atgacggtgg cttgttgcct acattcataa   26640
tggcagaaaa tgctaaattt tggttaagag tgaaaataaa gatgcatgtt ttcttcccat   26700
ccaagttctc agatgcacag gattccatcc acagactcca ggttgagaac tcccagtgat   26760
tgggtagagc acgttgaggt ggaggcagcg aagtaaatag ggggctgatc atccatagcc   26820
tggtaggcat gtagcaaggg gctgcaagca tggaatgatc acatctgtgc tccagattgt   26880
tcactgcccc attgcagggg gccagattga ggtaagatag gaatggaggc cacagggcca   26940
gttcagaggc catcatagtt ataagcaagg atacttcgaa gtgacttaaa tagtattgtt   27000
ttaggaatca ctggaaacat aaaatctggt ttgctgctta aacgatagac ctagagaagt   27060
actgaggtta tgggtaaaa gaaacaaaca aaaatgtctg cccagtggac accccataaa    27120
tgcatgtttc atcgtactaa actcacacac tgcaatgact catgcagaaa tccgttcatc   27180
tgcagagaga catttaatag ttctctggtc cctccctcta tttgaagaaa catttagatc   27240
acagtttttt gaactagtgt ctgggaaatc actgcactgc aggctgtgcc atgaagaagg   27300
cagtgcgaga cctggagccc atactgtgct gtgtcttatg agactttcca agagggagac   27360
gtggtaggca atattttctg gactgacttg atcatagaat gctctctttc atgccatatc   27420
tattagcatc atctggcaca gtctcctgcc aggcactggt ttgagaaaat ttgatttcaa   27480
```

```
tctgtcaaaa gaagtcttta gttggtctgc aagctatttg tttttgcttt tttcaaacca   27540
agagattatt ctgccagagg aaaacagcac catggagatc ctcctaacta gtctctattt   27600
gatgccacag ccaaatctgt cctaaaagga tatcctgtct tttgtgtggt gtggggata    27660 gaggtagaag ggcatatcat gcgtttttaa aataaagaat gatgtatatt agcaaggttt   27720
cagatgtgta tcacatgcat tctttcagcc ttttgtgagc aagaccagct aattaaaact   27780
tgtctgctga ggcccagatc aaaatgagat gctgttttgc atttgtttgt tgcctgaaaa   27840
gatagacctt ggtcaataga gtctgctctg aggcatatgg aaaagacatt ttgattaacc   27900
cgaggaacaa tgctagtgtg cgctctctag tttctacggc tgtgccctct ggagtcttag   27960
agaaactgat taaaatctga aatatggttt aaatttttt cctctggact caggagtagg     28020
aatttagtat cagtaactct agtacagctc taatttatag cagattattt ctcttgtccg   28080
cctagaacaa agcttagata tcaagtgagc atgttcaacc aaatgacaaa tactttgcta   28140
attgtattaa gaaaggctct gaatggctgg tatgtttgtt tggttttct gttttaaggg     28200 aaaaactaga tatttggcac tgagatatct ttaaatcttt atttcaaaag aaggagagaa   28260
ataagcagta tgaataggta gatctttcaa atatgtggca tatgttctac aagggtatg    28320 aagagtgatt ttaactaaag cgtgaacact ttttttttt tttgaaacgg gatctctgtt     28380
gcccaggctt tagtgaagtg gtgtgatcat agttcaccgc agccttgacc tcctgggctt   28440
aagtgatcct cccacttcag tttccaagta gctgggtcca caggctcatg ccaccattct   28500
tagctaatta aaaaaatt tttttagaga tgggatcatg ccatgttgcc caggctgatc      28560
tcaaccccct ggcctcaagg gatcctcctg ccttggtctc ccaaagtgct gggacaagca   28620
tgcaccactg tgcctggccc atattttaaa tttaatagtt atgagttaaa acatgtgaac   28680
tcttagaaaa gtgtttggca tatagtaaga aaataaaatg accgaagttt gagaaacttg   28740
tgattttgtt ttctcattac tctcaggaaa agtccaaagt tcttcccatg gattgtgggc   28800
cctgtaggat tcagagcatg ggcttttgaa ctggccagac ctggttttaa tgagctctgg   28860
gaccttgaat aagttgccct tgtgtcctgg tcagagattg ctggttgcga agaaatgtgc   28920
agtgaaactg gctcgagtta aaaggggatt attggggccc ggcatggtgg ctcatgcctg   28980
taatcccagc aatttgggag gccaaggtgg gtggatcacc tgaggtcagg agttctagac   29040
tagcctggcc aacatggtga accccatct ctactaaaaa atacaaaaaa tttggccaga    29100
catggtggcg cacacctgta gtaccagcta cttgggaagc tgaggcaaga gaatcctggc   29160
agttggaggt tgtagtgagt cgagatgtgt gagactccat ctaaacaaac aaacaaacaa   29220
acaaaaaatg gtagtgggga ttattgtagg gctgtaagag gatctcgtga agccaaggg    29280 cagaaagcag gtctgtggtg tatgtgtgca gtctgcaccc aggacgcaga agccagcctg   29340
aggtggggct gaaacccagg ctgtcctcca ccctgaggag ggaagggagt ctttatgtaa    29400
ttctttctga ggccgcagga caggccctgc cagaagtgct gaatggagct ttccctcgtg   29460
ggaactagag aagcctttgc taaggtctcc agcttgcttg ccccacagag tctttcattg   29520
gcttttcttg gagtcagctc cgttttccct ggtccttcat ggactgcttt ctttcctctt   29580
ccctggcttc tcactgccct ccacagtgga agtgccttga gcctttgtct tgctaggaag   29640
ctgatttact tggccctgac tctgtgactc cgtgggactt attggggttc aagagtgcac   29700
tattgtctaa ctagaatctc tgtgggtttg ggttgctgtc tctctctctc tctctgtgtg   29760
tgtgtgtgtg tgagagagag agagagagag agaaagagaa agagacagag acacagagag   29820
```

```
agggagaggc tgactggctg agcctagcct atggctttgc tgtcttaaac atttttttttt    29880 tttttttttt ttgagacaga atcttcctct gttgcccagg ctggagtgcg gtgacatgat    29940
ctcagctcac tgcgacctcc acctccccgg ttcaagcgat tctactcctt aggctatcaa    30000
gtagctggga ttacaggtgc atgccacaac gcccagctaa ttttcgtatt ttaaaaatag    30060
agacgaggtt tcaccatgtt ggccaggctg tcttgaact cctgacttca ggtgatctgt      30120
ccaccccggc ctcccaaagt gctgggatta caggcgtgag ccaccacacc tgactggctt    30180
ggctgtctct actcaggtgt ccagtcagct gtggtagtca gtcggggaga atcccatgtt    30240 gcggggaag gtgcaatcct ctcagaagtg tgagcagaca ggaactgaca tttctagaag     30300
ttccttgcta accctcattg cccttattgt gaaatgggaa taaaaggact gctttgaaga    30360
tcaaataagc taacctatat aaataccta tattagttcc ctaaggctgc cgtaacatat     30420
taccacaaac ttgatggctt aaaacaatag aaatttattc tctcagagct gtggagaccg    30480
gaagtctaaa tcaaggtgtt ggcagcacct catgccctct gaagactcta gcagagaatc    30540
tttccttgac tcttctagct tctagtggct gcagcagatc ctcggtgtgc gacaatgtca    30600
ctctcatgtc tgcctccatc ttcacgtgga catctttctg cgtgtctcct cttttgtctc    30660
aaatctccat ctgtctttct cctataagga cacttgtcat tgggtttagg gcccagctgg    30720
atagtccaga tatctcattt taagattctt gacattttca catcagcaaa gacttgtttt    30780
ccagataagg tagcatttat aggtcctggg gatttgatgt ggatatcttt tggggggccat   30840 tttttggcct ttcacaatat ctgacacagt gttttggttta ttatagtgat ggtccatata   30900
cagggccatt tttttaaaaa tttataattt taaaaaattt tattgtgata agaatgctta    30960
acatgagagc tactgttta ataaagtttt tagtgtacaa tacattatgg ttgactctaa     31020
gtacaatgtt gaatagcaga tctctagagc gtgttcattt tgcttgactg aaactttttc    31080
ccattaatta gtaactcctc atttccccct cccccagcac ctgacaacca tcattctact    31140
cttcaagtct atgaatttga ctattttagg tatgtcatgt aggtggaatc atgcagtatt    31200
tgtctttctg tgactggctc atttcactga gtgtaatgtc ctccaggttc atgccagttg    31260
ttacatcttg cagaattttc ttctttataa aagatgaata gtattccatt ggtgtgtata    31320
ccacatttcc ttttttttt ttttgagatg gggtcttact ctgtcaccca ggctggagtg     31380
cagtggcaca atcttggctc actgcaactt ccgcctccca ggttcaagcg attctcctgc    31440
cccagcctcc tgagtagttg ggattacagg catgtgccac catgccaggc taattttttat    31500 attttagta gagacggggt ttcaccacat tggccaggct ggtctcgaac tcctgacctc     31560
aagtgatcta cccgccttgg gctcccaaag tgctgggatt acaggcatga gccactgcgc    31620
ccagccacat tttctttatt catctgtcaa cgggcattca ggttttttcc acgtcttggc    31680
tattgtgaat aatgcttcag tgaacatggg ggtactaata tcttttttgga tcatgatttc    31740 aactcttttg gataaatacc cagaagtggg attgctaagt catacattcg ttctgttttt    31800
aagttttgga ggaacctctg tactgttccc atggtggctg cacccattcc caccaacagt    31860
atataagggc tttattttct cttcatccgc accaacactt cttgtctttt gtttttgata    31920
atggtcatcc taacaggtat aaagtgacgt cttatggtgg ttttgatttg catttccctg    31980
atggttagtg acattgaccg cctcttcatg tagatattgg ccatttattg gtcttctttg    32040
gagaaatgtc tattcaagtc tttagtccac tattatggtt ttaatgggtc tcaaatgaca    32100
atgaaagtca gttctcagca gcctaggggc tcttcttcat gtattattc tttcagagat     32160 tgacagaagc actatttccc cagagagaaa ggcatgagaa agggatgttg tgattgacaa    32220
```

```
ttagcagctg gttgaagtgg gagttagaga aagggtctag ttctccctct gtcttggatc   32280
ctcaggtaat tctgtggatc tgggcaaaga agtcttgtct ctccttagtg agaaaattaa   32340
gtctctccaa gcaatagaaa gaatatcgtg ttttggggtt aggcagatga gaggttttgt   32400
gtcccctttt ccttgcaaat agttgtatga ccttggacaa gtaaactaat ctctctaagc   32460
cttagtttcc tcatttgcaa ttacctctag gtgttttaaa gattaaagga ggaaatctgt   32520
agaaagcacc ttagtgaaat catattccac ctctgctcaa attttccaat ggttttcatt   32580
tctctttgtt taaaagccag agttccggtg atgtcttaaa gaacccttca tcattgtaac   32640
ctctcttgca ttaacaccta ttctcttcct cctcattcat taccctccag ctgtactgac   32700
atactgcttt tcctctaaca cgcaagacac aaccctacct tgggtccttt gtacttgctg   32760
tttctctgcc tggaaagctc acatctcaaa tgaccatatg acttgctccc ttcctttctt   32820
taggtcttta cttaaaactc atcttctcag tgaagacttc cctggccgtt ctatctaaaa   32880
tttaccccac cacactgcca tccaacactt catattccct tcccttcttt atttttcat    32940 cttattgctg gttaccatct aactctgcct gtaattgttt atcacctgct atctccactg   33000
gcatcttcaa aatggcagga gtcactacag ctgttcactg ctgtacccca gtgcatagaa   33060
ctatgcgtgt tacacaataa acacaaaata cagatttggt gagctgattt gaattaatga   33120
tagctagcta gttcctttt accattgagc ttcaactttc taatccgtaa aatgagaaat   33180
agagagtata ggccaaagtg gcttggactg tgagctccta gaaggcaaag acaatgcttg   33240
tttgagtctg tatttacact gtccagcacc taacattgca ttcaggaagc acaggacgaa   33300
cgttgaacag atgggcggat aaatatgtaa taacttgtga caggaaaata agataagcag   33360
tgatgaaaat ttataaaaca tagtatgttg ataattagga accctcttac tccatatttg   33420
cattttgata tcaaaaagct ttacaaagcc attcatttat tcattcattt ggcgaataca   33480
cacttgtacc ttctatgttc ccaggcgttt gatttaggta ctaagactat aagtcaaaca   33540
ggacatggct gctatcttag agtttcttgg tgccctgtgt gggaaattga catgtggatg   33600
tccattcact gaagacagca ctgtgttggt gccatggctg tgggaccaaa ggtctgtaag   33660
acaagcccaa gaaaagggga ccagttcaat tttcgggatt caggaagttt cctctgagga   33720
aggaccattt acaatgagtc taaaaagaat gagttacttt acctgggaaa gaatatgagg   33780
aaagggattc cagccctaga gaatcacatt ttcaatggcc taagggttgt ggaaggttgt   33840
gttgttgcta ttgccatcag catagtatca gtaatggctg ctaacattta ttgagtctac   33900
actgtgtgcc agtcactatc ctaatctgtt acatgcaaaa tctctaagca gagagataac   33960
ctactagaaa tattcatgcc atttatcccc acacatccta tggataggta gaatgggctt   34020
tattgtcctc attaagaaat gagagactta agactctaat tctctttgtg ctatcacaaa   34080
actggcatct gaataatgta gtaaataact tagtagcccc ccaaaacccc attttttgtt   34140
ttattcacaa gctattttat tttctcctta gcattcattg ctattttgtg ttttttctct   34200
ctgtgtatat acatatatac acacacatta tatatattat atatatatag agagagacac   34260
acacacatta gatatatgta ttttagaga caggagcttg ctctgtcact cccactggag   34320
tgcagtgtgt gtttgtagct taccttaacc ttgaccaact cctgggttcc agggatcctc   34380
ccatctcaac ctcctgagta gctaggacta caggcacaca ccaccacacc tgctagatt    34440 tgtattatta ttattattat tattattatt actattgaga tggagtctct ctcagtcacc   34500
caggctggag tgtagtggtg tgatcttggc tcactacaac ctctgcctct tgggttcaag   34560
```

-continued

```
tgattctcct gcctcagcct cccaagtagc tgggattaca ggcgtctgcc accacaccca    34620 gctgatttt  atattttag  tagagatggg  atttcaccat  gttggctagg  ctggtctcaa    34680
actcctgacc  tcaaatgatc  cacccacctc  tatctcccaa  agtgctggga  ttacaggcgt    34740
gagccattgc  acctggccta  gctggctaga  ttttgattt   tttgtagaga  tggggtctcg    34800
ccacgttgcc  caggctggtc  ttgagctcct  ggcctcaagt  aatcctcttg  cctaggcctt    34860
ccaaagcatt  gggattacag  gtgtgagtca  ccatgaccat  aatataaat   acatatatat    34920 ttaaatttgt  acataatctc  ttattacaag  gtgaaatcta  tgagagcagg  acttttgtt    34980 tgtttgtttc  attttttttt  tttgagatgg  agtctcactc  tgttgcccaa  gctggaatgc    35040
agtggtgcaa  tctcagctca  ctgcaaattc  catctcccag  gttcatgcca  ttctcctgcc    35100
tcagcttcct  gagtagctgg  gagtacaggt  gcccgccacc  acgcccggct  aattttttt     35160 gtattttag   tagagatggg  gtttcaccgt  gttagccagg  atggtctgga  tctcctgacc    35220
tcgtgatcca  cccgcctcag  cctcccaaag  tgctgggatt  acaggtgtga  gccaccgcac    35280
ccggccggtt  ttgttttta   agatggggtt  tcactctgtt  gcccaggctg  gagtgcattg    35340
gcactatctt  ggctcactgc  agccttgacc  tcctgggctc  aagccaggag  ctcaagcca     35400 ggctgaggtc  ccacctcagc  ctcctaaata  actgggacta  caggcacaca  ccactacgcc    35460
tggcccagga  cttttgcttg  ctgctatccc  caagtatgta  agatgccctc  cataagtatg    35520
tgttaaataa  atgaaaaaag  aaagacctca  tgaggtaatt  attgtgtagg  ctcattggta    35580
aaaaatggtt  gtcagccttt  ttctaacaaa  cacaactata  tctgatttct  catttccaga    35640
cagcacagtt  taactgggat  ccagaaacag  tgggccttat  ccatggatct  tttttctggg    35700
gctatattat  gacacaaatt  ccaggtggtt  tcatttcaaa  caagtttgct  gctaacaggt    35760
aagataaatt  gatataacat  gatacaaacc  aatgaaatgt  ggctttgtac  ctataaattc    35820
tgcatagctg  gctctcaatt  tggggtgca   gaatgaaaaa  caggagccat  ctggatagat    35880
gcaattcaca  gatactgatc  ccaaatgacc  ctgatcttaa  tttattttta  tttttatttt    35940
tgagacggtg  tctcactctg  tcacccaggc  tggagtgcag  tggtgtgatc  ttggctcact    36000
gcaacctctg  ccccacccccc tcccccaccc  cactcggcat  tcaagcaact  ctggttcctc    36060
agcctcctga  acagttggga  ttaaaagtgt  gcaccactac  acccagctaa  cttttgtatt    36120
tttggtagag  acgaggtttc  accatgttgg  ccaggctgat  ctcaaactct  tgacctcaag    36180
tgatccaccc  gccttagcct  cccaaagtac  tgggattgca  ggcgtgtgag  acaccagcgc    36240
ccagtcaaga  gtttctttt   atttcgtttt  tcatccaatt  aaatttacct  tgcaactctt    36300
caagtgatta  tgtggtaaaa  agaccaatca  actctgagtc  aggagaaatg  gttcctgccc    36360
cctaactgga  tcactgggtg  acctctattg  agtcactttc  cttccctccc  tgggcctcag    36420
tttcttcatc  tgtgaaatga  acattggac   tagattgtat  ttcagttccc  cttgaccagt    36480
gacattctgt  aatcttaggt  taatatcacc  cagtaccata  aaggttttct  cagatgagtg    36540 gtggggctt   gcctctagac  tgcaagatgt  gtctctaatg  tccttgagac  tctgtagtgg    36600
gtgtttgagc  aattaaaagt  acccaagaac  agagtgagct  gtctcaagaa  gcagtgagtt    36660
ctctgtcacc  ggaggtattc  aagcagagga  ggatggccac  ttgggggaga  tgttgtagaa    36720
tgtatcatgt  attagaaaag  gagtgaacta  aatctctcca  ggtcgcttcc  aatttgtattt   36780 cccatatgac  tttccataaa  tggatttcat  gaagtgcatt  ccattttaa   aaagtggttt    36840 ttttttcaa   attctaaagc  acaactcatt  agatagttgt  gaaaacaata  taatgattta    36900
ccaatgagca  ttttaaaaa   agagagaaat  agaagaaaag  ataatcaaat  agaataaaat    36960
```

-continued

```
agaaaatatc tgaatgcatt gcacataagg gtaaatattg gttttttgaga cttgtttcag    37020 ttacatttgt atgtatgagt atggactggg ttgcaatata aaatatattt tgtttatggg    37080
ttaaggtaaa aaaattggaa gccactacca taagatctaa ataggaataa gcatatattt    37140
atttaggttc ttgtctaatt tatgtctttt atttattgtt agttatctat tgtattcttt    37200
ttaaaaagtg ataaaatatt ggttgctatg gtttcctggg ttaccgctta cacctcagcc    37260
ttgaaaaaaa atcacacata atctaatttc ccagcacata aaaagagtgg aaacatcatc    37320
aacataagtg agagggggaag aaaatgctgc ttgctctctt ttcccagggc accctgagct    37380
ggccaggaaa tgggagctaa gacaggtaca caacctgtct tgtgcttggc tggtcccagg    37440
acatacaatg cttcttggat agtcagtgtt tctgactctg ggaagcagga aacaacctca    37500
aacatacagt aacagtcaga aaagatcagt cggtggggaa ccaggcagga tggtaggtct    37560
ctagcaagct tacctgaacc tggccaatct ccaacttttc aggacatcat ccaggcagga    37620
catccctgtg ccaccaaaaa tttgttcata gttggtccag gggccagagc ttgggaatca    37680
aagaagccca agagtctagc ttggggtgca ctagacccta acacatctat ttctccaaat    37740
tacaggtgcc agccgccatg cctggctaat ttttttgtatt tttagtagag atggggttca    37800
ccatgttggc caggctggtc tcaaactcct gacctcaggt gatccaccca cctcagcctc    37860
ccaaagtgct gggattacag gtacgatctt ccacaggga tttccacagg gatctttcat    37920
gaactgttag gtttgtttct ggtgcttagc tgaagtagca catccatcag cagacctgcc    37980
gaataacaca atgctttggt ccccccagggt ctttggagct gccatcttct taacatcgac    38040
tctgaacatg tttattccct ctgcagccag agtgcattac ggatgcgtca tgtgtgtcag    38100
aattctgcaa ggtttagtgg aggtaggaga tactttcctt acagtttttg atattgctag    38160
agacagcgca gtcctttaga aaattcacct tctgaagaaa atcccccttta ctcagttttt    38220 ttctatattt tcttccttttt cctgctgttt ccattctctg gtaatggcta aaattgcaag    38280 aatttttaatt aaaatgcctt gtgtgattttt acatttatga acaataaagt acccttgcat    38340
aatgatctta gagataatct aacctgaccc tcttcatttt aatagatagt gtaactgaag    38400
cccaaatcta cagttcacat agcagaggct cattccacta aaacaattta agtggattca    38460
ttaataaatc tgtacatttt caagggtgta gtctgatgca gagatttaat tcaatgaagg    38520
aggcagcatg atatggagcc agaaggtaaa tattttggac tttacaggcc ttacagtgtc    38580
tgttgcatct actcaaccct gctgttatag tgcaaaagca gccagagaca atatggaaac    38640
aaatgggcat ggctacgttc caattaaaca ttttacaaac tgaaatttga acttcatatg    38700
attgttgtgt gccattaaat attactcttc ttttgatttt ttttctcacc attttaaaat    38760
gtaaaaaaga ttcttagctt gtgggctata caaaaacaga tggtgaacca attggcccat    38820
agtttgccaa ccctcgatat acagcaatgt ttcccaaaca cagtcattca cctctgacct    38880
tcgccagttt gttatgccca tgtacaactt gtactattat ttgcctattg ttttccccta    38940
gatcgactca tttaaaacaa aaaacaaaag atacctatta ctctaagcaa taccatcttt    39000
gaaatcatgg gtttgatgtg ttagttacat cttttccttt tttttttttt tttttttgag    39060
atagagtctc gctctgtagc ccaggctgaa gtgcggtggc atgatctcgg cccgttgcaa    39120
catctgcctc ccaggttcaa gcgattctcc tgcctcagcc tcctgagtag ctgggactac    39180
aggtgccagt taccacaccc ggctaatttt ttgtatttttt agtagagatg gggttttacc    39240
atgttggcca ggctggtctt gaactcctga cctcaggtga tccgcccacc tcagcctccc    39300
```

```
aaaatgctgg gattacaggt gttagccacc acacccagcc actagttaca tcttttcaa    39360 agcatacata tatatagtag aattatatat aaatttaatt atatatagat taattataac    39420
atatatacta gtgtatatat gtatatataa tatatacata tatagtatat ataatatata    39480
tatagtgtat atatatactg tatcatatat agtgtatgta tataatatac atacactagt    39540
atatatatta taattaaaaa tgtaagttgt tatatcattt caaatccaac tctagtccca    39600
ctagagggac atatatgaca ctttgggatg tacccgtgta gtggaaagaa cacgatatta    39660
gcatccatga agactaaatt ttagtcactt aacagccctg agtctcaggt tctgtatctt    39720
gaaatgagtg gatggaccaa ctgattgtgg aaggctcttc ctacactgat agtctatgat    39780
aatatgaaat ataaatataa agaccttttc ccccatctcc taccatgctt acatgtgaag    39840
tgtatttgaa tttcagcatc tgtactgtga gtcaaaatag ctcaatcatg ctgtttagtg    39900
tctgttttag tccatttggg cttctacaga ataccataaa ctaggtaggt tataaacaaa    39960
agaatttttt tttttttttt tgagacagag tctcactgtg tcaccgaggc tggaggcagt    40020
ggtgtgatct cagctcactg caacctctgc ctcccaggtt caagcgattc ttctgcttca    40080
gcctcctgca tagctgggat aacaggcaca tgccactgca cccggctaat tttgtattt    40140 ttggtagaga taggattttg ccatgttggc caggctggtc tcgaactcct gacttaggtg    40200
atccgcccac ctcggcctcc caaactgttg ggattacaag cataagccac tgtgcctggc    40260
cttttttttt tttcagtctc gctctgttgc ccaggctgaa gtgcagtggt gcaatctcag    40320
ctcactgcaa tctctgcctc ctgggttcag gcgattcttg tgcctcagcc tcccaagtag    40380
ttgggattac aggcatgcac caccatgccc aactagtttt tgtatttta gtagagatgg    40440 ggtttcatca cgttggctag gctggtcttg aactcctggc ttcaagtgat ccacccacct    40500
cggcctctca aagtgctggg actacaggcg tgagccaccg ctcctggcct agaaatgtat    40560
ttcttacagt tctggaggct gaggagtcaa agatcaaggt gctggcagat cggtgacttg    40620
ggagagctag cttcctggtt cataaacaac taccttctct ttgtctgccc atggcagaac    40680
ggatgaggga gctctctgga gtttctttta caaggcacta atctcattca tgagggctac    40740
acccttatta cttagtcact tcccaaaggt ccatctccaa ataccatcac attgggaatt    40800
aggttttaac ataggaattt ggtggggaca caaacattca acctacaaca gtgtctgtaa    40860
attgggcttt tatattgtag cctgtgtgaa gaagcagcat ccatattta aacacaagca    40920 gaaactcag tcaaatcaac taatctattt tcaactcttc tgccagggtg tgacctaccc    40980
agcctgccat gggatgtgga gtaagtgggc accacctttg gagagaagcc gactggccac    41040
aacctctttt tgtggtgggt atattagaat cgtaacaaat tttatttatg aatgcttttt    41100
ttgggttcat gcagtggctc acgcctgtaa tctcagcact ttagggaggc cgaggcagga    41160
ggatccctgg agcccaggag ttcgagatca gcctggacaa tatagtgaca cttcgtcttt    41220
aaaaaaaaaa aaaaaaatta gccgagcatg gaggtgtgtg cctgggatcc tagctactag    41280
ggaggctgag gcaggaggac tgcttgagcc tgggaggttg aggctgcatt aagctatgat    41340
ggccacagca ctccagcctg agtgacagag tgagaccttg tatctaaaaa gaaaaaagaa    41400 aaagaaatg gaatgctttt ttggcttcaa gcaactgaaa accctactaa gggcttaaa    41460 atgagtctat ttatttata taacagaatt ctaaaggtga gtggtggcta gtgttggttc    41520
tgctgctcaa aaatccatcc agggcctagg catgttctga cttctactc tgctatcctc    41580 agacatagct tttatttac ttctgtgctt attccatctg tccctttcat caggaaaaca    41640
aaagctttcc caaagccccc taccaaacctt ccactttaat ttctttggcc ctaactgtat    41700
```

-continued

```
catatgcttt actaaatgca gaggaggcta ggcaagcaga tgcctagctt caccagcctc    41760
ttcaggagtg aagggaagg gagaaagggt tggaagtggt tgttggatta gccaacaaat     41820
gacatttgct aaggacaaaa gtggaaagat gggatcatca agcatcccac gcctcttctt    41880
tttatatgaa actaaagttc agtgacttgc ccaagatcat ggagctagaa caagacctga    41940
actgttgatc tggaactttc cttacttcac gctcctacca tgtacacatt gtcatataga    42000
aatgtaaatt aatttttgtc attatatccc agataataag aagtagagac catccatctt    42060
atctgaaagt aaatgagtag ccccaagta gtatgtgact ttaattcctg catctccaaa     42120
cttcaccttg ctgaggttgc catctccaag ctacccctgt gggacaggcc tctctaggtg    42180
tggctgggtc cctaggaatc aatcaacaac agaacaacaa cagcacatgc cgctgccatc    42240
aacacagtgg taaatgtgtc gggggaaggg gcccatgaag gtaaaagtac cttagaccag    42300
ccaggcatgg tggctcacac ctgtaatccc agcactttgg gaggctgagg tggaggattg    42360
cttgagccta ggagtttgag accaacctgg gcaacatggt gaaacccat ctctaccaaa     42420 aatacaaaaa attagctggg tgcggtggct catgtctgtg gtcccagcta ctcaggaggc    42480
caaggtggga ggatcgcttg agcccggagg tggaggttgc agtgagccga tcacacca      42540 ttgtactcca gcctgggtga cagaggaaga ccccgtctca aaaaaaaaaa aaagtacctt    42600
agaccacaaa agtcacagtg tggcctaggc agtgtgaatt acagcttagg tctgtctgat    42660
tttcaaacta gcacactttt cctaagatat tcttctttgc taagggaga aagatagctt     42720 tctatttatt tctgcatatg ttttaatttt cctcttcctg ctggcctttt acctccttga    42780
aataataata aagtaatcct gagaatgtgg tgtgaggtat tcaccgctat gcctactttg    42840
tgcctcgttg ggaattgcat gctcagctga gatgtcttta catattcagt gtctcttgtc    42900
cttagaaacc atctccatcc gctcatttgc agtttaagca tctccatccc tactactgtg    42960
cttataccaa ctctagaaga ggataagact caccccagct ggccttgtgg cttgttagat    43020
ccttgacctt actttctttg gatggtttat ttgtaagacc tttcattttg atttgccagc    43080
aaaatgagca tgactagcag ccactcccca ttcttagtgt gttttttatag ccctaaaagg    43140 gctgatttaa gaaatggttt gactctcaag gaaagttacc tgatcaagga cacaggcctc    43200
attacatgtc ccagctaagg tgtggccttg gtttcaaaga acagccaaag gaaaatgtgg    43260
aagaaggaaa cccaggcttg gagtgtataa attcttaatc tcaaaagata ttggagttag    43320
aagggattct agaaaacatc cagtgatatg gtttggctct gtcgccaccc aaatctcatc    43380
ttgtagctcc cataattccc atgtgttatg ggagggacct ggtgggaatt gattgaatca    43440
tgggggtggg tctttcccat gcttttctcg tggtagtgaa tgggtctcat gagatctgat    43500
ggttttaaaa acgggagttt ctctgcacaa gctctctctt tgcttgccgc catccacgta    43560
agatgtgact tgctcttcta tgccttccgc catgattgtg aggcctcccc cgccacgtgg    43620
aactgtgagt ccaattaaac ctcttctttt tgtaaattgc tcacacttgg gtttgtcttt    43680
atcagcagca tgaaatcaga ctaatacatc cagttacaac ccattgtttt atagttgagg    43740
aaactgaggc tgagggagga aaaagattt aaattcttac agctagtgag ggccgaaccg     43800 ggggctctttt ctcaccccca gttctgttct tccttctttg cataccattc aacaatcatc    43860
tgaggcccag gggactgagc tgcagtctgc tccccagggc agtctgggag cagctggggg    43920
cagctgcagt aagggctgag tgccctgttg tttgctcaag gggctgtgtc taataggaac    43980
tgacattgga gaatgtctaa aaggatgagg aagattttt ctgatagaaa agaagggtag     44040
```

```
tttaggtcac attgtgtatt agtctgtttt cacataacta taaagaacca cctgagactg    44100
ggtaatttat aaaagaaaga ggtttaatca actcacagtt ctgcatggct ggggaggcct    44160
caaggaactt acaatcacgg caggaggcaa aaggggaggc aaggcacatc ttacatggtg    44220
gcaggagaga gagagagaga gtgaagggga aggtgccaca cttttaaacc atcagatctc    44280
atgagatctc actcactatc gtaagaacag cacgggggaa atccgccccc atgacccagt    44340
cacctcccac caggttcttc cctcaacaca tggggattac aatttgagat gcaatttggg    44400
tagggacaca gagccaagcc atatcacatt gtaaagtttc cccaatgata gaatgctttt    44460
tactatgtaa ggggaattat taggtgcttt tgagtgaagg aggcatgact gaatgattaa    44520
ataagagtaa gggctttggg gttccacaga cctgggctcc tgtcctgtga cttgtcactt    44580
ctacctgtgt gacctcaggc aatctgcctc ccctcctcca gcctggcttt tccttataa    44640 aatggggtc atattggtac ttaccttgtc aggttaagg agagttaaac aaagtcatag     44700
gtacagtata cttagcatgg tactaggcac ccagaaagca ctcagtgcat cttagttggt    44760
ggggttattc tctacctgcc cctgtcccag gcattctttt gcattaccta aaccagactc    44820
acccacccca cctcccaggg tatttggcct ggggacaaag gccaccctat ctccacgcac    44880
agcagaatga gacctgcagc ccattttcaa cacatgcctg gagtgctcac cttattggtt    44940
tgaggagccc tgagattgtt ttttgagtgt gttgtcattc tgtacatgat aatagcggta    45000
atagctggca tttgtgtaac ccattatagc ttacaaagca tcttcacata catagtttat    45060
ttgaatctca aaacaacccc ttgagatgga tatttcattc ccatcttatc tctgaggaaa    45120
atgagtctct tgacttcctc gggtgtcatg atgttcagat tccagatctc aggctgggcc    45180
tttcaccgag ggtcaggctc accttggaaa gatgtgattt aatctatttc tctggaagat    45240
ccccaacctc ccatttccta agatcttcc ttagcatcaa attctgggat atagaatttc     45300 cttttcaccac tcactttttc tgaagcaaga gttttttcat tcacagccca gggggagttt    45360
cagagagtaa cttctccttt cagctaataa ctcccaataa tgggaggtca cagggctcat    45420 cttttccctac cagacgtcca gaggatagca gaggtcagct cactgcctct agtcacaatt    45480
atcttgtcta gacaagataa acattcacac acaggtaagc atttgcaagg ttaagtttta    45540
caaagtaaga aatacatgta aaaatgtacc cattcaggag ctgaatggag acagcagccc    45600
tcttgccatc tggaatttaa ttgttcaccc ctcacctttt tttttttttt tttttttgat    45660
acagtcactc tgtcacccag gctggagtgc agtggtgaga tcttggctca ctgcaacctc    45720
cgcctcacgg gttcaagcaa ttcccgtgcc tcagccgccc aagtagctgg gattacaggc    45780
acgcgccacc atgccaggct aattttttgt attttttagta gagatggggt tttgctatgt    45840
tgaccaggct ggtcttgaac tcctggcctc aagtgatctg tccacctcag cctcccaaag    45900
tgttaggatt acaggtgtga gccaccgtgc ctggcaaccc tctccttttt tttttaatc    45960 aagactttaa aaatcatgat cttttaaata attcaatgtc cctcatttaa agatctggat    46020
gagaatcctc ccagtcctcc taagcaaatt ttgtatgttc ctttgcttgc tctttttagc    46080
ttccaatatt gcgcctggtt gaattttcaa aatttctctt agattttttt catcttctga    46140
ttccattctc tcatgtaatt ccaaactgtg atgctggagc aatctttgtc taaatcctgt    46200
gtggtctctg gatgaagtta aagggcatct tggtgacctt cctctcctgg aagccctgtt    46260
ctgtggcaca ctgggagttt gcctgtctct gcacggaggc agtctgattc ctgctcagtt    46320
tgattaattc ctgactttac catatgaatt ctaaatgagc tgaaaaggct tgcatgatga    46380
ttggtcagat tccctcaatc ttttcttgtt ccaggttcct atgcaggggc agtggttgcc    46440
```

```
atgcccctgg ctggggtgtt ggtgcagtac attggatggt cctctgtctt ttatatttat    46500
ggtgagtgat ttgacttcac aagttcacat gtgactcata gagatggtat tttactgcat    46560
atgggtttgg ctcagagttc attacatcaa aatagagatt actaaaacaa gtttattgta    46620
taaatggaat actttatcta tgatttgatt aatatttata ttaaagttga cctaaaaaaa    46680
taagtagaac attgtctttc tttaaatacc agttaacaag aggaacgtca acaaaatact    46740 taccccctagc tgaacatact gccatttgga aatattgtaa agatccttttt gtagttcata   46800 aatgtgataa ttgggtgttc acgtgcatgt atgagatgtc tgagtccctc aaaccttgtt    46860
acaacattgg tacattaccc attttacctg aaaaaaatat atatggtaaa aattgaaaaa    46920
tttagaaacg gaagaaaatg agaccatata acccagcctt ttcttttttta actgcaggca   46980 tgtttgggat tatttggtac atgttttggc tgttgcaggc ctatgagtgc ccagcagctc    47040
atccaacaat atccaatgag gagaagacct atatagagac aagcatagga gagggggcca   47100
acgtggttag tctaagtgta agtataaaaa gtcagatgaa gacttacctt ttttcataag    47160
tgattgtgtt gccttcttac agaaaaaatg tcaatatctt tactaaaaat atcatggtat    47220
ttttactccc tagaaatttta gtaccccatg gaaaagattt ttcacatctt tgccggttta   47280
tgcaatcatt gtggcaaatt tttgcagaag ctggacctttt tatttgctcc tcataagtca   47340
gcctgcttat tttgaagagg tctttggatt tgcaataagt aaggtaaaca cacagatgct    47400 ccaaatatttt ttgaactttta aatctcttga ttctacagag aataactttg tatgataaaa   47460
taattaaatt gctgatcata attcataaca gttctgtgac acctaatagc ctggctgtca    47520
gacaagttat acattctatg catagtatgc atagctgttt aatttcttct tagcaaggat    47580
cagagccgta ttaagctgct ttaaagattt atgttgtacc caatcttaga gtgttttttga   47640 agctagctca aggacggcat attaggcaag gataaaaaga tttgagggtg tgggttttct    47700
ttttttcctg taagctactc agtgagtagc agtaagaacc ttaccattca ttttgcagaa    47760
caccccttct ccataatggt ggctatagca gtaacaatca ttgcttgcaa tgggttagaa    47820
agaacctctt tctgccaggc gtggtggctc acgcctataa tcccagcatt tgggaagcc    47880 aaggctggcg gatcacctga ggttaggacc agcctgacca acatggcaaa accctgcctc    47940
tactaaaaat acaaaaatta gctgggcgta gtgatgcaca cctgtgatcc tagttactca    48000
ggaggctgag acaggagaat cacttgaacc caggaggcag aggttgcagt gaggcgagat    48060
tgcaccactg cactccagcc tgggcaacag agcaagactc tgtctaaaaa aaaaaaagaa    48120
gaagaaaaaa taaacagaaa aaaagaaag aacctctttc aatgctccca gacattatca     48180
tcaagccaat tgtgttttag ggaggaaggg tgtggatagt gaatcatcaa ccatcatcat    48240
aagataaacc tctttcctac aagggaaaga acagcagccg agcaaacaca aatgtctgcc    48300
tagctacaga tactgtcaga agtgaccatg gaagagctgg cataatcatg aaatggtggc    48360
tgtcatcagt catcagtgct cactgggtgc caagtgcttt atctcccatg tgccatgccc    48420
tctgtgatga ataaaagtca tcgctgccct caaggagctt ccaatctggt agaggacaca    48480
gataggtcta aaatcattcg ctcattcatc atttatttat tatgaaattc aggcctaccc    48540
agctcccaca taattagatg cttaaatttg gtggtggtag gtaggggggc tgtggagtgg    48600
aggtgggcaa gggaattagg gaggcccctc tctcagaaat aatgacaaac tgcttactgt    48660
ttctttccct tccaggtggg tctcttgtca gcagtcccac acatggttat gacaatcgtt    48720
gtacctattg gaggacaatt ggctgattat ttaagaagca gacaaatttt aaccacaact    48780
```

```
gctgtcagaa aaatcatgaa ctgtggaggt actgtggatt tcatagatgg cttaggcagc   48840
ttttgtagaa ttagggtaaa ctgaactgca gagcatatat taagaagtga catttagtca   48900
ttggagtgga tcttaaagac ctctaagtct gtccctcagc agacacttga gtgttgtcca   48960
tcacagtgct gccaagaggt catccagctg ggaccttttcc atacatcctt ccacatttat   49020
tgtttgctta tgtagtttat tcccttctct gcttaccttt ctacctatcc atatgttttg   49080
gtaagaaaca gaagaaaagt agtctttcct cctagcctat gcttgtgcat gggacacaca   49140
cacacacaca cacacacaca cacacacaca ccatttttctt tcttgatttt atttagctcc   49200
tgctttatgt tttaattttg taaagacaaa gtgaatgtta ggtgatttcc caaaagaggt   49260
aggcgaaagt aattgtgaac ccctacaatg ttcatgagtg cttttttaaaa aactcatctt   49320 ttttgtttag cttttaaaat taacatttat tgaatgcttt ctgtgccaga cactaagcta   49380
aatcttctac atacattatt ttatttaatc ttcataacca ccatgtggag caggtactat   49440
tactatatgc aatttgcaat gaggaaacag aggtaaaata aagggacttg ctcaagtagc   49500
agatccctgc aaggtatcag gtaggccgga gcctaccgcc aaagctctta gtttgcggct   49560 accccctctgg aggactagtc aggatgagcg agcaggaggt agaggatagc gccacctatg   49620
ggcaagagct cacaactgtg atattaagtt gaaagggacg gattgcgtat gctctgacag   49680
atagctaggt ctggcacatt tagaagtgaa gactataccg agggacacag gagcaggcat   49740
gatctgatcc catagcattt cgggaagaaa gcctaagagt ctgttggcac ctgttctccc   49800
agttccttga ctgctggtcc caggcaggga tgtgtgggcc tgaccttagc ttgaactttc   49860
ttgtagagga ctgagggtta gcggatatag gcctgctatc tggtgggcag gaggtgaagc   49920
tctgggacat tgcattcaag tcctctccaa gagagctgta gcagctagaa taatgcccat   49980
gtcctaatcc tcagaagctg tgaatatgtt tccttacatg tcaaaaggga ctttgcaggt   50040
gggattaaat tgaggttctt gagatgggag tttatcctgc attatctagg tgggcccaat   50100
ataatcacaa taatccttat aaaaggagga aggagggtca gagtcagaaa agaagatgtg   50160
atggtggagg caagagtcag agtgatgcag ccacaaacca aggaatgcaa gcagacccta   50220
gaagctggag aagacaagaa gagattccgc catagcacct ctagaaggaa tgcaactctg   50280
taggctgctg ccttgacttt agccctgtac cattttggat ttttggcctc cagaactgta   50340
caatagtgca gagagtattt tagaggtgac atctaatcat tggaatagat cttaaagacc   50400
cctaagtcta tccctcagca gatacttgat atttgtgttg ttttgagcca ctgagtttgt   50460
ggtaatttat tacagcagca aatgaaaact aacacagcgg taggcagggt gcagtggctc   50520
actcctgcaa tcctagcact tgggaggtt gaggcgggca gaccacttga gctcaggagt   50580
tcgaaatcag tcagggcaat agtgagaact tttctctatt aaaaaataaa acatttataa   50640
aatgaaaact aatacagtag ccaaagcctc acccttctaa tgataaaatt ctgctccagc   50700
tgaacagccc tcacccaagc cctgaacata tctttctgtc tctgactttg cccactccct   50760 ttctcttttcc ctgtgagttc tcaccttcac ctctcaatcc agtcctctct atacatccag   50820
ctcaattctt ctcctcttat gtttccttaa agccatgcca ttctccagtg atccctctga   50880
atatgtccac atggctagat tggcaactca tcatgtggtg ccttattgca gctctctcag   50940
gaaaagattt taggcagagg gaatagtatg tgcaatgacc ctggggcagg caggaatgtg   51000
gcctgtgtga gaatagaagg aaggggagtc agaatggctg agtgacggga gacgggatcg   51060
ggatgttttt ctagggtcag atcatggcag gccttgtcgg cgtatgcaga gcttgggttt   51120
tatttgaagt acattgagat gcagatgatt taaagcacgg aatggatatg atctcatttt   51180
```

```
tttttttttt tgagacagag tctcgctctg ttacccaggc tggagtgcag tggtgcaatc   51240
tcagctcact gcaacctccg cctcttgggt tcaagtgatt ctcctgcctc agcttcctga   51300
gtagctggga ttacaggcat gggccaccat gcctggctaa tcttttgtat ttttgtagag   51360
acagggtttc actatattgg ccaggctggt ctcaaactcc tgacctcaag taatccgccc   51420
gcctcggcct tccaaagtgc tgggattaca ggcatgagcc acctcgcctg gccttgctta   51480
tttattttta atctggggaa ttatgcaggg tacaagagta aagaaggga gaccaggtag    51540 gaggtgattt cagttgtcct gtctagagaa gatggtggct tagacaaatg aggtggcaat   51600
ggagatggag agagggggt caatttctaa attctcagag ccaacagttc tcatctttaa    51660
attacataat aatatttact tcagaggata gttatgagag ttaaatgata caacgtatga   51720
atgcacctag tgcggtgttc aacctataaa aagttctcaa caaatgttaa tgctgctttt   51780
tttctcctat gttcaagaca caaaaaacac agaagttttt caaagagttc tttaacaaat   51840
atctgtgatt gtatttcctt tggacaaaaa aatgtacttc taaactggca actttaaata   51900
agtttctgga ttttaaacac tatttgcaca acctcttcta aacccagatg cattggatat   51960
tcttgagcat attttgtggg aatgtcttgt tcctatttaa ttctgcccca gtacctctgc   52020
tgtttctcca taattggtgg tgattatgtt atgttgtggt gatgagaact ttcaaagatg   52080
tttaattgct aacaaagtgc ctgttgagag gaaatagttt ttttctgca gaaactagaa    52140 ggcatatgtg gaatctttct gcctcatctc ccatctttaa aaaatacctc ttcacatggc   52200
ttttcatgtt catatatata tatatttttt ttgtttgttt gttttgtttt gttttgtttt   52260
tgagatggag tctcgctctg tcacccaggc tggagtgcag tggcgtgatc tcagctcact   52320
gcaagttccg cctcccaggt tcacaccatt ctcctgcctc agcctcccga gtagctggga   52380
ctacaggcac cgccaccac acccggctaa tttttttgtat tttttagtag aggcggggtt    52440
tcaccgtgtt agccagggta gtctcgatct cctgaccttg tgatccaccc acctcggcct   52500
cccaaagtgc tgggattaca ggcatgagcc accgtgcccg gccattcttt tatattttga   52560
catagtagga ccagtgagtt atatatagaa aataaaattt ttaaaaagac cataatggtc   52620
ccactttttc tgcttaaata cagagatgct agagcagaga taactacatg aaaacaaagt   52680
tttgtgccat cagtgaagaa tgcaggttga tttggaaatg atgaagcact ggtatgatct   52740
tccagagaat tttggttggc ttttttggttt cctactaaga aatatagaag gcatttctca   52800
tctgagaagg atcacacata tcttggagcc tgtcatcttt tatttccata gatttttaata   52860 tgccattaaa atcatttaaa gcaaaacaga tcacttaaga catgatgttc aattcattct   52920
gaatcagggt ctacgtctat gatgcttaaa gacagatgcc aaattcttgt cctgccccct   52980
ctatagaaca tgcaaagtgt aactgaggtc aaaaattcta ttctggctga atcagttgca   53040
agtgtgaact tcagattatt ttaatatgaa ataaaatatt tcttaggcct ttaagtccta   53100
gttttgtttt tcttgtcaac tctaaatagg ttcaatttta aggatctcct gattacccct   53160
aaagttgaaa ttttatcctt aagctcctga aacatgcagc cctgtctcta gtattttaac   53220
tgtcagtaga aaccatttag gctcttaaat gcttttttt ccactggcaa tctgctattt    53280
ggccaaaatt tttttttctta cagatgaact gatgtatcat ttgtaagttt tattctttat   53340
acaatgtcat cattctaatt ctttggggga attgactttc tgcatgcttc tgttcagagt   53400
gtaaaaataa aagaagtttc agccagatgc cttgttattt aggataggca cttctaagac   53460
acatatagtt agtatatgaa acactagcta ttttttccta tgtgtagtct taaatgttga   53520
```

```
aacaaaatta agaacaagta gcaatgatat aaagcctata gttttaaaag taagacttcc   53580
ctaattacat ttcatcctct ttagaagcca tttaaaacaa ttattagttc ttgcccttct   53640
ttatagtagt gttgaagaaa taggttcaaa aaggtaaata ttaataactt aaccatcatt   53700
tacggtaagt acttcagctt gtgaatctta ttttcttctt tctgggtccc atttcctttc   53760
ctttgcatta attcattaaa cgttatgtat gtatgtatgt atgtatgtat gtatgtatgt   53820
atgtatgtat gtatttagag acagagtctc actctgttgc ccaggctgga gtgcagtggt   53880
gcaatcttgg ctcactgcaa cctccacctc ccggtttcaa gtgattctcc cgcctcagcc   53940
tcctgagtag ctgggattac aggcacatgc aaccatgcct ggctaacttt catatgttta   54000
gtagagaagg ggttttgcca tgttgcccag gctggtcttg aactcctgac gtcaggtgat   54060
ccgcctgcct cgtcctccca aagagctgga attataggtg tgcaccacca tgcctggcca   54120
aacgttattt attgagtgca tactacatgc tagacagact ctgtgttaaa tatacagttt   54180
tgtgggagag gcagaaacac aaatgaaaag ttacaaagca atattgaaaa gttctataaa   54240
atgatgagaa ggtgatgtca gcttcattgg ttgagggtag ggagagggtt gttagggaag   54300 cttttctagag gaggcactat ttaatctgga ctttaaaaat agtaagattt atccagaaaa   54360
agagaaaatg atgagagaag agtatcccag gtaaagaaac aatgtgtgaa aatatgtaca   54420
ggcatgagat agtattgtgt ggttagaaaa cagctaatag aggagtatgt ctgtggcaca   54480
gagggctatc cacagaatgg gggcagtaag caaagagatg agggctggaa gaagatgaaa   54540
ctggaacagc aggaggtatt cattatagaa cactatactc atgatatgga gctcatgaca   54600
aacacgttaa gcacaggagc aaataatgag gtgtgtggct tagaaagaca gtggtattga   54660
gaatgcatca gaggaggacg agttgggaag actaccaaag tggcttattg tggctgagca   54720
tggtggctta ggcctgtaat cccagcactt tgggaggcca aggcaggcag atcacctgag   54780
gtcagaagtt ggagaccagc ctggccaaca tggggaaacc cggcctctac taaaaataca   54840
aaaattagac tgggcgtggt ggctcacgcc tgtaatccca gcactttggg aggctgaggt   54900
gggtggatca cgaggtcagg agactgagac catcctggct aacacggtga accccatct   54960 ctactaaaata tataaacaat tagctgggca tggtggtggg tgcctatagt cccagctact   55020
caggaggctg aggcaggaga agggcacgaa cccgggaggc agagcttgca gtgagccaag   55080
atcgcgctgc tgccctccag cctgggtgac agagcaggac tccatctcaa aaaaaaaaa   55140 aagttagccg ggcgtggtgg tggactataa tcccagcgac gggggaggct gagtcaggag   55200
aaccacttgc acccgggagg cagaggttgt aatgagctga gattgcacca ctgcactcca   55260
gtctgggtga cagagcacga ctccatctca aacaaaagaa gaaaaaaagg tggcttattg   55320
cagttttcct ggtaagaggt cacggggcct ggaactaaag cagtgacagg ggaggggaaa   55380
gtggcagttg cactgacag atgtttccga ggccaaacct gcagatttgt atatgaaagc   55440
tcaggcagga ggagaagtcc aaggtagttc tgaagtttct gcatcggact tctggctatc   55500
atttgttgag ctgtgcccat gtgccacact cagtacctca tataccaatt tcatttactt   55560
ttccgatacc tcacaaggct gtggtactat ctccagcttt tggatgagga atctaagagg   55620
tgtagtaact tgttcaaggt cacaaaatta gtgattttga agtggaaagt gaacccatac   55680
cagtttgact ctaaagattg ggttctaaac acagaatatg gaagattaat ttagaggaga   55740
agaaagcacg tggtggcgat ggtttggtga tggtttgctt gtttgtttag gagtaaaaaa   55800
ataggggaag aggccagggg tggtggctca tgcctgtaat cccagcactt gggaggctg   55860 aagtgggcgg accacctgag gtcaggagtg gccagcctgg ccaacatggt gaaaccagcc   55920
```

```
tggccaacat ggtgaaaccc caactctact aaaaatacaa aattagctgg gcgtggtagc   55980
acatgcccat aatcccagct acttgggagg ctgaggcagg agaatcattt gaacttggga   56040
ggcagaagtt gcagtgagcc aagatcatgc cgttgcactc cagcctgggt gataagagca   56100
agactctgtc tcaaagaaaa aataaataaa taaataaata aaaatagggg atgagagaat   56160
tgatttgggc atgttgcctt tgaggtactg tagaacaatt gtgtggagat gtctggaatc   56220
agcagacagt ctccaaatga agcaccacta attgtctctt cccctccta aggcactcta    56280 tatacttgga aatgatattt atatcatttt tctgtctgtt gtcagctgaa cttttttttc   56340
gggtgagaag gaacttcttc ataatttcct cattcttttt attttttatt gtgctagact   56400
cacttattct gaatgaaagg aacagaaagt acttttgttc tgcaatattt tctgtgcaaa   56460
attctcatgt attgtttgtt tttttttttt ttaagaggcc tgagagcttg gtgaactttg   56520
aaatagaaaa attttgactt ttgctttaca agggtgaag tgctgttttt gtttgtttct    56580
ttgtttgttt ttgtttcaga tatttgctac agttttctgg ttgcttttgg caataaatat   56640
tagagtgttg tcattttact tttaagggaa aggccataac tagtcaaagg ggaatcatta   56700
ccacagttat atagtagagt tttagtattt aacaatggca gggacagcta cccatgaagc   56760
aactaataat taacatccct catctcagga gcatcattgg aacctattgg gaccgtgtgg   56820
tgttcaaggt gcaccgcgat aatgttagaa agtttgtgaa cacccaggga atattagcaa   56880
agtcatgtag tcatgaaagt cctgggtggc attgtaagca ctgtaccaga atgtaggtct   56940
gtggaggaac agaaaaccaa acactgcatt tccccactca taagtgggag atgaacaatg   57000
agaacacatg gatacaggga ggggatcatc acacactggg gcctgctagg gggcaagggg   57060
agggacagca ttagggcaaa tacctaatgc atgtggggcc caaaacctag atgatgggtt   57120
gataggtgga gcaaaccatc atggcacatg tatacctatg taataaacct gcacattctg   57180
cacatgtatc cctgaactta aatcccagaa cttcaagtaa agttaaaaaa aaaaaaaaaa   57240
aaacttaaat tccagaactt aaagtaaaaa aaaacatag acacaaacaa aataaactta    57300
ggtctgtgga attataggtt agttcttatt tgataaataa atgaacttgg gttgaccgat   57360
atgaaaatga catttttttc ccttgctgtt tccatttgca ggttttggca tggaggcaac   57420
cttactcctg gtggttggct tttcgcatac caaagggtg gctatctcct ttctggtact    57480
tgctgtagga tttagtggct tcgctatttc aggtaatgtg tcctttgggt ttccagatct   57540
tgactataga ttcaacaagt cccaggaaga aggaaggaca aggatattgt agcaccttct   57600
ttcagtagcc agtccattct cagagagcag gaccaccgtc cagagaatgt gatctagtgg   57660
gggtgatttt gtaagatcac tgagaactgg gcttgggagc tcagttaagg tggaattttt   57720
cctacttact tgttacggg aaaagacaca aagtgcagat gacccttctg agacacgagc    57780
agaggcccaa gcatatgtcc tgggtgaagt ggactttcat actttagcac catgtcaccc   57840
tacctgacag aggctcctgt gacttttca gcctcgccc tcttgctaga gaactgcgag     57900
tgtcattaca gtcataggat cagaagtttt tttaagagtg aaaaccttct ttagatttt    57960 gtctactcca ttgctttcat tttccaaaca agaaaatgcg ggtccataga ggggaagtga   58020
ctttctgaac agggtaaaga ataatgacaa tgatgatgtg agctagcgat gaccaagcac   58080
agattctgtg ccagggaata ttccatgaga tctgcatata ttaagccctg tctctctcac   58140
aactaccctg ctgggtatca gtgctattac ggtcccatt ttacaggagc agaaaccagt    58200
ctactatatg tgagagaaag gccagagtgc aatcatatca gaagcttcct atgcaaaact   58260
```

-continued

```
gggtcaaaga gtgaaattta gttgtttgtc tatctttaaa acatcgtaat aagaatatgg   58320
ttactggccg ggtgcgctgg cttacgcgtg taatcgcagc actttgggag accgagacga   58380
atggatcact tgagcccagg agttcaagac cagcctgggc aacatggcaa accccatct   58440
ctacaaaaaa tacaaaaagt tagctaagtg taatggcgca cacctgcagt cccagttagt   58500
caggaggttg aggtgagagg atggcttgag cctgggagtt ggaggttgcg gtgagctgag   58560
ttcgtgccac tgcattccag cctggatgac aaagcgagac cccttctcaa gaaaaaaata   58620
aataaataaa ataaaaataa aaaatggtta cttaaagaaa atttcacata tattgtatat   58680
atatcataac attgtgaagc aagtagtagt atatcactat gctactgggt ttttcactat   58740
tttactaaag ctcagaaaaa tttgatactt tcttaatatc acacagttag tggcaaagga   58800
aggatgacag aacagttctg cctggcccaa aggccgtgct ccttccatta ttccaggttg   58860
ccttaaatat caaacagtgt tagtgtccca gaatagaaaa atatggaacc tctggtctaa   58920
actgccctaa gacaggggct tgtatctttc aaaataaata gagttgatga ataaattaga   58980
aaataaagta aaagtctaaa ttaaaagtaa cttgcagcta gtaatttgg tttagagatg   59040
catagacctg ggtttgaggc cctctttact atttactatt tataaaataa aaaatttgct   59100
aaattatgaa aactctcaag cttcagtttt ctcatctaga gattggagag atgaaacagc   59160
aacctcatag ggttgttggg aggataaact tagataattc atgtatttcc ccgcacttct   59220
tgtgggctgg gcattattct tagcactggg gatattgcag tgaataaatg aaagtgtcca   59280
tccccataaa gtttacattc tagtggaaat acttattcaa ataaaaacct tagctgtatt   59340
tatttgaagt ccttagcaca gtgccagatg cataacaaaa ttaatgagtg ttcaccatta   59400
ttgttctatt agtacacaca ccagcccagt gcctctcaaa gtgttatgtg aaatcaccat   59460
aagatatttc agaatgcaga ttctgatttg gtagctctag ggtggagcct gagattctgc   59520
agttttagca agttccccag agctgctgct gctgcagggc agtccacact ttgagtagca   59580
agggcagagc aatcacgatt tgcttccagt aggaagcgga ggaacgcctt cccttgataa   59640
ctttgtgatg caaaagagat ccatatcctg ttcccagaga tactgaaatg ttcaagttca   59700
tattgcttcc tttcccccga ttgccaatta agtcacaatc tgaaggagag aaacccaata   59760
ctccaaatca cataaactgc ttttttgttt tcctttttttt ttagacaggg tctcttgcct   59820
tgtgcagtgt ctcatgacta taatcccagc actttgggag gccgaggcag atggatcacc   59880
tgagatccag gagttcgaga ccaacctggc caacatggtg aaaccgcatg tctactaaaa   59940
atacaaaaac tagttggttg tggtggtatg tgcctgtagt cccagctact ggggaggctg   60000
aggttgcagt gagccaagat tgcaccactg cactccagcc tgggtgacaa agagagattc   60060
tgtctcaaaa aaaaaaaaaa aatagacagg gtctcgctct gacacacagg ctggtgtgca   60120
gtggcatgat cgcggatcat tgcagcctct acctcccatg ctcaactgat tctcctgcct   60180
cagcctcctg agtagctggg gctacaggca tgtgccacca cttccagata tatatatatt   60240
ttttcgagac agggtctcac gatgttgccc aagctggtct cgaactcctg gcctcaagtg   60300
attctcctgc cttggcctct caaagtattg agattacagg catgagccac cacacctggc   60360
cttcttgcca ctttttaaac atgatttcat ttaatcctca ttgcaacctt gatgagaaag   60420
gtattgctat attcacttta ttggtgggga accaaagtg tggtttaact tgccgagtga   60480
agtggctggg agtgtggaat aaaggtctgt tggtcccagc aatgcactg tgggagggat   60540
tgcagccaca ggggcaataa ttcctcagaa tctactgtct gccaactttt aaggaataa   60600
acatagatgt cagggaagac tgactggcac aatttaggag ctgattatag acaagactgc   60660
```

-continued

```
tgagatagat gaagttaaaa ataggcaaga gatgagtgat gcctgttttg ggaaatgtcc    60720
tatacagaag atagattctc tcagtttatg tgtaattttt ttatctgcta taaaaatcta    60780
tcaatatctc aatttctcag tgattttccc ccctccccaa atgtcaggat tgtgcagcta    60840
gaaacctaaa tggcttttcc cacattatct ttagctgaat gcagatgccc aggctttgta    60900
tcagagcata atactcaaca atcatattaa ttgcttctta tctctggatt cttttctaat    60960
aaagtgttta tcacattcaa atccatggta agattaatga acttgcagct gttttatatt    61020
ctgatcattt ggcacattga cctgaaagat aaggtatgtt tattattacc aaaaagtttt    61080
ctcaaaattt ctccctgaag ggaagtagga aagacaacca accagtgtgc cagattagaa    61140
caaaaaaatg ttttaagtcc tattttcagt tttttttttt gcacagaata gagaaataaa    61200
aagcaaagca aaggaagaca aaaagatgaa taaagcctac aacccttgc tataatttca     61260 gtagctgaag ctggtaatta atttagcaac tatttattga gtgactacaa tgtgccaggc    61320
actttgctag ttcaggggag atggtggtaa acaagacgga tggctaacca cctgtaaaga    61380
gcatgcatgt tggtttacac gtctatgcac catgtagtta acatacatta tttaacttaa    61440
ttcctacatc aattttataa gaatcattat cccgttatgt agatgaaact aaggttcagg    61500
aagtttaaat ccttggtcta ggcttgcatc tcaactaagc tgccagaact gaggtctgtc    61560
tgatttgaac atgcacccct gcaatatatt gacaaagtca gatctcagct cgctgtaacc    61620
tccaactcct gggttcaagt gattctcctg tctcagcctc ccaagtagct gggattacag    61680
gcatgtgcca ccatgcctgg ctaattttg tattttagt agaggtgagg ttttgccatg      61740
ttggccaggc tggtcttgaa cttctgacct caggtgatcc acccgcctca gcctcccaaa    61800
gtgctgagat tataggcgtg agcaaccatg cccggccagc agcattatct tttgatagaa    61860
gacctcaaag agagggagtt actttgcaat ggcagcagaa ggtagcagta gtagtagtgg    61920
tagttagcat agctttgata tttgccaagg gcttcacata cctatttccc ctgagtctct    61980
atcacagcac ctctgtgaag tgaatagtaa tattatcctc atattggaga tgaagaaaca    62040
aaggccccca aattacttgt ttacatagta gaaataagat tcaagtccag atttacagac    62100
tccaaatcaa gtaggtgtgt gaaagtgttt cataaattac agaaggttct cccaatgttt    62160
gtgcaaatgt ttcattaaaa agcacccttt tcattgtgtg aaaatgtggc catgtggcca    62220
ataaagtagg cttaccctttg gctgccttttt aagagtaagt caggggtagg agtgggaata  62280
ttataaagca aggtttggtc tagtcatact gtatgtgatt gtatgattat ttactctgaa    62340
taaatgtgat tcaggcttta ggcttttcaa tattgtgcca aacaccgtat tttgaattc     62400 agaacctaca aggtagagat gccataattc tctttataga gagagccctt gatagatatc    62460
cataatcaat tccagcattg tctaccagtg ctgctttgtg cagacacagc ctcttgaacc    62520
cagtcctctt ggtctggaaa ctagtcatat actagaggaa accaaacaga ttggtaaagg    62580
ctggggcaac tgagtatttt ccaaagcata tttgaaattc tgttcttgac tctgattttg    62640
aggttttggc ttcactgtag gttttaatgt caaccacctg acattgccc cacgctatgc     62700 cagcattctc atggggatct caaacggagt gggaaccctc tctggaatgg tctgtcccct    62760
cattgtcggt gcaatgacca ggcacaaggt aaaggtctcc tttgtggcta tgggttacaa    62820
tatcagagga ctggagctct acacaaactt gagatttcaa ggctctactg cagtctgtaa    62880
atgtgtatgt ccttgacctt gactgagtca gctgaacttc ttttttttttt cttccttctt   62940 ctgattttca aatcattgct tatcaatggc accaaggcta gttgttgttt tgttctatgt    63000
```

```
tttctcaatt gaggaataat agtctgggga gagggggatgg gccatagaaa ctgtttagag   63060
acccaaagaa gaaactgagg cagtcaactt gggataaatg agttactgaa gattgttttc   63120
tcattctcag tgattaaacc ttatagccta tttccatcca ttgcttagca tgtttcagca   63180
taaaaagatg agtgctattc tacttccttg ttaagaataa aataaacagg acattgataa   63240
cctacccagt tgttactgag cctttgtgaa tttagacaag ggtggatggt agaggcagat   63300
ccatccagag ttcaaccaca gcccacatga tttctttatc tttgtcactg aaacgtctca   63360
agatgctgct ttctgcaaat aagaattctt tgataccatg ggatttttt cccccatcta   63420 ttttcttagt tggattgcct attacaaata taacttcaga agttttgca gcttcctgca    63480 gaagaaagtg tgagataaat tttcttactt tttgacagaa aaggtaggat tttataggca   63540
gagaattcat gttttccatc tctgttcatg aaatgatagg attgataacc tgactattaa   63600
atccaagata tcttccccca accttagaca caaattccca ttattttttg acatactttt   63660
ttttacactg aaaatattat aaagttcttg tcagtcaagg gtgagaactt taatggctca   63720
aatattgtta tgtatccaac aacaagcaag aaggagactt ctgatattta aaacggtggg   63780
ttcctaaaac aatttaatt tagctgacta tgtgaaggga aaccccattt gagtattcaa    63840
aaagctatgc aatggtgctg caggtattaa tatttgtata tgttgtttat tttaaatgt    63900 attttcttgt aatcccagca ctttgggagg ccaaggcggg tggatcatga ggtcaggaga   63960
tcgagaccat cctggctaac acagtgaaac cccgcctcta ctaaaaatac aaaaaattag   64020
ccaggcgtgg tggcgggcac ctgtagtccc agctactcag aggctgaggc aggagaatgg   64080
tgtgaaccca ggaggcggag cttgcagtga gccgagatcg cgccactgca ctctagcctg   64140
ggtgacagag cgagactcca tctcaaaaaa aaaaaaaaga attttctaaa ttaaaaaaat   64200
acgtatttat tgttttgtct aactttcata ttcattgttg tcttaacttt catttttaa    64260 gttttctttt taaatttggt ttgaatcccg gatggtgctt ctgacacacg tcctcccgcc   64320
caaggagcct ctagagcatc gccttccaaa tgggcaggtg ctttttcaca gtggaggcct   64380
ccaggacata ctggtaatct ctagttttag ttaaaacatt aattggcact ttatttcctt   64440
atttagaccc gtgaagaatg gcagaatgtg ttcctcatag ctgccctggt gcattacagt   64500
ggtgtgatct tctatgggt cttttgcttct ggggagaaac aggagtgggc tgacccagag    64560
aatctctctg aggagaaatg tggaatcatt gaccaggacg aattagctga ggagatagaa   64620
ctcaaccatg agagttttgc gagtcccaaa agaagatgt cttatggagc cacctcccag    64680
aattgtgaag tccagaagaa ggaatggaaa ggacagagag gagcgaccct tgatgaggaa   64740
gagctgacat cctaccagaa tgaagagaga aacttctcaa ctatatccta atgtctgaga   64800
ggcacttctg tcttctcctt actttagaaa cagaaagtat ccatacctat tgccttttctt  64860 gtagcccagc ttgccagagg tccaaatatt gggaggggga aagatctaac cagcaacagg   64920
gaaaagagaa atattatctt tcaatgacat gtataggtaa ggagctgcgc tcagttgata   64980
acatagttga taatacatat ttttgaatt gacagttgac ccttctctca aagagctaaa    65040
cttattcaga aaggaatgac tagaagaaaa aggagacaat accatgttgt tcaaagaaac   65100
attgaaggaa attgggatgt ttggccagaa ggaatgtaaa cagtagtagt agctgccacc   65160
acatctctag ggtagccatg cagaggaggg cttcatattc caataaacc ccacgttgtg    65220 gcaggtgctt tataaacact cttatttaat ctccacacct ttatgacaca catttcttat   65280
ccccatttta caaccaaggc atctaaagca acaagaaatg aacttgccca aggtcatctg   65340
ccagggtcag tgctgagact gttgaagctc tcaataggtg gcagttttag ggaagatttc   65400
```

```
cattcagtgt agggaagaca tttgtaataa tgaaaactga aaatggagta attgtgagta    65460
actcaccact ttagcaggtg ttggggaagg gaaacatttg ggttgatgag gcagagggga    65520
ttcaaatgtg tgagaggcta gattcaaaga ccctcagtgt tctatgttat ctgaagagtc    65580
aaatggtttt gtgactccat agttttttaaa gtaataaggg tcaaagacta catcagagat    65640
tcaaataggt ttttaaagaa aagctaagca agagagccaa atttttagaa atctgatggt    65700
caaaatagct gaaagcagta aacaagagat tggctattaa atttcaactt tccataatat    65760
taagaatgta gctaaatgat gtcccaaact acttacaaac ttttaagaca tttaataatt    65820
taagaagtag gttcatgtgt tttcttaggt aaagttcttc tgaaagaatt ttctattttt    65880
aaaaaatgta tctctttagc cttttctgct ggagattata ttaggaagtt tcatcagatt    65940
gtataaaatt atgattttgt atcaaaagta ttcatgatga ctctatttgg aatgatattc    66000
agggaaatca caataatata gcagtagtta tacagagaaa tactcaatg aaaacatttg     66060 gggcaattag acctacagtt actgttgaaa aattcacctt tgattgcata aggcaattac    66120
atggatactt ttagatatat ttaaaatttt aacattggca tctaaagtgt tatttgaaaa    66180
taaaattatt ttcctgttca ttgattttaa acattttatt cctactttca gaagaaaaat    66240
ataatacgga aaaaattata gatttacttg tagcttatta ttgtaaagtg gtttttttt     66300 tttttttttt ttttctaatt tctcccacat gtatttctgg tccccagtga tactagctga    66360
gttgtagtgt atttataaa tggaataatc ttggggaaaa attgcgattc ttcattaaat      66420
aatattcttt atgtcactag catacaattt atgttagtag acatctttaa atctctttaa    66480
tgagtgaatc catgcaagcc ccataaaaca gttcctagca tgcagaaaat gcccacgtaa    66540
atagctgtca tcatcattat cttttaacat tttgggggac tttccagttg aaaagaaaac    66600
atgctatgtc attttttatcc attatccctg gaacttattg tgaaagttgt gctgttttct    66660
aagtaaaata aaaaataaaa aattagcaat ttatgatagc cagtgttta ttttgtgtgt      66720 gtgttagtaa agtcaaataa ttgtatttta aaaactcacg ataatcctta aggtagtatt    66780
gtatattgtg acacaaagtt gtat                                            66804
```

<210> SEQ ID NO 4
<211> LENGTH: 578
<212> TYPE: PRT
<213> ORGANISM: Rattus norvegicus

<400> SEQUENCE: 4

```
Glu Ser Val Lys Gln Arg Ile Leu Ala Pro Gly Lys Glu Gly Ile Lys
 1               5                  10                  15

Asn Phe Ala Gly Lys Ser Leu Gly Gln Ile Tyr Arg Val Leu Glu Lys
                20                  25                  30

Lys Gln Asp Asn Arg Glu Thr Ile Glu Leu Thr Glu Asp Gly Lys Pro
            35                  40                  45

Leu Glu Val Pro Glu Lys Lys Ala Pro Leu Cys Asp Cys Thr Cys Phe
        50                  55                  60

Gly Leu Pro Arg Arg Tyr Ile Ile Ala Ile Met Ser Gly Leu Gly Phe
65                  70                  75                  80

Cys Ile Ser Phe Gly Ile Arg Cys Asn Leu Gly Val Ala Ile Val Asp
                85                  90                  95

Met Val Asn Asn Ser Thr Ile His Arg Gly Gly Lys Val Ile Lys Glu
               100                 105                 110

Lys Ala Lys Phe Asn Trp Asp Pro Glu Thr Val Gly Met Ile His Gly
           115                 120                 125
```

```
Ser Phe Phe Trp Gly Tyr Ile Ile Thr Gln Ile Pro Gly Gly Tyr Ile
130                 135                 140

Ala Ser Arg Leu Ala Ala Asn Arg Val Phe Gly Ala Ala Ile Leu Leu
145                 150                 155                 160

Thr Ser Thr Leu Asn Met Leu Ile Pro Ser Ala Ala Arg Val His Tyr
                165                 170                 175

Gly Cys Val Ile Phe Val Arg Ile Leu Gln Gly Leu Val Glu Gly Val
                180                 185                 190

Thr Tyr Pro Ala Cys His Gly Ile Trp Ser Lys Trp Ala Pro Pro Leu
            195                 200                 205

Glu Arg Ser Arg Leu Ala Thr Thr Ser Phe Cys Gly Ser Tyr Ala Gly
210                 215                 220

Ala Val Ile Ala Met Pro Leu Ala Gly Ile Leu Val Gln Tyr Thr Gly
225                 230                 235                 240

Trp Ser Ser Val Phe Tyr Val Tyr Gly Ser Phe Gly Met Val Trp Tyr
                245                 250                 255

Met Phe Trp Leu Leu Val Ser Tyr Glu Ser Pro Ala Lys His Pro Thr
                260                 265                 270

Ile Thr Asp Glu Glu Arg Arg Tyr Ile Glu Glu Ser Ile Gly Glu Ser
            275                 280                 285

Ala Asn Leu Leu Gly Ala Met Glu Lys Phe Lys Thr Pro Trp Arg Lys
290                 295                 300

Phe Phe Thr Ser Met Pro Val Tyr Ala Ile Ile Val Ala Asn Phe Cys
305                 310                 315                 320

Arg Ser Trp Thr Phe Tyr Leu Leu Leu Ile Ser Gln Pro Ala Tyr Phe
                325                 330                 335

Glu Glu Val Phe Gly Phe Glu Ile Ser Lys Val Gly Met Leu Ser Ala
                340                 345                 350

Val Pro His Leu Val Met Thr Ile Val Pro Ile Gly Gly Gln Ile
                355                 360                 365

Ala Asp Phe Leu Arg Ser Lys Gln Ile Leu Ser Thr Thr Val Arg
            370                 375                 380

Lys Ile Met Asn Cys Gly Gly Phe Gly Met Glu Ala Thr Leu Leu
385                 390                 395                 400

Val Val Gly Tyr Ser His Thr Arg Gly Val Ala Ile Ser Phe Leu Val
                405                 410                 415

Leu Ala Val Gly Phe Ser Gly Phe Ala Ile Ser Gly Phe Asn Val Asn
                420                 425                 430

His Leu Asp Ile Ala Pro Arg Tyr Ala Ser Ile Leu Met Gly Ile Ser
            435                 440                 445

Asn Gly Val Gly Thr Leu Ser Gly Met Val Cys Pro Ile Ile Val Gly
450                 455                 460

Ala Met Thr Lys Asn Lys Ser Arg Glu Glu Trp Gln Tyr Val Phe Leu
465                 470                 475                 480

Ile Ala Ala Leu Val His Tyr Gly Gly Val Ile Phe Tyr Ala Leu Phe
                485                 490                 495

Ala Ser Gly Glu Lys Gln Pro Trp Ala Asp Pro Glu Glu Thr Ser Glu
            500                 505                 510

Glu Lys Cys Gly Phe Ile His Glu Asp Glu Leu Asp Glu Glu Thr Gly
            515                 520                 525

Asp Ile Thr Gln Asn Tyr Ile Asn Tyr Gly Thr Thr Lys Ser Tyr Gly
530                 535                 540
```

```
-continued

Ala Thr Ser Gln Glu Asn Gly Gly Trp Pro Asn Gly Trp Glu Lys Lys
545                 550                 555                 560

Glu Glu Phe Val Gln Glu Ser Ala Gln Asp Ala Tyr Ser Tyr Lys Asp
                565             570                 575

Arg Asp
```

ISOLATED HUMAN TRANSPORTER PROTEINS, NUCLEIC ACID MOLECULES ENCODING HUMAN TRANSPORTER PROTEINS, AND USES THEREOF

RELATED APPLICATIONS

The present application claims priority to provisional applications U.S. Ser. No. 60/251,035 filed Dec. 5, 2000.

FIELD OF THE INVENTION

The present invention is in the field of transporter proteins that are related to the differentation-associated Na-dependent inorganic phosphate cotransporter (a type of neurotransmitter transporter) subfamily, recombinant DNA molecules, and protein production. The present invention specifically provides novel peptides and proteins that effect ligand transport and nucleic acid molecules encoding such peptide and protein molecules, all of which are useful in the development of human therapeutics and diagnostic compositions and methods.

BACKGROUND OF THE INVENTION

Transporters

Transporter proteins regulate many different functions of a cell, including cell proliferation, differentiation, and signaling processes, by regulating the flow of molecules such as ions and macromolecules, into and out of cells. Transporters are found in the plasma membranes of virtually every cell in eukaryotic organisms. Transporters mediate a variety of cellular functions including regulation of membrane potentials and absorption and secretion of molecules and ion across cell membranes. When present in intracellular membranes of the Golgi apparatus and endocytic vesicles, transporters, such as chloride channels, also regulate organelle pH. For a review, see Greger, R. (1988) Annu. Rev. Physiol. 50:111–122.

Transporters are generally classified by structure and the type of mode of action. In addition, transporters are sometimes classified by the molecule type that is transported, for example, sugar transporters, chlorine channels, potassium channels, etc. There may be many classes of channels for transporting a single type of molecule (a detailed review of channel types can be found at Alexander, S. P. H. and J. A. Peters: Receptor and transporter nomenclature supplement. Trends Pharmacol. Sci., Elsevier, pp. 65–68 (1997) and http://www-biology.ucsd.edu/~msaier/transport/titlepage2.html.

The following general classification scheme is known in the art and is followed in the present discoveries.

Channel-type transporters. Transmembrane channel proteins of this class are ubiquitously found in the membranes of all types of organisms from bacteria to higher eukaryotes. Transport systems of this type catalyze facilitated diffusion (by an energy-independent process) by passage through a transmembrane aqueous pore or channel without evidence for a carrier-mediated mechanism. These channel proteins usually consist largely of a-helical spanners, although b-strands may also be present and may even comprise the channel. However, outer membrane porin-type channel proteins are excluded from this class and are instead included in class 9.

Carrier-type transporters. Transport systems are included in this class if they utilize a carrier-mediated process to catalyze uniport (a single species is transported by facilitated diffusion), antiport (two or more species are transported in opposite directions in a tightly coupled process, not coupled to a direct form of energy other than chemiosmotic energy) and/or symport (two or more species are transported together in the same direction in a tightly coupled process, not coupled to a direct form of energy other than chemiosmotic energy).

Pyrophosphate bond hydrolysis-driven active transporters. Transport systems are included in this class if they hydrolyze pyrophosphate or the terminal pyrophosphate bond in ATP or another nucleoside triphosphate to drive the active uptake and/or extrusion of a solute or solutes. The transport protein may or may not be transiently phosphorylated, but the substrate is not phosphorylated.

PEP-dependent, phosphoryl transfer-driven group translocators. Transport systems of the bacterial phosphoenolpyruvate:sugar phosphotransferase system are included in this class. The product of the reaction, derived from extracellular sugar, is a cytoplasmic sugar-phosphate.

Decarboxylation-driven active transporters. Transport systems that drive solute (e.g., ion) uptake or extrusion by decarboxylation of a cytoplasmic substrate are included in this class.

Oxidoreduction-driven active transporters. Transport systems that drive transport of a solute (e.g., an ion) energized by the flow of electrons from a reduced substrate to an oxidized substrate are included in this class.

Light-driven active transporters. Transport systems that utilize light energy to drive transport of a solute (e.g., an ion) are included in this class.

Mechanically-driven active transporters. Transport systems are included in this class if they drive movement of a cell or organelle by allowing the flow of ions (or other solutes) through the membrane down their electrochemical gradients.

Outer-membrane porins (of b-structure). These proteins form transmembrane pores or channels that usually allow the energy independent passage of solutes across a membrane. The transmembrane portions of these proteins consist exclusively of b-strands that form a b-barrel. These porin-type proteins are found in the outer membranes of Gram-negative bacteria, mitochondria and eukaryotic plastids.

Methyltransferase-driven active transporters. A single characterized protein currently falls into this category, the $Na^+$-transporting methyltetrahydromethanopterin:coenzyme M methyltransferase.

Non-ribosome-synthesized channel-forming peptides or peptide-like molecules. These molecules, usually chains of L- and D-amino acids as well as other small molecular building blocks such as lactate, form oligomeric transmembrane ion channels. Voltage may induce channel formation by promoting assembly of the transmembrane channel. These peptides are often made by bacteria and fungi as agents of biological warfare.

Non-Proteinaceous Transport Complexes. Ion conducting substances in biological membranes that do not consist of or are not derived from proteins or peptides fall into this category.

Functionally characterized transporters for which sequence data are lacking. Transporters of particular physiological significance will be included in this category even though a family assignment cannot be made.

Putative transporters in which no family member is an established transporter. Putative transport protein families are grouped under this number and will either be classified elsewhere when the transport function of a member becomes established, or will be eliminated from the TC classification system if the proposed transport function is disproven. These families include a member or members for which a transport function has been suggested, but evidence for such a function is not yet compelling.

Auxiliary transport proteins. Proteins that in some way facilitate transport across one or more biological membranes but do not themselves participate directly in transport are included in this class. These proteins always function in conjunction with one or more transport proteins. They may provide a function connected with energy coupling to transport, play a structural role in complex formation or serve a regulatory function.

Transporters of unknown classification. Transport protein families of unknown classification are grouped under this number and will be classified elsewhere when the transport process and energy coupling mechanism are characterized. These families include at least one member for which a transport function has been established, but either the mode of transport or the energy coupling mechanism is not known.

Ion Channels

An important type of transporter is the ion channel. Ion channels regulate many different cell proliferation, differentiation, and signaling processes by regulating the flow of ions into and out of cells. Ion channels are found in the plasma membranes of virtually every cell in eukaryotic organisms. Ion channels mediate a variety of cellular functions including regulation of membrane potentials and absorption and secretion of ion across epithelial membranes. When present in intracellular membranes of the Golgi apparatus and endocytic vesicles, ion channels, such as chloride channels, also regulate organelle pH. For a review, see Greger, R. (1988) Annu. Rev. Physiol. 50:111–122.

Ion channels are generally classified by structure and the type of mode of action. For example, extracellular ligand gated channels (ELGs) are comprised of five polypeptide subunits, with each subunit having 4 membrane spanning domains, and are activated by the binding of an extracellular ligand to the channel. In addition, channels are sometimes classified by the ion type that is transported, for example, chlorine channels, potassium channels, etc. There may be many classes of channels for transporting a single type of ion (a detailed review of channel types can be found at Alexander, S. P. H. and J. A. Peters (1997). Receptor and ion channel nomenclature supplement. Trends Pharmacol. Sci., Elsevier, pp. 65–68 and http://www-biology.ucsd.edu/~msaier/transport/toc.html.

There are many types of ion channels based on structure. For example, many ion channels fall within one of the following groups: extracellular ligand-gated channels (ELG), intracellular ligand-gated channels (ILG), inward rectifying channels (INR), intercellular (gap junction) channels, and voltage gated channels (VIC). There are additionally recognized other channel families based on ion-type transported, cellular location and drug sensitivity. Detailed information on each of these, their activity, ligand type, ion type, disease association, drugability, and other information pertinent to the present invention, is well known in the art.

Extracellular ligand-gated channels, ELGs, are generally comprised of five polypeptide subunits, Unwin, N. (1993), Cell 72: 31–41; Unwin, N. (1995), Nature 373: 37–43; Hucho, F., et al., (1996) J. Neurochem. 66: 1781–1792; Hucho, F., et al., (1996) Eur. J. Biochem. 239: 539–557; Alexander, S. P. H. and J. A. Peters (1997), Trends Pharmacol. Sci., Elsevier, pp. 4–6; 36–40; 42–44; and Xue, H. (1998) J. Mol. Evol. 47: 323–333. Each subunit has 4 membrane spanning regions: this serves as a means of identifying other members of the ELG family of proteins. ELG bind a ligand and in response modulate the flow of ions. Examples of ELG include most members of the neurotransmitter-receptor family of proteins, e.g., GABAI receptors. Other members of this family of ion channels include glycine receptors, ryandyne receptors, and ligand gated calcium channels.

The Voltage-gated Ion Channel (VIC) Superfamily

Proteins of the VIC family are ion-selective channel proteins found in a wide range of bacteria, archaea and eukaryotes Hille, B. (1992), Chapter 9: Structure of channel proteins; Chapter 20: Evolution and diversity. In: Ionic Channels of Excitable Membranes, 2nd Ed., Sinaur Assoc. Inc., Pubs., Sunderland, Mass.; Sigworth, F. J. (1993), Quart. Rev. Biophys. 27: 1–40; Salkoff, L. and T. Jegla (1995), Neuron 15: 489–492; Alexander, S. P. H. et al., (1997), Trends Pharmacol. Sci., Elsevier, pp. 76–84; Jan, L. Y. et al., (1997), Annu. Rev. Neurosci. 20: 91–123; Doyle, D. A, et al., (1998) Science 280: 69–77; Terlau, H. and W. Stühmer (1998), Naturwissenschaften 85: 437–444. They are often homo- or heterooligomeric structures with several dissimilar subunits (e.g., a1-a2-d-b $Ca^{2+}$ channels, $ab_1b_2$ $Na^+$ channels or $(a)_4$-b $K^+$ channels), but the channel and the primary receptor is usually associated with the a (or al) subunit. Functionally characterized members are specific for $K^+$, $Na^+$ or $Ca^{2+}$. The $K^+$ channels usually consist of homotetrameric structures with each a-subunit possessing six transmembrane spanners (TMSs). The al and a subunits of the $Ca^{2+}$ and $Na^+$ channels, respectively, are about four times-as large and possess 4 units, each with 6 TMSs separated by a hydrophilic loop, for a total of 24 TMSs. These large channel proteins form heterotetra-unit structures equivalent to the homotetrameric structures of most $K^+$ channels. All four units of the $Ca^{2+}$ and $Na^+$ channels are homologous to the single unit in the homotetrameric $K^+$ channels. Ion flux via the eukaryotic channels is generally controlled by the transmembrane electrical potential (hence the designation, voltage-sensitive) although some are controlled by ligand or receptor binding.

Several putative $K^+$-selective channel proteins of the VIC family have been identified in prokaryotes. The structure of one of them, the KcsA $K^+$ channel of *Streptomyces lividans*, has been solved to 3.2 Å resolution. The protein possesses four identical subunits, each with two transmembrane helices, arranged in the shape of an inverted teepee or cone. The cone cradles the "selectivity filter" P domain in its outer end. The narrow selectivity filter is only 12 Å long, whereas the remainder of the channel is wider and lined with hydrophobic residues. A large water-filled cavity and helix dipoles stabilize $K^+$ in the pore. The selectivity filter has two bound $K^+$ ions about 7.5 Å apart from each other. Ion conduction is proposed to result from a balance of electrostatic attractive and repulsive forces.

In eukaryotes, each VIC family channel type has several subtypes based on pharmacological and electrophysiological data. Thus, there are five types of $Ca^{2+}$ channels (L, N, P, Q and T). There are at least ten types of $K^+$ channels, each responding in different ways to different stimuli: voltage-sensitive [Ka, Kv, Kvr, Kvs and Ksr], $Ca^{2+}$-sensitive [$BK_{Ca}$, $IK_{Ca}$ and $SK_{Ca}$] and receptor-coupled [$K_M$ and $K_{ACh}$]. There are at least six types of $Na^+$ channels (I, II, III, μ1, H1 and PN3). Tetrameric channels from both prokaryotic and eukaryotic organisms are known in which each a-subunit possesses 2 TMSs rather than 6, and these two TMSs are homologous to TMSs 5 and 6 of the six TMS unit found in the voltage-sensitive channel proteins. KcsA of *S. lividans* is an example of such a 2 TMS channel protein. These channels may include the $K_{Na}$ ($Na^+$-activated) and $K_{Vol}$ (cell volume-sensitive) $K^+$ channels, as well as distantly related channels such as the Tok1 $K^+$ channel of yeast, the TWIK-1 inward rectifier $K^+$ channel of the mouse and the TREK-1 $K^+$ channel of the mouse. Because of insufficient sequence similarity with proteins of the VIC family, inward rectifier $K^+$ IRK channels (ATP-regulated; G-protein-activated) which possess a P domain and two flanking TMSs are placed in a distinct family. However, substantial sequence similarity in the P region suggests that they are homologous. The b, g and d subunits of VIC family members, when present, frequently play regulatory roles in channel activation/deactivation.

The Eithelial $Na^+$ Channel (ENaC) Family

The ENaC family consists of over twenty-four sequenced proteins (Canessa, C. M., et al., (1994), Nature 367: 463–467, Le, T. and M. H. Saier, Jr. (1996), Mol. Membr. Biol. 13: 149–157; Garty, H. and L. G. Palmer (1997), Physiol. Rev. 77: 359–396; Waldmann, R., et al., (1997), Nature 386:173–177; Darboux, I., et al., (1998), J. Biol. Chem. 273: 9424–9429; Firsov, D., et al., (1998), EMBO J. 17: 344–352; Horisberger, J. -D. (1998). Curr. Opin. Struc. Biol. 10: 443–449). All are from animals with no recognizable homologues in other eukaryotes or bacteria. The vertebrate ENaC proteins from epithelial cells cluster tightly together on the phylogenetic tree: voltage-insensitive ENaC homologues are also found in the brain. Eleven sequenced *C. elegans* proteins, including the degenerins, are distantly related to the vertebrate proteins as well as to each other. At least some of these proteins form part of a mechanotransducing complex for touch sensitivity. The homologous *Helix aspersa* (FMRF-amide)-activated $Na^+$ channel is the first peptide neurotransmitter-gated ionotropic receptor to be sequenced.

Protein members of this family all exhibit the same apparent topology, each with N- and C-termini on the inside of the cell, two amphipathic transmembrane spanning segments, and a large extracellular loop. The extracellular domains contain numerous highly conserved cysteine residues. They are proposed to serve a receptor function.

Mammalian ENaC is important for the maintenance of $Na^+$ balance and the regulation of blood pressure. Three homologous ENaC subunits, alpha, beta, and gamma, have been shown to assemble to form the highly $Na^+$-selective channel. The stoichiometry of the three subunits is $alpha_2$, beta 1, gamma 1 in a heterotetrameric architecture.

The Chloride Channel (ClC) Family

The ClC family is a large family consisting of dozens of sequenced proteins derived from Gram-negative and Gram-positive bacteria, cyanobacteria, archaea, yeast, plants and animals (Steinmeyer, K., et al., (1991), Nature 354: 301–304; Uchida, S., et al., (1993), J. Biol. Chem. 268: 3821–3824; Huang, M. -E., et al., (1994), J. Mol. Biol. 242: 595–598; Kawasaki, M., et al, (1994), Neuron 12: 597–604; Fisher, W. E., et al., (1995), Genomics. 29:598–606; and Foskett, J. K. (1998), Annu. Rev. Physiol. 60: 689–717). These proteins are essentially ubiquitous, although they are not encoded within genomes of *Haemophilus influenzae*, *Mycoplasma genitalium*, and *Mycoplasma pneumoniae*. Sequenced proteins vary in size from 395 amino acyl residues (*M. jannaschii*) to 988 residues (man). Several organisms contain multiple ClC family paralogues. For example, Synechocystis has two paralogues, one of 451 residues in length and the other of 899 residues. *Arabidopsis thaliana* has at least four sequenced paralogues, (775–792 residues), humans also have at least five paralogues (820–988 residues), and *C. elegans* also has at least five (810–950 residues). There are nine known members in mammals, and mutations in three of the corresponding genes cause human diseases. *E. coli, Methanococcus jannaschii* and *Saccharomyces cerevisiae* only have one ClC family member each. With the exception of the larger Synechocystis paralogue, all bacterial proteins are small (395–492 residues) while all eukaryotic proteins are larger (687–988 residues). These proteins exhibit 10–12 putative transmembrane a-helical spanners (TMSs) and appear to be present in the membrane as homodimers. While one member of the family, Torpedo ClC-O, has been reported to have two channels, one per subunit, others are believed to have just one.

All functionally characterized members of the ClC family transport chloride, some in a voltage-regulated process. These channels serve a variety of physiological functions (cell volume regulation; membrane potential stabilization; signal transduction; transepithelial transport, etc.). Different homologues in humans exhibit differing anion selectivities, i.e., ClC4 and ClC5 share a $NO_3^->Cl^->Br^->I^-$ conductance sequence, while ClC3 has an $I^->Cl^-$ selectivity. The ClC4 and ClC5 channels and others exhibit outward rectifying currents with currents only at voltages more positive than +20 mV.

Animal Inward Rectifier $K^+$ Channel (IRK-C) Family

IRK channels possess the "minimal channel-forming structure" with only a P domain, characteristic of the channel proteins of the VIC family, and two flanking transmembrane spanners (Shuck, M. E., et al., (1994), J. Biol. Chem. 269: 24261–24270; Ashen, M. D., et al., (1995), Am. J. Physiol. 268: H506–H511; Salkoff, L. and T. Jegla (1995), Neuron 15: 489–492; Aguilar-Bryan, L., et al., (1998), Physiol. Rev. 78: 227–245; Ruknudin, A., et al., (1998), J. Biol. Chem. 273: 14165–14171). They may exist in the membrane as homo- or heterooligomers. They have a greater tendency to let $K^+$ flow into the cell than out. Voltage-dependence may be regulated by external $K^+$, by internal $Mg^{2+}$, by internal ATP and/or by G-proteins. The P domains of IRK channels exhibit limited sequence similarity to those of the VIC family, but this sequence similarity is insufficient to establish homology. Inward rectifiers play a role in setting cellular membrane potentials, and the closing of these channels upon depolarization permits the occurrence of long duration action potentials with a plateau phase. Inward rectifiers lack the intrinsic voltage sensing helices found in VIC family channels. In a few cases, those of Kir1.1 a and Kir6.2, for example, direct interaction with a member of the ABC superfamily has been proposed to confer unique functional and regulatory properties to the heteromeric complex, including sensitivity to ATP. The SUR1 sulfonylurea receptor (spQ09428) is the ABC protein that regulates the Kir6.2 channel in response to ATP, and CFTR may regulate Kir1.1 a. Mutations in SUR1 are the cause of familial persistent hyperinsulinemic hypoglycemia in infancy (PHHI), an autosomal recessive disorder characterized by unregulated insulin secretion in the pancreas.

ATP-gated Cation Channel (ACC) Family

Members of the ACC family (also called P2X receptors) respond to ATP, a functional neurotransmitter released by exocytosis from many types of neurons (North, R. A. (1996), Curr. Opin. Cell Biol. 8: 474–483; Soto, F., M. Garcia-Guzman and W. Stühmer (1997), J. Membr. Biol. 160: 91–100). They have been placed into seven groups (P2X$_1$–P2X$_7$) based on their pharmacological properties. These channels, which function at neuron—neuron and neuron-smooth muscle junctions, may play roles in the control of blood pressure and pain sensation. They may also function in lymphocyte and platelet physiology. They are found only in animals.

The proteins of the ACC family are quite similar in sequence (>35% identity), but they possess 380–1000 amino acyl residues per subunit with variability in length localized primarily to the C-terminal domains. They possess two transmembrane spanners, one about 30–50 residues from their N-termini, the other near residues 320–340. The extracellular receptor domains between these two spanners (of about 270 residues) are well conserved with numerous conserved glycyl and cysteyl residues. The hydrophilic C-termini vary in length from 25 to 240 residues. They resemble the topologically similar epithelial Na$^+$ channel (ENaC) proteins in possessing (a) N- and C-termini localized intracellularly, (b) two putative transmembrane spanners, (c) a large extracellular loop domain, and (d) many conserved extracellular cysteyl residues. ACC family members are, however, not demonstrably homologous with them. ACC channels are probably hetero- or homomultimers and transport small monovalent cations (Me$^+$). Some also transport Ca$^{2+}$; a few also transport small metabolites.

The Ryanodine-Inositol 1,4,5-triphosphate Receptor Ca$^{2+}$ Channel (RIR-CaC) Family Ryanodine (Ry)-sensitive and inositol 1,4,5-triphosphate (IP3)-sensitive Ca$^{2+}$-release channels function in the release of Ca$^{2+}$ from intracellular storage sites in animal cells and thereby regulate various Ca$^{2+}$-dependent physiological processes (Hasan, G. et al., (1992) Development 116: 967–975; Michikawa, T., et al., (1994), J. Biol. Chem. 269: 9184–9189; Tunwell, R. E. A., (1996), Biochem. J. 318: 477–487; Lee, A. G. (1996) Biomembranes, Vol. 6, Transmembrane Receptors and Channels (A. G. Lee, ed.), JAI Press, Denver, Colo., pp 291–326; Mikoshiba, K., et al., (1996) J. Biochem. Biomem. 6: 273–289). Ry receptors occur primarily in muscle cell sarcoplasmic reticular (SR) membranes, and IP3 receptors occur primarily in brain cell endoplasmic reticular (ER) membranes where they effect release of Ca$^{2+}$ into the cytoplasm upon activation (opening) of the channel.

The Ry receptors are activated as a result of the activity of dihydropyridine-sensitive Ca$^+$ channels. The latter are members of the voltage-sensitive ion channel (VIC) family. Dihydropyridine-sensitive channels are present in the T-tubular systems of muscle tissues.

Ry receptors are homotetrameric complexes with each subunit exhibiting a molecular size of over 500,000 daltons (about 5,000 amino acyl residues). They possess C-terminal domains with six putative transmembrane a-helical spanners (TMSs). Putative pore-forming sequences occur between the fifth and sixth TMSs as suggested for members of the VIC family. The large N-terminal hydrophilic domains and the small C-terminal hydrophilic domains are localized to the cytoplasm. Low resolution 3-dimensional structural data are available. Mammals possess at least three isoforms that probably arose by gene duplication and divergence before divergence of the mammalian species. Homologues are present in humans and *Caenorabditis elegans*.

IP$_3$ receptors resemble Ry receptors in many respects. (1) They are homotetrameric complexes with each subunit exhibiting a molecular size of over 300,000 daltons (about 2,700 amino acyl residues). (2) They possess C-terminal channel domains that are homologous to those of the Ry receptors. (3) The channel domains possess six putative TMSs and a putative channel lining region between TMSs 5 and 6. (4) Both the large N-terminal domains and the smaller C-terminal tails face the cytoplasm. (5) They possess covalently linked carbohydrate on extracytoplasmic loops of the channel domains. (6) They have three currently recognized isoforms (types 1, 2, and 3) in mammals which are subject to differential regulation and have different tissue distributions.

IP$_3$ receptors possess three domains: N-terminal IP$_3$-binding domains, central coupling or regulatory domains and C-terminal channel domains. Channels are activated by IP$_3$ binding, and like the Ry receptors, the activities of the IP$_3$ receptor channels are regulated by phosphorylation of the regulatory domains, catalyzed by various protein kinases. They predominate in the endoplasmic reticular membranes of various cell types in the brain but have also been found in the plasma membranes of some nerve cells derived from a variety of tissues.

The channel domains of the Ry and IP$_3$ receptors comprise a coherent family that in spite of apparent structural similarities, do not show appreciable sequence similarity of the proteins of the VIC family. The Ry receptors and the IP$_3$ receptors cluster separately on the RIR-CaC family tree. They both have homologues in *Drosophila*. Based on the phylogenetic tree for the family, the family probably evolved in the following sequence: (1) A gene duplication event occurred that gave rise to Ry and IP$_3$ receptors in invertebrates. (2) Vertebrates evolved from invertebrates. (3) The three isoforms of each receptor arose as a result of two distinct gene duplication events. (4) These isoforms were transmitted to mammals before divergence of the mammalian species.

The Organellar Chloride Channel (O-CIC) Family

Proteins of the O-CIC family are voltage-sensitive chloride channels found in intracellular membranes but not the plasma membranes of animal cells (Landry, D, et al., (1993), J. Biol. Chem. 268: 14948–14955; Valenzuela, Set al., (1997), J. Biol. Chem. 272: 12575–12582; and Duncan, R. R., et al., (1997), J. Biol. Chem. 272: 23880–23886).

They are found in human nuclear membranes, and the bovine protein targets to the microsomes, but not the plasma membrane, when expressed in *Xenopus laevis* oocytes. These proteins are thought to function in the regulation of the membrane potential and in transepithelial ion absorption and secretion in the kidney. They possess two putative transmembrane a-helical spanners (TMSs) with cytoplasmic N- and C-termini and a large luminal loop that may be glycosylated. The bovine protein is 437 amino acyl residues in length and has the two putative TMSs at positions 223–239 and 367–385. The human nuclear protein is much smaller (241 residues). A *C. elegans* homologue is 260 residues long.

The Glutamate-gated Ion Channel (GIC) Family of Neurotransmitter Receptors

Members of the GIC family are heteropentameric complexes in which each of the 5 subunits is of 800–1000 amino acyl residues in length (Nakanishi, N., et al, (1990), Neuron 5: 569–581; Unwin, N. (1993), Cell 72: 31–41; Alexander, S. P. H. and J. A. Peters (1997) Trends Pharmacol. Sci., Elsevier, pp. 36–40). These subunits may span the membrane three or five times as putative a-helices with the N-termini (the glutamate-binding domains) localized extracellularly and the C-termini localized cytoplasmically. They may be distantly related to the ligand-gated ion channels, and if so, they may possess substantial b-structure in their transmembrane regions. However, homology between these two families cannot be established on the basis of sequence comparisons alone. The subunits fall into six subfamilies: a, b, g, d, e and z.

The GIC channels are divided into three types: (1) a-amino-3-hydroxy-5-methyl-4-isoxazole propionate (AMPA)-, (2) kainate- and (3) N-methyl-D-aspartate (NMDA)-selective glutamate receptors. Subunits of the AMPA and kainate classes exhibit 35–40% identity with each other while subunits of the NMDA receptors exhibit 22–24% identity with the former subunits. They possess large N-terminal, extracellular glutamate-binding domains that are homologous to the periplasmic glutamine and glutamate receptors of ABC-type uptake permeases of Gram-negative bacteria. All known members of the GIC family are from animals. The different channel (receptor) types exhibit distinct ion selectivities and conductance properties. The NMDA-selective large conductance channels are highly permeable to monovalent cations and $Ca^{2+}$. The AMPA- and kainate-selective ion channels are permeable primarily to monovalent cations with only low permeability to $Ca^{2+}$.

The brain-specific $Na^+$-dependent inorganic phosphate transporter (BNPI) belongs to a family of proteins that use the inwardly directed $Na^+$ gradient across the plasma membrane to cotransport inorganic phosphate (Pi). Originally identified as a sequence up-regulated by the exposure of cerebellar granule cells to subtoxic concentrations of N-methyl-D-aspartate, BNPI mediates the $Na^+$-dependent accumulation of Pi in Xenopus oocytes. BNPI has been implicated in adenosine 5'-triphosphate (ATP) production by neurons and protection against excitotoxic injury. However, BNPI is only expressed by glutamatergic neurons, militating against a general metabolic role in all neuronal populations. In Caenorhabditis elegans, genetic screens for multiple behavioral defects have identified mutants in the BNPI ortholog eat-4, and recent studies indicate a specific role for eat-4 in glutamatergic neurotransmission. The glutamatergic defect in eat-4 mutants appears to be presynaptic, consistent with the localization of BNPI to excitatory nerve terminals. The accumulation of cytoplasmic Pi mediated by BNPI may activate the phosphate-activated glutaminase responsible for biosynthesis of the bulk of glutamate released as a neurotransmitter. However, the family of proteins including BNPI/EAT-4 may have functions in addition to Pi transport.

BNPI shows sequence similarity to type I but not type II $Na^+$/Pi cotransporters. In contrast to the type II transporters that exhibit robust $Na^+$-dependent Pi uptake, the accumulation of Pi by type I transporters is less striking. Rather, the type I transporter NaPi-1 transports organic anions, including phenol red and penicillin G, with substantially higher apparent affinity than Pi. Human genetic studies have shown that mutations in another protein closely related to BNPI and NaPi-1 account for disorders of sialic acid storage. In these conditions, sialic acid accumulates in lysosomes because of a defect in proton-driven export. Although the sialin protein has not been demonstrated to mediate sialic acid transport, these observations together with the report that NaPi-1 accumulates organic anions with high apparent affinity suggest that BNPI might also transport organic anions. Localization to glutamatergic nerve terminals raises the possibility that it transports glutamate. In addition, BNPI is localized to synaptic vesicles in the brain and to intracellular membranes in transfected cells, suggesting a role for BNPI in the transport of glutamate into synaptic vesicles for regulated exocytotic release.

Glutamate transport into synaptic vesicles exhibits a number of properties that distinguish it from glutamate uptake by other transport systems. First, in contrast to plasma membrane glutamate uptake, the accumulation of glutamate in synaptic vesicles does not rely on a $Na^+$ electrochemical gradient. Consistent with this, glutamate was transported by BNPI in the absence of $Na^+$. Second, vesicular glutamate transport has a substantially lower apparent affinity (Km of ~1 mM) than the plasma membrane excitatory amino acid transporters (Km of ~10 to 100 EM). Glutamate transport by BNPI is saturated with a Km of ~2 mM, in the same range as transport by synaptic vesicles. Third, plasma membrane glutamate transporters recognize both aspartate and glutamate as substrates, whereas vesicular glutamate transport does not recognize aspartate. D-Glutamate partially inhibited the transport of 3H-glutamate, and L-glutamine had no effect, also consistent with prior work. Fourth, low micromolar concentrations of the dye Evans blue inhibited the transport of glutamate into both synaptic vesicles and membranes expressing BNPI.

For a review associated with the differentation-associated Na-dependent inorganic phosphate cotransporter, see references Bellocchio et al., Science, 289:957–960, 2000, Aihara et al., J. Neurochem. 74: 2622–2625, 2000, Ni et al., J. Neurochem, 66: 2f227–2238, 1996, Takamori et al., Nature 407: 189–194, 2000.

Transporter proteins, particularly members of the differentiation-associated Na-dependent inorganic phosphate cotransporter subfamily, are a major target for drug action and development. Accordingly, it is valuable to the field of pharmaceutical development to identify and characterize previously unknown transport proteins. The present invention advances the state of the art by providing previously unidentified human transport proteins.

SUMMARY OF THE INVENTION

The present invention is based in part on the identification of amino acid sequences of human transporter peptides and proteins that are related to the differentiation-associated Na-dependent inorganic phosphate cotransporter subfamily, as well as allelic variants and other mammalian orthologs thereof. These unique peptide sequences, and nucleic acid sequences that encode these peptides, can be used as models for the development of human therapeutic targets, aid in the identification of therapeutic proteins, and serve as targets for the development of human therapeutic agents that modulate transporter activity in cells and tissues that express the transporter.

DESCRIPTION OF THE FIGURE SHEETS

FIG. 1 provides the nucleotide sequence of a cDNA molecule or transcript sequence that encodes the transporter protein of the present invention. In addition structure and functional information is provided, such as ATG start, stop and tissue distribution, where available, that allows one to readily determine specific uses of inventions based on this molecular sequence. Experimental data as provided in FIG. 1 indicates expression in the pooled human melanocyte, fetal heart, and pregnant uterus and human leukocytes.

FIG. 2 provides the predicted amino acid sequence of the transporter of the present invention. In addition structure and functional information such as protein family, function, and modification sites is provided where available, allowing one to readily determine specific uses of inventions based on this molecular sequence.

FIG. 3 provides genomic sequences that span the gene encoding the transporter protein of the present invention. In addition structure and functional information, such as intron/ exon structure, promoter location, etc., is provided where available, allowing one to readily determine specific uses of inventions based on this molecular sequence. 69 SNPs, including 14 indels, have been identified in the gene encoding the transporter protein provided by the present invention and are given in FIG. 3.

DETAILED DESCRIPTION OF THE INVENTION

General Description

The present invention is based on the sequencing of the human genome. During the sequencing and assembly of the human genome, analysis of the sequence information revealed previously unidentified fragments of the human genome that encode peptides that share structural and/or sequence homology to protein/peptide/domains identified and characterized within the art as being a transporter protein or part of a transporter protein and are related to the differentation-associated Na-dependent inorganic phosphate cotransporter subfamily. Utilizing these sequences, additional genomic sequences were assembled and transcript and/or cDNA sequences were isolated and characterized. Based on this analysis, the present invention provides amino acid sequences of human transporter peptides and proteins that are related to the differentation-associated Na-dependent inorganic phosphate cotransporter subfamily, nucleic acid sequences in the form of transcript sequences, cDNA sequences and/or genomic sequences that encode these transporter peptides and proteins, nucleic acid variation (allelic information), tissue distribution of expression, and information about the closest art known protein/peptide/domain that has structural or sequence homology to the transporter of the present invention.

In addition to being previously unknown, the peptides that are provided in the present invention are selected based on their ability to be used for the development of commercially important products and services. Specifically, the present peptides are selected based on homology and/or structural relatedness to known transporter proteins of the differentation-associated Na-dependent inorganic phosphate cotransporter subfamily and the expression pattern observed. Experimental data as provided in FIG. 1 indicates expression in the pooled human melanocyte, fetal heart, and pregnant uterus and human leukocytes. The art has clearly established the commercial importance of members of this family of proteins and proteins that have expression patterns similar to that of the present gene. Some of the more specific features of the peptides of the present invention, and the uses thereof, are described herein, particularly in the Background of the Invention and in the annotation provided in the Figures, and/or are known within the art for each of the known differentation-associated Na-dependent inorganic phosphate cotransporter family or subfamily of transporter proteins.

Specific Embodiments

Peptide Molecules

The present invention provides nucleic acid sequences that encode protein molecules that have been identified as being members of the transporter family of proteins and are related to the differentation-associated Na-dependent inorganic phosphate cotransporter subfamily (protein sequences are provided in FIG. 2, transcript/cDNA sequences are provided in FIG. 1 and genomic sequences are provided in FIG. 3). The peptide sequences provided in FIG. 2, as well as the obvious variants described herein, particularly allelic variants as identified herein and using the information in FIG. 3, will be referred herein as the transporter peptides of the present invention, transporter peptides, or peptides/proteins of the present invention.

The present invention provides isolated peptide and protein molecules that consist of, consist essentially of, or comprising the amino acid sequences of the transporter peptides disclosed in the FIG. 2, (encoded by the nucleic acid molecule shown in FIG. 1, transcript/cDNA or FIG. 3, genomic sequence), as well as all obvious variants of these peptides that are within the art to make and use. Some of these variants are described in detail below.

As used herein, a peptide is said to be "isolated" or "purified" when it is substantially free of cellular material or free of chemical precursors or other chemicals. The peptides of the present invention can be purified to homogeneity or other degrees of purity. The level of purification will be based on the intended use. The critical feature is that the preparation allows for the desired function of the peptide, even if in the presence of considerable amounts of other components (the features of an isolated nucleic acid molecule is discussed below).

In some uses, "substantially free of cellular material" includes preparations of the peptide having less than about 30% (by dry weight) other proteins (i.e., contaminating protein), less than about 20% other proteins, less than about 10% other proteins, or less than about 5% other proteins. When the peptide is recombinantly produced, it can also be substantially free of culture medium, i.e., culture medium represents less than about 20% of the volume of the protein preparation.

The language "substantially free of chemical precursors or other chemicals" includes preparations of the peptide in which it is separated from chemical precursors or other chemicals that are involved in its synthesis. In one embodiment, the language "substantially free of chemical precursors or other chemicals" includes preparations of the transporter peptide having less than about 30% (by dry weight) chemical precursors or other chemicals, less than about 20% chemical precursors or other chemicals, less than about 10% chemical precursors or other chemicals, or less than about 5% chemical precursors or other chemicals.

The isolated transporter peptide can be purified from cells that naturally express it, purified from cells that have been altered to express it (recombinant), or synthesized using known protein synthesis methods. Experimental data as provided in FIG. 1 indicates expression in the pooled human melanocyte, fetal heart, and pregnant uterus and human leukocytes. For example, a nucleic acid molecule encoding the transporter peptide is cloned into an expression vector, the expression vector introduced into a host cell and the protein expressed in the host cell. The protein can then be isolated from the cells by an appropriate purification scheme using standard protein purification techniques. Many of these techniques are described in detail below.

Accordingly, the present invention provides proteins that consist of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). The amino acid sequence of such a protein is provided in FIG. 2. A protein consists of an amino acid sequence when the amino acid sequence is the final amino acid sequence of the protein.

The present invention further provides proteins that consist essentially of the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein consists essentially of an amino acid sequence when such an amino acid sequence is present with only a few additional amino acid residues, for example from about 1 to about 100 or so additional residues, typically from 1 to about 20 additional residues in the final protein.

The present invention further provides proteins that comprise the amino acid sequences provided in FIG. 2 (SEQ ID NO:2), for example, proteins encoded by the transcript/cDNA nucleic acid sequences shown in FIG. 1 (SEQ ID NO:1) and the genomic sequences provided in FIG. 3 (SEQ ID NO:3). A protein comprises an amino acid sequence when the amino acid sequence is at least part of the final amino acid sequence of the protein. In such a fashion, the protein can be only the peptide or have additional amino acid molecules, such as amino acid residues (contiguous encoded sequence) that are naturally associated with it or heterologous amino acid residues/peptide sequences. Such a protein can have a few additional amino acid residues or can comprise several hundred or more additional amino acids. The preferred classes of proteins that are comprised of the transporter peptides of the present invention are the naturally occurring mature proteins. A brief description of how various types of these proteins can be made/isolated is provided below.

The transporter peptides of the present invention can be attached to heterologous sequences to form chimeric or fusion proteins. Such chimeric and fusion proteins comprise a transporter peptide operatively linked to a heterologous protein having an amino acid sequence not substantially homologous to the transporter peptide. "Operatively linked" indicates that the transporter peptide and the heterologous protein are fused in-frame. The heterologous protein can be fused to the N-terminus or C-terminus of the transporter peptide.

In some uses, the fusion protein does not affect the activity of the transporter peptide per se. For example, the fusion protein can include, but is not limited to, enzymatic fusion proteins, for example beta-galactosidase fusions, yeast two-hybrid GAL fusions, poly-His fusions, MYC-tagged, HI-tagged and Ig fusions. Such fusion proteins, particularly poly-His fusions, can facilitate the purification of recombinant transporter peptide. In certain host cells (e.g., mammalian host cells), expression and/or secretion of a protein can be increased by using a heterologous signal sequence.

A chimeric or fusion protein can be produced by standard recombinant DNA techniques. For example, DNA fragments coding for the different protein sequences are ligated together in-frame in accordance with conventional techniques. In another embodiment, the fusion gene can be synthesized by conventional techniques including automated DNA synthesizers. Alternatively, PCR amplification of gene fragments can be carried out using anchor primers which give rise to complementary overhangs between two consecutive gene fragments which can subsequently be annealed and re-amplified to generate a chimeric gene sequence (see Ausubel et al, *Current Protocols in Molecular Biology*, 1992). Moreover, many expression vectors are commercially available that already encode a fusion moiety (e.g., a GST protein). A transporter peptide-encoding nucleic acid can be cloned into such an expression vector such that the fusion moiety is linked in-frame to the transporter peptide.

As mentioned above, the present invention also provides and enables obvious variants of the amino acid sequence of the proteins of the present invention, such as naturally occurring mature forms of the peptide, allelic/sequence variants of the peptides, non-naturally occurring recombinantly derived variants of the peptides, and orthologs and paralogs of the peptides. Such variants can readily be generated using art-known techniques in the fields of recombinant nucleic acid technology and protein biochemistry. It is understood, however, that variants exclude any amino acid sequences disclosed prior to the invention.

Such variants can readily be identified/made using molecular techniques and the sequence information disclosed herein. Further, such variants can readily be distinguished from other peptides based on sequence and/or structural homology to the transporter peptides of the present invention. The degree of homology/identity present will be based primarily on whether the peptide is a functional variant or non-functional variant, the amount of divergence present in the paralog family and the evolutionary distance between the orthologs.

To determine the percent identity of two amino acid sequences or two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). In a preferred embodiment, at least 30%, 40%, 50%, 60%, 70%, 80%, or 90% or more of a reference sequence is aligned for comparison purposes. The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The comparison of sequences and determination of percent identity and similarity between two sequences can be accomplished using a mathematical algorithm. (*Computational Molecular Biology*, Lesk, A. M., ed., Oxford University Press, New York, 1988; *Biocomputing: Informatics and Genome Projects*, Smith, D. W., ed., Academic Press, New York, 1993; *Computer Analysis of Sequence Data*, Part 1, Griffin, A. M., and Griffin, H. G., eds., Humana Press, New Jersey, 1994; *Sequence Analysis in Molecular Biology*, von Heinje, G., Academic Press, 1987; and *Sequence Analysis Primer*, Gribskov, M. and Devereux, J., eds., M Stockton Press, New York, 1991). In a preferred embodiment, the percent identity between two amino acid sequences is determined using the Needleman and Wunsch (*J. Mol. Biol.* (48):444–453 (1970)) algorithm which has been incorporated into the GAP program in the GCG software package (available at http://www.gcg.com), using either a Blossom 62 matrix or a PAM250 matrix, and a gap weight of 16, 14, 12, 10, 8, 6, or 4 and a length weight of 1, 2, 3, 4, 5, or 6. In yet another preferred embodiment, the percent identity between two nucleotide sequences is determined using the GAP program in the GCG software package (Devereux, J., et al., *Nucleic Acids Res.* 12(1):387 (1984)) (available at http://www.gcg.com), using a NWS-gapdna.CMP matrix and a gap weight of 40, 50, 60, 70, or 80 and a length weight of 1, 2, 3, 4, 5, or 6. In another embodiment, the percent identity between two amino acid or nucleotide sequences is determined using the algorithm of E. Myers and W. Miller (CABIOS, 4:11–17 (1989)) which has been incorporated into the ALIGN program (version 2.0), using a PAM120 weight residue table, a gap length penalty of 12 and a gap penalty of 4.

The nucleic acid and protein sequences of the present invention can further be used as a "query sequence" to perform a search against sequence databases to, for example, identify other family members or related sequences. Such searches can be performed using the NBLAST and XBLAST programs (version 2.0) of Altschul, et al. (*J. Mol. Biol.* 215:403–10 (1990)). BLAST nucleotide searches can be performed with the NBLAST program, score=100, wordlength=12 to obtain nucleotide sequences homologous to the nucleic acid molecules of the invention. BLAST protein searches can be performed with the XBLAST program, score=50, wordlength=3 to obtain amino acid sequences homologous to the proteins of the invention. To obtain gapped alignments for comparison purposes, Gapped BLAST can be utilized as described in Altschul et al. (*Nucleic Acids Res.* 25(17):3389–3402 (1997)). When utilizing BLAST and gapped BLAST programs, the default parameters of the respective programs (e.g., XBLAST and NBLAST) can be used.

Full-length pre-processed forms, as well as mature processed forms, of proteins that comprise one of the peptides of the present invention can readily be identified as having complete sequence identity to one of the transporter peptides of the present invention as well as being encoded by the same genetic locus as the transporter peptide provided herein.

Allelic variants of a transporter peptide can readily be identified as being a human protein having a high degree (significant) of sequence homology/identity to at least a portion of the transporter peptide as well as being encoded by the same genetic locus as the transporter peptide provided herein. Genetic locus can readily be determined based on the genomic information provided in FIG. 3, such as the genomic sequence mapped to the reference human. As indicated by the data presented in FIG. 3, the map position was determined to be on chromosome 12 by ePCR, and confirmed with radiation hybrid mapping. As used herein, two proteins (or a region of the proteins) have significant homology when the amino acid sequences are typically at least about 70–80%, 80–90%, and more typically at least about 90–95% or more homologous. A significantly homologous amino acid sequence, according to the present invention, will be encoded by a nucleic acid sequence that will hybridize to a transporter peptide encoding nucleic acid molecule under stringent conditions as more fully described below.

FIG. 3 provides information on SNPs that have been identified in a gene encoding the transporter protein of the present invention. 69 SNP variants were found, including 14 indels (indicated by a "–") and 1 SNPs in exons.

Paralogs of a transporter peptide can readily be identified as having some degree of significant sequence homology/identity to at least a portion of the transporter peptide, as being encoded by a gene from humans, and as having similar activity or function. Two proteins will typically be considered paralogs when the amino acid sequences are typically at least about 60% or greater, and more typically at least about 70% or greater homology through a given region or domain. Such paralogs will be encoded by a nucleic acid sequence that will hybridize to a transporter peptide encoding nucleic acid molecule under moderate to stringent conditions as more fully described below.

Orthologs of a transporter peptide can readily be identified as having some degree of significant sequence homology/identity to at least a portion of the transporter peptide as well as being encoded by a gene from another organism. Preferred orthologs will be isolated from mammals, preferably primates, for the development of human therapeutic targets and agents. Such orthologs will be encoded by a nucleic acid sequence that will hybridize to a transporter peptide encoding nucleic acid molecule under moderate to stringent conditions, as more fully described below, depending on the degree of relatedness of the two organisms yielding the proteins.

Non-naturally occurring variants of the transporter peptides of the present invention can readily be generated using recombinant techniques. Such variants include, but are not limited to deletions, additions and substitutions in the amino acid sequence of the transporter peptide. For example, one class of substitutions are conserved amino acid substitution. Such substitutions are those that substitute a given amino acid in a transporter peptide by another amino acid of like characteristics. Typically seen as conservative substitutions are the replacements, one for another, among the aliphatic amino acids Ala, Val, Leu, and Ile; interchange of the hydroxyl residues Ser and Thr; exchange of the acidic residues Asp and Glu; substitution between the amide residues Asn and Gln; exchange of the basic residues Lys and Arg; and replacements among the aromatic residues Phe and Tyr. Guidance concerning which amino acid changes are likely to be phenotypically silent are found in Bowie et al., *Science* 247:1306–1310 (1990).

Variant transporter peptides can be fully functional or can lack function in one or more activities, e.g. ability to bind ligand, ability to transport ligand, ability to mediate signaling, etc. Fully functional variants typically contain only conservative variation or variation in non-critical residues or in non-critical regions. FIG. 2 provides the result of protein analysis and can be used to identify critical domains/regions. Functional variants can also contain substitution of similar amino acids that result in no change or an insignificant change in function. Alternatively, such substitutions may positively or negatively affect function to some degree.

Non-functional variants typically contain one or more non-conservative amino acid substitutions, deletions, insertions, inversions, or truncation or a substitution, insertion, inversion, or deletion in a critical residue or critical region.

Amino acids that are essential for function can be identified by methods known in the art, such as site-directed mutagenesis or alanine-scanning mutagenesis (Cunningham et al., *Science* 244:1081–1085 (1989)), particularly using the results provided in FIG. 2. The latter procedure introduces single alanine mutations at every residue in the molecule. The resulting mutant molecules are then tested for biological activity such as transporter activity or in assays such as an in vitro proliferative activity. Sites that are critical for binding partner/substrate binding can also be determined by structural analysis such as crystallization, nuclear magnetic resonance or photoaffinity labeling (Smith et al., *J. Mol. Biol.* 224:899–904 (1992); de Vos et al. *Science* 255:306–312 (1992)).

The present invention further provides fragments of the transporter peptides, in addition to proteins and peptides that comprise and consist of such fragments, particularly those comprising the residues identified in FIG. 2. The fragments to which the invention pertains, however, are not to be construed as encompassing fragments that may be disclosed publicly prior to the present invention.

As used herein, a fragment comprises at least 8, 10, 12, 14, 16, or more contiguous amino acid residues from a transporter peptide. Such fragments can be chosen based on the ability to retain one or more of the biological activities of the transporter peptide or could be chosen for the ability to perform a function, e.g. bind a substrate or act as an immunogen. Particularly important fragments are biologically active fragments, peptides that are, for example, about 8 or more amino acids in length. Such fragments will typically comprise a domain or motif of the transporter peptide, e.g., active site, a transmembrane domain or a substrate-binding domain. Further, possible fragments include, but are not limited to, domain or motif containing fragments, soluble peptide fragments, and fragments containing immunogenic structures. Predicted domains and functional sites are readily identifiable by computer programs well known and readily available to those of skill in the art (e.g., PROSITE analysis). The results of one such analysis are provided in FIG. 2.

Polypeptides often contain amino acids other than the 20 amino acids commonly referred to as the 20 naturally occurring amino acids. Further, many amino acids, including the terminal amino acids, may be modified by natural processes, such as processing and other post-translational modifications, or by chemical modification techniques well known in the art. Common modifications that occur naturally in transporter peptides are described in basic texts, detailed monographs, and the research literature, and they are well known to those of skill in the art (some of these features are identified in FIG. 2).

Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as *Proteins—Structure and Molecular Properties*, 2nd Ed., T. E. Creighton, W. H. Freeman and Company, New York (1993). Many detailed reviews are available on this subject, such as by Wold, F., *Posttranslational Covalent Modification of Proteins*, B. C. Johnson, Ed., Academic Press, New York 1–12 (1983); Seifter et al. (*Meth. Enzymol.* 182: 626–646 (1990)) and Rattan et al. (*Ann. N.Y. Acad. Sci.* 663:48–62 (1992)).

Accordingly, the transporter peptides of the present invention also encompass derivatives or analogs in which a substituted amino acid residue is not one encoded by the genetic code, in which a substituent group is included, in which the mature transporter peptide is fused with another compound, such as a compound to increase the half-life of the transporter peptide (for example, polyethylene glycol), or in which the additional amino acids are fused to the mature transporter peptide, such as a leader or secretory sequence or a sequence for purification of the mature transporter peptide or a pro-protein sequence.

Protein/Peptide Uses

The proteins of the present invention can be used in substantial and specific assays related to the functional information provided in the Figures; to raise antibodies or to elicit another immune response; as a reagent (including the labeled reagent) in assays designed to quantitatively determine levels of the protein (or its binding partner or ligand) in biological fluids; and as markers for tissues in which the corresponding protein is preferentially expressed (either constitutively or at a particular stage of tissue differentiation or development or in a disease state). Where the protein binds or potentially binds to another protein or ligand (such as, for example, in a transporter-effector protein interaction or transporter-ligand interaction), the protein can be used to identify the binding partner/ligand so as to develop a system to identify inhibitors of the binding interaction. Any or all of these uses are capable of being developed into reagent grade or kit format for commercialization as commercial products.

Methods for performing the uses listed above are well known to those skilled in the art. References disclosing such methods include "Molecular Cloning: A Laboratory Manual", 2d ed., Cold Spring Harbor Laboratory Press, Sambrook, J., E. F. Fritsch and T. Maniatis eds., 1989, and "Methods in Enzymology: Guide to Molecular Cloning Techniques", Academic Press, Berger, S. L. and A. R. Kimmel eds., 1987.

Substantial chemical and structural homology exists between the differentation-associated Na-dependent inorganic phosphate cotransporter protein described herein and brain-specific $Na^+$-dependent inorganic phosphate transporter (BNPI) (see FIG. 1). As discussed in the background, brain-specific $Na^+$-dependent inorganic phosphate transporter is known in the art to be involved in transporting glutamate into native synaptic vesicles from the brain and it is also a phosphate transporter, presumably at the plasma membrane. Using fluorescence in situ hybridization, the BNPI gene is to be located on th elong arm of 19q13, in close proximity to the late-onset familial Alzheimer disease locus (Ni et al., *J. Neurochem,* 66: 2f227–2238, 1996), Accordingly, the differentation-associated Na-dependent inorganic phosphate cotransporter protein, and the encoding gene, provided by the present invention is useful for treating, preventing, and/or diagnosing neurotransmitter related disease, brain diseases such as Alzheimer and other disorders associated with this BNPI.

The potential uses of the peptides of the present invention are based primarily on the source of the protein as well as the class/action of the protein. For example, transporters isolated from humans and their human/mammalian orthologs serve as targets for identifying agents for use in mammalian therapeutic applications, e.g. a human drug, particularly in modulating a biological or pathological response in a cell or tissue that expresses the transporter. Experimental data as provided in FIG. 1 indicates that transporter proteins of the present invention are expressed in the pooled human melanocyte, fetal heart, and pregnant uterus detected by a virtual northern blot. In addition, PCR-based tissue screening panel indicates expression in human leukocytes. A large percentage of pharmaceutical agents are being developed that modulate the activity of transporter proteins, particularly members of the differentiation-associated Na-dependent inorganic phosphate cotransporter subfamily (see Background of the Invention). The structural and functional information provided in the Background and Figures provide specific and substantial uses for the molecules of the present invention, particularly in combination with the expression information provided in FIG. 1. Experimental data as provided in FIG. 1 indicates expression in the pooled human melanocyte, fetal heart, and pregnant uterus and human leukocytes. Such uses can readily be determined using the information provided herein, that known in the art and routine experimentation.

The proteins of the present invention (including variants and fragments that may have been disclosed prior to the present invention) are useful for biological assays related to transporters that are related to members of the differentation-associated Na-dependent inorganic phosphate cotransporter subfamily. Such assays involve any of the known transporter functions or activities or properties useful for diagnosis and treatment of transporter-related conditions that are specific for the subfamily of transporters that the one of the present invention belongs to, particularly in cells and tissues that express the transporter. Experimental data as provided in FIG. 1 indicates that transporter proteins of the present invention are expressed in the pooled human melanocyte, fetal heart, and pregnant uterus detected by a virtual northern blot. In addition, PCR-based tissue screening panel indicates expression in human leukocytes.

The proteins of the present invention are also useful in drug screening assays, in cell-based or cell-free systems ((Hodgson, Bio/technology, Sep. 10, 1992 (9);973–80). Cell-based systems can be native, i.e., cells that normally express the transporter, as a biopsy or expanded in cell culture. Experimental data as provided in FIG. 1 indicates expression in the pooled human melanocyte, fetal heart, and pregnant uterus and human leukocytes. In an alternate embodiment, cell-based assays involve recombinant host cells expressing the transporter protein.

The polypeptides can be used to identify compounds that modulate transporter activity of the protein in its natural state or an altered form that causes a specific disease or pathology associated with the transporter. Both the transporters of the present invention and appropriate variants and fragments can be used in high-throughput screens to assay candidate compounds for the ability to bind to the transporter. These compounds can be further screened against a functional transporter to determine the effect of the compound on the transporter activity. Further, these compounds can be tested in animal or invertebrate systems to determine activity/effectiveness. Compounds can be identified that activate (agonist) or inactivate (antagonist) the transporter to a desired degree.

Further, the proteins of the present invention can be used to screen a compound for the ability to stimulate or inhibit interaction between the transporter protein and a molecule that normally interacts with the transporter protein, e.g. a substrate or a component of the signal pathway that the transporter protein normally interacts (for example, another transporter). Such assays typically include the steps of combining the transporter protein with a candidate compound under conditions that allow the transporter protein, or fragment, to interact with the target molecule, and to detect the formation of a complex between the protein and the target or to detect the biochemical consequence of the interaction with the transporter protein and the target, such as any of the associated effects of signal transduction such as changes in membrane potential, protein phosphorylation, cAMP turnover, and adenylate cyclase activation, etc.

Candidate compounds include, for example, 1) peptides such as soluble peptides, including Ig-tailed fusion peptides and members of random peptide libraries (see, e.g., Lam et al., Nature 354:82–84 (1991); Houghten et al., Nature 354:84–86 (1991)) and combinatorial chemistry-derived molecular libraries made of D- and/or L-configuration amino acids; 2) phosphopeptides (e.g., members of random and partially degenerate, directed phosphopeptide libraries, see, e.g., Songyang et al., Cell 72:767–778 (1993)); 3) antibodies (e.g., polyclonal, monoclonal, humanized, anti-idiotypic, chimeric, and single chain antibodies as well as Fab, F(ab')$_2$, Fab expression library fragments, and epitope-binding fragments of antibodies); and 4) small organic and inorganic molecules (e.g., molecules obtained from combinatorial and natural product libraries).

One candidate compound is a soluble fragment of the receptor that competes for ligand binding. Other candidate compounds include mutant transporters or appropriate fragments containing mutations that affect transporter function and thus compete for ligand. Accordingly, a fragment that competes for ligand, for example with a higher affinity, or a fragment that binds ligand but does not allow release, is encompassed by the invention.

The invention further includes other end point assays to identify compounds that modulate (stimulate or inhibit) transporter activity. The assays typically involve an assay of events in the signal transduction pathway that indicate transporter activity. Thus, the transport of a ligand, change in cell membrane potential, activation of a protein, a change in the expression of genes that are up- or down-regulated in response to the transporter protein dependent signal cascade can be assayed.

Any of the biological or biochemical functions mediated by the transporter can be used as an endpoint assay. These include all of the biochemical or biochemical/biological events described herein, in the references cited herein, incorporated by reference for these endpoint assay targets, and other functions known to those of ordinary skill in the art or that can be readily identified using the information provided in the Figures, particularly FIG. 2. Specifically, a biological function of a cell or tissues that expresses the transporter can be assayed. Experimental data as provided in FIG. 1 indicates that transporter proteins of the present invention are expressed in the pooled human melanocyte, fetal heart, and pregnant uterus detected by a virtual northern blot. In addition, PCR-based tissue screening panel indicates expression in human leukocytes.

Binding and/or activating compounds can also be screened by using chimeric transporter proteins in which the amino terminal extracellular domain, or parts thereof, the entire transmembrane domain or subregions, such as any of the seven transmembrane segments or any of the intracellular or extracellular loops and the carboxy terminal intracellular domain, or parts thereof, can be replaced by heterologous domains or subregions. For example, a ligand-binding region can be used that interacts with a different ligand then that which is recognized by the native transporter. Accordingly, a different set of signal transduction components is available as an end-point assay for activation. This allows for assays to be performed in other than the specific host cell from which the transporter is derived.

The proteins of the present invention are also useful in competition binding assays in methods designed to discover compounds that interact with the transporter (e.g. binding partners and/or ligands). Thus, a compound is exposed to a transporter polypeptide under conditions that allow the compound to bind or to otherwise interact with the polypeptide. Soluble transporter polypeptide is also added to the mixture. If the test compound interacts with the soluble transporter polypeptide, it decreases the amount of complex formed or activity from the transporter target. This type of assay is particularly useful in cases in which compounds are sought that interact with specific regions of the transporter. Thus, the soluble polypeptide that competes with the target transporter region is designed to contain peptide sequences corresponding to the region of interest.

To perform cell free drug screening assays, it is sometimes desirable to immobilize either the transporter protein, or fragment, or its target molecule to facilitate separation of complexes from uncomplexed forms of one or both of the proteins, as well as to accommodate automation of the assay.

Techniques for immobilizing proteins on matrices can be used in the drug screening assays. In one embodiment, a fusion protein can be provided which adds a domain that allows the protein to be bound to a matrix. For example, glutathione-S-transferase fusion proteins can be adsorbed onto glutathione sepharose beads (Sigma Chemical, St. Louis, Mo.) or glutathione derivatized microtitre plates, which are then combined with the cell lysates (e.g., $^{35}$S-labeled) and the candidate compound, and the mixture incubated under conditions conducive to complex formation (e.g., at physiological conditions for salt and pH). Following incubation, the beads are washed to remove any unbound label, and the matrix immobilized and radiolabel determined directly, or in the supernatant after the complexes are dissociated. Alternatively, the complexes can be dissociated from the matrix, separated by SDS-PAGE, and the level of transporter-binding protein found in the bead fraction quantitated from the gel using standard electrophoretic techniques. For example, either the polypeptide or its target molecule can be immobilized utilizing conjugation of biotin and streptavidin using techniques well known in the art. Alternatively, antibodies reactive with the protein but which do not interfere with binding of the protein to its target molecule can be derivatized to the wells of the plate, and the protein trapped in the wells by antibody conjugation. Preparations of a transporter-binding protein and a candidate compound are incubated in the transporter protein-presenting wells and the amount of complex trapped in the well can be quantitated. Methods for detecting such complexes, in addition to those described above for the GST-immobilized complexes, include immunodetection of complexes using antibodies reactive with the transporter protein target molecule, or which are reactive with transporter protein and compete with the target molecule, as well as enzyme-linked assays which rely on detecting an enzymatic activity associated with the target molecule.

Agents that modulate one of the transporters of the present invention can be identified using one or more of the above assays, alone or in combination. It is generally preferable to use a cell-based or cell free system first and then confirm activity in an animal or other model system. Such model systems are well known in the art and can readily be employed in this context.

Modulators of transporter protein activity identified according to these drug screening assays can be used to treat a subject with a disorder mediated by the transporter pathway, by treating cells or tissues that express the transporter. Experimental data as provided in FIG. 1 indicates expression in the pooled human melanocyte, fetal heart, and pregnant uterus and human leukocytes. These methods of treatment include the steps of administering a modulator of transporter activity in a pharmaceutical composition to a subject in need of such treatment, the modulator being identified as described herein.

In yet another aspect of the invention, the transporter proteins can be used as "bait proteins" in a two-hybrid assay or three-hybrid assay (see, e.g., U.S. Pat. No. 5,283,317; Zervos et al. (1993) Cell 72:223–232; Madura et al. (1993) J. Biol. Chem. 268:12046–12054; Bartel et al. (1993) Biotechniques 14:920–924; Iwabuchi et al. (1993) Oncogene 8:1693–1696; and Brent WO94/10300), to identify other proteins, which bind to or interact with the transporter and are involved in transporter activity. Such transporter-binding proteins are also likely to be involved in the propagation of signals by the transporter proteins or transporter targets as, for example, downstream elements of a transporter-mediated signaling pathway. Alternatively, such transporter-binding proteins are likely to be transporter inhibitors.

The two-hybrid system is based on the modular nature of most transcription factors, which consist of separable DNA-binding and activation domains. Briefly, the assay utilizes two different DNA constructs. In one construct, the gene that codes for a transporter protein is fused to a gene encoding the DNA binding domain of a known transcription factor (e.g., GAL-4). In the other construct, a DNA sequence, from a library of DNA sequences, that encodes an unidentified protein ("prey" or "sample") is fused to a gene that codes for the activation domain of the known transcription factor. If the "bait" and the "prey" proteins are able to interact, in vivo, forming a transporter-dependent complex, the DNA-binding and activation domains of the transcription factor are brought into close proximity. This proximity allows transcription of a reporter gene (e.g., LacZ) which is operably linked to a transcriptional regulatory site responsive to the transcription factor. Expression of the reporter gene can be detected and cell colonies containing the functional transcription factor can be isolated and used to obtain the cloned gene which encodes the protein which interacts with the transporter protein.

This invention further pertains to novel agents identified by the above-described screening assays. Accordingly, it is within the scope of this invention to further use an agent identified as described herein in an appropriate animal model. For example, an agent identified as described herein (e.g., a transporter-modulating agent, an antisense transporter nucleic acid molecule, a transporter-specific antibody, or a transporter-binding partner) can be used in an animal or other model to determine the efficacy, toxicity, or side effects of treatment with such an agent. Alternatively, an agent identified as described herein can be used in an animal or other model to determine the mechanism of action of such an agent. Furthermore, this invention pertains to uses of novel agents identified by the above-described screening assays for treatments as described herein.

The transporter proteins of the present invention are also useful to provide a target for diagnosing a disease or predisposition to disease mediated by the peptide. Accordingly, the invention provides methods for detecting the presence, or levels of, the protein (or encoding mRNA) in a cell, tissue, or organism. Experimental data as provided in FIG. 1 indicates expression in the pooled human melanocyte, fetal heart, and pregnant uterus and human leukocytes. The method involves contacting a biological sample with a compound capable of interacting with the transporter protein such that the interaction can be detected. Such an assay can be provided in a single detection format or a multi-detection format such as an antibody chip array.

One agent for detecting a protein in a sample is an antibody capable of selectively binding to protein. A biological sample includes tissues, cells and biological fluids isolated from a subject, as well as tissues, cells and fluids present within a subject.

The peptides of the present invention also provide targets for diagnosing active protein activity, disease, or predisposition to disease, in a patient having a variant peptide, particularly activities and conditions that are known for other members of the family of proteins to which the present one belongs. Thus, the peptide can be isolated from a biological sample and assayed for the presence of a genetic mutation that results in aberrant peptide. This includes amino acid substitution, deletion, insertion, rearrangement, (as the result of aberrant splicing events), and inappropriate post-translational modification. Analytic methods include altered electrophoretic mobility, altered tryptic peptide digest, altered transporter activity in cell-based or cell-free assay, alteration in ligand or antibody-binding pattern, altered isoelectric point, direct amino acid sequencing, and any other of the known assay techniques useful for detecting mutations in a protein. Such an assay can be provided in a single detection format or a multi-detection format such as an antibody chip array.

In vitro techniques for detection of peptide include enzyme linked immunosorbent assays (ELISAs), Western blots, immunoprecipitations and immunofluorescence using a detection reagent, such as an antibody or protein binding agent. Alternatively, the peptide can be detected in vivo in a subject by introducing into the subject a labeled anti-peptide antibody or other types of detection agent. For example, the antibody can be labeled with a radioactive marker whose presence and location in a subject can be detected by standard imaging techniques. Particularly useful are methods that detect the allelic variant of a peptide expressed in a subject and methods which detect fragments of a peptide in a sample.

The peptides are also useful in pharmacogenomic analysis. Pharmacogenomics deal with clinically significant hereditary variations in the response to drugs due to altered drug disposition and abnormal action in affected persons. See, e.g., Eichelbaum, M. (*Clin. Exp. Pharmacol. Physiol.* 23(10–11):983–985 (1996)), and Linder, M. W. (*Clin. Chem.* 43(2):254–266 (1997)). The clinical outcomes of these variations result in severe toxicity of therapeutic drugs in certain individuals or therapeutic failure of drugs in certain individuals as a result of individual variation in metabolism. Thus, the genotype of the individual can determine the way a therapeutic compound acts on the body or the way the body metabolizes the compound. Further, the activity of drug metabolizing enzymes effects both the intensity and duration of drug action. Thus, the pharmacogenomics of the individual permit the selection of effective compounds and effective dosages of such compounds for prophylactic or therapeutic treatment based on the individual's genotype. The discovery of genetic polymorphisms in some drug metabolizing enzymes has explained why some patients do not obtain the expected drug effects, show an exaggerated drug effect, or experience serious toxicity from standard drug dosages. Polymorphisms can be expressed in the phenotype of the extensive metabolizer and the phenotype of the poor metabolizer. Accordingly, genetic polymorphism may lead to allelic protein variants of the transporter protein in which one or more of the transporter functions in one population is different from those in another population. The peptides thus allow a target to ascertain a genetic predisposition that can affect treatment modality. Thus, in a ligand-based treatment, polymorphism may give rise to amino terminal extracellular domains and/or other ligand-binding regions that are more or less active in ligand binding, and transporter activation. Accordingly, ligand dosage would necessarily be modified to maximize the therapeutic effect within a given population containing a polymorphism. As an alternative to genotyping, specific polymorphic peptides could be identified.

The peptides are also useful for treating a disorder characterized by an absence of, inappropriate, or unwanted expression of the protein. Experimental data as provided in FIG. 1 indicates expression in the pooled human melanocyte, fetal heart, and pregnant uterus and human leukocytes. Accordingly, methods for treatment include the use of the transporter protein or fragments.

Antibodies

The invention also provides antibodies that selectively bind to one of the peptides of the present invention, a protein comprising such a peptide, as well as variants and fragments thereof. As used herein, an antibody selectively binds a target peptide when it binds the target peptide and does not significantly bind to unrelated proteins. An antibody is still considered to selectively bind a peptide even if it also binds to other proteins that are not substantially homologous with the target peptide so long as such proteins share homology with a fragment or domain of the peptide target of the antibody. In this case, it would be understood that antibody binding to the peptide is still selective despite some degree of cross-reactivity.

As used herein, an antibody is defined in terms consistent with that recognized within the art: they are multi-subunit proteins produced by a mammalian organism in response to an antigen challenge. The antibodies of the present invention include polyclonal antibodies and monoclonal antibodies, as well as fragments of such antibodies, including, but not limited to, Fab or $F(ab')_2$, and Fv fragments.

Many methods are known for generating and/or identifying antibodies to a given target peptide. Several such methods are described by Harlow, Antibodies, Cold Spring Harbor Press, (1989).

In general, to generate antibodies, an isolated peptide is used as an immunogen and is administered to a mammalian organism, such as a rat, rabbit or mouse. The full-length protein, an antigenic peptide fragment or a fusion protein can be used. Particularly important fragments are those covering functional domains, such as the domains identified in FIG. 2, and domain of sequence homology or divergence amongst the family, such as those that can readily be identified using protein alignment methods and as presented in the Figures.

Antibodies are preferably prepared from regions or discrete fragments of the transporter proteins. Antibodies can be prepared from any region of the peptide as described herein. However, preferred regions will include those involved in function/activity and/or transporter/binding partner interaction. FIG. 2 can be used to identify particularly important regions while sequence alignment can be used to identify conserved and unique sequence fragments.

An antigenic fragment will typically comprise at least 8 contiguous amino acid residues. The antigenic peptide can comprise, however, at least 10, 12, 14, 16 or more amino acid residues. Such fragments can be selected on a physical property, such as fragments correspond to regions that are located on the surface of the protein, e.g., hydrophilic regions or can be selected based on sequence uniqueness (see FIG. 2).

Detection on an antibody of the present invention can be facilitated by coupling (i.e., physically linking) the antibody to a detectable substance. Examples of detectable substances include various enzymes, prosthetic groups, fluorescent materials, luminescent materials, bioluminescent materials, and radioactive materials. Examples of suitable enzymes include horseradish peroxidase, alkaline phosphatase, β-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and aequorin, and examples of suitable radioactive material include $^{125}I$, $^{131}I$, $^{35}S$ or $^{3}H$.

Antibody Uses

The antibodies can be used to isolate one of the proteins of the present invention by standard techniques, such as affinity chromatography or immunoprecipitation. The antibodies can facilitate the purification of the natural protein from cells and recombinantly produced protein expressed in host cells. In addition, such antibodies are useful to detect the presence of one of the proteins of the present invention in cells or tissues to determine the pattern of expression of the protein among various tissues in an organism and over the course of normal development. Experimental data as provided in FIG. 1 indicates that transporter proteins of the present invention are expressed in the pooled human melanocyte, fetal heart, and pregnant uterus detected by a virtual northern blot. In addition, PCR-based tissue screening panel indicates expression in human leukocytes. Further, such antibodies can be used to detect protein in situ, in vitro, or in a cell lysate or supernatant in order to evaluate the abundance and pattern of expression. Also, such antibodies can be used to assess abnormal tissue distribution or abnormal expression during development or progression of a biological condition. Antibody detection of circulating fragments of the full length protein can be used to identify turnover.

Further, the antibodies can be used to assess expression in disease states such as in active stages of the disease or in an individual with a predisposition toward disease related to the protein's function. When a disorder is caused by an inappropriate tissue distribution, developmental expression, level of expression of the protein, or expressed/processed form, the antibody can be prepared against the normal protein. Experimental data as provided in FIG. 1 indicates expression in the pooled human melanocyte, fetal heart, and pregnant uterus and human leukocytes. If a disorder is characterized by a specific mutation in the protein, antibodies specific for this mutant protein can be used to assay for the presence of the specific mutant protein.

The antibodies can also be used to assess normal and aberrant subcellular localization of cells in the various tissues in an organism. Experimental data as provided in FIG. 1 indicates expression in the pooled human melanocyte, fetal heart, and pregnant uterus and human leukocytes. The diagnostic uses can be applied, not only in genetic testing, but also in monitoring a treatment modality. Accordingly, where treatment is ultimately aimed at correcting expression level or the presence of aberrant sequence and aberrant tissue distribution or developmental expression, antibodies directed against the protein or relevant fragments can be used to monitor therapeutic efficacy.

Additionally, antibodies are useful in pharmacogenomic analysis. Thus, antibodies prepared against polymorphic proteins can be used to identify individuals that require modified treatment modalities. The antibodies are also useful as diagnostic tools as an immunological marker for aberrant protein analyzed by electrophoretic mobility, isoelectric point, tryptic peptide digest, and other physical assays known to those in the art.

The antibodies are also useful for tissue typing. Experimental data as provided in FIG. 1 indicates expression in the pooled human melanocyte, fetal heart, and pregnant uterus and human leukocytes. Thus, where a specific protein has been correlated with expression in a specific tissue, antibodies that are specific for this protein can be used to identify a tissue type.

The antibodies are also useful for inhibiting protein function, for example, blocking the binding of the transporter peptide to a binding partner such as a ligand or protein binding partner. These uses can also be applied in a therapeutic context in which treatment involves inhibiting the protein's function. An antibody can be used, for example, to block binding, thus modulating (agonizing or antagonizing) the peptides activity. Antibodies can be prepared against specific fragments containing sites required for function or against intact protein that is associated with a cell or cell membrane. See FIG. 2 for structural information relating to the proteins of the present invention.

The invention also encompasses kits for using antibodies to detect the presence of a protein in a biological sample. The kit can comprise antibodies such as a labeled or labelable antibody and a compound or agent for detecting protein in a biological sample; means for determining the amount of protein in the sample; means for comparing the amount of protein in the sample with a standard; and instructions for use. Such a kit can be supplied to detect a single protein or epitope or can be configured to detect one of a multitude of epitopes, such as in an antibody detection array. Arrays are described in detail below for nucleic acid arrays and similar methods have been developed for antibody arrays.

Nucleic Acid Molecules

The present invention further provides isolated nucleic acid molecules that encode a transporter peptide or protein of the present invention (cDNA, transcript and genomic sequence). Such nucleic acid molecules will consist of, consist essentially of, or comprise a nucleotide sequence that encodes one of the transporter peptides of the present invention, an allelic variant thereof, or an ortholog or paralog thereof.

As used herein, an "isolated" nucleic acid molecule is one that is separated from other nucleic acid present in the natural source of the nucleic acid. Preferably, an "isolated" nucleic acid is free of sequences that naturally flank the nucleic acid (i.e., sequences located at the 5' and 3' ends of the nucleic acid) in the genomic DNA of the organism from which the nucleic acid is derived. However, there can be some flanking nucleotide sequences, for example up to about 5KB, 4KB, 3KB, 2KB, or 1KB or less, particularly contiguous peptide encoding sequences and peptide encoding sequences within the same gene but separated by introns in the genomic sequence. The important point is that the nucleic acid is isolated from remote and unimportant flanking sequences such that it can be subjected to the specific manipulations described herein such as recombinant expression, preparation of probes and primers, and other uses specific to the nucleic acid sequences.

Moreover, an "isolated" nucleic acid molecule, such as a transcript/cDNA molecule, can be substantially free of other cellular material, or culture medium when produced by recombinant techniques, or chemical precursors or other chemicals when chemically synthesized. However, the nucleic acid molecule can be fused to other coding or regulatory sequences and still be considered isolated.

For example, recombinant DNA molecules contained in a vector are considered isolated. Further examples of isolated DNA molecules include recombinant DNA molecules maintained in heterologous host cells or purified (partially or substantially) DNA molecules in solution. Isolated RNA molecules include in vivo or in vitro RNA transcripts of the isolated DNA molecules of the present invention. Isolated nucleic acid molecules according to the present invention further include such molecules produced synthetically.

Accordingly, the present invention provides nucleic acid molecules that consist of the nucleotide sequence shown in FIG. 1 or 3 (SEQ ID NO: 1, transcript sequence and SEQ ID NO:3, genomic sequence), or any nucleic acid molecule that encodes the protein provided in FIG. 2, SEQ ID NO:2. A nucleic acid molecule consists of a nucleotide sequence when the nucleotide sequence is the complete nucleotide sequence of the nucleic acid molecule.

The present invention further provides nucleic acid molecules that consist essentially of the nucleotide sequence shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule consists essentially of a nucleotide sequence when such a nucleotide sequence is present with only a few additional nucleic acid residues in the final nucleic acid molecule.

The present invention further provides nucleic acid molecules that comprise the nucleotide sequences shown in FIG. 1 or 3 (SEQ ID NO:1, transcript sequence and SEQ ID NO:3, genomic sequence), or any nucleic acid molecule that encodes the protein provided in FIG. 2, SEQ ID NO:2. A nucleic acid molecule comprises a nucleotide sequence when the nucleotide sequence is at least part of the final nucleotide sequence of the nucleic acid molecule. In such a fashion, the nucleic acid molecule can be only the nucleotide sequence or have additional nucleic acid residues, such as nucleic acid residues that are naturally associated with it or heterologous nucleotide sequences. Such a nucleic acid molecule can have a few additional nucleotides or can comprise several hundred or more additional nucleotides. A brief description of how various types of these nucleic acid molecules can be readily made/isolated is provided below.

In FIGS. 1 and 3, both coding and non-coding sequences are provided. Because of the source of the present invention, humans genomic sequence (FIG. 3) and cDNA/transcript sequences (FIG. 1), the nucleic acid molecules in the Figures will contain genomic intronic sequences, 5' and 3' non-coding sequences, gene regulatory regions and non-coding intergenic sequences. In general such sequence features are either noted in FIGS. 1 and 3 or can readily be identified using computational tools known in the art. As discussed below, some of the non-coding regions, particularly gene regulatory elements such as promoters, are useful for a variety of purposes, e.g. control of heterologous gene expression, target for identifying gene activity modulating compounds, and are particularly claimed as fragments of the genomic sequence provided herein.

The isolated nucleic acid molecules can encode the mature protein plus additional amino or carboxyl-terminal amino acids, or amino acids interior to the mature peptide (when the mature form has more than one peptide chain, for instance). Such sequences may play a role in processing of a protein from precursor to a mature form, facilitate protein trafficking, prolong or shorten protein half-life or facilitate manipulation of a protein for assay or production, among other things. As generally is the case in situ, the additional amino acids may be processed away from the mature protein by cellular enzymes.

As mentioned above, the isolated nucleic acid molecules include, but are not limited to, the sequence encoding the transporter peptide alone, the sequence encoding the mature peptide and additional coding sequences, such as a leader or secretory sequence (e.g., a pre-pro or pro-protein sequence), the sequence encoding the mature peptide, with or without the additional coding sequences, plus additional non-coding sequences, for example introns and non-coding 5' and 3' sequences such as transcribed but non-translated sequences that play a role in transcription, mRNA processing (including splicing and polyadenylation signals), ribosome binding and stability of mRNA. In addition, the nucleic acid molecule may be fused to a marker sequence encoding, for example, a peptide that facilitates purification.

Isolated nucleic acid molecules can be in the form of RNA, such as mRNA, or in the form DNA, including cDNA and genomic DNA obtained by cloning or produced by chemical synthetic techniques or by a combination thereof. The nucleic acid, especially DNA, can be double-stranded or single-stranded. Single-stranded nucleic acid can be the coding strand (sense strand) or the non-coding strand (antisense strand).

The invention further provides nucleic acid molecules that encode fragments of the peptides of the present invention as well as nucleic acid molecules that encode obvious variants of the transporter proteins of the present invention that are described above. Such nucleic acid molecules may be naturally occurring, such as allelic variants (same locus), paralogs (different locus), and orthologs (different organism), or may be constructed by recombinant DNA methods or by chemical synthesis. Such non-naturally occurring variants may be made by mutagenesis techniques, including those applied to nucleic acid molecules, cells, or organisms. Accordingly, as discussed above, the variants can contain nucleotide substitutions, deletions, inversions and insertions. Variation can occur in either or both the coding and non-coding regions. The variations can produce both conservative and non-conservative amino acid substitutions.

The present invention further provides non-coding fragments of the nucleic acid molecules provided in FIGS. 1 and 3. Preferred non-coding fragments include, but are not limited to, promoter sequences, enhancer sequences, gene modulating sequences and gene termination sequences. Such fragments are useful in controlling heterologous gene expression and in developing screens to identify gene-modulating agents. A promoter can readily be identified as being 5' to the ATG start site in the genomic sequence provided in FIG. 3.

A fragment comprises a contiguous nucleotide sequence greater than 12 or more nucleotides. Further, a fragment could at least 30, 40, 50, 100, 250 or 500 nucleotides in length. The length of the fragment will be based on its intended use. For example, the fragment can encode epitope bearing regions of the peptide, or can be useful as DNA probes and primers. Such fragments can be isolated using the known nucleotide sequence to synthesize an oligonucleotide probe. A labeled probe can then be used to screen a cDNA library, genomic DNA library, or mRNA to isolate nucleic acid corresponding to the coding region. Further, primers can be used in PCR reactions to clone specific regions of gene.

A probe/primer typically comprises substantially a purified oligonucleotide or oligonucleotide pair. The oligonucleotide typically comprises a region of nucleotide sequence that hybridizes under stringent conditions to at least about 12, 20, 25, 40, 50 or more consecutive nucleotides.

Orthologs, homologs, and allelic variants can be identified using methods well known in the art. As described in the Peptide Section, these variants comprise a nucleotide sequence encoding a peptide that is typically 60–70%, 70–80%, 80–90%, and more typically at least about 90–95% or more homologous to the nucleotide sequence shown in the Figure sheets or a fragment of this sequence. Such nucleic acid molecules can readily be identified as being able to hybridize under moderate to stringent conditions, to the nucleotide sequence shown in the Figure sheets or a fragment of the sequence. Allelic variants can readily be determined by genetic locus of the encoding gene. As indicated by the data presented in FIG. 3, the map position was determined to be on chromosome 12 by ePCR, and confirmed with radiation hybrid mapping.

FIG. 3 provides information on SNPs that have been identified in a gene encoding the transporter protein of the present invention. 69 SNP variants were found, including 14 indels (indicated by a "–") and 1 SNPs in exons.

As used herein, the term "hybridizes under stringent conditions" is intended to describe conditions for hybridization and washing under which nucleotide sequences encoding a peptide at least 60–70% homologous to each other typically remain hybridized to each other. The conditions can be such that sequences at least about 60%, at least about 70%, or at least about 80% or more homologous to each other typically remain hybridized to each other. Such stringent conditions are known to those skilled in the art and can be found in *Current Protocols in Molecular Biology*, John Wiley & Sons, N.Y. (1989), 6.3.1–6.3.6. One example of stringent hybridization conditions are hybridization in 6× sodium chloride/sodium citrate (SSC) at about 45 C., followed by one or more washes in 0.2× SSC, 0.1% SDS at 50–65C. Examples of moderate to low stringency hybridization conditions are well known in the art.

Nucleic Acid Molecule Uses

The nucleic acid molecules of the present invention are useful for probes, primers, chemical intermediates, and in biological assays. The nucleic acid molecules are useful as a hybridization probe for messenger RNA, transcript/cDNA and genomic DNA to isolate full-length cDNA and genomic clones encoding the peptide described in FIG. 2 and to isolate cDNA and genomic clones that correspond to variants (alleles, orthologs, etc.) producing the same or related peptides shown in FIG. 2. 69 SNPs, including 14 indels, have been identified in the gene encoding the transporter protein provided by the present invention and are given in FIG. 3.

The probe can correspond to any sequence along the entire length of the nucleic acid molecules provided in the Figures. Accordingly, it could be derived from 5' noncoding regions, the coding region, and 3' noncoding regions. However, as discussed, fragments are not to be construed as encompassing fragments disclosed prior to the present invention.

The nucleic acid molecules are also useful as primers for PCR to amplify any given region of a nucleic acid molecule and are useful to synthesize antisense molecules of desired length and sequence.

The nucleic acid molecules are also useful for constructing recombinant vectors. Such vectors include expression vectors that express a portion of, or all of, the peptide sequences. Vectors also include insertion vectors, used to integrate into another nucleic acid molecule sequence, such as into the cellular genome, to alter in situ expression of a gene and/or gene product. For example, an endogenous coding sequence can be replaced via homologous recombination with all or part of the coding region containing one or more specifically introduced mutations.

The nucleic acid molecules are also useful for expressing antigenic portions of the proteins.

The nucleic acid molecules are also useful as probes for determining the chromosomal positions of the nucleic acid molecules by means of in situ hybridization methods. As indicated by the data presented in FIG. 3, the map position was determined to be on chromosome 12 by ePCR, and confirmed with radiation hybrid mapping.

The nucleic acid molecules are also useful in making vectors containing the gene regulatory regions of the nucleic acid molecules of the present invention.

The nucleic acid molecules are also useful for designing ribozymes corresponding to all, or a part, of the mRNA produced from the nucleic acid molecules described herein.

The nucleic acid molecules are also useful for making vectors that express part, or all, of the peptides.

The nucleic acid molecules are also useful for constructing host cells expressing a part, or all, of the nucleic acid molecules and peptides.

The nucleic acid molecules are also useful for constructing transgenic animals expressing all, or a part, of the nucleic acid molecules and peptides.

The nucleic acid molecules are also useful as hybridization probes for determining the presence, level, form and distribution of nucleic acid expression. Experimental data as provided in FIG. 1 indicates that transporter proteins of the present invention are expressed in the pooled human melanocyte, fetal heart, and pregnant uterus detected by a virtual northern blot. In addition, PCR-based tissue screening panel indicates expression in human leukocytes.

Accordingly, the probes can be used to detect the presence of, or to determine levels of, a specific nucleic acid molecule in cells, tissues, and in organisms. The nucleic acid whose level is determined can be DNA or RNA. Accordingly, probes corresponding to the peptides described herein can be used to assess expression and/or gene copy number in a given cell, tissue, or organism. These uses are relevant for diagnosis of disorders involving an increase or decrease in transporter protein expression relative to normal results.

In vitro techniques for detection of mRNA include Northern hybridizations and in situ hybridizations. In vitro techniques for detecting DNA include Southern hybridizations and in situ hybridization.

Probes can be used as a part of a diagnostic test kit for identifying cells or tissues that express a transporter protein, such as by measuring a level of a transporter-encoding nucleic acid in a sample of cells from a subject e.g., mRNA or genomic DNA, or determining if a transporter gene has been mutated. Experimental data as provided in FIG. 1 indicates that transporter proteins of the present invention are expressed in the pooled human melanocyte, fetal heart, and pregnant uterus detected by a virtual northern blot. In addition, PCR-based tissue screening panel indicates expression in human leukocytes.

Nucleic acid expression assays are useful for drug screening to identify compounds that modulate transporter nucleic acid expression.

The invention thus provides a method for identifying a compound that can be used to treat a disorder associated with nucleic acid expression of the transporter gene, particularly biological and pathological processes that are mediated by the transporter in cells and tissues that express it. Experimental data as provided in FIG. 1 indicates expression in the pooled human melanocyte, fetal heart, and pregnant uterus and human leukocytes. The method typically includes assaying the ability of the compound to modulate the expression of the transporter nucleic acid and thus identifying a compound that can be used to treat a disorder characterized by undesired transporter nucleic acid expression. The assays can be performed in cell-based and cell-free systems. Cell-based assays include cells naturally expressing the transporter nucleic acid or recombinant cells genetically engineered to express specific nucleic acid sequences.

The assay for transporter nucleic acid expression can involve direct assay of nucleic acid levels, such as mRNA levels, or on collateral compounds involved in the signal pathway. Further, the expression of genes that are up- or down-regulated in response to the transporter protein signal pathway can also be assayed. In this embodiment the regulatory regions of these genes can be operably linked to a reporter gene such as luciferase.

Thus, modulators of transporter gene expression can be identified in a method wherein a cell is contacted with a candidate compound and the expression of mRNA determined. The level of expression of transporter mRNA in the presence of the candidate compound is compared to the level of expression of transporter mRNA in the absence of the candidate compound. The candidate compound can then be identified as a modulator of nucleic acid expression based on this comparison and be used, for example to treat a disorder characterized by aberrant nucleic acid expression. When expression of mRNA is statistically significantly greater in the presence of the candidate compound than in its absence, the candidate compound is identified as a stimulator of nucleic acid expression. When nucleic acid expression is statistically significantly less in the presence of the candidate compound than in its absence, the candidate compound is identified as an inhibitor of nucleic acid expression.

The invention further provides methods of treatment, with the nucleic acid as a target, using a compound identified through drug screening as a gene modulator to modulate transporter nucleic acid expression in cells and tissues that express the transporter. Experimental data as provided in FIG. 1 indicates that transporter proteins of the present invention are expressed in the pooled human melanocyte, fetal heart, and pregnant uterus detected by a virtual northern blot. In addition, PCR-based tissue screening panel indicates expression in human leukocytes. Modulation includes both up-regulation (i.e. activation or agonization) or down-regulation (suppression or antagonization) or nucleic acid expression.

Alternatively, a modulator for transporter nucleic acid expression can be a small molecule or drug identified using the screening assays described herein as long as the drug or small molecule inhibits the transporter nucleic acid expression in the cells and tissues that express the protein. Experimental data as provided in FIG. 1 indicates expression in the pooled human melanocyte, fetal heart, and pregnant uterus and human leukocytes.

The nucleic acid molecules are also useful for monitoring the effectiveness of modulating compounds on the expression or activity of the transporter gene in clinical trials or in a treatment regimen. Thus, the gene expression pattern can serve as a barometer for the continuing effectiveness of treatment with the compound, particularly with compounds to which a patient can develop resistance. The gene expression pattern can also serve as a marker indicative of a physiological response of the affected cells to the compound. Accordingly, such monitoring would allow either increased administration of the compound or the administration of alternative compounds to which the patient has not become resistant. Similarly, if the level of nucleic acid expression falls below a desirable level, administration of the compound could be commensurately decreased.

The nucleic acid molecules are also useful in diagnostic assays for qualitative changes in transporter nucleic acid expression, and particularly in qualitative changes that lead to pathology. The nucleic acid molecules can be used to detect mutations in transporter genes and gene expression products such as mRNA. The nucleic acid molecules can be used as hybridization probes to detect naturally occurring genetic mutations in the transporter gene and thereby to determine whether a subject with the mutation is at risk for a disorder caused by the mutation. Mutations include deletion, addition, or substitution of one or more nucleotides in the gene, chromosomal rearrangement, such as inversion or transposition, modification of genomic DNA, such as aberrant methylation patterns or changes in gene copy number, such as amplification. Detection of a mutated form of the transporter gene associated with a dysfunction provides a diagnostic tool for an active disease or susceptibility to disease when the disease results from overexpression, underexpression, or altered expression of a transporter protein.

Individuals carrying mutations in the transporter gene can be detected at the nucleic acid level by a variety of techniques. FIG. 3 provides information on SNPs that have been identified in a gene encoding the transporter protein of the present invention. 69 SNP variants were found, including 14 indels (indicated by a "–") and 1 SNPs in exons. As indicated by the data presented in FIG. 3, the map position was determined to be on chromosome 12 by ePCR, and confirmed with radiation hybrid mapping. Genomic DNA can be analyzed directly or can be amplified by using PCR prior to analysis. RNA or cDNA can be used in the same way. In some uses, detection of the mutation involves the use of a probe/primer in a polymerase chain reaction (PCR) (see, e.g. U.S. Pat. Nos. 4,683,195 and 4,683,202), such as anchor PCR or RACE PCR, or, alternatively, in a ligation chain reaction (LCR) (see, e.g., Landegran et al., *Science* 241:1077–1080 (1988); and Nakazawa et al., *PNAS* 91:360–364 (1994)), the latter of which can be particularly useful for detecting point mutations in the gene (see Abravaya et al., *Nucleic Acids Res.* 23:675–682 (1995)). This method can include the steps of collecting a sample of cells from a patient, isolating nucleic acid (e.g., genomic, mRNA or both) from the cells of the sample, contacting the nucleic acid sample with one or more primers which specifically hybridize to a gene under conditions such that hybridization and amplification of the gene (if present) occurs, and detecting the presence or absence of an amplification product, or detecting the size of the amplification product and comparing the length to a control sample. Deletions and insertions can be detected by a change in size of the amplified product compared to the normal genotype. Point mutations can be identified by hybridizing amplified DNA to normal RNA or antisense DNA sequences.

Alternatively, mutations in a transporter gene can be directly identified, for example, by alterations in restriction enzyme digestion patterns determined by gel electrophoresis.

Further, sequence-specific ribozymes (U.S. Pat. No. 5,498,531) can be used to score for the presence of specific mutations by development or loss of a ribozyme cleavage site. Perfectly matched sequences can be distinguished from mismatched sequences by nuclease cleavage digestion assays or by differences in melting temperature.

Sequence changes at specific locations can also be assessed by nuclease protection assays such as RNase and S1 protection or the chemical cleavage method. Furthermore, sequence differences between a mutant transporter gene and a wild-type gene can be determined by direct DNA sequencing. A variety of automated sequencing procedures can be utilized when performing the diagnostic assays (Naeve, C. W., (1995) *Biotechniques* 19:448), including sequencing by mass spectrometry (see, e.g., PCT International Publication No. WO 94/16101; Cohen et al., *Adv. Chromatogr.* 36:127–162 (1996); and Griffin et al., *Appl. Biochem. Biotechnol.* 38:147–159 (1993)).

Other methods for detecting mutations in the gene include methods in which protection from cleavage agents is used to detect mismatched bases in RNA/RNA or RNA/DNA duplexes (Myers et al., *Science* 230:1242 (1985)); Cotton et al., *PNAS* 85:4397 (1988); Saleeba et al., *Meth. Enzymol.* 217:286–295 (1992)), electrophoretic mobility of mutant and wild type nucleic acid is compared (Orita et al., *PNAS* 86:2766 (1989); Cotton et al., *Mutat. Res.* 285:125–144 (1993); and Hayashi et al., *Genet. Anal. Tech. Appl.* 9:73–79 (1992)), and movement of mutant or wild-type fragments in polyacrylamide gels containing a gradient of denaturant is assayed using denaturing gradient gel electrophoresis (Myers et al., *Nature* 313:495 (1985)). Examples of other techniques for detecting point mutations include selective oligonucleotide hybridization, selective amplification, and selective primer extension.

The nucleic acid molecules are also useful for testing an individual for a genotype that while not necessarily causing the disease, nevertheless affects the treatment modality. Thus, the nucleic acid molecules can be used to study the relationship between an individual's genotype and the individual's response to a compound used for treatment (pharmacogenomic relationship). Accordingly, the nucleic acid molecules described herein can be used to assess the mutation content of the transporter gene in an individual in order to select an appropriate compound or dosage regimen for treatment. FIG. 3 provides information on SNPs that have been identified in a gene encoding the transporter protein of the present invention. 69 SNP variants were found, including 14 indels (indicated by a and 1 SNPs in exons.

Thus nucleic acid molecules displaying genetic variations that affect treatment provide a diagnostic target that can be used to tailor treatment in an individual. Accordingly, the production of recombinant cells and animals containing these polymorphisms allow effective clinical design of treatment compounds and dosage regimens.

The nucleic acid molecules are thus useful as antisense constructs to control transporter gene expression in cells, tissues, and organisms. A DNA antisense nucleic acid molecule is designed to be complementary to a region of the gene involved in transcription, preventing transcription and hence production of transporter protein. An antisense RNA or DNA nucleic acid molecule would hybridize to the mRNA and thus block translation of mRNA into transporter protein.

Alternatively, a class of antisense molecules can be used to inactivate mRNA in order to decrease expression of transporter nucleic acid. Accordingly, these molecules can treat a disorder characterized by abnormal or undesired transporter nucleic acid expression. This technique involves cleavage by means of ribozymes containing nucleotide sequences complementary to one or more regions in the mRNA that attenuate the ability of the mRNA to be translated. Possible regions include coding regions and particularly coding regions corresponding to the catalytic and other functional activities of the transporter protein, such as ligand binding.

The nucleic acid molecules also provide vectors for gene therapy in patients containing cells that are aberrant in transporter gene expression. Thus, recombinant cells, which include the patient's cells that have been engineered ex vivo and returned to the patient, are introduced into an individual where the cells produce the desired transporter protein to treat the individual.

The invention also encompasses kits for detecting the presence of a transporter nucleic acid in a biological sample. Experimental data as provided in FIG. 1 indicates that transporter proteins of the present invention are expressed in the pooled human melanocyte, fetal heart, and pregnant uterus detected by a virtual northern blot. In addition, PCR-based tissue screening panel indicates expression in human leukocytes. For example, the kit can comprise reagents such as a labeled or labelable nucleic acid or agent capable of detecting transporter nucleic acid in a biological sample; means for determining the amount of transporter nucleic acid in the sample; and means for comparing the amount of transporter nucleic acid in the sample with a standard. The compound or agent can be packaged in a suitable container. The kit can further comprise instructions for using the kit to detect transporter protein mRNA or DNA.

Nucleic Acid Arrays

The present invention further provides nucleic acid detection kits, such as arrays or microarrays of nucleic acid molecules that are based on the sequence information provided in FIGS. 1 and 3 (SEQ ID NOS:1 and 3).

As used herein "Arrays" or "Microarrays" refers to an array of distinct polynucleotides or oligonucleotides synthesized on a substrate, such as paper, nylon or other type of membrane, filter, chip, glass slide, or any other suitable solid support. In one embodiment, the microarray is prepared and used according to the methods described in U.S. Pat. No. 5,837,832, Chee et al., PCT application WO95/11995 (Chee et al.), Lockhart, D. J. et al. (1996; Nat. Biotech. 14: 1675–1680) and Schena, M. et al. (1996; Proc. Natl. Acad. Sci. 93: 10614–10619), all of which are incorporated herein in their entirety by reference. In other embodiments, such arrays are produced by the methods described by Brown et al., U.S. Pat. No. 5,807,522.

The microarray or detection kit is preferably composed of a large number of unique, single-stranded nucleic acid sequences, usually either synthetic antisense oligonucleotides or fragments of cDNAs, fixed to a solid support. The oligonucleotides are preferably about 6–60 nucleotides in length, more preferably 15–30 nucleotides in length, and most preferably about 20–25 nucleotides in length. For a certain type of microarray or detection kit, it may be preferable to use oligonucleotides that are only 7–20 nucleotides in length. The microarray or detection kit may contain oligonucleotides that cover the known 5', or 3', sequence, sequential oligonucleotides that cover the fall length sequence; or unique oligonucleotides selected from particular areas along the length of the sequence. Polynucleotides used in the microarray or detection kit may be oligonucleotides that are specific to a gene or genes of interest.

In order to produce oligonucleotides to a known sequence for a microarray or detection kit, the gene(s) of interest (or an ORF identified from the contigs of the present invention) is typically examined using a computer algorithm which starts at the 5' or at the 3' end of the nucleotide sequence. Typical algorithms will then identify oligomers of defined length that are unique to the gene, have a GC content within a range suitable for hybridization, and lack predicted secondary structure that may interfere with hybridization. In certain situations it may be appropriate to use pairs of oligonucleotides on a microarray or detection kit. The "pairs" will be identical, except for one nucleotide that preferably is located in the center of the sequence. The second oligonucleotide in the pair (mismatched by one) serves as a control. The number of oligonucleotide pairs may range from two to one million. The oligomers are synthesized at designated areas on a substrate using a light-directed chemical process. The substrate may be paper, nylon or other type of membrane, filter, chip, glass slide or any other suitable solid support.

In another aspect, an oligonucleotide may be synthesized on the surface of the substrate by using a chemical coupling procedure and an ink jet application apparatus, as described in PCT application WO95/251116 (Baldeschweiler et al.) which is incorporated herein in its entirety by reference. In another aspect, a "gridded" array analogous to a dot (or slot) blot may be used to arrange and link cDNA fragments or oligonucleotides to the surface of a substrate using a vacuum system, thermal, UV, mechanical or chemical bonding procedures. An array, such as those described above, may be produced by hand or by using available devices (slot blot or dot blot apparatus), materials (any suitable solid support), and machines (including robotic instruments), and may contain 8, 24, 96, 384, 1536, 6144 or more oligonucleotides, or any other number between two and one million which lends itself to the efficient use of commercially available instrumentation.

In order to conduct sample analysis using a microarray or detection kit, the RNA or DNA from a biological sample is made into hybridization probes. The mRNA is isolated, and cDNA is produced and used as a template to make antisense RNA (aRNA). The aRNA is amplified in the presence of fluorescent nucleotides, and labeled probes are incubated with the microarray or detection kit so that the probe sequences hybridize to complementary oligonucleotides of the microarray or detection kit. Incubation conditions are adjusted so that hybridization occurs with precise complementary matches or with various degrees of less complementarity. After removal of nonhybridized probes, a scanner is used to determine the levels and patterns of fluorescence. The scanned images are examined to determine degree of complementarity and the relative abundance of each oligonucleotide sequence on the microarray or detection kit. The biological samples may be obtained from any bodily fluids (such as blood, urine, saliva, phlegm, gastric juices, etc.), cultured cells, biopsies, or other tissue preparations. A detection system may be used to measure the absence, presence, and amount of hybridization for all of the distinct sequences simultaneously. This data may be used for large-scale correlation studies on the sequences, expression patterns, mutations, variants, or polymorphisms among samples.

Using such arrays, the present invention provides methods to identify the expression of the transporter proteins/peptides of the present invention. In detail, such methods comprise incubating a test sample with one or more nucleic acid molecules and assaying for binding of the nucleic acid molecule with components within the test sample. Such assays will typically involve arrays comprising many genes, at least one of which is a gene of the present invention and or alleles of the transporter gene of the present invention. FIG. 3 provides information on SNPs that have been identified in a gene encoding the transporter protein of the present invention. 69 SNP variants were found, including 14 indels (indicated by a "–") and 1 SNPs in exons.

Conditions for incubating a nucleic acid molecule with a test sample vary. Incubation conditions depend on the format employed in the assay, the detection methods employed, and the type and nature of the nucleic acid molecule used in the assay. One skilled in the art will recognize that any one of the commonly available hybridization, amplification or array assay formats can readily be adapted to employ the novel fragments of the Human genome disclosed herein. Examples of such assays can be found in Chard, T, *An Introduction to Radioimmunoassay and Related Techniques*, Elsevier Science Publishers, Amsterdam, The Netherlands (1986); Bullock, G. R. et al., *Techniques in Immunocytochemistry*, Academic Press, Orlando, Fla. Vol. 1 (1982), Vol. 2 (1983), Vol. 3 (1985); Tijssen, P., *Practice and Theory of Enzyme Immunoassays: Laboratory Techniques in Biochemistry and Molecular Biology*, Elsevier Science Publishers, Amsterdam, The Netherlands (1985).

The test samples of the present invention include cells, protein or membrane extracts of cells. The test sample used in the above-described method will vary based on the assay format, nature of the detection method and the tissues, cells or extracts used as the sample to be assayed. Methods for preparing nucleic acid extracts or of cells are well known in the art and can be readily be adapted in order to obtain a sample that is compatible with the system utilized.

In another embodiment of the present invention, kits are provided which contain the necessary reagents to carry out the assays of the present invention.

Specifically, the invention provides a compartmentalized kit to receive, in close confinement, one or more containers which comprises: (a) a first container comprising one of the nucleic acid molecules that can bind to a fragment of the Human genome disclosed herein; and (b) one or more other containers comprising one or more of the following: wash reagents, reagents capable of detecting presence of a bound nucleic acid.

In detail, a compartmentalized kit includes any kit in which reagents are contained in separate containers. Such containers include small glass containers, plastic containers, strips of plastic, glass or paper, or arraying material such as silica. Such containers allows one to efficiently transfer reagents from one compartment to another compartment such that the samples and reagents are not cross-contaminated, and the agents or solutions of each container can be added in a quantitative fashion from one compartment to another. Such containers will include a container which will accept the test sample, a container which contains the nucleic acid probe, containers which contain wash reagents (such as phosphate buffered saline, Tris-buffers, etc.), and containers which contain the reagents used to detect the bound probe. One skilled in the art will readily recognize that the previously unidentified transporter gene of the present invention can be routinely identified using the sequence information disclosed herein can be readily incorporated into one of the established kit formats which are well known in the art, particularly expression arrays.

Vectors/host cells

The invention also provides vectors containing the nucleic acid molecules described herein. The term "vector" refers to a vehicle, preferably a nucleic acid molecule, which can transport the nucleic acid molecules. When the vector is a nucleic acid molecule, the nucleic acid molecules are covalently linked to the vector nucleic acid. With this aspect of the invention, the vector includes a plasmid, single or double stranded phage, a single or double stranded RNA or DNA viral vector, or artificial chromosome, such as a BAC, PAC, YAC, OR MAC.

A vector can be maintained in the host cell as an extra-chromosomal element where it replicates and produces additional copies of the nucleic acid molecules. Alternatively, the vector may integrate into the host cell genome and produce additional copies of the nucleic acid molecules when the host cell replicates.

The invention provides vectors for the maintenance (cloning vectors) or vectors for expression (expression vectors) of the nucleic acid molecules. The vectors can function in procaryotic or eukaryotic cells or in both (shuttle vectors).

Expression vectors contain cis-acting regulatory regions that are operably linked in the vector to the nucleic acid molecules such that transcription of the nucleic acid molecules is allowed in a host cell. The nucleic acid molecules can be introduced into the host cell with a separate nucleic acid molecule capable of affecting transcription. Thus, the second nucleic acid molecule may provide a trans-acting factor interacting with the cis-regulatory control region to allow transcription of the nucleic acid molecules from the vector. Alternatively, a trans-acting factor may be supplied by the host cell. Finally, a trans-acting factor can be produced from the vector itself. It is understood, however, that in some embodiments, transcription and/or translation of the nucleic acid molecules can occur in a cell-free system.

The regulatory sequence to which the nucleic acid molecules described herein can be operably linked include promoters for directing mRNA transcription. These include, but are not limited to, the left promoter from bacteriophage λ, the lac, TRP, and TAC promoters from *E. coli*, the early and late promoters from SV40, the CMV immediate early promoter, the adenovirus early and late promoters, and retrovirus long-terminal repeats.

In addition to control regions that promote transcription, expression vectors may also include regions that modulate transcription, such as repressor binding sites and enhancers. Examples include the SV40 enhancer, the cytomegalovirus immediate early enhancer, polyoma enhancer, adenovirus enhancers, and retrovirus LTR enhancers.

In addition to containing sites for transcription initiation and control, expression vectors can also contain sequences necessary for transcription termination and, in the transcribed region a ribosome binding site for translation. Other regulatory control elements for expression include initiation and termination codons as well as polyadenylation signals. The person of ordinary skill in the art would be aware of the numerous regulatory sequences that are useful in expression vectors. Such regulatory sequences are described, for example, in Sambrook et al., *Molecular Cloning: A Laboratory Manual.* 2nd. ed., Cold Spring Harbor Laboratory Press, Cold Spring Harbor, N.Y., (1989).

A variety of expression vectors can be used to express a nucleic acid molecule. Such vectors include chromosomal, episomal, and virus-derived vectors, for example vectors derived from bacterial plasmids, from bacteriophage, from yeast episomes, from yeast chromosomal elements, including yeast artificial chromosomes, from viruses such as baculoviruses, papovaviruses such as SV40, Vaccinia viruses, adenoviruses, poxviruses, pseudorabies viruses, and retroviruses. Vectors may also be derived from combinations of these sources such as those derived from plasmid and bacteriophage genetic elements, e.g. cosmids and phagemids. Appropriate cloning and expression vectors for prokaryotic and eukaryotic hosts are described in Sambrook et al., *Molecular Cloning: A Laboratory Manual.* 2nd. ed., Cold Spring Harbor Laboratory Press, Cold Spring Harbor, N.Y., (1989).

The regulatory sequence may provide constitutive expression in one or more host cells (i.e. tissue specific) or may provide for inducible expression in one or more cell types such as by temperature, nutrient additive, or exogenous factor such as a hormone or other ligand. A variety of vectors providing for constitutive and inducible expression in prokaryotic and eukaryotic hosts are well known to those of ordinary skill in the art.

The nucleic acid molecules can be inserted into the vector nucleic acid by well-known methodology. Generally, the DNA sequence that will ultimately be expressed is joined to an expression vector by cleaving the DNA sequence and the expression vector with one or more restriction enzymes and then ligating the fragments together. Procedures for restriction enzyme digestion and ligation are well known to those of ordinary skill in the art.

The vector containing the appropriate nucleic acid molecule can be introduced into an appropriate host cell for propagation or expression using well-known techniques. Bacterial cells include, but are not limited to, *E. coli*, Streptomyces, and *Salmonella typhimurium*. Eukaryotic cells include, but are not limited to, yeast, insect cells such as Drosophila, animal cells such as COS and CHO cells, and plant cells.

As described herein, it may be desirable to express the peptide as a fusion protein. Accordingly, the invention provides fusion vectors that allow for the production of the peptides. Fusion vectors can increase the expression of a recombinant protein, increase the solubility of the recombinant protein, and aid in the purification of the protein by acting for example as a ligand for affinity purification. A proteolytic cleavage site may be introduced at the junction of the fusion moiety so that the desired peptide can ultimately be separated from the fusion moiety. Proteolytic enzymes include, but are not limited to, factor Xa, thrombin, and enterotransporter. Typical fusion expression vectors include pGEX (Smith et al., *Gene* 67:31–40 (1988)), pMAL (New England Biolabs, Beverly, Mass.) and pRIT5 (Pharmacia, Piscataway, N.J.) which fuse glutathione S-transferase (GST), maltose E binding protein, or protein A, respectively, to the target recombinant protein. Examples of suitable inducible non-fusion *E. coli* expression vectors include pTrc (Amann et al., *Gene* 69:301–315 (1988)) and pET 11d (Studier et al., *Gene Expression Technology: Methods in Enzymology* 185:60–89 (1990)).

Recombinant protein expression can be maximized in host bacteria by providing a genetic background wherein the host cell has an impaired capacity to proteolytically cleave the recombinant protein. (Gottesman, S., *Gene Expression Technology: Methods in Enzymology* 185, Academic Press, San Diego, Calif. (1990)119–128). Alternatively, the sequence of the nucleic acid molecule of interest can be altered to provide preferential codon usage for a specific host cell, for example *E. coli*. (Wada et al., *Nucleic Acids Res.* 20:2111–2118 (1992)).

The nucleic acid molecules can also be expressed by expression vectors that are operative in yeast. Examples of vectors for expression in yeast e.g., *S. cerevisiae* include pYepSec1 (Baldari, et al., *EMBO J.* 6:229–234 (1987)), pMFa (Kurjan et al., *Cell* 30:933–943 (1982)), pJRY88 (Schultz et al., *Gene* 54:113–123 (1987)), and pYES2 (Invitrogen Corporation, San Diego, Calif.).

The nucleic acid molecules can also be expressed in insect cells using, for example, baculovirus expression vectors. Baculovirus vectors available for expression of proteins in cultured insect cells (e.g., Sf 9 cells) include the pAc series (Smith et al, *Mol. Cell Biol.* 3:2156–2165 (1983)) and the pVL series (Lucklow et al., *Virology* 170:31–39 (1989)).

In certain embodiments of the invention, the nucleic acid molecules described herein are expressed in mammalian cells using mammalian expression vectors. Examples of mammalian expression vectors include pCDM8 (Seed, B. *Nature* 329:840(1987)) and pMT2PC (Kaufman et al., *EMBO J.* 6:187–195 (1987)).

The expression vectors listed herein are provided by way of example only of the well-known vectors available to those of ordinary skill in the art that would be useful to express the nucleic acid molecules. The person of ordinary skill in the art would be aware of other vectors suitable for maintenance propagation or expression of the nucleic acid molecules described herein. These are found for example in Sambrook, J., Fritsh, E. F., and Maniatis, T. *Molecular Cloning: A Laboratory Manual.* 2nd, ed., Cold Spring Harbor Laboratory, Cold Spring Harbor Laboratory Press, Cold Spring Harbor, N.Y., 1989.

The invention also encompasses vectors in which the nucleic acid sequences described herein are cloned into the vector in reverse orientation, but operably linked to a regulatory sequence that permits transcription of antisense RNA. Thus, an antisense transcript can be produced to all, or to a portion, of the nucleic acid molecule sequences described herein, including both coding and non-coding regions. Expression of this antisense RNA is subject to each of the parameters described above in relation to expression of the sense RNA (regulatory sequences, constitutive or inducible expression, tissue-specific expression).

The invention also relates to recombinant host cells containing the vectors described herein. Host cells therefore include prokaryotic cells, lower eukaryotic cells such as yeast, other eukaryotic cells such as insect cells, and higher eukaryotic cells such as mammalian cells.

The recombinant host cells are prepared by introducing the vector constructs described herein into the cells by techniques readily available to the person of ordinary skill in the art. These include, but are not limited to, calcium phosphate transfection, DEAE-dextran-mediated transfection, cationic lipid-mediated transfection, electroporation, transduction, infection, lipofection, and other techniques such as those found in Sambrook, et al. (*Molecular Cloning: A Laboratory Manual.* 2nd, ed., Cold Spring Harbor Laboratory, Cold Spring Harbor Laboratory Press, Cold Spring Harbor, N.Y., 1989).

Host cells can contain more than one vector. Thus, different nucleotide sequences can be introduced on different vectors of the same cell. Similarly, the nucleic acid molecules can be introduced either alone or with other nucleic acid molecules that are not related to the nucleic acid molecules such as those providing trans-acting factors for expression vectors. When more than one vector is introduced into a cell, the vectors can be introduced independently, co-introduced or joined to the nucleic acid molecule vector.

In the case of bacteriophage and viral vectors, these can be introduced into cells as packaged or encapsulated virus by standard procedures for infection and transduction. Viral vectors can be replication-competent or replication-defective. In the case in which viral replication is defective, replication will occur in host cells providing functions that complement the defects.

Vectors generally include selectable markers that enable the selection of the subpopulation of cells that contain the recombinant vector constructs. The marker can be contained in the same vector that contains the nucleic acid molecules described herein or may be on a separate vector. Markers include tetracycline or ampicillin-resistance genes for prokaryotic host cells and dihydrofolate reductase or neomycin resistance for eukaryotic host cells. However, any marker that provides selection for a phenotypic trait will be effective.

While the mature proteins can be produced in bacteria, yeast, mammalian cells, and other cells under the control of the appropriate regulatory sequences, cell-free transcription and translation systems can also be used to produce these proteins using RNA derived from the DNA constructs described herein.

Where secretion of the peptide is desired, which is difficult to achieve with multi-transmembrane domain containing proteins such as transporters, appropriate secretion signals are incorporated into the vector. The signal sequence can be endogenous to the peptides or heterologous to these peptides.

Where the peptide is not secreted into the medium, which is typically the case with transporters, the protein can be isolated from the host cell by standard disruption procedures, including freeze thaw, sonication, mechanical disruption, use of lysing agents and the like. The peptide can then be recovered and purified by well-known purification methods including ammonium sulfate precipitation, acid extraction, anion or cationic exchange chromatography, phosphocellulose chromatography, hydrophobic-interaction chromatography, affinity chromatography, hydroxylapatite chromatography, lectin chromatography, or high performance liquid chromatography.

It is also understood that depending upon the host cell in recombinant production of the peptides described herein, the peptides can have various glycosylation patterns, depending upon the cell, or maybe non-glycosylated as when produced in bacteria. In addition, the peptides may include an initial modified methionine in some cases as a result of a host-mediated process.

Uses of Vectors and Host Cells

The recombinant host cells expressing the peptides described herein have a variety of uses. First, the cells are useful for producing a transporter protein or peptide that can be further purified to produce desired amounts of transporter protein or fragments. Thus, host cells containing expression vectors are useful for peptide production.

Host cells are also useful for conducting cell-based assays involving the transporter protein or transporter protein fragments, such as those described above as well as other formats known in the art. Thus, a recombinant host cell expressing a native transporter protein is useful for assaying compounds that stimulate or inhibit transporter protein function.

Host cells are also useful for identifying transporter protein mutants in which these functions are affected. If the mutants naturally occur and give rise to a pathology, host cells containing the mutations are useful to assay compounds that have a desired effect on the mutant transporter protein (for example, stimulating or inhibiting function)

which may not be indicated by their effect on the native transporter protein.

Genetically engineered host cells can be further used to produce non-human transgenic animals. A transgenic animal is preferably a mammal, for example a rodent, such as a rat or mouse, in which one or more of the cells of the animal include a transgene. A transgene is exogenous DNA that is integrated into the genome of a cell from which a transgenic animal develops and which remains in the genome of the mature animal in one or more cell types or tissues of the transgenic animal. These animals are useful for studying the function of a transporter protein and identifying and evaluating modulators of transporter protein activity. Other examples of transgenic animals include non-human primates, sheep, dogs, cows, goats, chickens, and amphibians.

A transgenic animal can be produced by introducing nucleic acid into the male pronuclei of a fertilized oocyte, e.g., by microinjection, retroviral infection, and allowing the oocyte to develop in a pseudopregnant female foster animal. Any of the transporter protein nucleotide sequences can be introduced as a transgene into the genome of a non-human animal, such as a mouse.

Any of the regulatory or other sequences useful in expression vectors can form part of the transgenic sequence. This includes intronic sequences and polyadenylation signals, if not already included. A tissue-specific regulatory sequence (s) can be operably linked to the transgene to direct expression of the transporter protein to particular cells.

Methods for generating transgenic animals via embryo manipulation and microinjection, particularly animals such as mice, have become conventional in the art and are described, for example, in U.S. Pat. Nos. 4,736,866 and 4,870,009, both by Leder et al., U.S. Pat. No. 4,873,191 by Wagner et al. and in Hogan, B., *Manipulating the Mouse Embryo*, (Cold Spring Harbor Laboratory Press, Cold Spring Harbor, N.Y., 1986). Similar methods are used for production of other transgenic animals. A transgenic founder animal can be identified based upon the presence of the transgene in its genome and/or expression of transgenic mRNA in tissues or cells of the animals. A transgenic founder animal can then be used to breed additional animals carrying the transgene. Moreover, transgenic animals carrying a transgene can further be bred to other transgenic animals carrying other transgenes. A transgenic animal also includes animals in which the entire animal or tissues in the animal have been produced using the homologously recombinant host cells described herein.

In another embodiment, transgenic non-human animals can be produced which contain selected systems that allow for regulated expression of the transgene. One example of such a system is the cre/loxP recombinase system of bacteriophage P1. For a description of the cre/loxP recombinase system, see, e.g., Lakso et al. *PNAS* 89:6232–6236 (1992). Another example of a recombinase system is the FLP recombinase system of *S. cerevisiae* (O'Gorman et al. *Science* 251:1351–1355 (1991). If a cre/loxP recombinase system is used to regulate expression of the transgene, animals containing transgenes encoding both the Cre recombinase and a selected protein is required. Such animals can be provided through the construction of "double" transgenic animals, e.g., by mating two transgenic animals, one containing a transgene encoding a selected protein and the other containing a transgene encoding a recombinase.

Clones of the non-human transgenic animals described herein can also be produced according to the methods described in Wilmut, I. et al. *Nature* 385:810–813 (1997) and PCT International Publication Nos. WO 97/07668 and WO 97/07669. In brief, a cell, e.g., a somatic cell, from the transgenic animal can be isolated and induced to exit the growth cycle and enter $G_o$ phase. The quiescent cell can then be fused, e.g., through the use of electrical pulses, to an enucleated oocyte from an animal of the same species from which the quiescent cell is isolated. The reconstructed oocyte is then cultured such that it develops to morula or blastocyst and then transferred to pseudopregnant female foster animal. The offspring born of this female foster animal will be a clone of the animal from which the cell, e.g., the somatic cell, is isolated.

Transgenic animals containing recombinant cells that express the peptides described herein are useful to conduct the assays described herein in an in vivo context. Accordingly, the various physiological factors that are present in vivo and that could effect ligand binding, transporter protein activation, and signal transduction, may not be evident from in vitro cell-free or cell-based assays. Accordingly, it is useful to provide non-human transgenic animals to assay in vivo transporter protein function, including ligand interaction, the effect of specific mutant transporter proteins on transporter protein function and ligand interaction, and the effect of chimeric transporter proteins. It is also possible to assess the effect of null mutations, that is mutations that substantially or completely eliminate one or more transporter protein functions.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the above-described modes for carrying out the invention which are obvious to those skilled in the field of molecular biology or related fields are intended to be within the scope of the following claims.

That which is claimed is:

1. An isolated nucleic acid molecule consisting of a nucleotide sequence selected from the group consisting of:
   (a) a nucleotide sequence that encodes a protein comprising the amino acid sequence of SEQ ID NO:2;
   (b) a nucleotide sequence consisting of the nucleic acid sequence of SEQ ID No:1; and
   (c) a nucleotide sequence that is completely complementary to a nucleotide sequence of (a)–(b).

2. A nucleic acid vector comprising a nucleic acid molecule of claim 1.

3. A host cell containing the vector of claim 2.

4. A process for producing a polypeptide comprising culturing the host cell of claim 3 under conditions sufficient for the production of said polypeptide, and recovering the peptide from the host cell culture.

5. An isolated polynucleotide consisting of a nucleotide sequence set forth in SEQ ID NO:1.

6. A vector according to claim 2, said vector is selected from the group consisting of a plasmid, virus, and bacteriophage.

7. A vector according to claim 2, wherein said isolated nucleic acid molecule is inserted into said vector in proper orientation and correct reading frame such that the protein of SEQ ID NO:2 may be expressed by a cell transformed with said vector.

8. A vector according to claim 7, wherein said isolated nucleic acid molecule is operatively linked to a promoter sequence.

9. An isolated nucleic acid molecule comprising a nucleotide sequence selected from the group consisting of:
   (a) a nucleotide sequence that encodes a protein comprising the amino acid sequence of SEQ ID NO:2;
   (b) a nucleotide sequence comprising the nucleic acid sequence of SEQ ID No:1; and
   (c) a nucleotide sequence that is completely complementary to a nucleotide sequence of(a)–(b).

10. A nucleic acid vector comprising a nucleic acid molecule of claim 9.

11. A host cell containing the vector of claim 10.

12. A process for producing a polypeptide comprising culturing the host cell of claim 11 under conditions sufficient for the production of said polypeptide, and recovering the peptide from the host cell culture.

13. An isolated polynucleotide comprising a nucleotide sequence set forth in SEQ ID NO:1.

14. A vector according to claim 10, wherein said vector is selected from the group consisting of a plasmid, virus, and bacteriophage.

15. A vector according to claim 10, wherein said isolated nucleic acid molecule is inserted into said vector in proper orientation and correct reading frame such that the protein of SEQ ID NO:2 may be expressed by a cell transformed with said vector.

16. A vector according to claim 15, wherein said isolated nucleic acid molecule is operatively linked to a promoter sequence.

17. An isolated nucleic acid molecule encoding a human transporter peptide, said nucleic acid molecule sharing at least 90 percent homology with a nucleic acid molecule shown in SEQ ID NO:1.

18. A nucleic acid vector comprising a nucleic acid molecule of claim 17.

19. A host cell containing the vector of claim 18.

20. A process for producing a polypeptide comprising culturing the host cell of claim 19 under conditions sufficient for the production of said polypeptide, and recovering the peptide from the host cell culture.

21. A vector according to claim 18, wherein said vector is selected from the group consisting of a plasmid, virus, and bacteriophage.

22. A vector according to claim 18, wherein said isolated nucleic acid molecule is inserted into said vector in proper orientation and correct reading frame such that the protein of SEQ ID NO:2 may be expressed by a cell transformed with said vector.

23. A vector according to claim 22, wherein said isolated nucleic acid molecule is operatively linked to a promoter sequence.

* * * * *